(12) United States Patent
Kang et al.

(10) Patent No.: US 9,682,973 B2
(45) Date of Patent: Jun. 20, 2017

(54) PHTALAZINONE DERIVATIVES AND MANUFACTURING PROCESS THEREOF

(71) Applicant: ILDONG PHARM CO., LTD., Seoul (KR)

(72) Inventors: Jae-Hoon Kang, Seoul (KR); Hong-Sub Lee, Gyeonggi-do (KR); Yoon-Suk Lee, Gyeonggi-do (KR); Joon-Tae Park, Gyeonggi-do (KR); Kyung-Mi An, Gyeonggi-do (KR); Jin-Ah Jeong, Seoul (KR); Kyung-Sun Kim, Gyeonggi-do (KR); Jeong-Geun Kim, Gyeonggi-do (KR); Chang-Hee Hong, Seoul (KR); Sun-Young Park, Gyeonggi-do (KR); Dong-Keun Song, Gyeonggi-do (KR); Yong-Don Yun, Gyeonggi-do (KR)

(73) Assignee: ILDONG PHARM CO., LTD (KR)

( * ) Notice: Subject to any disclaimer, the term of this patent is extended or adjusted under 35 U.S.C. 154(b) by 0 days.

(21) Appl. No.: 15/021,336

(22) PCT Filed: Sep. 12, 2014

(86) PCT No.: PCT/KR2014/008523
§ 371 (c)(1),
(2) Date: Mar. 11, 2016

(87) PCT Pub. No.: WO2015/037939
PCT Pub. Date: Mar. 19, 2015

(65) Prior Publication Data
US 2016/0222003 A1    Aug. 4, 2016

(30) Foreign Application Priority Data

Sep. 13, 2013  (KR) .................... 10-2013-0110170
Sep. 11, 2014  (KR) .................... 10-2014-0120152

(51) Int. Cl.
| C07D 417/14 | (2006.01) |
| C07D 401/14 | (2006.01) |
| C07D 403/08 | (2006.01) |
| C07D 403/14 | (2006.01) |
| C07D 403/10 | (2006.01) |

(52) U.S. Cl.
CPC ......... *C07D 417/14* (2013.01); *C07D 401/14* (2013.01); *C07D 403/08* (2013.01); *C07D 403/10* (2013.01); *C07D 403/14* (2013.01)

(58) Field of Classification Search
CPC .................................................. C07D 401/00
See application file for complete search history.

(56) References Cited

U.S. PATENT DOCUMENTS

| 7,834,015 B2 | 11/2010 | Jones et al. |
| 8,188,084 B2 | 5/2012 | Jones et al. |
| 2005/0059663 A1 | 3/2005 | Martin et al. |
| 2008/0161280 A1 | 7/2008 | Gandhi et al. |

FOREIGN PATENT DOCUMENTS

| EP | 1633724 B1 | 3/2006 |
| EP | 2799435 A1 | 5/2014 |
| JP | 2006-519827 A | 8/2006 |
| JP | 2009-538896 A | 11/2009 |
| JP | 2009-538897 A | 11/2009 |
| JP | 2010-514785 A | 5/2010 |
| WO | WO 02/36576 A1 | 5/2002 |
| WO | WO 03/093261 A1 | 11/2003 |
| WO | WO 2004/080976 A1 | 9/2004 |
| WO | WO 2007/138351 A2 | 12/2007 |
| WO | WO 2007/138355 A1 | 12/2007 |
| WO | WO 2009/063244 A1 | 5/2009 |
| WO | WO 2009/112832 A1 | 9/2009 |
| WO | WO 2012/014221 A1 | 2/2012 |
| WO | WO 2012/019427 A1 | 2/2012 |
| WO | WO 2012/019430 A1 | 2/2012 |
| WO | WO 2012019426 A1 | 2/2012 |
| WO | WO 2012/071684 A1 | 6/2012 |
| WO | WO 2012/072033 A1 | 6/2012 |
| WO | 2013078771 A1 | 6/2013 |

OTHER PUBLICATIONS

Pinedo et al. (2000).*
McMahon et al. (2000).*
Ye et al., "Design, Synthesis, and Biological Evaluation of a Series of Benzo[de][1,7]naphthyridin-7(8H)-ones Bearing a Functionalized Longer Chain Appendage as Novel PARP1 Inhibitors," *J. Med. Chem.*, 2013, 56:2885-2903.
Zhu et al., "Discovery and SAR of orally efficacious tetrahydropyridopyridazinone PARP inhibitors for the treatment of cancer", Bioorganic & Medicinal Chemistry vol. 20, No. 15, (2012) pp. 4635-4645.

* cited by examiner

*Primary Examiner* — Paul V Ward
(74) *Attorney, Agent, or Firm* — Riverside Law LLP

(57) ABSTRACT

The present invention relates to phthalazinone derivatives, including pharmaceutical compositions and for the preparation of phthalazinone derivatives. And more particularly the present invention provided a pharmaceutical composition of phthalazinone derivatives for inhibiting activity of the Poly(ADP-riboside) polymerase enzyme.

7 Claims, No Drawings

PHTALAZINONE DERIVATIVES AND MANUFACTURING PROCESS THEREOF

CROSS-REFERENCE TO RELATED APPLICATIONS

This application is the U.S. national phase application filed under 35 U.S.C. §371 claiming benefit to International Patent Application No. PCT/KR2014/008523, filed on Sep. 12, 2014, which is entitled to priority under 35 U.S.C. §119(a)-(d) to Korea application nos. 10-2013-0110170, filed Sep. 13, 2013 and 10-2014-0120152, filed Sep. 11, 2014, each of which application is hereby incorporated herein by reference in its entirety.

TECHNICAL FIELD

The present invention relates to phthalazinone derivates, isomers, pharmaceutically acceptable salt thereof and on its study for medicinal uses.

BACKGROUND ART

The interest in Poly ADP ribose polymerase (PARP) inhibitors is increasing in accordance with the detection of a high rate of BRCA1 or BRCA2 gene mutation due to the recent genetic breast and ovarian cancer. In general, with BRCA genetic mutations the breast cancer risk is 5 times higher, and one of them in particular, the probability of a considerable risk for TNBC (Triple-negative breast cancer) is increasing. TNBC accounted for 15% of breast cancer patients is related to the lacks of estrogen receptors, progesterone receptors. As there has been no special treatment until now, the target of TNBC contains significant market potential.

The PARP is the one of repairing enzyme for damaged single-stranded DNA breakes. In case of inhibition of PARP, the damage of single strand consecutively generates defects in double-stranded DNA. At this point, the defects of double strand can be recovered by BRCA protein complex. Thus in general, even though the one of the DNA repairing paths is not working, most of cell can be alive. But the cancer patients who inheritantly lost repairing path of BRCA protein complex by the mutation of BRCA1/BRCA2 can increase dependancy on the PARP pathway of DNA repairing. Especially, as the possibility of defects in DNA replication in case of cancer cell is higher than normal cell, the cancer cell has higher dependance on PARP path than normal cell. In other words, the PARP inhibitors fundamentally block the repairing system of cancer cell following apoptosis of cancer cell.

To date, 18 members of the PARP family have been identified and characterized, with PARP-1 being the most thoroughly studied and PARP-2 being its closest relative. Despite the large number of enzymes in this family, PARP-1 accounts for >90% of the ADP-ribosylation within the cell. Because of the structural homology between PARP-1 and PARP-2, most PARP-1 inhibitors also inhibit PARP-2. The PARP-1 enzyme is a 113 kDa protein with three major structural domains, a DNA binding domain with two zinc fingers, a 55 kDa catalytic domain, which utilizes nicotinamide adenine dinucleotide (NAD+) as a substrate to construct polymers of ADP-ribose on histones and other nuclear acceptor proteins including the automodification domain of PARP-1 itself. It is published and generally accepted that the catalytic activity of PARP-1 is stimulated by DNA damage caused by peroxidation, irradiation, and DNA-damaging chemicals, chemotherapeutic agents. Toward this end, PARP-1 enzyme binds to damaged DNA and stimulates polymerization of ADP-ribose resulting in the unwinding of DNA from histones and exposing the damaged DNA for repairing. Accordingly, PARP-1 is associated with DNA repairing and maintenance.

TNBC breast cancer is associated with BRCA1 and BRCA2 gene mutations. The central role of the BRCA gene is the recovery of double stranded brake (DSB) through homologous recombination (HR). PARP-1 inhibition will lead to an increase in single strand breaks (SSB), the preponderance of these SSBs will eventually lead to increased DSBs. The increase of DSBs in BRCA1/BRCA2 gene mutation cancer patients in the presence of HR deficient cell types leads to chromosomal aberrations and instability of the genome resulting in cell death.

A conventionally known PARP inhibitor Olaparib (WO2002036576, WO2003093261, US2004876080, US2005059663) are developed for the treatment of cancer, such as, specifically, stomach cancer, ovarian cancer, breast cancer.

Following four patents are published with modified phenyl group of phthalazinone structure (WO2007138351, WO2007138355, WO2009063244, and WO2009112832).

Since 2011 pharmaceutical companies from China and India published various patent with modified derivates of Olaparib (WO2012019426A1, WO2012019427A1, WO2012019430A1, WO2012071684A1, WO2012072033A1 and WO2012014221).

As anticancer agents PARP inhibitors, has been progressed with respect to the prior published clinical literature, has a new mechanism of action for the treatment of cancer. PARP inhibitors are development as first target for personalized medicine based on personal genetic mutation so that worldwide attention is focused. PARP inhibitors have been reported to exhibit in particular a significant effect on cancer caused by genetic mutations in BRCA1/2, and the present invention with new mechanism for the treatment of cancer patients with genetic variation in BRCA1/2 genes is expected to open a new chapter.

DISCLOSURE OF INVENTION

Technical Problem

An object of the present invention is to provide a novel phthalazinone derivative and a process method for preparing.

In addition, the object of the present invention is to provide medical use for useful treatment of diseases improved by PARP inhibition, or cancers caused by generic defect of BRCA1, BRCA2, and ERG fusion gene.

However, the technical objects to be achieved in the present invention are not limited to those stated above and other objects may be clearly understood to those skilled in the art from the following description.

Solution to Problem

To solve the problem described above, the present invention provides a compound represented by Formula I, racemic, enantiomer, diastereoisomer thereof, or pharmaceutically acceptable salt thereof.

[Formula I]

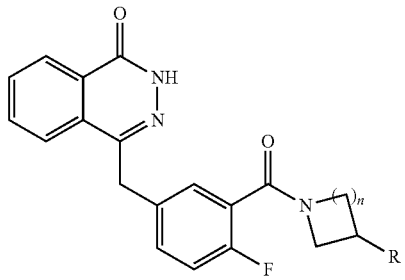

wherein, n is 1 or 2,

R is

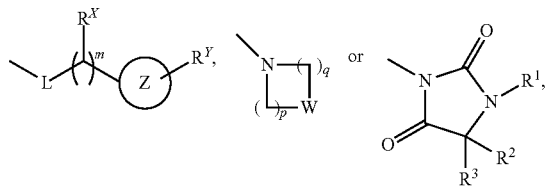

Wherein, when the R is

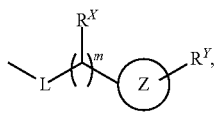

m is 0, 1 or 2,

L is oxygen, methylene, carbonyl, CONHCH$_2$, NR$^{c1}$CH$_2$, NR$^{c2}$CO, NR$^{c3}$, CONR$^{c4}$ or CH$_2$NR$^{c5}$ (especially, R$^{c1}$, R$^{c2}$, R$^{c3}$, R$^{c4}$ and R$^{c5}$ is each independently oxygen, C$_{1-4}$ alkylamine, C$_{1-6}$ alkyl, C$_{1-6}$ alkoxy, halo C$_{1-6}$ alkyl, C$_{2-6}$ alkenyl, C$_{2-6}$ alkynyl, C$_{3-8}$ cycloalkyl or 3-8 membered heterocycle), R$^X$ is hydrogen, cyano, hydroxyl, trifluoromethyl, C$_{1-6}$ alkyl or C$_{3-8}$ cycloalkyl, R$^Y$ is hydrogen, amide, cyano, hydroxyl, trifluoromethyl, halo, ester, C$_{1-4}$ alkylamine, C$_{1-6}$ alkyl, C$_{1-6}$ methoxyalkyl or C$_{2-6}$ alkynyl, Z is unsubstituted, C$_{1-6}$ alkyl, C$_{1-6}$ methoxyalkyl, C$_{2-6}$ alkenyl, C$_{2-6}$ alkynyl, C$_{3-8}$ cycloalkyl, C$_{3-8}$ cycloalkenyl, C$_{6-10}$ aromatic cycle or 3-8 membered heterocycle having 1-3 nitrogens, wherein, when the R is

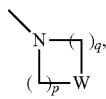

p and q is each independently from 1 to 3,

W is CR$^{d1}$R$^{d2}$ or NR$^{d3}$ (especially, R$^{d1}$, R$^{d2}$ and R$^{d3}$ is each independently hydrogen, fluoro or C$_{1-6}$ alkyl), wherein, when the R is

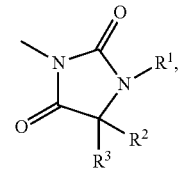

R$^1$, R$^2$ and R$^3$ is each independently hydrogen or C$_{1-6}$ alkyl.

The present invention provides a pharmaceutical composition for treating cancers comprising the compound represented by Formula I, racemic, enantiomer, diastereoisomer thereof, or pharmaceutically acceptable salt thereof.

The present invention provides a preparation method of the compound represented by Formula I, racemic, enantiomer, diastereoisomer thereof, or pharmaceutically acceptable salt thereof.

Advantageous Effects of Invention

The compounds of the present invention are highly active in the suppression of PARP, and according to its pharmaceutical compositions are expected to be useful for therapeutic applications which are improved by suppression of PARP activity, and cancer with mutated BRCA1, BRCA2 and ERG fusion gene in mono or combination treatment with radiation and with chemotherapy.

BEST MODE FOR CARRYING OUT THE INVENTION

Hereinafter, the present invention will be described in detail.

The present invention provides a compound represented by Formula I, racemic, enantiomer, diastereoisomer thereof, or pharmaceutically acceptable salt thereof.

[Formula I]

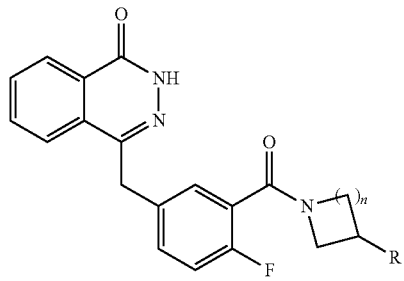

wherein, n is 1 or 2,

R is

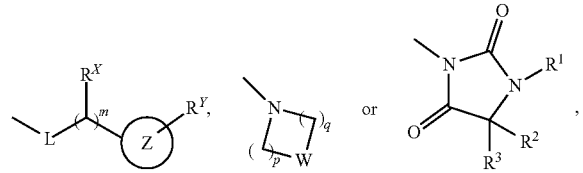

Wherein, when the R is m is 0, 1 or 2,
L is oxygen, methylene, carbonyl, CONHCH$_2$, NR$^{c1}$CH$_2$, NR$^{c2}$CO, NR$^{c3}$, CONR$^{c4}$ or CH$_2$NR$^{c5}$ (especially, R$^{c1}$, R$^{c2}$, R$^{c3}$, R$^{c4}$ and R$^{c5}$ is each independently oxygen, C$_{1-4}$ alkylamine, C$_{1-6}$ alkyl, C$_{1-6}$ alkoxy, halo C$_{1-6}$ alkyl, C$_{2-6}$ alkenyl, C$_{2-6}$ alkynyl, C$_{3-8}$ cycloalkyl or 3-8 membered heterocycle),
R$^X$ is hydrogen, cyano, hydroxyl, trifluoromethyl, C$_{1-6}$ alkyl or C$_{3-8}$ cycloalkyl,
R$^Y$ is hydrogen, amide, cyano, hydroxyl, trifluoromethyl, halo, ester, C$_{1-4}$ alkylamine, C$_{1-6}$ alkyl, C$_{1-6}$ methoxyalkyl or C$_{2-6}$ alkynyl,
Z is unsubstituted, C$_{1-6}$ alkyl, C$_{1-6}$ methoxyalkyl, C$_{2-6}$ alkenyl, C$_{2-6}$ alkynyl, C$_{3-8}$ cycloalkyl, C$_{3-8}$ cycloalkenyl, C$_{6-10}$ aromatic cycle or 3-8 membered heterocycle having 1-3 nitrogens,
wherein, when the R is p and q is each independently from 1 to 3,
W is CR$^{d1}$R$^{d2}$ or NR$^{d3}$ (especially, R$^{d1}$, R$^{d2}$ and R$^{d3}$ is each independently hydrogen, fluoro or C$_{1-6}$ alkyl),
wherein, when the R is R$^1$, R$^2$ and R$^3$ is each independently hydrogen or C$_{1-6}$ alkyl.
In the present invention, the compound of Formula I is preferably selected form i) or Vii) disclosed below:
i) In case, R is L is methylene, carbonyl, CONHCH$_2$, NR$^{c1}$CH$_2$, NR$^{c2}$CO, NR$^{c3}$, CONR$^{c4}$ or CH$_2$NR$^{c5}$ (especially, R$^{c1}$, R$^{c2}$, R$^{c3}$, R$^{c4}$ and R$^{c5}$ is each independently hydrogen, C$_{1-6}$ alkyl, C$_{2-6}$ alkynyl or C$_{3-8}$cycloalkyl), R$^X$ is hydrogen, cyano, hydroxyl, trifluoromethyl, methyl, ethyl or cyclopropyl, R$^Y$ is hydrogen, dimethylamide, cyano, hydroxyl, trifluoromethyl, halo, ethylester, dimethylamine, methyl, methoxymethyl or propargyl, Z is unsubstituted, C$_{1-6}$ alkyl, C$_{1-6}$ methoxyalkyl, C$_{2-6}$ alkynyl, C$_{3-8}$ cycloalkyl, C$_{6-10}$ aromatic cycle or 3-8 membered heterocycle having 1-3 nitrogens.

ii) In case, R is p and q is each independently from 1 to 2, W is CR$^{d1}$R$^{d2}$ or NR$^{d3}$ (especially R$^{d1}$, R$^{d2}$ and R$^{d3}$ is each independently hydrogen, fluoro or methyl).
iii) In case, R is R$^1$, R$^2$ and R$^3$ is each independently hydrogen, methyl or ethyl.
iv) In case, R is L is NR$^{c1}$CH$_2$, CONR$^{c4}$ or CH$_2$NR$^{c5}$ (especially, R$^{c1}$, R$^{c4}$ and R$^{c5}$ is each independently hydrogen, methyl, ethyl, propyl, propargyl or cyclopropyl),

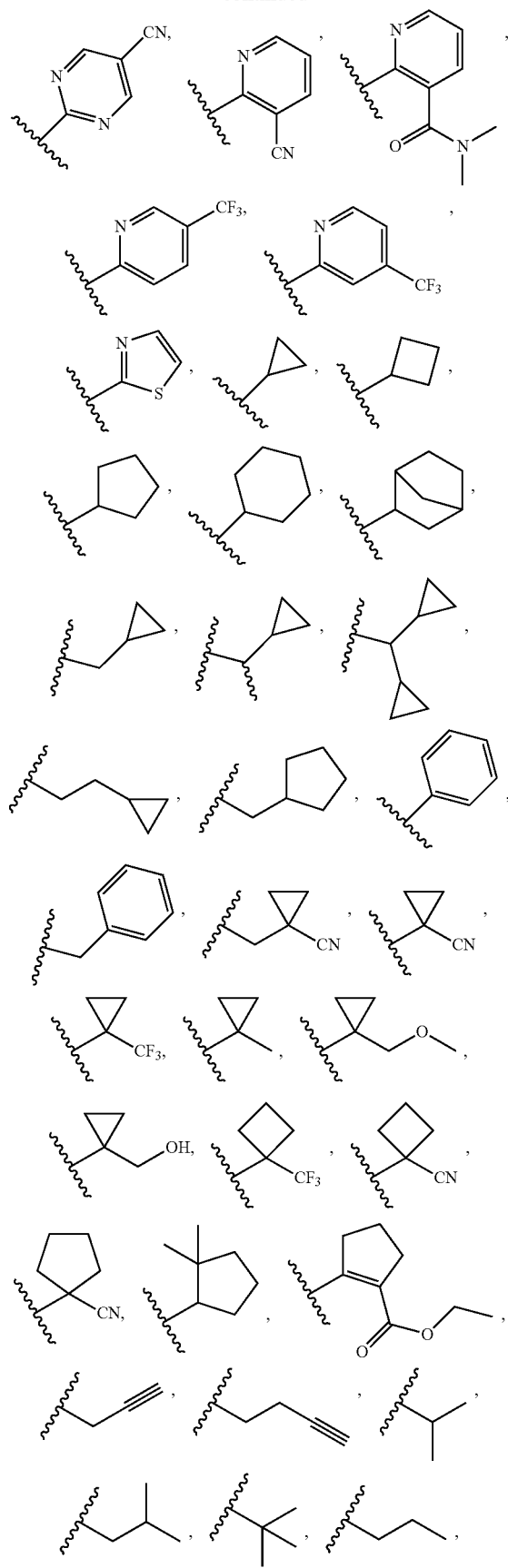
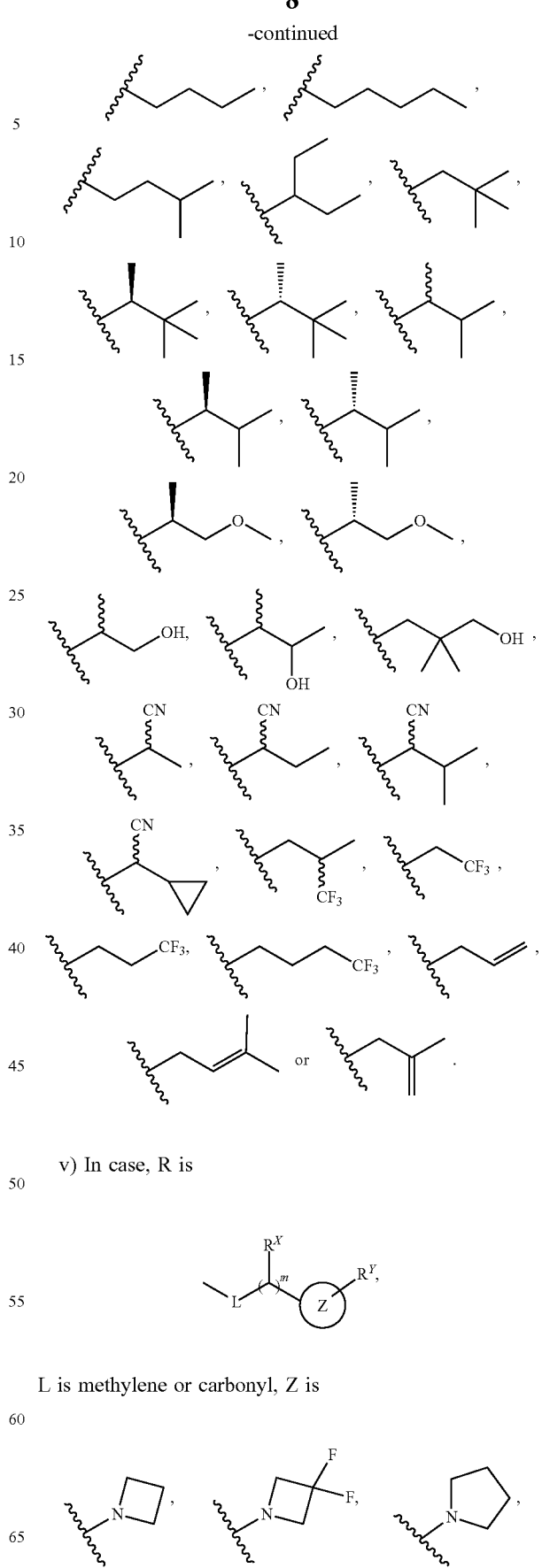
v) In case, R is
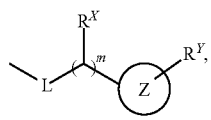
L is methylene or carbonyl, Z is
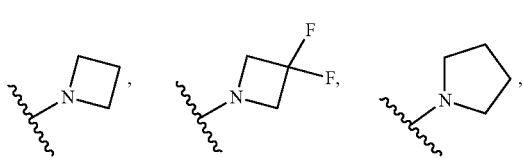

-continued

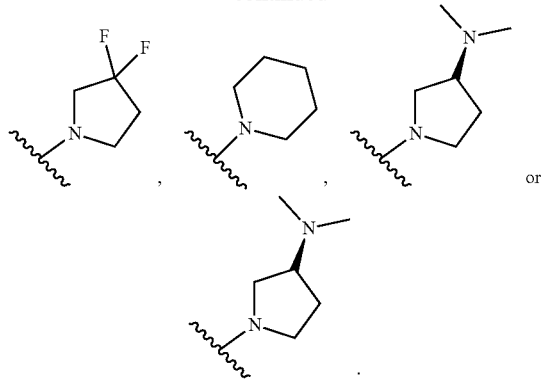

vi) In case, R is

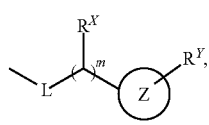

L is CONHCH$_2$ or NR$^{c2}$CO (especially, R$^{c2}$ is hydrogen, methyl, ethyl or propyl), Z is

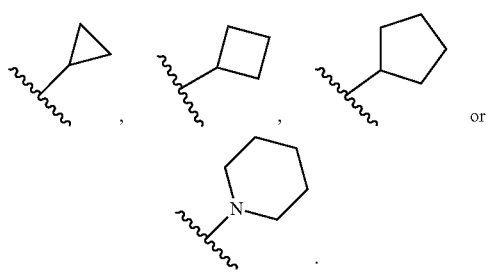

vii) In case, R is

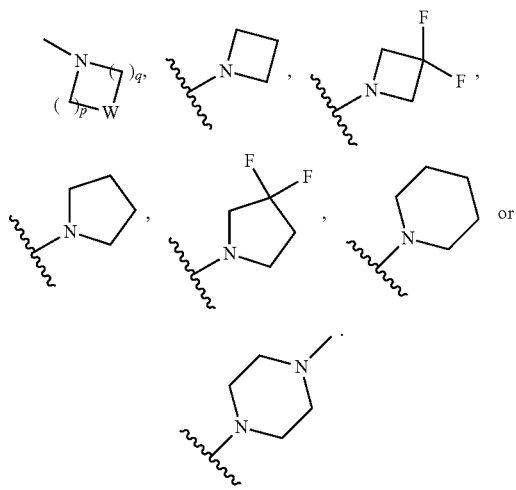

Particularly preferred examples of the compound of Formula I according to the present invention comprise the followings:

(R)-4-(3-(3-aminopyrrolidine-1-carbonyl)-4-fluorobenzyl) phthalazin-1(2H)-one; (I-1)
(S)-4-(3-(3-aminopyrrolidine-1-carbonyl)-4-fluorobenzyl) phthalazin-1(2H)-one; (I-2)
4-(3-(3-aminoazetidine-1-carbonyl)-4-fluorobenzyl) phthalazin-1(2H)-one; (I-3)
(R)-4-(4-fluoro-3-(3-hydroxypyrrolidine-1-carbonyl)benzyl)phthalazin-1(2H)-one; (I-4)
(S)-4-(4-fluoro-3-(3-hydroxypyrrolidine-1-carbonyl)benzyl)phthalazin-1(2H)-one; (I-5)
4-(4-fluoro-3-(3-hydroxyazetidine-1-carbonyl)benzyl) phthalazin-1(2H)-one; (I-6)
4-(4-fluoro-3-(3-(hydroxymethyl)azetidine-1-carbonyl)benzyl)phthalazin-1(2H)-one; (I-7)
(R)—N-(1-(2-fluoro-5-((4-oxo-3,4-dihydrophthalazin-1-yl) methyl)benzoyl)pyrrolidin-3-yl)cyclopropanecarboxamide; (I-8)
N-(1-(2-fluoro-5-((4-oxo-3,4-dihydrophthalazin-1-yl) methyl)benzoyl)azetidin-3-yl)cyclopropanecarboxamide; (I-9)
(S)—N-(1-(2-fluoro-5-((4-oxo-3,4-dihydrophthalazin-1-yl) methyl)benzoyl)pyrrolidin-3-yl)cyclopropanecarboxamide; (I-10)
(R)—N-(1-(2-fluoro-5-((4-oxo-3,4-dihydrophthalazin-1-yl) methyl)benzoyl)pyrrolidin-3-yl)-N-methylcyclopropanecarboxamide; (I-11)
N-(1-(2-fluoro-5-((4-oxo-3,4-dihydrophthalazin-1-yl) methyl)benzoyl)azetidin-3-yl)-N-methylcyclopropanecarboxamide; (I-12)
(S)—N-(1-(2-fluoro-5-((4-oxo-3,4-dihydrophthalazin-1-yl) methyl)benzoyl)pyrrolidin-3-yl)-N-methylcyclopropanecarboxamide; (I-13)
3-(1-(2-fluoro-5-((4-oxo-3,4-dihydrophthalazin-1-yl) methyl)benzoyl)azetidin-3-yl)-5,5-dimethylimidazolidine-2,4-dione; (I-14)
(R)-3-(1-(2-fluoro-5-((4-oxo-3,4-dihydrophthalazin-1-yl) methyl)benzoyl)pyrrolidin-3-yl)imidazolidine-2,4-dione; (I-15)
(R)-1-ethyl-3-(1-(2-fluoro-5-((4-oxo-3,4-dihydrophthalazin-1-yl)methyl)benzoyl)pyrrolidin-3-yl)imidazolidine-2,4-dione; (I-16)
4-(4-fluoro-3-(3-(4-fluoropiperidine-1-carbonyl)azetidine-1-carbonyl)benzyl)phthalazin-1(2H)-one; (I-17)
4-(3-(3-(3,3-difluoroazetidine-1-carbonyl)azetidine-1-carbonyl)-4-fluorobenzyl)phthalazin-1(2H)-one; (I-18)
4-(3-(3-(3,3-difluoropyrrolidine-1-carbonyl)azetidine-1-carbonyl)-4-fluorobenzyl)phthalazin-1(2H)-one; (I-19)
4-(3-(3-(3,3-difluoropyrrolidine-1-carbonyl)pyrrolidine-1-carbonyl)-4-fluorobenzyl)phthalazin-1(2H)-one; (I-20)
(R)—N-(cyclopropylmethyl)-1-(2-fluoro-5-((4-oxo-3,4-dihydrophthalazin-1-yl)methyl)benzoyl)pyrrolidine-3-carboxamide; (I-21)
4-(4-fluoro-3-(3-(pyrrolidine-1-carbonyl)azetidine-1-carbonyl)benzyl)phthalazin-1(2H)-one; (I-22)
(R)-4-(3-(3-((dimethylamino)pyrrolidine-1-carbonyl)azetidine-1-carbon yl)-4-fluorobenzyl)phthalazin-1(2H)-one; (I-23)
(S)-4-(3-(3-((dimethylamino)pyrrolidine-1-carbonyl)azetidine-1-carbon yl)-4-fluorobenzyl)phthalazin-1(2H)-one; (I-24)
4-(3-(3-(cyclobutylamino)azetidine-1-carbonyl)-4-fluorobenzyl)phthalazin-1(2H)-one; (I-25)
4-(3-(3-(cyclopropylamino)azetidine-1-carbonyl)-4-fluorobenzyl)phthalazin-1(2H)-one; (I-26)
4-(3-(3-(cyclopentylamino)azetidine-1-carbonyl)-4-fluorobenzyl)phthalazin-1(2H)-one; (I-27)

4-(3-(3-(cyclohexylamino)azetidine-1-carbonyl)-4-fluorobenzyl)phthalazin-1(2H)-one; (I-28)
(R)-4-(3-(3-(cyclopropylamino)pyrrolidine-1-carbonyl)-4-fluorobenzyl)phthalazin-1(2H)-one; (I-29)
(R)-4-(3-(3-(cyclobutylamino)pyrrolidine-1-carbonyl)-4-fluorobenzyl)phthalazin-1(2H)-one; (I-30)
(R)-4-(3-(3-(cyclopentylamino)pyrrolidine-1-carbonyl)-4-fluorobenzyl)phthalazin-1(2H)-one; (I-31)
4-(4-fluoro-3-(3-(isopropylamino)azetidine-1-carbonyl)benzyl)phthalazin-1(2H)-one; (I-32)
4-(3-(3-((cyclopropylmethyl)amino)azetidine-1-carbonyl)-4-fluorobenzyl)phthalazin-1(2H)-one; (I-33)
4-(3-(3-(bis(cyclopropylmethyl)amino)azetidine-1-carbonyl)-4-fluorobenzyl)phthalazin-1(2H)-one; (I-34)
4-(4-fluoro-3-(3-(isobutylamino)azetidine-1-carbonyl)benzyl)phthalazin-1(2H)-one; (I-35)
4-(4-fluoro-3-(3-((1-hydroxypropan-2-yl)amino)azetidine-1-carbonyl)benzyl)phthalazin-1(2H)-one; (I-36)
4-(4-fluoro-3-(3-(neopentylamino)azetidine-1-carbonyl)benzyl)phthalazin 1(2H)-one; (I-37)
4-(3-(3-((2,2-dimethylcyclopentyl)amino)azetidine-1-carbonyl)-4-fluorobenzyl)phthalazin-1(2H)-one; (I-38)
ethyl 2-((1-(2-fluoro-5-((4-oxo-3,4-dihydrophthalazin-1-yl)methyl)benzoyl)azetidin-3-yl)amino)cyclopent-1-enecarboxylate; (I-39)
4-(4-fluoro-3-(3-(pentan-3-ylamino)azetidine-1-carbonyl)benzyl)phthalazin-1(2H)-one; (I-40)
4-(4-fluoro-3-(3-((3-methylbutan-2-yl)amino)azetidine-1-carbonyl)benzyl)phthalazin-1(2H)-one; (I-41)
4-(3-(3-((1-cyclopropylethyl)amino)azetidine-1-carbonyl)-4-fluorobenzyl)phthalazin-1(2H)-one; (I-42)
4-(3-(3-(bicyclo[2.2.1]heptan-2-ylamino)azetidine-1-carbonyl)-4-fluorobenzyl)phthalazin-1(2H)-one; (I-43)
4-(3-(3-(sec-butylamino)azetidine-1-carbonyl)-4-fluorobenzyl)phthalazin-1(2H)-one; (I-44)
4-(3-(3-((dicyclopropylmethyl)amino)azetidine-1-carbonyl)-4-fluorobenzyl)phthalazin-1(2H)-one; (I-45)
4-(4-fluoro-3-(3-((4-methylpentan-2-yl)amino)azetidine-1-carbonyl)benzyl)phthalazin-1(2H)-one; (I-46)
4-(4-fluoro-3-(3-((3-hydroxybutan-2-yl)amino)azetidine-1-carbonyl)benzyl)phthalazin-1(2H)-one; (I-47)
4-(4-fluoro-3-(3-(pentan-2-ylamino)azetidine-1-carbonyl)benzyl)phthalazin-1(2H)-one; (I-48)
4-(4-fluoro-3-(3-((1-(1-methylcyclopropyl)ethyl)amino)azetidine-1-carbonyl)benzyl)phthalazin-1(2H)-one; (I-49)
4-(4-fluoro-3-(3-((3,3,3-trifluoro-2-methylpropyl)amino)azetidine-1-carbonyl)benzyl)phthalazin-1(2H)-one; (I-50)
4-(3-(3-(allylamino)azetidine-1-carbonyl)-4-fluorobenzyl)phthalazin-1-(2H)-one; (I-51)
4-(4-fluoro-3-(3-(isopentylamino)azetidine-1-carbonyl)benzyl)phthalazin-1(2H)-one; (I-52)
4-(3-(3-(butylamino)azetidine-1-carbonyl)-4-fluorobenzyl)phthalazin-1-(2H)-one; (I-53)
4-(4-fluoro-3-(3-((3-methylbut-2-en-yl)amino)azetidine-1-carbonyl)benzyl)phthalazin-1(2H)-one; (I-54)
4-(3-(3-((cyclopentylmethyl)amino)azetidine-1-carbonyl)-4-fluorobenzyl)phthalazin-1(2H)-one; (I-55)
4-(4-fluoro-3-(3-((4,4,4-trifluorobutyl)amino)azetidine-1-carbonyl)benzyl)phthalazin-1(2H)-one; (I-56)
4-(4-fluoro-3-(3-(pentylamino)azetidine-1-carbonyl)benzyl)phthalazin-1-(2H)-one; (I-57)
4-(3-(3-((2-cyclopropylethyl)amino)azetidine-1-carbonyl)-4-fluorobenzyl)phthalazin-1(2H)-one; (I-58)
4-(4-fluoro-3-(3-(propylamino)azetidine-1-carbonyl)benzyl)phthalazin-1-(2H)-one; (I-59)
4-(4-fluoro-3-(3-(methyl(pyridin-4-ylmethyl)amino)azetidine-1-carbonyl)benzyl)phthalazin-1(2H)-one; (I-60)
(R)-4-(4-fluoro-3-(3-(methyl(pyridin-4-ylmethyl)amino)pyrrolidine-1-carbonyl)benzyl)phthalazin-1(2H)-one; (I-61)
(S)-4-(4-fluoro-3-(3-(methyl(pyridin-4-ylmethyl)amino)pyrrolidine-1-carbonyl)benzyl)phthalazin-1(2H)-one; (I-62)
(S)-4-(4-fluoro-3-(3-(methyl(pyridin-2-ylmethyl)amino)pyrrolidine-1-carbonyl)benzyl)phthalazin-1(2H)-one; (I-63)
(R)-4-(4-fluoro-3-(3-(methyl(pyridin-2-ylmethyl)amino)pyrrolidine-1-carbonyl)benzyl)phthalazin-1(2H)-one; (I-64)
4-(4-fluoro-3-(3-(methyl(pyridin-2-ylmethyl)amino)azetidine-1-carbonyl)benzyl)phthalazin-1(2H)-one; (I-65)
4-(4-fluoro-3-(3-(methyl(pyridin-3-ylmethyl)amino)azetidine-1-carbonyl)benzyl)phthalazin-1(2H)-one; (I-66)
(S)-4-(4-fluoro-3-(3-(methyl(pyridin-3-ylmethyl)amino)pyrrolidine-1-carbonyl)benzyl)phthalazin-1(2H)-one; (I-67)
(R)-4-(4-fluoro-3-(3-(methyl(pyridin-3-ylmethyl)amino)pyrrolidine-1-carbonyl)benzyl)phthalazin-1(2H)-one; (I-68)
4-(3-(3-(cyclopropyl(methyl)amino)azetidine-1-carbonyl)-4-fluorobenzyl)phthalazin-1(2H)-one; (I-69)
4-(3-(3-(cyclopropyl(ethyl)amino)azetidine-1-carbonyl)-4-fluorobenzyl)phthalazin-1(2H)-one; (I-70)
4-(3-(3-(cyclobutyl(methyl)amino)azetidine-1-carbonyl)-4-fluorobenzyl)phthalazin-1(2H)-one; (I-71)
4-(3-(3-(cyclopentyl(prop-2-yn-1-yl)amino)azetidine-1-carbonyl)-4-fluorobenzyl)phthalazin-1(2H)-one; (I-72)
4-(3-(3-(3,3-difluoropyrrolidin-1-yl)azetidine-1-carbonyl)-4-fluorobenzyl)phthalazin-1(2H)-one; (I-73)
4-(4-fluoro-3-(3-(4-fluoropiperidin-1-yl)azetidine-1-carbonyl)benzyl)phthalazin-1(2H)-one; (I-74)
4-(3-([1,3'-biazetidine]-1'-carbonyl)-4-fluorobenzyl)phthalazin-1(2H)-one; (I-75)
4-(4-fluoro-3-(3-(pyrrolidin-1-yl)azetidine-1-carbonyl)benzyl)phthalazin-1(2H)-one; (I-76)
4-(4-fluoro-3-(3-(piperidin-1-yl)azetidine-1-carbonyl)benzyl)phthalazin-1(2H)-one; (I-77)
4-(4-fluoro-3-(3-(4-methylpiperazin-1-yl)azetidine-1-carbonyl)benzyl)phthalazin-1(2H)-one; (I-78)
4-(4-fluoro-3-(3-(phenylamino)azetidine-1-carbonyl)benzyl)phthalazin-1(2H)-one; (I-79)
4-(4-fluoro-3-(3-((1-(trifluoromethyl)cyclopropyl)amino)azetidine-1-carbonyl)benzyl)phthalazin-1(2H)-one; (I-80)
4-(4-fluoro-3-(3-(prop-2-yn-1-ylamino)azetidine-1-carbonyl)benzyl)phthalazin-1(2H)-one; (I-81)
(S)-4-(4-fluoro-3-(3-((1-methoxypropan-2-yl)amino)azetidine-1-carbonyl)benzyl)phthalazin-1(2H)-one; (I-82)
(R)-4-(4-fluoro-3-(3-((1-methoxypropan-2-yl)amino)azetidine-1-carbonyl)benzyl)phthalazin-1(2H)-one; (I-83)
4-(4-fluoro-3-(3-((1-(hydroxymethyl)cyclopropyl)amino)azetidine-1-carbonyl)benzyl)phthalazin-1(2H)-one; (I-84)
4-(4-fluoro-3-(3-((1-methylcyclopropyl)amino)azetidine-1-carbonyl)benzyl)phthalazin-1(2H)-one; (I-85)
(R)-4-(3-(3-((3,3-dimethylbutan-2-yl)amino)azetidine-1-carbonyl)-4-fluorobenzyl)phthalazin-1(2H)-one; (I-86)
(S)-4-(3-(3-((3,3-dimethylbutan-2-yl)amino)azetidine-1-carbonyl)-4-fluorobenzyl)phthalazin-1(2H)-one; (I-87)

(R)-4-(4-fluoro-3-(3-((3-methylbutan-2-yl)amino)azetidine-1-carbonyl)benzyl)phthalazin-1(2H)-one; (I-88)
(S)-4-(4-fluoro-3-(3-((3-methylbutan-2-yl)amino)azetidine-1-carbonyl)benzyl)phthalazin-1(2H)-one; (I-89)
4-(4-fluoro-3-(3-((1-(methoxymethyl)cyclopropyl)amino)azetidine-1-carbonyl)benzyl)phthalazin-1(2H)-one; (I-90)
4-(3-(3-(but-3-yn-1-ylamino)azetidine-1-carbonyl)-4-fluorobenzyl)phthalazin-1(2H)-one; (I-91)
4-(4-fluoro-3-(3-((2-methylallyl)amino)azetidine-1-carbonyl)benzyl)phthalazin-1(2H)-one; (I-92)
4-(4-fluoro-3-(3-((3-hydroxy-2,2-dimethylpropyl)amino)azetidine-1-carbonyl)benzyl)phthalazin-1(2H)-one; (I-93)
1-(((1-(2-fluoro-5-((4-oxo-3,4-dihydrophthalazin-1-yl)methyl)benzoyl)azetidin-3-yl)amino)methyl)cyclopropanecarbonitrile; (I-94)
4-(4-fluoro-3-(3-((2,2,2-trifluoroethyl)amino)azetidine-1-carbonyl)benzyl)phthalazin-1(2H)-one; (I-95)
(R)-4-(4-fluoro-3-(3-(pyrrolidin-3-ylamino)azetidine-1-carbonyl)benzyl)phthalazin-1(2H)-one; (I-96)
(S)-4-(4-fluoro-3-(3-(pyrrolidin-3-ylamino)azetidine-1-carbonyl)benzyl)phthalazin-1(2H)-one; (I-97)
1-((1-(2-fluoro-5-((4-oxo-3,4-dihydrophthalazin-1-yl)methyl)benzoyl)azetidin-3-yl)amino)cyclopentanecarbonitrile; (I-98)
1-((1-(2-fluoro-5-((4-oxo-3,4-dihydrophthalazin-1-yl)methyl)benzoyl)azetidin-3-yl)amino)cyclobutanecarbonitrile; (I-99)
2-((1-(2-fluoro-5-((4-oxo-3,4-dihydrophthalazin-1-yl)methyl)benzoyl)azetidin-3-yl)amino)propanenitrile; (I-100)
2-((1-(2-fluoro-5-((4-oxo-3,4-dihydrophthalazin-1-yl)methyl)benzoyl)azetidin-3-yl)amino)butanenitrile; (I-101)
2-((1-(2-fluoro-5-((4-oxo-3,4-dihydrophthalazin-1-yl)methyl)benzoyl)azetidin-3-yl)amino)-3-methylbutanenitrile; (I-102)
2-cyclopropyl-2-((1-(2-fluoro-5-((4-oxo-3,4-dihydrophthalazin-1-yl)methyl)benzoyl)azetidin-3-yl)amino)acetonitrile; (I-103)
4-(4-fluoro-3-(3-((1-(trifluoromethyl)cyclobutyl)amino)azetidine-1-carbonyl)benzyl)phthalazin-1(2H)-one; (I-104)
(S)-4-(4-fluoro-3-(3-(methyl(pyrimidin-2-yl)amino)pyrrolidine-1-carbonyl)benzyl)phthalazin-1(2H)-one; (I-105)
(S)-4-(4-fluoro-3-(3-(methyl(pyrimidin-2-yl)amino)pyrrolidine-1-carbonyl)benzyl)phthalazin-1(2H)-one; (I-106)
4-(4-fluoro-3-(3-(methyl(pyrimidin-2-yl)amino)azetidine-1-carbonyl)benzyl)phthalazin-1(2H)-one; (I-107)
4-(4-fluoro-3-(3-(methyl(pyrimidin-2-yl)amino)azetidine-1-carbonyl)benzyl)phthalazin-1(2H)-one; (I-108)
4-(4-fluoro-3-(3-(pyrimidin-2-ylamino)azetidine-1-carbonyl)benzyl)phthalazin-1(2H)-one; (I-109)
(S)-4-(4-fluoro-3-(3-(pyrimidin-2-ylamino)pyrrolidine-1-carbonyl)benzyl)phthalazin-1(2H)-one; (I-110)
(S)-4-(3-(3-((6-chloropyridazin-3-yl)(methyl)amino)pyrrolidine-1-carbonyl)-4-fluorobenzyl)phthalazin-1(2H)-one; (I-111)
(S)-4-(3-(3-((6-chloropyridazin-3-yl)amino)pyrrolidine-1-carbonyl)-4-fluorobenzyl)phthalazin-1(2H)-one; (I-112)
(S)-4-(4-fluoro-3-(3-(methyl(pyridazin-3-yl)amino)pyrrolidine-1-carbonyl)benzyl)phthalazin-1(2H)-one; (I-113)
4-(3-(3-((6-chloropyridazin-3-yl)amino)azetidine-1-carbonyl)-4-fluorobenzyl)phthalazin-1(2H)-one; (I-114)
4-(3-(3-((6-chloropyridazin-3-yl)(methyl)amino)azetidine-1-carbonyl)-4-fluorobenzyl)phthalazin-1(2H)-one; (I-115)
4-(3-(3-(cyclobutyl(pyrimidin-2-yl)amino)azetidine-1-carbonyl)-4-fluorobenzyl)phthalazin-1(2H)-one; (I-116)
4-(4-fluoro-3-(3-(pyridazin-3-ylamino)azetidine-1-carbonyl)benzyl)phthalazin-1(2H)-one; (I-117)
(R)-4-(3-(3-((6-chloropyridazin-3-yl)amino)pyrrolidine-1-carbonyl)-4-fluorobenzyl)phthalazin-1(2H)-one; (I-118)
(R)-4-(3-(3-((6-chloropyridazin-3-yl)(methyl)amino)pyrrolidine-1-carbonyl)-4-fluorobenzyl)phthalazin-1(2H)-one; (I-119)
(R)-4-(4-fluoro-3-(3-(pyrimidin-2-ylamino)pyrrolidine-1-carbonyl)benzyl)phthalazin-1(2H)-one; (I-120)
(R)-4-(3-(3-(methyl(pyrimidin-2-yl)amino)pyrrolidine-1-carbonyl)-4-fluorobenzyl)phthalazin-1(2H)-one; (I-121)
(R)-4-(4-fluoro-3-(3-(pyridazin-3-ylamino)pyrrolidine-1-carbonyl)benzyl)phthalazin-1(2H)-one; (I-122)
(R)-4-(4-fluoro-3-(3-(methyl(pyridazin-3-yl)amino)pyrrolidine-1-carbonyl)benzyl)phthalazin-1(2H)-one; (I-123)
(R)-4-(4-fluoro-3-(3-(thiazol-2-ylamino)pyrrolidine-1-carbonyl)benzyl)phthalazin-1(2H)-one; (I-124)
(R)-4-(3-(3-((5-ethynylpyrimidin-2-yl)amino)pyrrolidine-1-carbonyl)-4-fluorobenzyl)phthalazin-1(2H)-one; (I-125)
(R)-2-((1-(2-fluoro-5-((4-oxo-3,4-dihydrophthalazin-1-yl)methyl)benzoyl)pyrrolidin-3-yl)amino)pyrimidine-5-carbonitrile; (I-126)
(R)-2-((1-(2-fluoro-5-((4-oxo-3,4-dihydrophthalazin-1-yl)methyl)benzoyl)pyrrolidin-3-yl)amino)nicotinonitrile; (I-127)
(R)-4-(4-fluoro-3-(3-(pyridin-2-ylamino)pyrrolidine-1-carbonyl)benzyl)phthalazin-1(2H)-one; (I-128)
(R)-2-((1-(2-fluoro-5-((4-oxo-3,4-dihydrophthalazin-1-yl)methyl)benzoyl)pyrrolidin-3-yl)amino)-N,N-dimethylnicotinamiide; (I-129)
(R)-4-(3-(3-((5-bromopyrimidin-2-yl)amino)pyrrolidine-1-carbonyl)-4-fluorobenzyl)phthalazin-1(2H)-one; (I-130)
(R)-4-(4-fluoro-3-(3-((5-(trifluoromethyl)pyridin-2-yl)amino)pyrrolidine-1-carbonyl)benzyl)phthalazin-1(2H)-one; (I-131)
(R)-4-(4-fluoro-3-(3-((4-(trifluoromethyl)pyridin-2-yl)amino)pyrrolidine-1-carbonyl)benzyl)phthalazin-1(2H)-one; (I-132)
4-(3-(3-(benzylamino)azetidine-1-carbonyl)-4-fluorobenzyl)phthalazin-1(2H)-one; (I-133)
4-(4-fluoro-3-(3-((3,3,3-trifluoropropyl)amino)azetidine-1-carbonyl)benzyl)phthalazin-1(2H)-one; (I-134)
(R)-4-(3-(3-(azetidin-1-yl)pyrrolidine-1-carbonyl)-4-fluorobenzyl)phthalazin-1(2H)-one; (I-135)
(R)-4-(3-([1,3'-bipyrrolidine]-1'-carbonyl)-4-fluorobenzyl)phthalazin-1(2H)-one; (I-136)
(R)-4-(4-fluoro-3-(3-(piperidin-1-yl)pyrrolidine-1-carbonyl)benzyl)phthalazin-1(2H)-one; (I-137)
(R)-4-(4-fluoro-3-(3-(p-tolylamino)pyrrolidine-1-carbonyl)benzyl)phthalazin-1(2H)-one; (I-138)
(R)-4-(4-fluoro-3-(3-(phenylamino)pyrrolidine-1-carbonyl)benzyl)phthalazin-1(2H)-one; (I-139)
4-(4-fluoro-3-(3-(pyrrolidin-1-ylmethyl)azetidine-1-carbonyl)benzyl)phthalazin-1(2H)-one; (I-140)
4-(4-fluoro-3-(3-(piperidin-1-ylmethyl)azetidine-1-carbonyl)benzyl)phthalazin-1(2H)-one; (I-141)
4-(3-(3-(azetidin-1-ylmethyl)azetidine-1-carbonyl)-4-fluorobenzyl)phthalazin-1(2H)-one; (I-142)
4-(3-(3-((cyclopropylamino)methyl)azetidine-1-carbonyl)-4-fluorobenzyl)phthalazin-1(2H)-one; (I-143)
4-(4-fluoro-3-(3-((isopropylamino)methyl)azetidine-1-carbonyl)benzyl)phthalazin-1(2H)-one; (I-144)

4-(3-(3-(((cyclopropylmethyl)amino)methyl)azetidine-1-carbonyl)-4-fluorobenzyl)phthalazin-1(2H)-one; (I-145)

4-(4-fluoro-3-(3-((isobutylamino)methyl)azetidine-1-carbonyl)benzyl)phthalazin-1(2H)-one; (I-146)

4-(3-(3-((tert-butylamino)methyl)azetidine-1-carbonyl)-4-fluorobenzyl)phthalazin-1(2H)-one; (I-147)

4-(3-(3-((cyclobutylamino)methyl)azetidine-1-carbonyl)-4-fluorobenzyl)phthalazin-1(2H)-one; (I-148)

4-(4-fluoro-3-(3-((prop-2-yn-1-ylamino)methyl)azetidine-1-carbonyl)benzyl)phthalazin-1(2H)-one; (I-149)

4-(4-fluoro-3-(3-((phenylamino)methyl)azetidine-1-carbonyl)benzyl)phthalazin-1(2H)-one; (I-150)

1-((((1-(2-fluoro-5-((4-oxo-3,4-dihydrophthalazin-1-yl)methyl)benzoyl)azetidin-3-yl)methyl)amino)methyl)cyclopropanecarbonitrile; (I-151)

1-(((1-(2-fluoro-5-((4-oxo-3,4-dihydrophthalazin-1-yl)methyl)benzoyl)azetidin-3-yl)methyl)amino)cyclopropanecarbonitrile; (I-152)

4-(3-(3-((cyclopropyl(prop-2-yn-1-yl)amino)methyl)azetidine-1-carbonyl)-4-fluorobenzyl)phthalazin-1(2H)-one; (I-153)

4-(3-(3-((cyclopropyl(methyl)amino)methyl)azetidine-1-carbonyl)-4-fluorobenzyl)phthalazin-1(2H)-one; (I-154)

4-(3-(3-((cyclopropyl(ethyl)amino)methyl)azetidine-1-carbonyl)-4-fluoro benzyl)phthalazin-1(2H)-one; (I-155)

4-(3-(3-(cyclobutylamino)azetidine-1-carbonyl)-4-fluorobenzyl)phthalazin-1(2H)-one hydrochloride; (I-156)

4-(3-(3-(cyclopropyl amino)azetidine-1-carbonyl)-4-fluorobenzyl)phthalazin-1(2H)-one hydrochloride; (I-157)

4-(3-(3-(cyclopentyl amino)azetidine-1-carbonyl)-4-fluorobenzyl)phthalazin-1(2H)-one hydrochloride; (I-158)

4-(4-fluoro-3-(3-(isopropylamino)azetidine-1-carbonyl)benzyl)phthalazin-1(2H)-one hydrochloride; (I-159)

4-(3-(3-((cyclopropylmethyl)amino)azetidine-1-carbonyl)-4-fluorobenzyl)phthalazin-1(2H)-one hydrochloride; (I-160)

4-(4-fluoro-3-(3-(isobutylamino)azetidine-1-carbonyl)benzyl)phthalazin-1(2H)-one hydrochloride; (I-161)

4-(4-fluoro-3-(3-((1-hydroxypropan-2-yl)amino)azetidine-1-carbonyl)benzyl)phthalazin-1(2H)-one hydrochloride; (I-162)

4-(3-(3-(butylamino)azetidine-1-carbonyl)-4-fluorobenzyl)phthalazin-1(2H)-one hydrochloride; (I-163)

4-(3-([1,3'-biazetidine]-1'-carbonyl)-4-fluorobenzyl)phthalazin-1(2H)-one hydrochloride; (I-164)

(R)-4-(4-fluoro-3-(3-((1-methoxypropan-2-yl)amino)azetidine-1-carbonyl)benzyl)phthalazin-1(2H)-one hydrochloride; (I-165)

1-((1-(2-fluoro-5-((4-oxo-3,4-dihydrophthalazin-1-yl)methyl)benzoyl)azetidin-3-yl)amino)cyclobutanecarbonitrile hydrochloride; (I-166)

(R)-4-(3-(3-(azetidin-1-yl)pyrrolidine-1-carbonyl)-4-fluorobenzyl)phthalazin-1(2H)-one hydrochloride; (I-167)

4-(4-fluoro-3-(3-(pyrrolidin-1-ylmethyl)azetidine-1-carbonyl)benzyl)phthalazin-1(2H)-one hydrochloride; (I-168)

4-(4-fluoro-3-(3-(piperidin-1-ylmethyl)azetidine-1-carbonyl)benzyl)phthalazin-1(2H)-one hydrochloride; (I-169)

4-(3-(3-(azetidin-1-ylmethyl)azetidine-1-carbonyl)-4-fluorobenzyl)phthalazin-1(2H)-one hydrochloride; (I-170)

4-(3-(3-((cyclopropylamino)methyl)azetidine-1-carbonyl)-4-fluorobenzyl)phthalazin-1(2H)-one hydrochloride; (I-171)

4-(4-fluoro-3-(3-((isopropylamino)methyl)azetidine-1-carbonyl)benzyl)phthalazin-1(2H)-one hydrochloride; (I-172)

4-(3-(3-(((cyclopropylmethyl)amino)methyl)azetidine-1-carbonyl)-4-fluorobenzyl)phthalazin-1(2H)-one hydrochloride; (I-173)

4-(4-fluoro-3-(3-((isobutylamino)methyl)azetidine-1-carbonyl)benzyl)phthalazin-1(2H)-one hydrochloride; (I-174)

4-(3-(3-((cyclobutylamino)methyl)azetidine-1-carbonyl)-4-fluorobenzyl)phthalazin-1(2H)-one hydrochloride; (I-175) and 4-(4-fluoro-3-(3-((prop-2-yn-1-ylamino)methyl)azetidine-1-carbonyl)benzyl)phthalazin-1(2H)-one hydrochloride; (I-176).

In the present invention, "$C_{1-4}$ alkylamine" is a saturated hydrocarbonyl amine with linear or branched chains of 1-4 carbon atoms. Exemplary alkylamines include, but are not limited, to methylamine, ethylamine, propylamine, butylamine, 1-methylethylamine, diethylamine or dimethylamine.

In the present invention, "$C_{1-6}$ alkyl" is a saturated hydrocarbonyl amine with linear or branched chains of 1-6 carbon atoms. Exemplary alkyl include, but are not limited, to methyl, ethyl, propyl, butyl, pentyl, hexyl, 1-methylethyl, 1-methylpropyl, 2-methylpropyl, 1,1-dimethylethyl, 1-methylbutyl, 1,1-dimethylpropyl, 1-methylpentyl or 1,1-dimethylbutyl.

In the present invent ion, "$C_{1-6}$alkoxy" is an OR group with R as defined above. Exemplary alkoxy with 1-6 carbon atoms include, but are not limited, to methoxy, ethoxy, propoxy, butoxy, 1-methylethoxy, 1,1-dimethylethoxy, 1-methylpropoxy, 2-methylpropoxy or cyclopropylmethoxy.

In the present invent ion, "halo $C_{1-6}$alkyl" is intended as a $C_{1-6}$alkyl radical having one or more hydrogen atoms replaced by a halogen atoms defined above. Exemplary haloalkyl include, but are not limited, to difluoromethyl or trifluoromethyl.

In the present invention, "halo" is intended as bromine, fluorine, or chlorine atom.

In the present invent ion, "$C_{2-6}$ alkenyl" is intended as a linear or branched hydrocarbonyl chain of 2-6 carbon atoms and at least one carbon-carbon double bond. Alkenyls have a "cis" or "trans" and "E" or "Z" double bond configuration. Exemplary alkenyl include, but are not limited, to crotyl (—CH$_2$CH═CHCH$_3$), vinyl (—CH═CH$_2$) or allyl (—CH$_2$CH═CH$_2$).

In the present invent ion, "$C_{2-6}$ alkynyl" is intended as a linear or branched hydrocarbonyl radical with 2-6 carbon atoms and at least one carbon-carbon triple bond. Exemplary alkynyl include, but are not limited, to ethynyl(—C≡CH) or propargyl (—CH$_2$C≡CH).

In the present invention, "$C_{3-8}$ cycloalkyl" is intended as a saturated hydrocarbonyl ring with 3-8 carbon atoms. Exemplary cycloalkyl include, but are not limited, to cyclopropyl, cyclobutyl, cyclopentyl or cyclohexyl.

In the present invention, "$C_{3-8}$ cycloalkenyl" is intended as an unsaturated hydrocarbonyl ring with 3-8 carbon atoms and at least one carbon-carbon double bond. Alkenyls have a "cis" or "trans" and "E" or "Z" double bond configuration. Exemplary cycloalkenyl include, but are not limited, to cyclopropenyl, cyclobutenyl, cyclopentenyl, cyclohexenyl, 1,3-cyclohexadiene, 1,4-cyclohexadiene, cycloheptenyl, cyclooctenyl or 1,5-cyclooctadiene.

In the present invention, "$C_{6-10}$ aromatic cycle" is intended as an aromatic hydrocarbonyl radical with 6-10 carbon atoms. Exemplary aromatic ring include, but are not limited, to phenyl or naphthyl.

In the present invention, "heterocycle" is intended as a saturated or partially unsaturated hydrocarbonyl mono-tricyclic ring with at least one nitrogen atom. Exemplary mono heterocycles with 5-6 atoms include, but are not limited, to pyrrolidinyl, piperidinyl, pyrollyl, pyrazolyl, imidazolyl, oxazolyl, isoxazolyl, triazolyl, thiazolyl, pyridyl, pyridazinyl, pyrimidinyl, pyrazinyl, or triazinyl. Also, exemplary bicyclic aromatic ring include, but are not limited, to benzothiazolyl, benzoxazolyl, benzoxazinone, benzoxadiazolyl, 1,3-benzodioxolyl, benzofuryl, benzopyrazinyl, indolyl, indazolyl, benzimidazolyl, benzopyranyl, pyrolopyridanyl, furopyridinyl, or imidazothiazolyl.

The term "pharmaceutically acceptable," as used herein, when referring to a component of a pharmaceutical composition means that the component, when administered to an animal, does not have undue adverse effects such as excessive toxicity, irritation, or allergic response commensurate with a reasonable benefit/risk ratio.

The term "treatment" as used herein covers any treatment of a disease in a mammal, particularly a human, and includes inhibiting the disease, i.e., arresting its development; or relieving the disease, i.e. causing regression of the disease and/or its symptoms or conditions and slowing disease progression.

The term "therapeutically effective amount" means an amount of a compound of the present invention that ameliorates, attenuates or eliminates a particular disease or condition or prevents or delays the onset of a particular disease or condition. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic.

The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. A specific stereoisomer may also be referred to as an enantiomer, and a mixture of such isomers is often called an enantiomeric mixture. A 50:50 mixture of enantiomers is referred to as a racemic-mixture or a racemate.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In another aspect, the present invent ion provides a method of preparing the compound represented by Formula I or a pharmaceutically approved salt thereof.

A preparation method of the present invention is shown in the following.

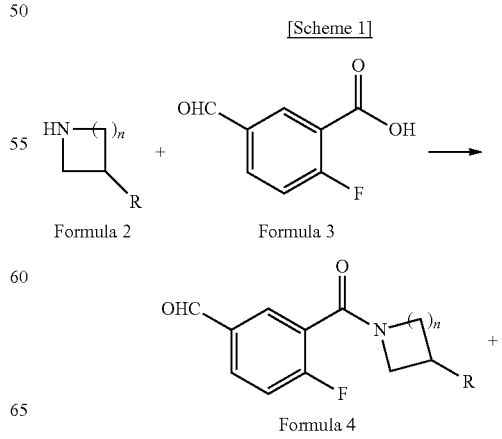

[Scheme 1]

Formula 2    Formula 3

Formula 4

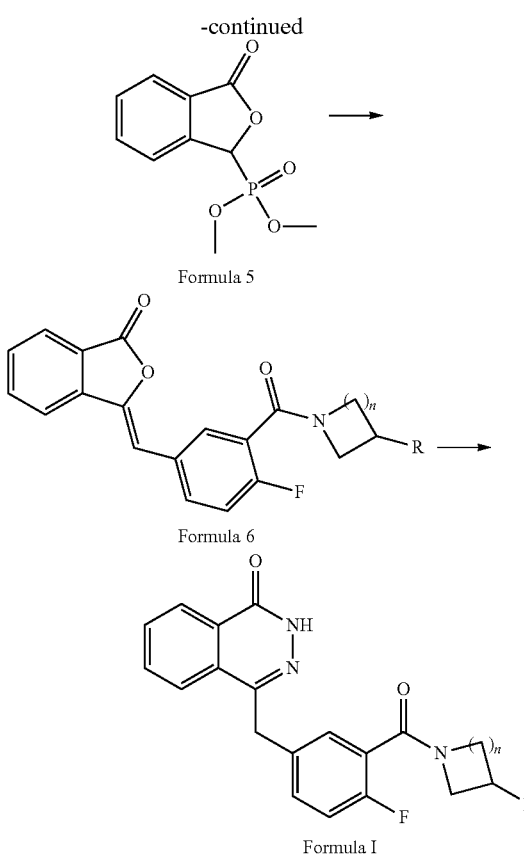

Formula 5

Formula 6

Formula I

The compound of Formula I of the present invention, as shown in Scheme 1, can be prepared by series of steps from the compound of Formula 2.

n and R, illustrated in Scheme 1, are defined as below:
Wherein,
n is 1 or 2;
R is

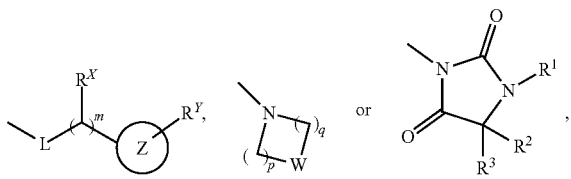

Wherein, when the R is,

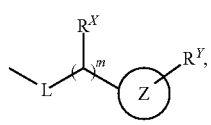

m is 0, 1 or 2,
L is oxygen, methylene, carbonyl, CONHCH$_2$, NR$^{c1}$CH$_2$, NR$^{c2}$CO, NR$^{c3}$, CONR$^{c4}$ or CH$_2$NR$^{c5}$ (especially, R$^{c1}$, R$^{c2}$, R$^{c3}$, R$^{c4}$ and R$^{c5}$ is each independently oxygen, C$_{1-4}$ alkylamine, C$_{1-6}$ alkyl, C$_{1-6}$ alkoxy, halo C$_{1-6}$ alkyl, C$_{2-6}$ alkenyl, C$_{2-6}$ alkynyl, C$_{3-8}$ cycloalkyl or 3-8 membered heterocycle),
R$^X$ is hydrogen, cyano, hydroxyl, trifluoromethyl, C$_{1-6}$ alkyl or C$_{3-8}$ cycloalkyl, R$^Y$ is hydrogen, amide, cyano, hydroxyl, trifluoromethyl, halo, ester, C$_{1-4}$ alkylamine, C$_{1-6}$ alkyl, C$_{1-6}$ methoxyalkyl or C$_{2-6}$ alkynyl,
Z is unsubstituted, C$_{1-6}$ alkyl, C$_{1-6}$ methoxyalkyl, C$_{2-6}$ alkenyl, C$_{2-6}$ alkynyl, C$_{3-8}$ cycloalkyl, C$_{3-8}$ cycloalkenyl, C$_{6-10}$ aromatic cycle or 3-8 membered heterocycle having 1-3 nitrogens,
wherein, when the R is

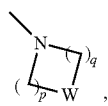

p and q is each independently from 1 to 3,
W is CR$^{d1}$R$^{d2}$ or NR$^{d3}$ (especially, R$^{d1}$, R$^{d2}$ and R$^{d3}$ is each independently hydrogen, fluoro or C$_{1-6}$alkyl),
wherein, when the R is

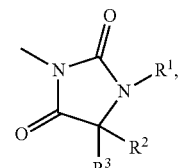

R$^1$, R$^2$ and R$^3$ is each independently hydrogen or C$_{1-6}$ alkyl.

The preparation method of the Formula I comprise:
Preparing a compound of Formula 4 from a compound of Formula 2 and 3 which reacted with amide coupling reaction (Step 1)
Preparing a compound of Formula 6 from a compound of Formula 4 and 5 which reacted with olefination reaction (Step 2)
Preparing a compound of Formula I from a compound of Formula 6 and hydrazine monohydrate which reacted with condensation reaction (Step 3)

Each step of the above preparation method is described in more detail as follows.

i) The compound of Formula 4 can be prepared from Formula 2 by amide coupling in the above Step 1. An Amide coupling reaction is carried out with 1-Ethyl-3-(3-dimethylaminopropyl)carbodiimide hydrochloride (EDCI) and 4-(Dimethylamino)pyridine (DMAP) or O-(benzotriazole-1-yl)-N,N,N',N'-tetramethyluronium hexafluorophosphate (HBTU) and N,N-diisopropyl ethylamine (DIPEA). Examples of solvents useful in the react ion include chloroform or dimethyl formamide. The react ion is heated to 20~35° C. for 1~30 hours, so as to obtain the compound of Formula 4.

Example of preparing the compound of Formula 4 from the compound of Formula 2 and 3 by amide coupling in the above Step 1 is illustrated below.

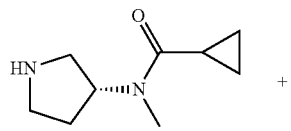 +

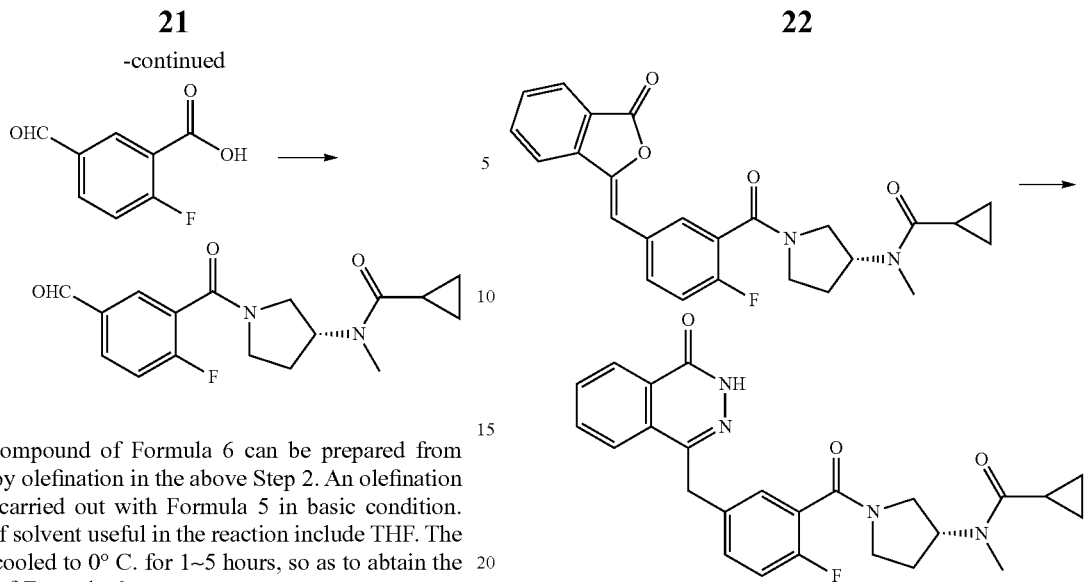

ii) The compound of Formula 6 can be prepared from Formula 4 by olefination in the above Step 2. An olefination reaction is carried out with Formula 5 in basic condition. Examples of solvent useful in the reaction include THF. The reaction is cooled to 0° C. for 1~5 hours, so as to abtain the compound of Formula 6.

Example of preparing the compound of Formula 6 from the compound of Formula 4 and 5 by olefination in the above Step 2 is illustrated below.

iii) The compound of Formula I can be prepared from Formula 6 by condensation in the above Step 3. A condensation reaction is carried out with hydrazine monohydrate. Example of solvent useful in the react ion includes water. The react ion is heated to 30~70° C. for 20 hours, so as to obtain the compound of Formula I.

Example of preparing the compound of Formula I from the compound of Formula 6 by condensation in the above Step 3 is illustrated below.

In another aspect, the present invention provides another method of preparing the compound represented by Formula I or a pharmaceutically approved salt thereof.

Besides, another preparation method of the present invention is shown in the following.

[Scheme 2]

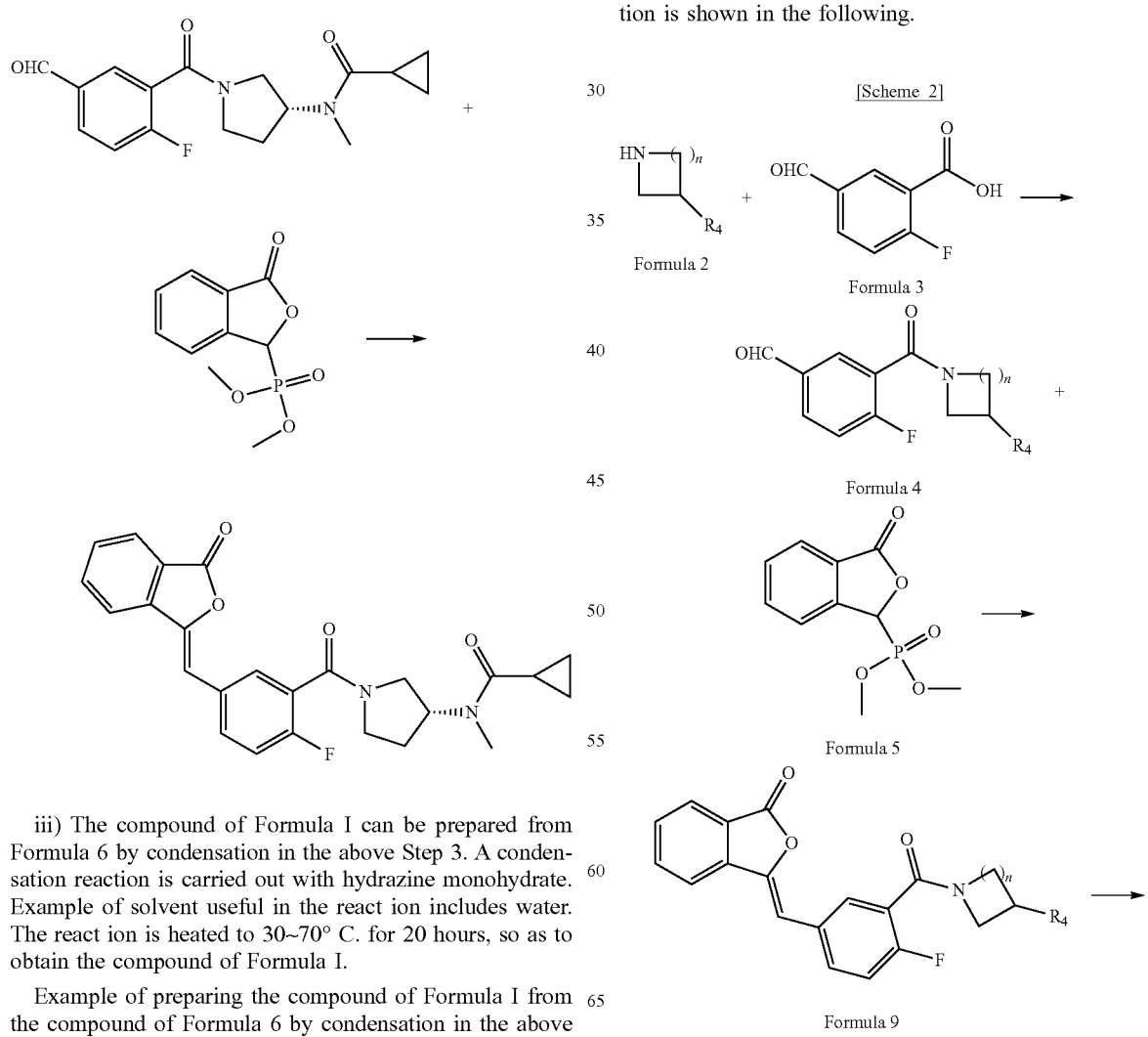

-continued

Formula 10

Formula 11

Formula 1

The compound of Formula I of the present invention, as shown in Scheme 2, can be prepared by series of steps from the compound of Formula 1.

n, $R_4$ and R, illustrated in Scheme 2, are defined as below:

Wherein, n is 1 or 2;

$R_4$ and $R_5$ is each independently tert-butyldimethylsiloxyl tert-butyldimethylsiloxymethyl benzylcarbamate, amine, $CH_2OH$ or hydroxyl;

R is wherein, when the R is m is 0, 1 or 2,

L is oxygen, methylene, carbonyl, $CONHCH_2$, $NR^{c1}CH_2$, $NR^{c2}CO$, $NR^{c3}$, $CONR^{c4}$ or $CH_2NR^{c5}$ (especially, $R^{c1}$, $R^{c2}$, $R^{c3}$, $R^{c4}$ and $R^{c5}$ is each independently oxygen, $C_{1-4}$ alkylamine, $C_{1-6}$ alkyl, $C_{1-6}$ alkoxy, halo $C_{1-6}$ alkyl, $C_{2-6}$ alkenyl, $C_{2-6}$ alkynyl, $C_{3-8}$ cycloalkyl or 3-8 membered heterocycle), $R^X$ is hydrogen, cyano, hydroxyl, trifluoromethyl, $C_{1-6}$ alkyl or $C_{3-8}$ cycloalkyl, $R^Y$ is hydrogen, amide, cyano, hydroxyl, trifluoromethyl, halo, ester, $C_{1-4}$ alkylamine, $C_{1-6}$ alkyl, $C_{1-6}$ methoxyalkyl or $C_{2-6}$ alkynyl, Z is unsubstituted, $C_{1-6}$ alkyl, $C_{1-6}$ methoxyalkyl, $C_{2-6}$ alkenyl, $C_{2-6}$ alkynyl, $C_{3-8}$ cycloalkyl, $C_{3-8}$ cycloalkenyl, $C_{6-10}$ aromatic cycle or 3-8 membered heterocycle having 1-3 nitrogens, wherein, when the R is p and q is each independently from 1 to 3, W is $CR^{d1}R^{d2}$ or $NR^{d3}$ (especially, $R^{d1}$, $R^{d2}$ and $R^{d3}$ is each independently hydrogen, fluoro or $C_{1-6}$alkyl), wherein, when the R is $R^1$, $R^2$ and $R^3$ is each independently hydrogen or $C_{1-6}$alkyl.

Another preparation method of the Formula I comprises

Preparing a compound of Formula 8 from a compound of Formula 7 and 3 which reacted with amide coupling reaction (Step 1)

Preparing a compound of Formula 9 from a compound of Formula 8 and 5 which reacted with olefination reaction (Step 2)

Preparing a compound of Formula 10 from a compound of Formula 9 and hydrazine monohydrate which reacted with condensation reaction (Step 3)

Preparing a compound of Formula 11 from a compound of Formula 10 which reacted with carboxybenzyl or tert-butyldimethylsiloxyl

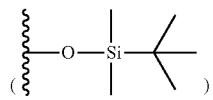

deprotection reaction (Step 4)

Preparing a compound of Formula I from a compound of Formula 11 which reacted with amide coupling, substitution and reductive amination reaction (Step 5)

Each step of the above preparation method is described in more detail as follows.

i) The compound of Formula 8 can be prepared from Formula 7 by amide coupling in the above Step 1. An Amide coupling reaction is carried out with 1-Ethyl-3-(3-dimethylaminopropyl)carbodiimide hydrochloride (EDCI) and 4-(Dimethylamino)pyridine (DMAP) or O-(benzotriazole-1-yl)-N,N,N',N'-tetramethyluronium hexafluorophosphate (HBTU) and N,N-diisopropyl ethylamine (DIPEA). Examples of solvents useful in the react ion include chloroform or dimethyl formamide. The react ion is heated to 20~35° C. for 1~30 hours, so as to obtain the compound of Formula 8.

Example of preparing the compound of Formula 8 from the compound of Formula 7 and 3 by amide coupling in the above Step 1 is illustrated below.

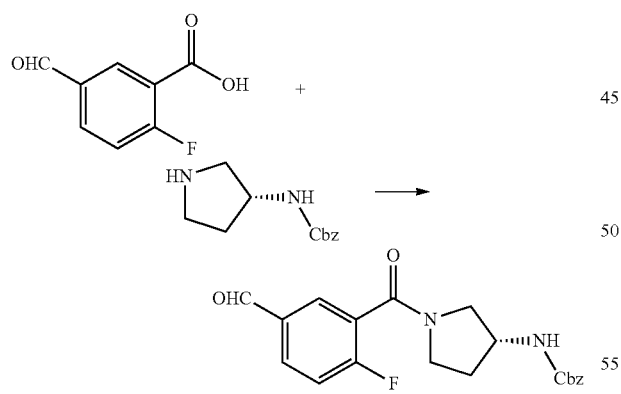

ii) The compound of Formula 9 can be prepared from Formula 8 by olefination in the above Step 2. An olefination reaction is carried out with Formula 5 in basic condition. Examples of solvent useful in the reaction include THF. The reaction is cooled to 0° C. for 1~5 hours, so as to abtain the compound of Formula 9.

Example of preparing the compound of Formula 9 from the compound of Formula 8 and 5 by olefination in the above Step 2 is illustrated below.

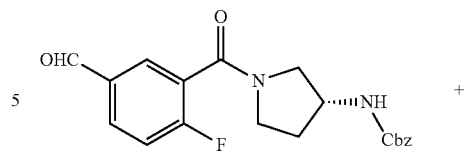

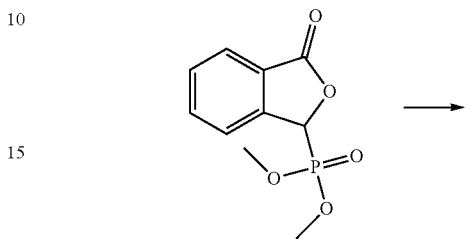

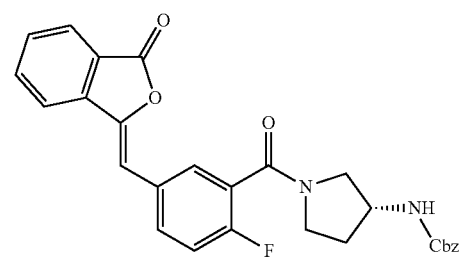

iii) The compound of Formula 10 can be prepared from Formula 9 by condensation in the above Step 3. A condensation reaction is carried out with hydrazine monohydrate. Example of solvent useful in the reaction includes water. The reaction is heated to 30~70° C. for 20 hours, so as to obtain the compound of Formula 10.

Example of preparing the compound of Formula 10 from the compound of Formula 9 by condensation in the above Step 3 is illustrated below.

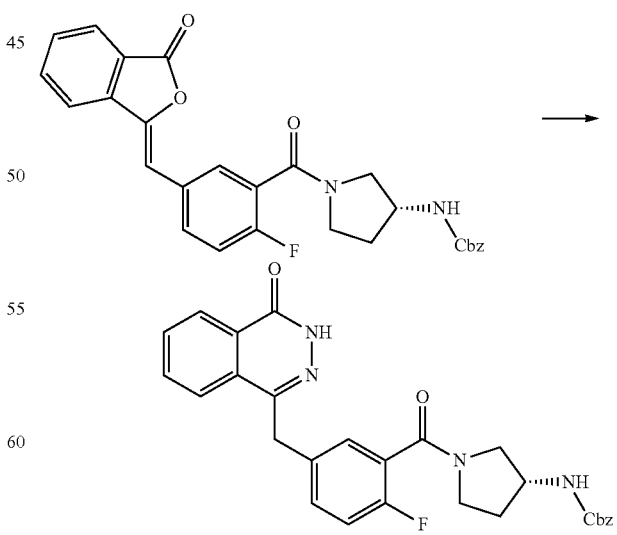

iv) The compound of Formula 11 can be prepared from Formula 10 by carboxybenzyl or tert-butyloxycarbonyl

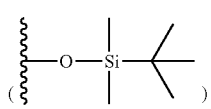

deprotection in the above

Step 4. A carboxybenzyl or tert-butyldimethylsiloxyl

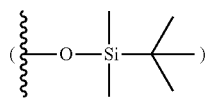

deprotection reaction is carried out with Pd/C under $N_2$ gas or 1M solution of tetra-n-butylammonium fluoride in THF (TBAF), so as to obtain the compound of Formula 11.

Example of preparing the compound of Formula 11 from the compound of Formula 10 by condensation in the above Step 4 is illustrated below.

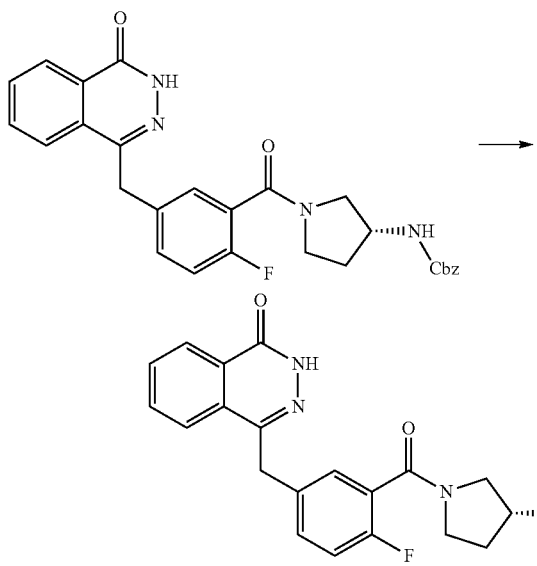

v) The compound of Formula I can be prepared from Formula 11 by amide coupling, substitution and reductive amination reaction.

A step 5 of the Scheme 2 is described in more detail as follows.

In Step 5 of the preparation method, the compound of Formula I can be prepared with amide coupling, substitution and reductive amination.

In the above amide coupling reaction, the reaction is carried out with 1-Ethyl-3-(3-dimethylaminopropyl)carbodiimide hydrochloride (EDCI) and 4-(Dimethylamino)pyridine (DMAP) or O-(benzotriazole-1-yl)-N,N,N',N'-tetramethyluronium hexafluorophosphate (HBTU) and N,N-diisopropyl ethylamine (DIPEA). Examples of solvents useful in the react ion include chloroform or dimethylformamide, so as to obtain the compound of Formula I. An example is illustrated below.

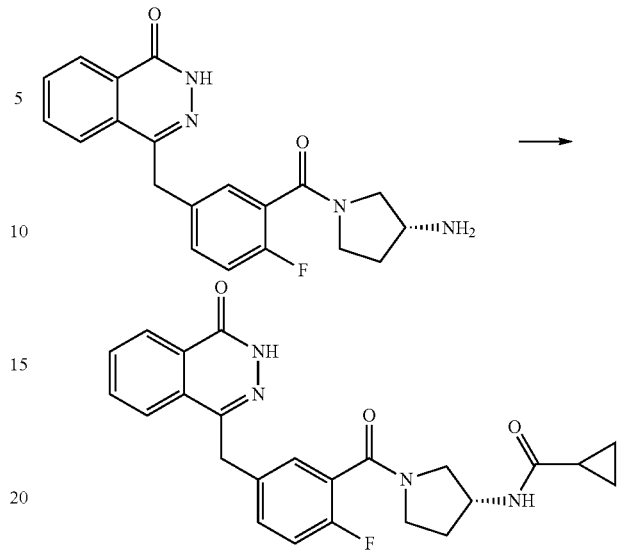

Besides, In the Step 5, the compound of Formula I can be prepared with from substitution.

In the above substitution reaction, mesylate compound is prepared from alcohol compound by reaction with methanesulfonyl chloride in dichloromethane. And then, desired functional group can be introduced by reaction of mesylate compound with

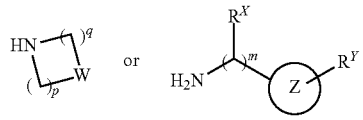

(In above Scheme, p, q, m, W, Z, $R^X$ and $R^Y$, are the same as defined in Formula I). An example of preparing the compound of Formula I form the compound of Formula 8 by substitution in the present invention is illustrated below (The $R^{c6}$ substitution is introduced with $K_2CO_3$ and $R^{c6}$—I).

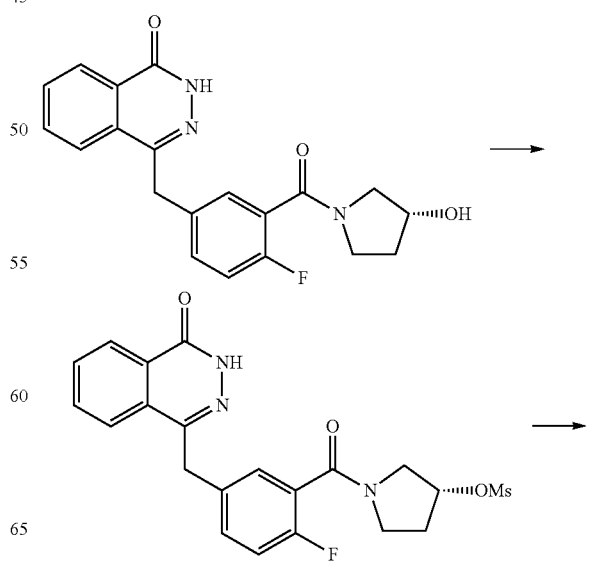

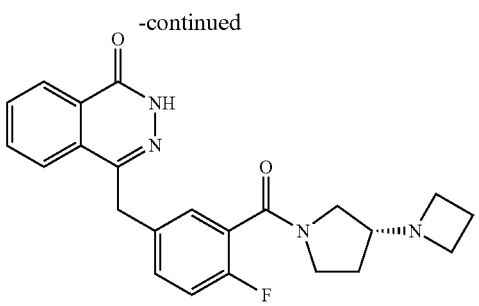

Besides, in the above reductive amination reaction, the compound of Formula I can be prepared form

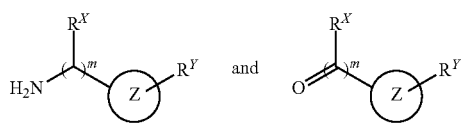

(In above Scheme, m, Z, $R^X$ and $R^Y$, are the same as defined in Formula I). The reaction is carried out with sodium triacetoxyborohydride and acetic acid for overnight. Examples of solvent useful in the reaction include chloroform or dichloromethane. An example of preparing the compound of Formula I is illustrated below (The $R^{c4}$ substitution is introduced with $K_2CO_3$ and $R^{c4}$—I in dimethylformamide).

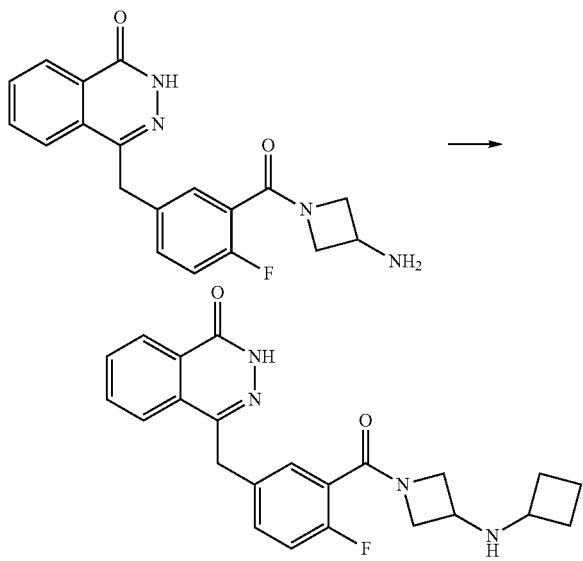

In addition, the present invention provides a pharmaceutical composition for treating cancers comprising the compound of Formula I, racemic, enantiomer, diastereoisomer thereof, or pharmaceutically acceptable salt thereof. The cancers may be caused by PARP activity, or generic defect of BRCA1, BRCA2, and ERG fusion gene. Exemplary cancers include, but are not limited to breast cancer, ovarian cancer, pancreatic cancer, gastric cancer, lung cancer, colorectal cancer, brain tumor, prostate cancer and Ewings sarcoma. As used herein, the term "generic defect" is intended as gene mutation, gene deficiency or defect of gene expression, but is not limited thereto.

The present invention provides a method of treating cancers in a subject in need thereof, comprising administering an effective amount of the pharmaceutical composition to the subject. The dosage of pharmaceutical composition of the present invention may vary depending on the patient's weight, age, gender, physical condition, diet, the time and mode of administration, excretion rates, and the severity of illness. Mammals (including human) are desirable for the individual without limit.

Compounds of the invention intended for pharmaceutical use may be administered as a solid or liquid, such as a tablet, capsule, solution or suspension. Pharmaceutical compositions suitable for the delivery of compounds of the present invention and methods for their preparation will be readily apparent to those skilled in the art. Such compositions and methods for their preparation may be found, for example, in Remingtons Pharmaceutical Sciences, 19th Edition (Mack Publishing Company, 1995).

The present invention provides compound, specifically, active in inhibiting the activity of PARP. Compounds of the invention can be used in cancer treatment through inhibition of PARP. Exemplary include lung cancer, gastrointestinal cancer, prostate cancer, uterine cancer, or especially breast cancer, or ovarian cancer.

Compounds of the invention may be combined in a pharmaceutical combination formulation, or dosing regimen as combination therapy, with a second compound having anti-cancer properties or at least two kinds of pharmaceutical active ingredients.

The examples of agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR®, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA®, Johnson & Johnson), ABRAXANE® (Cremophor-free), albumin-engineered nanoparticle formulations of paclitaxel (American Pharmaceutical Partners, Schaumberg, 1H), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclophosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gamma II, calicheamicin omega II (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

For instance, compounds of the invention, especially formula I or pharmaceutically acceptable salt can be administered simultaneously, gradually, or individually with at least one of therapeutic agents.

Oral Administration

In one embodiment, the compounds of the invent ion may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid plugs, solid microparticulates, semi-solid and liquid (including multiple phases or dispersed systems) such as tablets; soft or hard capsules containing multi- or nano-particulates, liquids, emulsions or powders; lozenges (including liquid-lled); chews; gels; fast dispersing dosage forms; lms; ovules; sprays; and buccal/mucoadhesive patches. Liquid (including multiple phases and dispersed systems) formulations include emulsions, suspensions, solutions, syrups and elixirs. Such formulations may be presented as llers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001).

The immediate release portion may comprise a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, powdered cellulose, lower alkyl-substituted hydroxypropyl cellulose, polacrilin potassium, starch, pregelatinized starch, sodium alginate, and mixtures thereof. Generally, the disintegrant will comprise from 1 wt % to 80 wt %, preferably from 5 wt % to 60 wt % of the layer.

Examples of matrix materials, fillers, or diluents include lactose, mannitol, xylitol, dextrose, sucrose, sorbitol, compressible sugar, microcrystalline cellulose, powdered cellulose, starch, pregelatinized starch, dextrates, dextran, dextrin, dextrose, maltodextrin, calcium carbonate, dibasic calcium phosphate, tribasic calcium phosphate, calcium sulfate, magnesium carbonate, magnesium oxide, poloxamers, polyethylene oxide, hydroxypropyl methyl cellulose and mixtures thereof.

When preparing dosage forms incorporating the compositions of the invent ion, the compounds may also be blended with conventional excipients such as binders, including gelatin, pregelatinized starch, and the like; lubricants, such as hydrogenated vegetable oil, stearic acid, and the like; diluents, such as lactose, mannose, and sucrose; disintegrants, such as carboxymethylcellulose and sodium starch glycolate; suspending agents, such as povidone, polyvinyl alcohol, and the like; absorbants, such as silicon dioxide; preservatives, such as methylparaben, propylparaben, and sodium benzoate; surfactants; such as sodium lauryl sulfate, polysorbate 80, and the like; flavorants; and sweeteners. If present, the surfactants would comprise of 0.2 wt % to 5 wt % and the absorbants would comprise from 0.2 wt % to 1 wt %. Another excipients include one or more of: anti-oxidants, colourants, flavouring agents, preservatives and taste-masking agents.

Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in "Pharmaceutical Dosage Forms: Tablets, Vol. 1", by H. Lieberman and L. Lachman, Marcel Dekker, N.Y., N.Y., 1980 (ISBN 0-8247-6918-X).

Sol id formulations for oral administration may be formulated to be immediate and/or modified release. Modified release formulations include delayed-, sustained-, pulsed-, controlled-, targeted and programmed release Parenteral Administration The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous.

Suitable devices for parenteral administration includes needle (including microneedle) injectors, needle-free injectors and infusion techniques. An example of a needle free injection is Powderject™.

Parenteral formulations are typically aqueous solutions which may contain excipients such as salts, carbohy-drates and buffering agents (preferably, to a pH of from 3 to 9), but, for some applications, they may be more suitably formulated as a sterile nonaqueous solution or as a powdered, dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

A proper dosage form such as combination with solubility enhancer can increase solubility of compound of formula I used in non-oral solution.

Formulations for parenteral administration may be formulated to be immediate and/or modified/controlled release. Controlled/modified release formulations include delayed-, sustained-, pulsed-, controlled-, targeted and programmed release. Thus compounds of the invent ion may be formulated as a solid, semi-solid, or thixotropic liquid for administration as an implanted depot providing modified release of the active compound. Examples of such formulations include drug-coated stents and PGLA microspheres.

Local Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Li-posomes may also be used.

Does

In human patients, the precise daily dose administered depends on various factors such as the age, sex, weight and condition of the patient being treated. The amount of dose can be selected within the bounds of goal achieving treatment effect without harmful or serious adverse effect.

For instance, the dosage of the compound of invention may be administered in an effective amount raging from 0.05 to 1000 mg daily on patients. The following dosage levels and other dosage levels herein are for the average human subject having a weight range of about 65 to 70 kg. The skilled person will readily be able to determine the dosage levels required for a subject whose weight falls outside this range, such as children and the elderly.

The present invention explain, but are not limited, in detail through the following examples and experimental examples.

EXAMPLE

Example 1

(R)-4-(3-(3-aminopyrrolidine-1-carbonyl)-4-fluorobenzyl)phthalazin-1(2H)-one; (I-1)

Step 1: Preparation of ((R)-benzyl(1-(2-fluoro-5-formylbenzoyl)pyrrolidin-3-yl)carbamate 2-fluoro-5-formylbenzoic acid (220 mg, 0.91 mmol), O-(benzotriazole-1-yl)-N,N,N',N'-tetramethyluronium hexafluorophosphate (HBTU, 384 mg, 1.01 mmol) and N,N-diisopropyl ethylamine (DIPEA, 0.52 mL, 2.98 mmol) was added to a solution of (R)-benzyl pyrrolidin-3-ylcarbamate (200 mg, 0.91 mmol) in DMF (5 mL) and stirred for 12 hours. The react ion mixture was concentrated in vacuum, added dichloromethane and washed sat. $NH_4Cl$ (aq) and water. The combined organic layers were dried over $MgSO_4$, filtered, evaporated in vacuum and purified using silica chromatography to give the intermediate compound (R)-benzyl (1-(2-fluoro-5-formylbenzoyl)pyrrolidin-3-yl)carbamate (229 mg, 68%).

Step 2: Preparation of (R,Z)-benzyl(1-(2-fluoro-5-((3-oxoisobenzofuran-1(3H)-ylidene)methyl)benzoyl)pyrrolidin-3-yl)carbamate The intermediate compound (Step 1)(236 mg, 0.62 mmol) and triethylamine (0.12 mL, 0.81 mmol) was added to a solution of dimethyl (3-oxo-1,3-dihydroisobenzofuran-1-yl) phosphonate (220 mg, 0.91 mmol) in THF (1.7 mL) and stirred for 5 hours at 0° C. The reaction mixture was concentrated in vacuum then the white residue was slurried in water for 30 minutes, filtered, washed with water, hexane and ether, and dried to yield the intermediate compound (R,Z)-benzyl (1-(2-fluoro-5-((3-oxoisobenzofuran-1(3H)-ylidene)methyl)benzoyl)pyrrolidin-3-yl)carbamate (164 mg, 59%).

Step 3: Preparation of (R)-benzyl(1-(2-fluoro-5-((4-oxo-3,4-dihydrophthalazin-1-yl)methyl)benzoyl) pyrrolidin-3-yl)carbamate Hydrazine monohydrate (19 uL, 0.38 mmol) was added to a suspension of the intermediate compound (Step 2)(164 mg, 0.35 mmol) in water (1.5 mL) and stirred for 2 hours at 40° C. The reaction was cooled to room temperature and concentrated in vacuum. Water was added to the react ion mixture and the product was extracted into dichloromethane. The combined organic layers were dried over $MgSO_4$, filtered, evaporated in vacuum and purified using silica chromatography to give (R)-benzyl(1-(2-fluoro-5-((4-oxo-3,4-dihydrophthalazin-1-yl)methyl)benzoyl)pyrrolidin-3-yl)carbamate (100 mg, 47%).

Step 4: Preparation of (R)-4-(3-(3-aminopyrrolidine-1-carbonyl)-4-fluorobenzyl)phthalazin-1(2H)-one The intermediate compound (step 3)(100 mg, 0.20 mmol) and 10 wt. % Pd/C (10 mg) in methanol (30 mL) was hydrogenated at atmosphere for 6 h. The reaction mixture was filtered, evaporated in vacuum and purified using silica chromatography to afford the title compound (63 mg, 85%).

$^1$H-NMR (DMSO, 400 MHz): δ 12.60 (s, 1H), 8.26 (d, 1H), 7.97 (d, 1H), 7.89 (t, 1H), 7.83 (t, 1H), 7.50-7.44 (m,

1H), 7.40 (d, 1H), 7.21 (t, 1H), 4.37 (s, 2H), 3.79-3.67 (m, 1H), 3.59-3.33 (m, 3H), 3.29-3.06 (m, 3H).

Example 2

(S)-4-(3-(3-aminopyrrolidine-1-carbonyl)-4-fluorobenzyl)phthalazin-1(2H)-one; (I-2)

Step 1: Preparation of (S)-benzyl(1-(2-fluoro-5-formylbenzoyl)pyrrolidin-3-yl)carbamate This compound was made using the procedure described for example 1 (Step 1). Thus, (S)-benzylpyrrolidine-3-yl-carbamate (150 mg, 0.68 mmol) was reacted with 2-fluoro-5-formyl benzoic acid (114 mg, 0.68 mmol), O-(benzotriazole-1-yl)-N,N,N',N'-tetramethyluronium hexafluorophosphate (HBTU, 335 mg, 0.88 mmol) and N,N-diisopropyl ethyl amine (DIPEA, 0.24 mL, 1.36 mmol) to afford the intermediate compound (S)-benzyl (1-(2-fluoro-5-formylbenzoyl)pyrrolidin-3-yl)carbamate (156 mg, 62%).

Step 2: Preparation of (S,Z)-benzyl(1-(2-fluoro-5-((3-oxoisobenzofuran-1(3H)-ylidene)methyl)benzoyl)pyrrolidin-3-yl)carbamate This compound was made using the procedure described for example 1 (Step 2). Thus, this intermediate compound (Step 1) was reacted with dimethyl (3-oxo-1,3-dihydroisobenzofuran-1-yl)phosphonate (102 mg, 0.42 mmol) and triethyl amine (88 uL, 0.63 mmol) to afford the intermediate compound (S,Z)-benzyl (1-(2-fluoro-5-((3-oxoisobenzofuran-1(3H)-ylidene)methyl)benzoyl)pyrrolidin-3-yl)carbamate (117 mg, 57%).

Step 3: Preparation of (S)-benzyl(1-(2-fluoro-5-((4-oxo-3,4-dihydrophthalazin-1-yl)methyl)benzoyl)pyrrolidin-3-yl)carbamate This compound was made using the procedure described for example 1 (Step 3). Thus, this intermediate compound (Step 2) was reacted with hydrazine monohydrate (24 uL, 0.48 mmol) to afford the intermediate compound (S)-benzyl (1-(2-fluoro-5-((4-oxo-3,4-dihydrophthalazin-1-yl)methyl)benzoyl)pyrrolidin-3-yl)carbamate (58 mg, 48%).

Step 4: Preparation of (S)-4-(3-(3-aminopyrrolidine-1-carbonyl)-4-fluorobenzyl)phthalazin-1(2H)-one This compound was made using the procedure described for example 1 (Step 4). Thus, this intermediate compound (Step 3)(58 mg, 0.12 mmol) was reacted with 10 wt. Pd/C (6 mg) to afford the title compound (39 mg, 88%).
$^1$H-NMR (DMSO, 400 MHz): δ 12.60 (s, 1H), 8.26 (d, 1H), 7.97 (d, 1H), 7.89 (t, 1H), 7.83 (t, 1H), 7.50-7.44 (m, 1H), 7.40 (d, 1H), 7.21 (t, 1H), 4.37 (s, 2H), 3.79-3.67 (m, 1H), 3.59-3.33 (m, 3H), 3.29-3.06 (m, 3H).

Example 3

4-(3-(3-aminoazetidine-1-carbonyl)-4-fluorobenzyl)phthalazin-1(2H)-one; (I-3)

Step 1: Preparation of benzyl(1-(2-fluoro-5-formylbenzoyl)azetidin-3-yl)carbamate This compound was made using the procedure described for example 1 (Step 1). Thus, benzyl azetidine-3-ylcarbamate (500 mg, 2.42 mmol) was reacted with 2-fluoro-5-formyl benzoic acid (408 mg, 2.42 mmol), O-(benzotriazole-1-yl)-N,N,N',N'-tetramethyluronium hexafluorophosphate (HBTU, 1.20 g, 3.15 mmol) and N,N-diisopropyl ethylamine (DIPEA, 0.84 mL, 4.85 mmol) to affoed the intermediate compound benzyl (1-(2-fluoro-5-formylbenzoyl)azetidin-3-yl)carbamate (604 mg, 70%).

Step 2: Preparation of (Z)-benzyl(1-(2-fluoro-5-((3-oxoisobenzofuran-1(3H)-ylidene)methyl)benzoyl)azetidin-3-yl)carbamate This compound was made using the procedure described for example 1 (Step 2). Thus, this intermediate compound (Step 1)(604 mg, 1.69 mmol) was reacted with dimethyl(3-oxo-1,3-dihydroisobenzofuran-1-yl)phosphonate (410 mg, 1.69 mmol) and triethylamine (0.35 mL, 2.54 mmol) to afford the intermediate compound (Z)-benzyl (1-(2-fluoro-5-((3-oxoisobenzofuran-1(3H)-ylidene)methyl)benzoyl) azetidin-3-yl)carbamate (497 mg, 62%).

Step 3: Preparation of benzyl(1-(2-fluoro-5-((4-oxo-3,4-dihydrophthalazin-1-yl)methyl)benzoyl)azetidin-3-yl)carbamate This compound was made using the procedure described for example 1 (Step 3). Thus, this intermediate compound (Step 2)(497 mg, 1.05 mmol) was reacted with hydrazine monohydrate (0.1 mL, 2.1 mmol) to afford the intermediate compound benzyl (1-(2-fluoro-5-((4-oxo-3,4-dihydrophthalazin-1-yl)methyl)benzoyl)azetidin-3-yl)carbamate (261 mg, 51%).

Step 4: Preparation of 4-(3-(3-aminoazetidine-1-carbonyl)-4-fluorobenzyl)phthalazin-1(2H)-one This compound was made using the procedure described for example 1 (Step 4). Thus, this intermediate compound (Step 3)(261 mg, 0.54 mmol) was reacted with 10 wt. % Pd/C (30 mg) to afford the title compound (174 mg, 91%).
$^1$H-NMR (DMSO, 400 MHz): δ 12.61 (s, 1H), 8.27-8.25 (m, 1H), 7.97 (d, 1H), 7.91-7.81 (m, 2H), 7.48-7.44 (m, 1H), 7.41-7.39 (m, 1H), 7.21 (t, 1H), 4.33 (s, 2H), 4.15-4.10 (m, 2H), 3.66-3.59 (m, 3H).

Example 4

(R)-4-(4-fluoro-3-(3-hydroxypyrrolidine-1-carbonyl)benzyl)phthalazin-1(2H)-one; (I-4)

Step 1: Preparation of (R)-3-(3-((tert-butyldimethylsilyl)oxy)pyrrolidine-1-carbonyl)-4-fluorobenzaldehyde This compound was made using the procedure described for example 1 (Step 1). Thus, (R)-3-((tert-butyldimethylsilyl)oxy)pyrrolidine (300 mg, 1.49 mmol) was reacted with 2-fluoro-5-formyl benzoic acid (250 mg, 1.49 mmol), O-(benzotriazole-1-yl)-N,N,N',N'-tetramethyluronium hexafluorophosphate (HBTU, 734 mg, 1.93 mmol) and N,N-diisopropyl ethylamine (DIPEA, 0.52 mL, 2.97 mmol) to afford the intermediate compound (R)-3-(3-((tert-butyldimethylsilyl)oxy)pyrrolidine-1-carbonyl)-4-fluorobenzaldehyde (377 mg, 72%).

Step 2: Preparation of (R,Z)-3-(3-(3-((tert-butyldimethylsilyl)oxy)pyrrolidine-1-carbonyl)-4-fluorobenzylidene)isobenzofuran-1(3H)-one This compound was made using the procedure described for example 1 (Step 2). Thus, this intermediate compound (Step 1)(377 mg, 1.07 mmol) was reacted with dimethyl(3-oxo-1,3-dihydroisobenzofuran-1-yl)phosphonate (260 mg, 1.07 mmol) and triethylamine (0.22 mL, 1.61 mmol) to afford the intermediate compound (R,Z)-3-(3-(3-((tert-butyldimethylsilyl)oxy)pyrrolidine-1-carbonyl)-4-fluorobenzyidene)isobenzofuran-1(3H)-one (300 mg, 60%).

Step 3: Preparation of ((R)-4-(3-(3-((tert-butyldimethylsilyl)oxy)pyrrolidine-1-carbonyl)-4-fluorobenzyl)phthalazin-1(2H)-one This compound was made using the procedure described for example 1 (Step 3). Thus, this intermediate compound (Step 2)(300 mg, 0.64 mmol) was reacted with hydrazine monohydrate (63 uL, 1.28 mmol) to afford the intermediate compound (R)-4-(3-(3-((tert-butyldimethylsilyl)oxy)pyrrolidine-1-carbonyl)-4-fluorobenzyl)phthalazin-1(2H)-one (148 mg, 48%).

Step 4: Preparation of (R)-4-(4-fluoro-3-(3-hydroxypyrrolidine-1-carbonyl)benzyl)phthalazin-1(2H)-one The intermediate compound (step 3)(148 mg, 0.30 mmol) in THF (3 mL) cooled to 0° C. was added 1M solution of tetra-n-butylammonium fluoride in THF (TBAF, 0.60 mL, 0.60 mmol), and the mixture was stirred at room temperature for 3 h. The reaction mixture was concentrated in vacuum, added dichloromethane and washed with sat. NH$_4$Cl (ag) and water. The combined organic layers were dried over MgSO$_4$, filtered, evaporated in vacuum and purified using silica chromatography to afford the title compound (101 mg, 92%).
$^1$H-NMR (DMSO, 400 MHz): δ 12.61 (s, 1H), 8.25 (d, 1H), 7.98 (d, 1H), 7.87 (t, 1H), 7.82 (t, 1H), 7.51-7.45 (m, 1H), 7.40 (d, 1H), 7.21 (t, 1H), 4.37 (s, 2H), 3.79-3.65 (m, 2H), 3.59-3.28 (m, 5H).

Example 5

(S)-4-(4-fluoro-3-(3-hydroxypyrrolidine-1-carbonyl)benzyl)phthalazin-1(2H)-one

Step 1: Preparation of (S)-3-(3-((tert-butyldimethylsilyl)oxy)pyrrolidine-1-carbonyl)-4-fluorobenzaldehyde This compound was made using the procedure described for example 1 (Step 1). Thus, (S)-3-((tert-butyldimethylsilyl)oxy)pyrrolidine (300 mg, 1.49 mmol) was reacted with 2-fluoro-5-formyl benzoic acid (250 mg, 1.49 mmol), O-(benzotriazole-1-yl)-N,N,N',N'-tetramethyluronium hexafluorophosphate (HBTU, 734 mg, 1.93 mmol) and N,N-diisopropyl ethylamine (DIPEA, 0.52 mL, 2.97 mmol) to afford the intermediate compound (S)-3-(3-((tert-butyldimethylsilyl)oxy)pyrrolidine-1-carbonyl)-4-fluorobenzaldehyde (377 mg, 72%).

Step 2: Preparation of (S,Z)-3-(3-(3-((tert-butyldimethylsilyl)oxy)pyrrolidine-1-carbonyl)-4-fluorobenzylidene)isobenzofuran-1(3H)-one This compound was made using the procedure described for example 1 (Step 2). Thus, this intermediate compound (Step 1)(377 mg, 1.07 mmol) was reacted with dimethyl(3-oxo-1,3-dihydroisobenzofuran-1-yl)phosphonate (260 mg, 1.07 mmol) and triethylamine (0.22 mL, 1.61 mmol) to afford the intermediate compound (S,Z)-3-(3-(3-((tert-butyldimethylsilyl)oxy)pyrrolidine-1-carbonyl)-4-fluorobenzylidene)isobenzofuran-1(3H)-one (300 mg, 60%).

Step 3: Preparation of (S)-4-(3-(3-((tert-butyldimethylsilyl)oxy)pyrrolidine-1-carbonyl)-4-fluorobenzyl)phthalazin-1(2H)-one This compound was made using the procedure described for example 1 (Step 3). Thus, this intermediate compound (Step 2)(300 mg, 0.64 mmol) was reacted with hydrazine monohydrate (63 uL, 1.28 mmol) to afford the intermediate compound (S)-4-(3-(3-((tert-butyldimethylsilyl)oxy)pyrrolidine-1-carbonyl)-4-fluorobenzyl)phthalazin-1(2H)-one (148 mg, 48%).

Step 4: Preparation of (S)-4-(4-fluoro-3-(3-hydroxypyrrolidine-1-carbonyl)benzyl)phthalazin-1(2H)-one This compound was made using the procedure described for example 4 (Step 4). Thus, this intermediate compound (Step 3)(144 mg, 0.30 mmol) was reacted with a 1M solution of tetra-n-butylammonium fluoride in THF (TBAF, 0.60 mL, 0.60 mmol) to afford the title compound (101 mg, 92%).
$^1$H-NMR (DMSO, 400 MHz): δ 12.61 (s, 1H), 8.25 (d, 1H), 7.98 (d, 1H), 7.87 (t, 1H), 7.82 (t, 1H), 7.51-7.45 (m, 1H), 7.40 (d, 1H), 7.21 (t, 1H), 4.37 (s, 2H), 3.79-3.65 (m, 2H), 3.59-3.28 (m, 5H).

Example 6

4-(4-fluoro-3-(3-hydroxyazetidine-1-carbonyl)benzyl)phthalazin-1(2H)-one; (I-6)

Step 1: Preparation of 3-(3-((tert-butyldimethylsilyl)oxy)azetidine-1-carbonyl)-4-fluorobenzaldehyde This compound was made using the procedure described for example 1 (Step 1). Thus, 3-((tert-butyldimethylsilyl)oxy)azetidine (300 mg, 1.60 mmol) was reacted with 2-fluoro-5-formyl benzoic acid (269 mg, 1.60 mmol), O-(benzotriazole-1-yl)-N,N,N',N'-tetramethyluronium hexafluorophosphate (HBTU, 789 mg, 2.08 mmol) and N,N-diisopropyl ethylamine (DIPEA, 0.56 mL, 3.20 mmol) to afford the intermediate compound 3-(3-((tert-butyldimethylsilyl)oxy)azetidine-1-carbonyl)-4-fluorobenzaldehyde (378 mg, 70%).

Step 2: Preparation of (Z)-3-(3-(3-((tert-butyldimethylsilyl)oxy)azetidine-1-carbonyl)-4-fluorobenzylidene)isobenzofuran-1(3H)-one This compound was made using the procedure described for example 1 (Step 2). Thus, this intermediate compound (Step 1)(378 mg, 1.12 mmol) was reacted with dimethyl(3-oxo-1,3-dihydroisobenzofuran-1-yl)phosphonate (271 mg, 1.12 mmol) and triethylamine (0.23 mL, 1.68 mmol) to afford the intermediate compound (Z)-3-(3-(3-((tert-butyldimethylsilyl)oxy)azetidine-1-carbonyl)-4-fluorobenzylidene)isobenzofuran-1(3H)-one (284 mg, 56%).

Step 3: Preparation of 4-(3-(3-((tert-butyldimethylsilyl)oxy)azetidine-1-carbonyl)-4-fluorobenzyl)phthalazin-1(2H)-one This compound was made using the procedure described for example 1 (Step 3). Thus, this intermediate compound (Step 2)(284 mg, 0.62 mmol) was reacted with hydrazine monohydrate (61 uL, 1.26 mmol) to afford the intermediate compound 4-(3-(3-(((tert-butyldimethylsilyl)oxy)azetidine-1-carbonyl)-4-fluorobenzyl)phthalazin-1(2H)-one (149 mg, 51%).

Step 4: Preparation of 4-(4-fluoro-3-(3-hydroxyazetidine-1-carbonyl)benzyl)phthalazin-1(2H)-one This compound was made using the procedure described for example 4 (Step 4). Thus, this intermediate compound (Step 3)(149 mg, 0.32 mmol) was reacted with a 1M solution of tetra-n-butylammonium fluoride in THF (TBAF, 0.64 mL, 0.64 mmol) to afford the title compound (98 mg, 92%).

$^1$H-NMR (DMSO, 400 MHz): δ 12.60 (s, 1H), 8.27-8.26 (m, 1H), 7.96 (d, 1H), 7.91-7.81 (m, 2H), 7.48-7.45 (m, 1H), 7.41-7.39 (m, 1H), 7.20 (t, 1H), 4.33 (s, 2H), 4.15-4.11 (m, 3H), 3.66-3.58 (m, 2H).

Example 7

4-(4-fluoro-3-(3-(hydroxyethyl)azetidine-1-carbonyl)benzyl)phthalazin-1(2H)-one; (I-7)

Step 1: Preparation of 3-(3-(((tert-butyldimethylsilyl)oxy)methyl)azetidine-1-carbonyl)-4-fluorobenzaldehyde This compound was made using the procedure described for example 1 (Step 1). Thus, 3-(((tert-butyldimethylsilyl)oxy)methyl)azetidine (300 mg, 1.60 mmol) was reacted with 2-fluoro-5-formyl benzoic acid (269 mg, 1.60 mmol), O-(benzotriazole-1-yl)-N,N,N',N'-tetramethyluronium hexafluorophosphate (HBTU, 789 mg, 2.08 mmol) and N,N-diisopropyl ethylamine (DIPEA, 0.56 mL, 3.20 mmol) to afford the intermediate compound 3-(3-(((tert-butyldimethylsilyl)oxy)methyl)azetidine-1-carbonyl)-4-fluorobenzaldehyde (378 mg, 72%).

Step 2: Preparation of (Z)-3-(3-(3-(((tert-butyldimethylsilyl)oxy)methyl)azetidine-1-carbonyl)-4-fluorobenzylidene)isobenzofuran-1(3H)-one This compound was made using the procedure described for example 1 (Step 2). Thus, this intermediate compound (Step 1)(378 mg, 1.12 mmol) was reacted with dimethyl(3-oxo-1,3-dihydroisobenzofuran-1-yl)phosphonate (271 mg, 1.12 mmol) and trietylamine (0.23 mL, 1.68 mmol) to afford the intermediate compound (Z)-3-(3-(3-(((tert-butyldimethylsilyl)oxy)methyl)azetidine-1-carbonyl)-4-fluorobenzylidene)isobenzofuran-1(3H)-one (284 mg, 56%).

Step 3: Preparation of 4-(3-(3-(((tert-butyldimethylsilyl)oxy)methyl)azetidine-1-carbonyl)-4-fluorobenzyl)phthalazin-1(2H)-one This compound was made using the procedure described for example 1 (Step 3). Thus, this intermediate compound (Step 2)(284 mg, 0.63 mmol) was reacted with hydrazine monohydrate (61 uL, 1.25 mmol) to afford the intermediate compound 4-(3-(3-(((tert-butyldimethylsilyl)oxy)methyl)azetidine-1-carbonyl)-4-fluorobenzyl)phthalazin-1(2H)-one (149 mg, 51%).

Step 4: Preparation of 4-(4-fluoro-3-(3-(hydroxymethyl)azetidine-1-carbonyl)benzyl)phthalazin-1(2H)-one This compound was made using the procedure described for example 4 (Step 4). Thus, this intermediate compound (Step 3)(149 mg, 0.32 mmol) was reacted with a 1M solution of tetra-n-butylammonium fluoride in THF (TBAF, 0.64 mL, 0.64 mmol) to afford the title compound (98 mg, 92%).

$^1$H-NMR (DMSO, 400 MHz): δ 12.61 (s, 1H), 8.28-8.26 (m, 1H), 7.97 (d, 1H), 7.92-7.81 (m, 2H), 7.49-7.45 (m, 1H), 7.42-7.39 (m, 1H), 7.21 (t, 1H), 4.33 (s, 2H), 4.15-4.11 (m, 3H), 3.66-3.58 (m, 2H), 3.47 (m, 2H).

Example 8

(R)—N-(1-(2-fluoro-5-((4-oxo-3,4-dihydrophthalazin-1-yl)methyl)benzoyl)pyrrolidin-3-yl)cyclopropanecarboxamide; (I-8)

Step 1: Preparation of (R)—N-(1-(2-fluoro-5-((4-oxo-3,4-dihydrophthalazin-1-yl)methyl)benzoyl)pyrrolidin-3-yl)cyclopropanecarboxamide Cyclopropanecarboxylic acid (20 uL, 0.28 mmol), 1-Ethyl-3-(3-dimethylaminopropyl)carbodiimide hydrochloride (EDCI, 66 mg, 0.42 mmol) and 4-(Dimethylamino)pyridine (DMAP, 68 mg, 0.56 mmol) was added to a solution of (R)-4-(3-(3-aminopyrrolidine-1-carbonyl)-4-fluorobenzyl)phthalazin-1(2H)-one (example 1)(100 mg, 0.28 mmol) in dichloromethane (1.5 mL) and stirred for 12 hours. The reaction mixture was concentrated in vacuum, added dichloromethane and washed sat. NH$_4$Cl (aq) and water. The combined organic layers were dried over MgSO$_4$, filtered, evaporated in vacuum and purified using silica chromatography to afford title compound (83 mg, 68%).

$^1$H-NMR (CDCl$_3$, 400 MHz): δ 10.36 (d, 1H), 8.46 (m, 1H), 7.79 (m, 2H), 7.71 (m, 1H), 7.35 (m, 1H), 7.32 (m, 1H), 7.04 (q, 1H), 5.89 (m, 1H), 4.60 (q, 0.3H), 4.45 (q, 0.7H), 4.26 (d, 2H), 3.82 (m, 1H), 3.65 (m, 1H), 3.51 (m, 1H), 3.40 (m, 1H), 3.18 (m, 1H), 2.28 (m, 2H), 1.61 (m, 1H), 0.98 (m, 11H), 0.96 (m, 2H), 0.74 (m, 2H).

Example 9

N-(1-(2-fluoro-5-((4-oxo-3,4-dihydrophthalazin-1-yl)methyl)benzoyl)azetidin-3-yl)cyclopropanecarboxamide; (I-9)

Step 1: Preparation of N-(1-(2-fluoro-5-((4-oxo-3,4-dihydrophthalazin-1-yl)methyl)benzoyl)azetidin-3-yl)cyclopropanecarboxamide This compound was made using the procedure described for example 8 (Step 1). Thus, 4-(3-(3-aminoazetidine-1-carbonyl)-4-fluorobenzyl)phthalazin-1(2H)-one (example 3)(100 mg, 0.28 mmol) was reacted with cyclopropanecarboxylic acid (20 uL, 0.28 mmol), 1-Ethyl-3-(3-dimethylaminopropyl)carbodiimide hydrochloride (EDCI, 66 mg, 0.42 mmol) and 4-(Dimethylamino)pyridine (DMAP, 68 mg, 0.56 mmol) to afford the title compound (78 mg, 62%).

$^1$H-NMR (MeOD, 400 MHz): δ 8.39 (dd, 1H), 7.94 (dd, 1H), 7.85-7.80 (m, 2H), 7.52-7.45 (m, 2H), 7.17-7.12 (m, 1H), 4.63-4.53 (m, 1H), 4.44-4.37 (m, 3H), 4.30-4.21 (m, 1H), 4.01-3.89 (m, 2H), 1.59-1.52 (m, 1H), 0.92-0.78 (m, 4H).

Example 10

(S)—N-(1-(2-fluoro-5-((4-oxo-3,4-dihydrophthalazin-1-yl)methyl)benzoyl)pyrrolidin-3-yl)cyclopropanecarboxamide; (I-10)

Step 1: Preparation of (S)—N-(1-(2-fluoro-5-((4-oxo-3,4-dihydrophthalazin-1-yl)methyl)benzoyl)pyrrolidin-3-yl)cyclopropanecarboxamide This compound was made using the procedure described for example 8 (Step 1). Thus, (S)-4-(3-(3-aminopyrrolidine-1-carbonyl)-4-fluorobenzyl)phthalazin-1(2H)-one (example 2)(100 mg, 0.28 mmol) was reacted with cyclopropanecarboxylic acid (20 uL, 0.28 mmol), 1-Ethyl-3-(3-dimethylaminopropyl)carbodiimide hydrochloride (EDCI, 66 mg, 0.42 mmol) and 4-(Dimethylamino)pyridine (DMAP, 68 mg, 0.56 mmol) to afford the title compound (77 mg, 65%).

$^1$H-NMR (CDCl$_3$, 400 MHz): δ 9.55 (s, 0.6H), 9.52 (s, 0.6H), 8.46 (d, 1H), 7.82-7.71 (m, 3H), 7.38-7.26 (m, 2H), 7.04 (q, 1H), 5.75 (m, 1H), 4.60 (m, 0.4H), 4.42 (m, 0.6H), 4.28 (s, 0.8H), 4.27 (s, 1.2H), 3.92-3.64 (m, 2.4H), 3.56-3.33 (m, 1H), 3.17 (dd, 0.6H), 2.33-2.16 (m, 1H), 1.93 (m, 1H), 1.32 (m, 1H), 0.96 (m, 2H), 0.75 (m, 2H).

Example 11

(R)—N-(1-(2-fluoro-5-((4-oxo-3,4-dihydrophthalazin-1-yl)methyl)benzoyl)pyrrolidin-3-yl)-N-methylcyclopropanecarboxamide; (I-11)

Step 1: Preparation of (R)—N-(1-(2-fluoro-5-formylbenzoyl)pyrrolidin-3-yl)-N-methylcyclopropanecarboxamide 2-fluoro-5-formylbenzoic acid (350 mg, 2.08 mmol), O-(benzotriazole-1-yl)-N,N,N',N'-tetramethyluronium hexafluorophosphate (HBTU, 1.02 g, 2.79 mmol) and N,N-diisopropyl ethylamine (DIPEA, 0.72 mL, 4.16 mmol) was added to a solution of (R)—N-methyl-N-(pyrrolidin-3-yl)cyclopropanecarboxamide (350 mg, 2.08 mmol) in DMF (5 mL) and stirred for 12 hours. The react ion mixture was concentrated in vacuum, added dichloromethane and washed sat. NH$_4$Cl (aq) and water. The combined organic layers were dried over MgSO$_4$, filtered, evaporated in vacuum and purified using silica chromatography to afford the intermediate compound (R)—N-(1-(2-fluoro-5-formylbenzoyl)pyrrolidin-3-yl)-N-methylcyclopropanecarboxamide (470 mg, 72%). (R)-benzyl(1-(2-fluoro-5-formylbenzoyl)pyrrolidin-3-yl)carbamate (229 mg, 68%).

Step 2: Preparation of (R,Z)—N-(1-(2-fluoro-5-((3-oxoisobenzofuran-1(3H)-ylidene)methyl)benzoyl)pyrrolidin-3-yl)-N-methylcyclopropanecarboxamide Trietylamine (0.38 mL, 2.21 mmol) was added drop-wide to a solution of the intermediate compound (Step 1)(470 mg, 1.48 mmol) and dimethyl (3-oxo-1,3-dihydroisobenzofuran-1-yl)phosphonate (357 mg, 1.48 mmol) in THF (1.7 mL) and stirred for 5 hours at 0° C. The reaction mixture was concentrated in vacuum then the white residue was slurried in water for 30 minutes, filtered, washed with water, hexane and ether, and dried to afford the intermediate compound (R,Z)—N-(1-(2-fluoro-5-((3-oxoisobenzofuran-1(3H)-ylidene)methyl)benzoyl)pyrrolidin-3-yl)-N-methylcyclopropanecarboxamide (398 mg, 62%).

Step 3: Preparation of (R)—N-(1-(2-fluoro-5-((4-oxo-3,4-dihydrophthalazin-1-yl)methyl)benzoyl)pyrrolidin-3-yl)-N-methylcyclopropanecarboxamide Hydrazine monohydrate (90 uL, 1.83 mmol) was added to a suspension of the intermediate compound (Step 2)(398 mg, 0.92 mmol) in ethanol (1.5 mL) and stirred at 40° C. for 2 hours. The reaction was cooled to room temperature and concentrated in vacuum. Water was added to the react ion mixture and the product was extracted into dichloromethane. The combined organic layers were dried over MgSO$_4$, filtered, evaporated in vacuum and purified using silica chromatography to afford the title compound (184 mg, 45%).

$^1$H-NMR (CDCl$_3$, 400 MHz): δ 5.35 (q, 0.7H), 4.78 (q, 0.3H), 3.65 (m, 1H), 3.51 (m, 1H), 3.40 (m, 1H), 3.01 (s, 3H), 2.28 (m, 2H), 1.61 (m, 1H), 0.98 (m, 1H), 0.96 (m, 2H), 0.74 (m, 2H).

Example 12

N-(1-(2-fluoro-5-((4-oxo-3,4-dihydrophthalazin-1-yl)ethyl)benzoyl)azetidin-3-yl)-N-ethylcyclopropanecarboxamide; (I-12)

Step 1: Preparation of N-(1-(2-fluoro-5-formylbenzoyl)azetidin-3-yl)-N-methylcyclopropanecarboxamide This compound was made using the procedure described for example 11 (Step 1). Thus, N-(azetidin-3-yl)-N-methylcyclopropanecarboxamide (200 mg, 1.30 mmol) was reacted with 2-fluoro-5-formyl benzoic acid (218 mg, 1.30 mmol), O-(benzotriazole-1-yl)-N,N,N',N'-tetramethyluronium hexafluorophosphate (HBTU, 640 mg, 1.68 mmol) and N,N-diisopropyl ethylamine (DIPEA, 0.45 mL, 2.59 mmol) to afford the intermediate compound N-(1-(2-fluoro-5-formylbenzoyl)azetidin-3-yl)-N-methylcyclopropanecarboxamide (256 mg, 65%).

Step 2: Preparation of (Z)—N-(1-(2-fluoro-5-((3-oxoisobenzofuran-1(3H)-ylidene)methyl)benzoyl)azetidin-3-yl)-N-methylcyclopropanecarboxamide This compound was made using the procedure described for example 11 (Step 2). Thus, this intermediate compound (Step 1)(256 mg, 0.84 mmol) was reacted with dimethyl(3-oxo-1,3-dihydroisobenzofuran-1-yl)phosphonate (204 mg, 0.84 mmol) and trietylamine (0.17 mL, 1.26 mmol) to afford the intermediate compound (Z)—N-(1-(2-fluoro-5-((3-oxoisobenzofuran-1(3H)-ylidene)methyl)benzoyl)azetidin-3-yl)-N-methylcyclopropanecarboxamide (202 mg, 57%).

Step 3: Preparation of N-(1-(2-fluoro-5-((4-oxo-3,4-dihydrophthalazin-1-yl)methyl)benzoyl)azetidin-3-yl)-N-methylcyclopropanecarboxamide This compound was made using the procedure described for example 11 (Step 3). Thus, this intermediate compound (Step 2)(202 mg, 0.48 mmol) was reacted with hydrazine monohydrate (46 uL, 0.96 mmol) to afford the title compound (106 mg, 51%).

$^1$H-NMR (MeOD, 400 MHz): δ 8.39 (dd, 1H), 7.94 (dd, 1H), 7.85-7.80 (m, 2H), 7.52-7.45 (m, 2H), 7.17-7.12 (m, 1H), 4.63-4.53 (m, 1H), 4.44-4.37 (m, 3H), 4.30-4.21 (m, 1H), 4.01-3.89 (m, 2H), 3.26 (s, 3H), 1.59-1.52 (m, 1H), 0.92-0.78 (m, 4H).

Example 13

(S)—N-(1-(2-fluoro-5-((4-oxo-3,4-dihydrophthalazin-1-yl)ethyl)benzoyl)pyrrolidin-3-yl)-N-methylcyclopropanecarboxamide; (I-13)

Step 1: Preparation of (S)—N-(1-(2-fluoro-5-formylbenzoyl)pyrrolidin-3-yl)-N-methylcyclopropanecarboxamide This compound was made using the procedure described for example 11 (Step 1). Thus, (S)—N-methyl-N-(pyrrolidin-3-yl)cyclopropanecarboxamide (350 mg, 2.08 mmol) was reacted with 2-fluoro-5-formyl benzoic acid (349 mg, 2.08 mmol), O-(benzotriazole-1-yl)-N,N,N',N'-tetramethyluronium hexafluorophosphate (HBTU, 1.02 mg, 2.70 mmol) and N,N-diisopropyl ethylamine (DIPEA, 0.72 mL, 4.16 mmol) to afford the intermediate compound (S)—N-(1-(2-fluoro-5-formylbenzoyl)pyrrolidin-3-yl)-N-methylcyclopropanecarboxamide (470 mg, 71%).

Step 2: Preparation of (S,Z)—N-(1-(2-fluoro-5-((3-oxoisobenzofuran-1(3H)-ylidene)methyl)benzoyl)pyrrolidin-3-yl)-N-methylcyclopropanecarboxamide This compound was made using the procedure described for example 11 (Step 2). Thus, this intermediate compound (Step 1)(470 mg, 1.48 mmol) was reacted with dimethyl(3-oxo-1,3-dihydroisobenzofuran-1-yl)phosphonate (357 mg, 1.48 mmol) and triethylamine (0.31 mL, 2.12 mmol) to afford the intermediate compound (S,Z)—N-(1-(2-fluoro-5-((3-oxoisobenzofuran-1(3H)-ylidene)methyl)benzoyl)pyrrolidin-3-yl)-N-methylcyclopropanecarboxamide (397 mg, 62%).

Step 3: Preparation of (S)—N-(1-(2-fluoro-5-((4-oxo-3,4-dihydrophthalazin-1-yl)methyl)benzoyl)pyrrolidin-3-yl)-N-methylcyclopropanecarboxamide This compound was made using the procedure described for example 11 (Step 3). Thus, this intermediate compound (Step 2)(397 mg, 0.92 mmol) was reacted with hydrazine monohydrate (90 uL, 1.83 mmol) to afford the title compound (185 mg, 45%).

$^1$H-NMR (CDCl$_3$, 400 MHz): δ 10.13 (s, 0.5H), 9.97 (s, 0.5H), 8.46 (s, 1H), 7.81-7.70 (m, 3H), 7.37 (m, 1H), 7.30 (m, 1H), 7.03 (q, 1H), 5.34 (m, 0.5H), 5.13 (m, 0.5H), 4.27 (d, 2H), 3.88 (m, 0.5H), 3.78 (m, 0.5H), 3.66-3.34 (m, 3H), 3.20-3.14 (m, 3.5H), 2.98-2.82 (m, 0.5H), 2.20-2.06 (m, 1H), 1.78-1.65 (m, 1H), 1.06-0.92 (m, 2H), 0.81 (m, 2H).

Example 14

3-(1-(2-fluoro-5-((4-oxo-3,4-dihydrophthalazin-1-yl)ethyl)benzoyl)azetidin-3-yl)-5,5-dimethylimidazolidine-2,4-dione; (I-14)

Step 1: Preparation of 3-(3-(4,4-dimethyl-2,5-dioxoimidazolidin-1-yl)azetidine-1-carbonyl)-4-fluorobenzaldehyde This compound was made using the procedure described for example 11 (Step 1). Thus, 3-(azetidin-3-yl)-5,5-dimethylimidazolidine-2,4-dione (150 mg, 0.82 mmol) was reacted with 2-fluoro-5-formyl benzoic acid (137 mg, 0.82 mmol), O-(benzotriazole-1-yl)-N,N,N',N'-tetramethyluronium hexafluorophosphate (HBTU, 403 mg, 1.06 mmol) and N,N-diisopropyl ethylamine (DIPEA, 0.29 mL, 1.63 mmol) to afford the intermediate compound 3-(3-(4,4-dimethyl-2,5-dioxoimidazolidin-1-yl)azetidine-1-carbonyl)-4-fluorobenzaldehyde (152 mg, 56%).

Step 2: Preparation of (Z)-3-(1-(2-fluoro-5-((3-oxoisobenzofuran-1(3H)-ylidene)methyl)benzoyl)azetidin-3-yl)-5,5-dimethylimidazolidine-2,4-dione This compound was made using the procedure described for example 11 (Step 2). Thus, this intermediate compound (Step 1)(152 mg, 0.45 mmol) was reacted with dimethyl(3-oxo-1,3-dihydroisobenzofuran-1-yl)phosphonate (111 mg, 0.45 mmol) and triethylamine (96 uL, 0.68 mmol) to afford the intermediate compound (Z)-3-(1-(2-fluoro-5-((3-oxoisobenzofuran-1(3H)-ylidene)methyl)benzoyl)azetidin-3-yl)-5,5-dimethylimidazolidine-2,4-dione (89 mg, 43%).

Step 3: Preparation of 3-(1-(2-fluoro-5-((4-oxo-3,4-dihydrophthalazin-1-yl)methyl)benzoyl)azetidin-3-yl)-5,5-dimethylimidazolidine-2,4-dione This compound was made using the procedure described for example 11 (Step 3). Thus, this intermediate compound (Step 2)(89 mg, 0.19 mmol) was reacted with hydrazine monohydrate (20 uL, 0.39 mmol) to afford the title compound (47 mg, 51%).

$^1$H-NMR (MeOD, 400 MHz): δ 8.36-8.35 (m, 1H), 7.92 (t, 1H), 7.98 (d, 1H), 7.90-7.82 (m, 2H), 7.48-7.43 (m, 2H), 7.22 (t, 1H), 4.34 (s, 2H), 4.07-4.03 (m, 1H), 3.94 (t, 1H), 3.85-3.76 (m, 2H), 3.27-3.23 (m, 1H), 1.32 (s, 6H).

Example 15

(R)-3-(1-(2-fluoro-5-((4-oxo-3,4-dihydrophthalazin-1-yl)ethyl)benzoyl)pyrrolidin-3-yl)imidazolidine-2,4-dione; (I-15)

Step 1: Preparation of (R)-3-(3-(2,5-dioxoimidazolidin-1-yl)pyrrolidine-1-carbonyl)-4-fluorobenzaldehyde This compound was made using the procedure described for example 11 (Step 1). Thus, (R)-3-(pyrrolidin-3-yl)imidazolidine-2,4-dione (150 mg, 0.88 mmol) was reacted with 2-fluoro-5-formyl benzoic acid (149 mg, 0.88 mmol), O-(benzotriazole-1-yl)-N,N,N',N'-tetramethyluronium hexafluorophosphate (HBTU, 437 mg, 1.15 mmol) and N,N-diisopropyl ethylamine (DIPEA, 0.31 mL, 1.77 mmol) to afford the intermediate compound (R)-3-(3-(2,5-dioxoimidazolidin-1-yl)pyrrolidine-1-carbonyl)-4-fluorobenzaldehyde (158 mg, 56%).

Step 2: Preparation of (R,Z)-3-(1-(2-fluoro-5-((3-oxoisobenzofuran-1(3H)-ylidene)methyl)benzoyl)pyrrolidin-3-yl)imidazolidine-2,4-dione This compound was made using the procedure described for example 11 (Step 2). Thus, this intermediate compound (Step 1)(158 mg, 0.50 mmol) was reacted with dimethyl(3-oxo-1,3-dihydroisobenzofuran-1-yl)phosphonate (120 mg, 0.50 mmol) and triethylamine (58 uL, 0.42 mmol) to afford the intermediate compound (R,Z)-3-(1-(2-fluoro-5-((3-oxoisobenzofuran-1(3H)-ylidene)methyl)benzoyl)pyrrolidin-3-yl)imidazolidine-2,4-dione (93 mg, 43%).

Step 3: Preparation of (R)-3-(1-(2-fluoro-5-((4-oxo-3,4-dihydrophthalazin-1-yl)methyl)benzoyl)pyrrolidin-3-yl)imidazolidine-2,4-dione This compound was made using the procedure described for example 11 (Step 3). Thus, this intermediate compound (Step 2)(93 mg, 0.21 mmol) was reacted with hydrazine monohydrate (21 uL, 0.43 mmol) to afford the title compound (54 mg, 56%).

$^1$H-NMR (MeOD, 400 MHz): δ 8.35-8.32 (m, 1H), 7.91 (t, 1H), 7.86-7.77 (m, 2H), 7.47-7.38 (m, 2H), 7.16-7.10 (m, 1H), 4.80-4.58 (m, 1H), 4.35 (d, 2H), 3.98-3.94 (m, 2H), 3.68-3.60 (m, 1H), 3.51-3.45 (m, 2H), 2.50-2.32 (m, 1H), 2.24-2.12 (m, 2H).

Example 16

(R)-1-ethyl-3-(1-(2-fluoro-5-((4-oxo-3,4-dihydrophthalazin-1-yl)methyl)benzoyl)pyrrolidin-3-yl)imidazolidine-2,4-dione; (I-16)

Step 1: Preparation of (R)-3-(3-(3-ethyl-2,5-dioxoimidazolidin-1-yl)pyrrolidine-1-carbonyl)-4-fluorobenzaldehyde This compound was made using the procedure described for example 11 (Step 1). Thus, (R)-1-ethyl-3-(pyrrolidin-3-yl)imidazolidine-2,4-dione (200 mg, 1.01 mmol) was reacted with 2-fluoro-5-formyl benzoic acid (170 mg, 1.01 mmol), O-(benzotriazole-1-yl)-N,N,N',N'-tetramethyluronium hexafluorophosphate (HBTU, 500 mg, 1.31 mmol) and N,N-diisopropyl ethylamine (DIPEA, 0.35 mL, 2.02 mmol) to afford the intermediate compound (R)-3-(3-(3-ethyl-2,5-dioxoimidazolidin-1-yl)pyrrolidine-1-carbonyl)-4-fluoro benzaldehyde (197 mg, 56%).

Step 2: Preparation of (R,Z)-1-ethyl-3-(1-(2-fluoro-5-((3-oxoisobenzofuran-1(3H)-ylidene)methyl)benzoyl)pyrrolidin-3-yl)imidazolidine-2,4-dione This compound was made using the procedure described for example 11 (Step 2). Thus, this intermediate compound (Step 1)(197 mg, 0.56 mmol) was reacted with dimethyl(3-oxo-1,3-dihydroisobenzofuran-1-yl)phosphonate (137 mg, 0.56 mmol) and triethylamine (0.12 mL, 0.85 mmol) to afford the intermediate compound (R,Z)-1-ethyl-3-(1-(2-fluoro-5-((3-oxoisobenzofuran-1(3H)-ylidene)methyl)benzoyl)pyrrolidin-3-yl)imidazolidine-2,4-dione (134 mg, 51%).

Step 3: Preparation of (R)-1-ethyl-3-(1-(2-fluoro-5-((4-oxo-3,4-dihydrophthalazin-1-yl)methyl)benzoyl)pyrrolidin-3-yl)imidazolidine-2,4-dione This compound was made using the procedure described for example 11 (Step 3). Thus, this intermediate compound (Step 2)(134 mg, 0.29 mmol) was reacted with hydrazine monohydrate (28 uL, 0.58 mmol) to afford the title compound (66 mg, 48%).

$^1$H-NMR (MeOD, 400 MHz): δ 8.37-8.34 (m, 1H), 7.92 (t, 1H), 7.87-7.80 (m, 2H), 7.49-7.43 (m, 1H), 7.41-7.39 (m, 1H), 7.17-7.11 (m, 1H), 4.78-4.59 (m, 1H), 4.37 (d, 2H), 3.94 (s, 2H), 3.87 (d, 2H), 3.84-3.79 (m, 1H), 3.67-3.60 (m, 1H), 3.47-3.35 (m, 2H), 2.59-2.44 (m, 1H), 2.19 (d, 2H), 1.20-1.13 (m, 3H).

Example 17

4-(4-fluoro-3-(3-(4-fluoropiperidine-1-carbonyl)azetidine-1-carbonyl)benzyl)phthalazin-1(2H)-one; (I-17)

Step 1: Preparation of 4-fluoro-3-(3-(4-fluoropiperidine-1-carbonyl)azetidine-1-carbonyl)benzaldehyde This compound was made using the procedure described for example 11 (Step 1). Thus, azetidin-3-yl(4-fluoropiperidin-1-yl)methanone (200 mg, 1.07 mmol) was reacted with 2-fluoro-5-formyl benzoic acid (180 mg, 1.07 mmol), O-(benzotriazole-1-yl)-N,N,N',N'-tetramethyluronium hexafluorophosphate (HBTU, 529 mg, 1.40 mmol) and N,N-diisopropyl ethylamine (DIPEA, 0.37 mL, 2.14 mmol) to afford the intermediate compound 4-fluoro-3-(3-(4-fluoropiperidine-1-carbonyl)azetidine-1-carbonyl)benzaldehyde (216 mg, 60%).

Step 2: Preparation of (Z)-3-(4-fluoro-3-(3-(4-fluoropiperidine-1-carbonyl)azetidine-1-carbonyl)benz ylidene)isobenzofuran-1(3H)-one This compound was made using the procedure described for example 11 (Step 2). Thus, this intermediate compound (Step 1)(261 mg, 0.64 mmol) was reacted with dimethyl(3-oxo-1,3-dihydroisobenzofuran-1-yl)phosphonate (156 mg, 0.64 mmol) and trietyhlamine (0.13 mL, 0.96 mmol) to afford the intermediate compound (Z)-3-(4-fluoro-3-(3-(4-fluoropiperidine-1-carbonyl)azetidine-1-carbonyl)benz ylidene)isobenzofuran-1(3H)-one (140 mg, 48%).

Step 3: Preparation of 4-(4-fluoro-3-(3-(4-fluoropiperidine-1-carbonyl)azetidine-1-carbonyl)benzyl)phthalazin-1(2H)-one This compound was made using the procedure described for example 11 (Step 3). Thus, this intermediate compound (Step 2)(140 mg, 0.31 mmol) was reacted with hydrazine monohydrate (30 uL, 0.62 mmol) to afford the title compound (76 mg, 53%).

$^1$H-NMR (MeOD, 400 MHz): δ 8.36 (d, 1H), 7.95 (d, 1H), 7.79-7.90 (m, 2H), 7.45-7.60 (m, 2H), 7.15 (t, 1H), 4.37 (s, 2H), 4.32 (d, 1H), 4.15-4.27 (m, 3H), 3.70-3.88 (m, 2H), 3.41-3.62 (m, 2H), 3.27-3.36 (m, 2H), 1.76-1.94 (m, 4H).

Example 18

4-(3-(3-(3,3-difluoroazetidine-1-carbonyl)azetidine-1-carbonyl)-4-fluorobenzyl)phthalazin-1(2H)-one; (I-18)

Step 1: Preparation of 3-(3-(3,3-difluoroazetidine-1-carbonyl)azetidine-1-carbonyl)-4-fluorobenzaldehyde This compound was made using the procedure described for example 11 (Step 1). Thus, azetidin-3-yl(3,3-difluoroazetidin-1-yl)methanone (200 mg, 1.14 mmol) was reacted with 2-fluoro-5-formyl benzoic acid (190 mg, 1.14 mmol), O-(benzotriazole-1-yl)-N,N,N',N'-tetramethyluronium hexafluorophosphate (HBTU, 560 mg, 1.47 mmol) and N,N-diisopropyl ethylamine (DIPEA, 0.41 mL, 2.27 mmol) to afford the intermediate compound 3-(3-(3,3-difluoroazetidine-1-carbonyl)azetidine-1-carbonyl)-4-fluorobenzaldehyde (222 mg, 60%).

Step 2: Preparation of (Z)-3-(3-(3-(3,3-difluoroazetidine-1-carbonyl)azetidine-1-carbonyl)-4-fluorobenzylidene)isobenzofuran-1(3H)-one This compound was made using the procedure described for example 11 (Step 2). Thus, this intermediate compound (Step 1)(222 mg, 0.68 mmol) was reacted with dimethyl(3-oxo-1,3-dihydroisobenzofuran-1-yl)phosphonate (164 mg, 0.68 mmol) and trietylamine (0.14 mL, 1.02 mmol) to afford the intermediate (Z)-3-(3-(3-(3,3-difluoroazetidine-1-carbonyl)azetidine-1-carbonyl)-4-fluorobenzylidene)isobenzofuran-1(3H)-one (145 mg, 48%).

Step 3: Preparation of 4-(3-(3-(3,3-difluoroazetidine-1-carbonyl)azetidine-1-carbonyl)-4-fluorobenzyl)phthalazin-1(2H)-one This compound was made using the procedure described for example 11 (Step 3). Thus, this intermediate compound (Step 2)(145 mg, 0.33 mmol) was reacted with hydrazine monohydrate (31 uL, 0.65 mmol) to afford the title compound (79 mg, 53%).

$^1$H-NMR (MeOD, 400 MHz): δ 8.36 (d, 1H), 7.94 (d, 1H), 7.79-7.89 (m, 2H), 7.46-7.58 (m, 2H), 7.14 (t, 1H), 4.46-4.64 (m, 2H), 4.25-4.40 (m, 5H), 4.05-4.23 (m, 3H), 3.51-3.59 (m, 1H).

Example 19

4-(3-(3-(3,3-difluoropyrrolidine-1-carbonyl)azetidine-1-carbonyl)-4-fluorobenzyl)phthalazin-1(2H)-one; (I-19)

Step 1: Preparation of 3-(3-(3,3-difluoropyrrolidine-1-carbonyl)azetidine-1-carbonyl)-4-fluorobenzaldehyde This compound was made using the procedure described for example 11 (Step 1). Thus, azetidin-3-yl(3,3-difluoropyrrolidin-1-yl)methanone (200 mg, 1.05 mmol) was reacted with 2-fluoro-5-formyl benzoic acid (176 mg, 1.05 mmol), O-(benzotriazole-1-yl)-N,N,N',N'-tetramethyluronium hexafluorophosphate (HBTU, 518 mg, 1.05 mmol) and N,N-diisopropyl ethylamine (DIPEA, 0.37 mL, 1.37 mmol) to afford the intermediate compound 3-(3-(3,3-difluoropyrrolidine-1-carbonyl)azetidine-1-carbonyl)-4-fluorobenzaldehyde (214 mg, 60%).

Step 2: Preparation of (Z)-3-(3-(3-(3,3-difluoropyrrolidine-1-carbonyl)azetidine-1-carbonyl)-4-fluorobenzylidene)isobenzofuran-1(3H)-one This compound was made using the procedure described for example 11 (Step 2). Thus, this intermediate compound (Step 1)(214 mg, 0.63 mmol) was reacted with dimethyl(3-oxo-1,3-dihydroisobenzofuran-1-yl)phosphonate (152 mg, 0.63 mmol) and trietylamine (0.13 mL, 0.94 mmol) to afford the intermediate compound (Z)-3-(3-(3-(3,3-difluoropyrrolidine-1-carbonyl)azetidine-1-carbonyl)-4-fluorobenzylidene)isobenzofuran-1(3H)-one (138 mg, 48%).

Step 3: Preparation of 4-(3-(3-(3,3-difluoropyrrolidine-1-carbonyl-carbonyl)-4-fluorobenzyl)phthalazin-1(2H)-one This compound was made using the procedure described for example 11 (Step 3). Thus, this intermediate compound (Step 2)(138 mg, 0.31 mmol) was reacted with hydrazine monohydrate (30 uL, 0.62 mmol) to afford the title compound (75 mg, 53%).

$^1$H-NMR (MeOD, 400 MHz): δ 8.36 (d, 1H), 7.95 (d, 1 Hz), 7.80-7.90 (m, 2H), 7.45-7.54 (m, 2H), 7.15 (t, 1H), 4.38 (s, 2H), 4.29-4.36 (m, 2H), 4.16-4.28 (m, 3H), 3.58-3.85 (m, 4H), 2.36-2.51 (m, 2H).

Example 20

4-(3-(3-(3,3-difluoropyrrolidine-1-carbonyl)pyrrolidine-1-carbonyl)-4-fluorobenzyl)phthalazin-1(2H)-one; (I-20)

Step 1: Preparation of 3-(3-(3,3-difluoropyrrolidine-1-carbonyl)pyrrolidine-1-carbonyl)-4-fluorobenzaldehyde This compound was made using the procedure described for example 11 (Step 1). Thus, (3,3-difluoropyrrolidin-1-yl)(pyrrolidin-3-yl)methanone (210 mg, 1.03 mmol) was reacted with 2-fluoro-5-formyl benzoic acid (172 mg, 1.03 mmol), O-(benzotriazole-1-yl)-N,N,N',N'-tetramethyluronium hexafluorophosphate (HBTU, 507 mg, 1.33 mmol) and N,N-diisopropyl ethylamine (DIPEA, 0.36 mL, 2.05 mmol) to afford the intermediate compound 3-(3-(3,3-difluoropyrrolidine-1-carbonyl)pyrrolidine-1-carbonyl)-4-fluorobenzaldehyde (218 mg, 60%).

Step 2: Preparation of (Z)-3-(3-(3-(3,3-difluoropyrrolidine-1-carbonyl)pyrrolidine-1-carbonyl)-4-fluorobenzylidene)isobenzofuran-1(3H)-one This compound was made using the procedure described for example 11 (Step 2). Thus, this intermediate compound (Step 1)(218 mg, 0.62 mmol) was reacted with dimethyl(3-oxo-1,3-dihydroisobenzofuran-1-yl)phosphonate (149 mg, 0.62 mmol) and trietylamine (0.13 mL, 0.93 mmol) to afford the intermediate compound (Z)-3-(3-(3-(3,3-difluoropyrrolidine-1-carbonyl)pyrrolidine-1-carbonyl)-4-fluorobenzylidene)isobenzofuran-1(3H)-one (139 mg, 48%).

Step 3: Preparation of 4-(3-(3-(3,3-difluoropyrrolidine-1-carbonyl)pyrrolidine-1-carbonyl)-4-fluorobenzyl)phthalazin-1(2H)-one This compound was made using the procedure described for example 11 (Step 3). Thus, this intermediate compound (Step 2)(139 mg, 0.30 mmol) was reacted with hydrazine monohydrate (29 uL, 0.59 mmol) to afford the title compound (76 mg, 53%).

$^1$H-NMR (DMSO, 400 MHz): δ 12.60 (s, 1H), 8.26 (d, 1H), 7.98 (d, 1H), 7.90 (t, 1H), 7.86-7.80 (m, 1H), 7.46-7.37 (m, 2H), 7.22 (t, 1H), 4.33 (s, 2H), 4.08-3.98 (m, 1H), 3.79-3.67 (m, 2H), 3.64-3.42 (m, 3H), 3.32-3.16 (m, 2H), 2.49-2.32 (m, 2H), 2.23-2.04 (m, 1H), 1.97-1.87 (m, 1H), 1.18 (t, 1H).

Example 21

(R)—N-(cyclopropylmethyl)-1-(2-fluoro-5-((4-oxo-3,4-dihydrophthalazin-1-yl)ethyl)benzoyl)pyrrolidine-3-carboxamide; (I-21)

Step 1: Preparation of (R)—N-(cyclopropylmethyl)-1-(2-fluoro-5-formylbenzoyl)pyrrolidine-3-carboxamide This compound was made using the procedure described for example 11 (Step 1). Thus, (R)—N-(cyclopropylmethyl)

pyrrolidine-3-carboxamide (300 mg, 1.78 mmol) was reacted with 2-fluoro-5-formyl benzoic acid (299 mg, 1.78 mmol), O-(benzotriazole-1-yl)-N,N,N',N'-tetramethyluronium hexafluorophosphate (HBTU, 879 mg, 2.32 mmol) and N,N-diisopropyl ethylamine (DIPEA, 0.63 mL, 3.57 mmol) to afford the intermediate compound (R)—N-(cyclopropylmethyl)-1-(2-fluoro-5-formylbenzoyl)pyrrolidine-3-carboxamide (266 mg, 47%).

Step 2: Preparation of (R,Z)—N-(cyclopropylmethyl)-1-(2-fluoro-5-((3-oxoisobenzofuran-1(3H)-ylidene)methyl)benzoyl)pyrrolidine-3-carboxamide This compound was made using the procedure described for example 11 (Step 2). Thus, this intermediate compound (Step 1)(266 mg, 0.84 mmol) was reacted with dimethyl(3-oxo-1,3-dihydroisobenzofuran-1-yl)phosphonate (203 mg, 0.84 mmol) and trietylamine (0.18 mL, 1.26 mmol) to afford the intermediate compound (R,Z)—N-(cyclopropylmethyl)-1-(2-fluoro-5-((3-oxoisobenzofuran-1(3H)-ylidene)methyl) benzoyl)pyrrolidine-3-carboxamide (186 mg, 51%).

Step 3: Preparation of (R)—N-(cyclopropylmethyl)-1-(2-fluoro-5-((4-oxo-3,4-dihydrophthalazin-1-yl)methyl)benzoyl)pyrrolidine-3-carboxamide This compound was made using the procedure described for example 11 (Step 3). Thus, this intermediate compound (Step 2)(186 mg, 0.43 mmol) was reacted with hydrazine monohydrate (42 uL, 0.85 mmol) to afford the title compound (84 mg, 44%).
$^1$H-NMR (MeOD, 400 MHz): δ 8.36-8.34 (m, 1H), 7.93 (t, 1H), 7.88-7.78 (m, 2H), 7.47-7.39 (m, 2H), 7.14 (t, 1H), 4.37 (s, 2H), 3.82-3.53 (m, 2H), 3.49-3.33 (m, 2H), 3.12-2.96 (m, 3H), 2.22-1.96 (m, 2H), 0.99-0.88 (m, 1H), 0.52-0.44 (m, 2H), 2.24-2.02 (m, 2H).

Example 22

4-(4-fluoro-3-(3-(pyrrolidine-1-carbonyl)azetidine-1-carbonyl)benzyl)phthalazin-1(2H)-one; (I-22)

Step 1: Preparation of 4-fluoro-3-(3-(pyrrolidine-1-carbonyl)azetidine-1-carbonyl)benzaldehyde This compound was made using the procedure described for example 11 (Step 1). Thus, azetidin-3-yl(pyrrolidin-1-yl)methanone (200 mg, 1.30 mmol) was 2-fluoro-5-formyl benzoic acid (218 mg, 1.30 mmol), O-(benzotriazole-1-yl)-N,N,N',N'-tetramethyluronium hexafluorophosphate (HBTU, 639 mg, 1.69 mmol) and N,N-diisopropyl ethylamine (DIPEA, 0.45 mL, 2.59 mmol) to afford the intermediate 4-fluoro-3-(3-(pyrrolidine-1-carbonyl)azetidine-1-carbonyl)benzaldehyde (244 mg, 62%).

Step 2: Preparation of (Z)-3-(4-fluoro-3-(3-(pyrrolidine-1-carbonyl)azetidine-1-carbonyl)benzylidene)isobenzofuran-1(3H)-one This compound was made using the procedure described for example 11 (Step 2). Thus, this intermediate compound (Step 1)(244 mg, 0.80 mmol) was reacted with dimethyl(3-oxo-1,3-dihydroisobenzofuran-1-yl)phosphonate (194 mg, 0.80 mmol) and trietylamine (0.17 mL, 1.21 mmol) to afford the intermediate compound (Z)-3-(4-fluoro-3-(3-(pyrrolidine-1-carbonyl)azetidine-1-carbonyl)benzylidene)isobenzofuran-1(3H)-one (172 mg, 51%).

Step 3: Preparation of 4-(4-fluoro-3-(3-(pyrrolidine-1-carbonyl)benzyl)phthalazin-1(2H)-one This compound was made using the procedure described for example 11 (Step 3). Thus, this intermediate compound (Step 2)(172 mg, 0.42 mmol) was reacted with hydrazine monohydrate (40 uL, 0.82 mmol) to afford the title compound (97 mg, 55%).
$^1$H-NMR (DMSO, 400 MHz): δ 12.61 (s, 1H), 8.37 (m, 1H), 7.24 (d, 1H), 7.80-7.90 (m, 2H), 7.49 (m, 2H), 7.14 (t, 1H), 4.37 (s, 2H), 4.32 (t, 1H), 4.22 (m, 3H), 3.71 (m, 1H), 3.44 (m, 2H), 3.30-3.44 (m, 2H), 1.86-1.97 (m, 4H).

Example 23

(R)-4-(3-(3-(3-(dimethylamino)pyrrolidine-1-carbonyl)azetidine-1-carbonyl)-4-fluorobenzyl)phthalazin-1(2H)-one; (I-23)

Step 1: Preparation of (R)-3-(3-(3-(dimethylamino)pyrrolidine-1-carbonyl)azetidine-1-carbonyl)-4-fluorobenzaldehyde This compound was made using the procedure described for example 11 (Step 1). Thus, (R)-azetidin-3-yl(3-(dimethylamino)pyrrolidin-1-yl)methanone (200 mg, 1.05 mmol) was reacted with 2-fluoro-5-formyl benzoic acid (176 mg, 2.05 mmol), O-(benzotriazole-1-yl)-N,N,N',N'-tetramethyluronium hexafluorophosphate (HBTU, 515 mg, 1.36 mmol) and N,N-diisopropyl ethylamine (DIPEA, 0.52 mL, 2.98 mmol) to afford the intermediate compound (R)-3-(3-(3-(dimethylamino)pyrrolidine-1-carbonyl)azetidine-1-carbonyl)-4-fluorobenzaldehyde (150 mg, 42%).

Step 2: Preparation of (R,Z)-3-(3-(3-(3-(dimethylamino)pyrrolidine-1-carbonyl)azetidine-1-carbonyl)-4-fluorobenzylidene)isobenzofuran-1(3H)-one This compound was made using the procedure described for example 11 (Step 2). Thus, this intermediate compound (Step 1)(150 mg, 0.44 mmol) was reacted with dimethyl(3-oxo-1,3-dihydroisobenzofuran-1-yl)phosphonate (106 mg, 0.44 mmol) and trietylamine (92 uL, 0.65 mmol) to afford the intermediate compound (R,Z)-3-(3-(3-(dimethylamino)pyrrolidine-1-carbonyl)azetidine-1-carbonyl)-4-fluorobenzylidene)isobenzofuran-1(3H)-one (102 mg, 51%).

Step 3: Preparation of (R)-4-(3-(3-(3-(dimethylamino)pyrrolidine-1-carbonyl)azetidine-1-carbonyl)-4-fluorobenzyl)phthalazin-1(2H)-one This compound was made using the procedure described for example 11 (Step 3). Thus, this intermediate compound (Step 2)(102 mg, 0.22 mmol) was reacted with hydrazine monohydrate (21 uL, 0.45 mmol) to afford the title compound (53 mg, 50%).
$^1$H-NMR (MeOD, 400 MHz): δ 8.36 (m, 1H), 7.94-7.92 (m, 1H), 7.89-7.80 (m, 2H), 7.56-7.39 (m, 2H), 7.16 (t, 1H), 4.36 (s, 2H), 4.20-4.03 (m, 2H), 3.96-3.80 (m, 2H), 3.67 (m, 1H), 3.44 (t, 2H), 3.39-3.32 (m, 2H), 2.98-2.90 (m, 1H), 2.10 (s, 6H), 1.82-1.80 (m, 2H).

Example 24

(S)-4-(3-(3-(3-(dimethylamino)pyrrolidine-1-carbonyl)azetidine-1-carbonyl)-4-fluorobenzyl)phthalazin-1(2H)-one; (I-24)

Step 1: Preparation of (S)-3-(3-(3-(dimethylamino)pyrrolidine-1-carbonyl)azetidine-1-carbonyl)-4-fluorobenzaldehyde This compound was made using the procedure described for example 11 (Step 1). Thus, (S)-azetidin-3-yl(3-(dimethylamino)pyrrolidin-1-yl)methanone (200 mg, 1.05 mmol) was reacted with 2-fluoro-5-formyl benzoic acid (176 mg, 2.05 mmol), O-(benzotriazole-1-yl)-N,N,N',N'-tetramethyluronium hexafluorophosphate (HBTU, 515 mg, 1.36 mmol) and N,N-diisopropyl ethylamine (DIPEA, 0.52 mL, 2.98 mmol) to afford the intermediate compound (S)-3-(3-(3-(dimethylamino)pyrrolidine-1-carbonyl)azetidine-1-carbonyl)-4-fluorobenzaldehyde (150 mg, 42%).

Step 2: Preparation of (S,Z)-3-(3-(3-(3-(dimethylamino)pyrrolidine-1-carbonyl)azetidine-1-carbonyl)-4-fluorobenzylidene)isobenzofuran-1(3H)-one This compound was made using the procedure described for example 11 (Step 2). Thus, this intermediate compound (Step 1)(150 mg, 0.44 mmol) was reacted with dimethyl(3-oxo-1,3-dihydroisobenzofuran-1-yl)phosphonate (106 mg, 0.44 mmol) and trietylamine (92 uL, 0.65 mmol) to afford the intermediate compound (S,Z)-3-(3-(3-(3-(dimethylamino)pyrrolidine-1-carbonyl)azetidine-1-carbonyl)-4-fluorobenzylidene)isobenzofuran-1(3H)-one (102 mg, 51%).

Step 3: Preparation of (S)-4-(3-(3-(3-(dimethylamino)pyrrolidine-1-carbonyl)azetidine-1-carbonyl)-4-fluorobenzyl)phthalazin-1(2H)-one This compound was made using the procedure described for example 11 (Step 3). Thus, this intermediate compound (Step 2)(102 mg, 0.22 mmol) was reacted with hydrazine monohydrate (21 uL, 0.45 mmol) to afford the title compound (53 mg, 50%).

$^1$H-NMR (MeOD, 400 MHz): δ 8.36 (m, 1H), 7.94-7.92 (m, 1H), 7.89-7.80 (m, 2H), 7.56-7.39 (m, 2H), 7.16 (t, 1H), 4.36 (s, 2H), 4.20-4.03 (m, 2H), 3.96-3.80 (m, 2H), 3.67 (m, 1H), 3.44 (t, 2H), 3.39-3.32 (m, 2H), 2.98-2.90 (m, 1H), 2.10 (s, 6H), 1.82-1.80 (m, 2H).

Example 25

4-(3-(3-(cyclobutyl amino)azetidine-1-carbonyl)-4-fluorobenzyl)phthalazin-1(2H)-one; (I-25)

Step 1: Preparation of 4-(3-(3-(cyclobutylamino)azetidine-1-carbonyl)-4-fluorobenzyl)phthalazin-1(2H)-one Cyclobutanone (42 uL, 0.57 mmol) was added to a solution of 4-(3-(3-aminoazetidine-1-carbonyl)-4-fluorobenzyl)phthalazin-1(2H)-one (example 3)(100 mg, 0.28 mmol) in 1,2-dichloroethane (2 mL) and stirred for 30 min then acetic acid (32 uL, 0.56 mmol) and triacetoxyborohydride (118 mg, 0.56 mmol) was added to the reaction mixture at 0° C. and stirred for 12 hours. The reaction mixture was concentrated in vacuum, added 2N NaOH(aq) and extracted into dichloromethane. The combined organic layers were dried over MgSO$_4$, filtered, evaporated in vacuum and purified using silica chromatography to afford the title compound (82 mg, 72%).

$^1$H-NMR (DMSO, 400 MHz): δ 12.61 (s, 1H), 8.26 (d, 1H), 7.97 (d, 1H), 7.89 (t, 1H), 7.83 (t, 1H), 7.50-7.21 (m, 2H), 7.21 (t, 1H), 4.33 (s, 2H), 4.10 (t, 1H), 3.97 (t, 1H), 3.67-3.51 (m, 3H), 3.08 (m, 1H), 2.76 (m, 1H), 1.99 (t, 2H), 1.69-1.46 (m, 4H).

Example 26

4-(3-(3-(cyclopropylamino)azetidine-1-carbonyl)-4-fluorobenzyl)phthalazin-1(2H)-one; (I-26)

Step 1: Preparation of 4-(3-(3-(cyclopropylamino)azetidine-1-carbonyl)-4-fluorobenzyl)phthalazin-1(2H)-one This compound was made using the procedure described for example 25 (Step 1). Thus, 4-(3-(3-aminoazetidine-1-carbonyl)-4-fluorobenzyl)phthalazin-1(2H)-one (example 3)(200 mg, 0.57 mmol) was reacted with (1-ethoxycyclopropoxy)trimethylsilane(51 uL, 0.57 mmol) and sodium triacetoxyborohydride (248 mg, 1.17 mmol) to afford the title compound (152 mg, 68%).

$^1$H-NMR (MeOD, 400 MHz): δ 8.36 (d, 1H), 7.93 (d, 1H), 7.79-7.89 (m, 2H), 7.48-7.54 (m, 1H), 7.42 (d, 1H), 7.15 (t, 1H), 4.00-4.05 (m, 2H), 3.75-3.80 (m, 2H), 3.34-3.39 (m, 1H), 3.12 (s, 2H), 1.32-1.36 (m, 1H), 0.64-0.72 (m, 2H), 0.41-0.46 (m, 2H).

Example 27

4-(3-(3-(cyclopentylamino)azetidine-1-carbonyl)-4-fluorobenzyl)phthalazin-1(2H)-one; (I-27)

Step 1: Preparation of 4-(3-(3-(cyclopentylamino)azetidine-1-carbonyl)-4-fluorobenzyl)phthalazin-1(2H)-one This compound was made using the procedure described for example 25 (Step 1). Thus, 4-(3-(3-aminoazetidine-1-carbonyl)-4-fluorobenzyl)phthalazin-1(2H)-one (example 3)(200 mg, 0.57 mmol) was reacted with cyclopentanone (51 uL, 0.57 mmol) and sodium triacetoxyborohydride (248 mg, 1.178 mmol) to afford the title compound (240 mg, 66%).

$^1$H-NMR (DMSO, 400 MHz): δ 12.60 (s, 1H), 8.26 (d, 1H), 7.97 (d, 1H), 7.89 (t, 1H), 7.83 (t, 1H), 7.44-7.50 (m, 1H), 7.40 (d, 1H), 7.21 (t, 1H), 4.33 (s, 2H), 4.13 (t, 1H), 4.00 (t, 1H), 3.54-3.70 (m, 3H), 2.82-2.91 (m, 1H), 1.52-1.67 (m, 4H), 1.43 (brs, 2H), 1.10-1.27 (m, 2H).

Example 28

4-(3-(3-(cyclohexylamino)azetidine-1-carbonyl)-4-fluorobenzyl)phthalazin-1(2H)-one; (I-28)

Step 1: Preparation of 4-(3-(3-(cyclohexylamino)azetidine-1-carbonyl)-4-fluorobenzyl)phthalazin-1(2H)-one This compound was made using the procedure described for example 25 (Step 1). Thus, 4-(3-(3-aminoazetidine-1-carbonyl)-4-fluorobenzyl)phthalazin-1(2H)-one (example 3)(200 mg, 0.57 mmol) was reacted with cyclohexanone (59 uL, 0.57 mmol) and sodium triacetoxyborohydride (247 mg, 1.17 mmol) to afford the title compound (203 mg, 82%).

$^1$H-NMR (DMSO, 400 MHz): δ 12.61 (s, 1H), 8.26 (d, 1H), 7.97 (d, 1H), 7.91-7.81 (m, 2H), 7.49-7.45 (m, 1H), 7.41-7.39 (m, 1H), 7.21 (t, 1H), 4.33 (s, 2H), 4.16-3.98 (m, 2H), 3.67-3.58 (m, 3H), 2.33-2.26 (m, 1H), 1.72-1.61 (m, 4H), 1.52 (d, 1H), 1.23-1.06 (m, 3H), 1.00-0.90 (m, 2H).

Example 29

(R)-4-(3-(3-(cyclopropylamino)pyrrolidine-1-carbonyl)-4-fluorobenzyl)phthalazin-1(2H)-one; (I-29)

Step 1: Preparation of (R)-4-(3-(3-(cyclopropylamino)pyrrolidine-1-carbonyl)-4-fluorobenzyl)phthalazin-1(2H)-one This compound was made using the procedure described for example 25 (Step 1). Thus, (R)-4-(3-(3-aminopyrrolidine-1-carbonyl)-4-fluorobenzyl)phthalazin-1(2H)-one (example 1)(200 mg, 0.54 mmol) was reacted with (1-ethoxycyclopropoxy)tri methylsilane(49 uL, 0.54 mmol) and sodium triacetoxyborohydride (247 mg, 1.17 mmol) to afford the title compound (142 mg, 65%).

$^1$H-NMR (DMSO, 400 MHz): δ 12.60 (s, 1H), 8.27-8.25 (m, 1H), 7.97 (d, 1H), 7.89-7.82 (m, 2H), 7.44-7.33 (m, 2H), 7.22 (t, 1H), 4.32 (s, 2H), 3.29-3.23 (m, 2H), 3.15-2.99 (m, 1H), 2.06-1.73 (m, 3H), 1.24 (s, 1H), 0.39-0.13 (m, 4H).

Example 30

(R)-4-(3-(3-(cyclobutylamino)pyrrolidine-1-carbonyl)-4-fluorobenzyl)phthalazin-1(2H)-one; (I-30)

Step 1: Preparation of (R)-4-(3-(3-(cyclobutylamino)pyrrolidine-1-carbonyl)-4-fluorobenzyl)phthalazin-1(2H)-one This compound was made using the procedure described for example 25 (Step 1). Thus, (R)-4-(3-(3-aminopyrrolidine-1-carbonyl)-4-fluorobenzyl)phthalazin-1(2H)-one (example 1)(200 mg, 0.54 mmol) was reacted with cyclobutanone (41 uL, 0.54 mmol) and sodium triacetoxyborohydride (247 mg, 1.17 mmol) to afford the title compound (163 mg, 72%).

$^1$H-NMR (DMSO, 400 MHz): δ 12.60 (s, 1H), 8.26 (d, 1H), 7.97 (d, 1H), 7.89 (t, 1H), 7.83 (t, 1H), 7.44-7.50 (m, 1H), 7.40 (d, 1H), 7.21 (t, 1H), 4.37 (s, 2H), 3.79-3.67 (m, 1H), 3.59-3.33 (m, 3H), 3.29-3.06 (m, 3H), 2.76 (m, 1H), 1.99 (t, 2H), 1.69-1.46 (m, 4H).

Example 31

(R)-4-(3-(3-(cyclopentylamino)pyrrolidine-1-carbonyl)-4-fluorobenzyl)phthalazin-1(2H)-one; (I-31)

Step 1: Preparation of (R)-4-(3-(3-(cyclopentylamino)pyrrolidine-1-carbonyl)-4-fluorobenzyl)phthalazin-1(2H)-one This compound was made using the procedure described for example 25 (Step 1). Thus, (R)-4-(3-(3-aminopyrrolidine-1-carbonyl)-4-fluorobenzyl)phthalazin-1(2H)-one (example 1)(200 mg, 0.54 mmol) was reacted with cyclopentanone (48 uL, 0.54 mmol) and sodium triacetoxyborohydride (247 mg, 1.17 mmol) to afford the title compound (190 mg, 81%).

$^1$H-NMR (DMSO, 400 MHz): δ 12.60 (s, 1H), 8.26 (d, 1H), 7.97 (d, 1H), 7.89 (t, 1H), 7.83 (t, 1H), 7.44-7.50 (m, 1H), 7.40 (d, 1H), 7.21 (t, 1H), 4.37 (s, 2H), 3.79-3.67 (m, 1H), 3.59-3.33 (m, 3H), 3.29-3.06 (m, 3H), 2.82-2.91 (m, 1H), 1.52-1.67 (m, 4H), 1.43 (brs, 2H), 1.10-1.27 (m, 2H).

Example 32

4-(4-fluoro-3-(3-(isopropylamino)azetidine-1-carbonyl)benzyl)phthalazin-1(2H)-one; (I-32)

Step 1: Preparation of 4-(4-fluoro-3-(3-(isopropylamino)azetidine-1-carbonyl)benzyl)phthalazin-1(2H)-one This compound was made using the procedure described for example 25 (Step 1). Thus, 4-(3-(3-aminoazetidine-1-carbonyl)-4-fluorobenzyl)phthalazin-1(2H)-one (example 3)(200 mg, 0.57 mmol) was reacted with acetone (42 uL, 0.57 mmol) and sodium triacetoxyborohydride (247 mg, 1.17 mmol) to afford the title compound (123 mg, 55%).

$^1$H-NMR (DMSO, 400 MHz): δ 12.61 (s, 1H), 8.27-8.25 (m, 1H), 7.97 (d, 1H), 7.91-7.81 (m, 2H), 7.48-7.44 (m, 1H), 7.41-7.39 (m, 1H), 7.21 (t, 1H), 4.33 (s, 2H), 4.15-4.10 (m, 2H), 3.66-3.59 (m, 3H), 3.17 (d, 1H), 2.68-2.61 (m, 1H), 0.92-0.83 (m, 6H).

Example 33

4-(3-(3-((cyclopropylmethyl)amino)azetidine-1-carbonyl)-4-fluorobenzyl)phthalazin-1(2H)-one; (I-33)

Step 1: Preparation of 4-(3-(3-((cyclopropylmethyl)amino)azetidine-1-carbonyl)-4-fluorobenzyl)phthalazin-1(2H)-one This compound was made using the procedure described for example 25 (Step 1). Thus, 4-(3-(3-aminoazetidine-1-carbonyl)-4-fluorobenzyl)phthalazin-1(2H)-one (example 3)(200 mg, 0.57 mmol) was reacted with cyclopropanecarbaldehyde (42 uL, 0.57 mmol) and sodium triacetoxyborohydride (247 mg, 1.17 mmol) to afford the title compound (153 mg, 66%).

$^1$H-NMR (DMSO, 400 MHz): δ 12.61 (s, 1H), 8.28-7.97 (m, 2H), 7.91-7.81 (m, 2H), 7.48-7.40 (m, 2H), 7.22 (m, 1H), 4.33 (s, 2H), 4.13-3.98 (m, 2H), 3.70-3.56 (m, 3H), 2.29 (m, 2H), 0.83-0.72 (m, 1H), 0.37-0.32 (m, 2H), 0.06 (m, 2H).

Example 34

4-(3-(3-(bis(cyclopropylethyl)amino)azetidine-1-carbonyl)-4-fluorobenzyl)phthalazin-1(2H)-one; (I-34)

Step 1: Preparation of 4-(3-(3-(bis(cyclopropylmethyl)amino)azetidine-1-carbonyl)-4-fluorobenzyl)phthalazin-1(2H)-one This compound was made using the procedure described for example 25 (Step 1). Thus, 4-(3-(3-aminoazetidine-1-carbonyl)-4-fluorobenzyl)phthalazin-1(2H)-one (example 3)(200 mg, 0.57 mmol) was reacted with cyclopropanecarbaldehyde (84 uL, 1.14 mmol) and sodium triacetoxyborohydride (247 mg, 1.17 mmol) to afford the title compound (116 mg, 43%).

¹H-NMR (DMSO, 400 MHz): δ 12.57 (s, 1H), 8.23 (m, 1H), 7.97-7.77 (m, 3H), 7.47-7.36 (m, 2H), 7.18 (m, 1H), 4.29 (s, 2H), 3.99 (m, 1H), 3.88-3.58 (m, 4H), 2.38-2.31 (m, 4H), 0.77 (m, 2H), 0.38 (s, 2H), 0.36 (s, 2H), 0.01 (s, 4H).

Example 35

4-(4-fluoro-3-(3-(isobutylamino)azetidine-1-carbonyl)benzyl)phthalazin-1(2H)-one; (I-35)

Step 1: Preparation of 4-(4-fluoro-3-(3-(isobutylamino)azetidine-1-carbonyl)benzyl)phthalazin-1(2H)-one This compound was made using the procedure described for example 25 (Step 1). Thus, 4-(3-(3-aminoazetidine-1-carbonyl)-4-fluorobenzyl)phthalazin-1(2H)-one (example 3)(200 mg, 0.57 mmol) was reacted with isobutyraldehyde (52 uL, 0.57 mmol) and sodium triacetoxyborohydride (247 mg, 1.17 mmol) to afford the title compound (194 mg, 83%).

¹H-NMR (MeOD, 400 MHz): δ 8.38-8.35 (m, 1H), 7.95-7.93 (m, 1H), 7.89-7.82 (m, 2H), 7.51-7.49 (m, 1H), 7.45-7.43 (m, 1H), 7.15 (t, 1H), 4.38 (s, 2H), 4.28-4.26 (m, 1H), 4.16-4.12 (m, 1H), 3.88-3.84 (m, 1H), 3.79-3.75 (m, 1H), 3.66-3.64 (m, 1H), 2.31-2.28 (m, 2H), 1.71-1.68 (m, 1H), 0.91 (dd, 6H).

Example 36

4-(4-fluoro-3-(3-((1-hydroxypropan-2-yl)amino)azetidine-1-carbonyl)benzyl)phthalazin-1(2H)-one; (I-36)

Step 1: Preparation of 4-(4-fluoro-3-(3-((1-hydroxypropan-2-yl)amino)azetidine-1-carbonyl)benzyl)phthalazin-1(2H)-one This compound was made using the procedure described for example 25 (Step 1). Thus, 4-(3-(3-aminoazetidine-1-carbonyl)-4-fluorobenzyl)phthalazin-1(2H)-one (example 3)(200 mg, 0.57 mmol) was reacted with 1-hydroxypropan-2-one (39 uL, 0.57 mmol) and sodium triacetoxyborohydride (247 mg, 1.17 mmol) to afford the title compound (82 mg, 35%).

¹H-NMR (MeOD, 400 MHz): δ 8.36-8.34 (m, 1H), 7.94-7.92 (m, 1H), 7.88-7.81 (m, 2H), 7.50-7.49 (m, 1H), 7.46-7.44 (m, 1H), 7.16-7.11 (m, 1H), 4.36 (s, 2H), 4.35-4.33 (m, 1H), 4.20-4.17 (m, 1H), 3.90-3.3.83 (m, 3H), 3.46-3.43 (m, 1H), 3.39-3.36 (m, 1H), 2.77-2.75 (m, 1H), 1.95 (s, 1H), 1.02 (q, 3H).

Example 37

4-(4-fluoro-3-(3-(neopentyl amino)azetidine-1-carbonyl)benzyl)phthalazin-1(2H)-one; (I-37)

Step 1: Preparation of 4-(4-fluoro-3-(3-(neopentylamino)azetidine-1-carbonyl)benzyl)phthalazin-1(2H)-one This compound was made using the procedure described for example 25 (Step 1). Thus, 4-(3-(3-aminoazetidine-1-carbonyl)-4-fluorobenzyl)phthalazin-1(2H)-one (example 3)(200 mg, 0.57 mmol) was reacted with pivalaldehyde (62 uL, 0.57 mmol) and sodium triacetoxyborohydride (247 mg, 1.17 mmol) to afford the title compound (185 mg, 77%).

¹H-NMR (MeOD, 400 MHz): δ 8.34 (m, 1H), 7.92-7.78 (m, 3H), 7.50-7.43 (m, 2H), 7.13 (t, 1H), 4.35 (s, 2H), 4.29-4.10 (m, 2H), 3.88-3.75 (m, 2H), 3.62 (m, 1H), 2.23 (m, 2H), 0.91 (s, 9H).

Example 38

4-(3-(3-((2,2-dimethylcyclopentyl)amino)azetidine-1-carbonyl)-4-fluorobenzyl)phthalazin-1(2H)-one; (I-38)

Step 1: Preparation of 4-(3-(3-((2,2-dimethylcyclopentyl)amino)azetidine-1-carbonyl)-4-fluorobenzyl)phthalazin-1(2H)-one This compound was made using the procedure described for example 25 (Step 1). Thus, 4-(3-(3-aminoazetidine-1-carbonyl)-4-fluorobenzyl)phthalazin-1(2H)-one (example 3)(200 mg, 0.57 mmol) was reacted with 2,2-dimethylcyclopentanone (72 uL, 0.57 mmol) and sodium triacetoxyborohydride (247 mg, 1.17 mmol) to afford the title compound (99 mg, 39%).

¹H-NMR (MeOD, 400 MHz): δ 8.35 (m, 1H), 7.93-7.79 (m, 3H), 7.51-7.42 (m, 2H), 7.14 (t, 1H), 4.36 (s, 2H), 4.30-4.10 (m, 2H), 3.90-3.68 (m, 3H), 2.43 (m, 1H), 1.95-1.82 (m, 1H), 1.68-1.28 (m, 5H), 1.01 (d, 3H), 0.84 (s, 3H).

Example 39 ethyl 2-((1-(2-fluoro-5-((4-oxo-3,4-dihydrophthalazin-1-yl)methyl)benzoyl)azetidin-3-yl)amino)cyclopent-1-enecarboxylate; (I-39)

Step 1: Preparation of ethyl 2-((1-(2-fluoro-5-((4-oxo-3,4-dihydrophthalazin-1-yl)methyl)benzoyl)azetidin-3-yl)amino)cyclopent-1-enecarboxylate This compound was made using the procedure described for example 25 (Step 1). Thus, 4-(3-(3-aminoazetidine-1-carbonyl)-4-fluorobenzyl)phthalazin-1(2H)-one (example 3)(200 mg, 0.57 mmol) was reacted with ethyl 2-oxocyclopentanecarboxylate (85 uL, 0.57 mmol) and sodium triacetoxyborohydride (247 mg, 1.17 mmol) to afford the title compound (64 mg, 23%).

¹H-NMR (CDCl₃, 400 MHz): δ 11.44 (s, 1H), 8.48 (m, 1H), 7.80-7.73 (m, 3H), 7.55 (m, 1H), 7.34-7.28 (m, 1H), 7.01 (t, 1H), 4.50 (t, 1H), 4.39-4.27 (m, 4H), 4.15 (m, 2H), 4.01 (m, 2H), 2.52-2.38 (m, 4H), 1.86-1.80 (m, 2H), 1.28 (t, 3H).

Example 40

4-(4-fluoro-3-(3-(pentan-3-yl amino)azetidine-1-carbonyl)benzyl)phthalazin-1(2H)-one; (I-40)

Step 1: Preparation of 4-(4-fluoro-3-(3-(pentan-3-ylamino)azetidine-1-carbonyl)benzyl)phthalazin-1(2H)-one This compound was made using the procedure described for example 25 (Step 1). Thus, 4-(3-(3-aminoazetidine-1-carbonyl)-4-fluorobenzyl)phthalazin-1(2H)-one (example 3)(200 mg, 0.57 mmol) was reacted with pentan-3-one (48 uL, 0.57 mmol) and sodium triacetoxyborohydride (247 mg, 1.17 mmol) to afford the title compound (46 mg, 19%).

¹H-NMR (CDCl₃, 400 MHz): δ 11.32 (br, 1H), 8.47 (m, 1H), 7.77-7.72 (m, 3H), 7.51 (m, 1H), 7.32-7.31 (m, 1H), 7.00 (t, 1H), 4.39 (m, 1H), 4.29 (s, 2H), 4.17 (m, 1H), 3.85-3.74 (m, 3H), 2.36 (m, 1H), 2.06 (br, 1H), 1.38 (m, 4H), 0.87 (dd, 6H).

Example 41

4-(4-fluoro-3-(3-((3-ethylbutan-2-yl)amino)azetidine-1-carbonyl)benzyl)phthalazin-1(2H)-one; (I-41)

Step 1: Preparation of 4-(4-fluoro-3-(3-((3-methylbutan-2-yl)amino)azetidine-1-carbonyl)benzyl)phthalazin-1(2H)-one This compound was made using the procedure described for example 25 (Step 1). Thus, 4-(3-(3-aminoazetidine-1-carbonyl)-4-fluorobenzyl)phthalazin-1(2H)-one (example 3)(200 mg, 0.57 mmol) was reacted with 3-methylbutan-2-one (61 uL, 0.57 mmol) and sodium triacetoxyborohydride (247 mg, 1.17 mmol) to afford the title compound (125 mg, 52%).

$^1$H-NMR (CDCl$_3$, 400 MHz): δ 11.22 (s, 1H), 8.50-8.45 (m, 1H), 7.79-7.71 (m, 3H), 7.52-7.50 (m, 1H), 7.33-7.29 (m, 1H), 7.01 (t, 1H), 4.38 (m, 1H), 4.29 (s, 2H), 4.21-4.13 (m, 1H), 3.86-3.72 (m, 3H), 2.50-2.40 (m, 1H), 1.66-1.55 (m, 1H), 0.94-0.84 (m, 9H).

Example 42

4-(3-(3-((1-cyclopropylethyl)amino)azetidine-1-carbonyl)-4-fluorobenzyl)phthalazin-1(2H)-one; (I-42)

Step 1: Preparation of 4-(3-(3-((1-cyclopropylethyl)amino)azetidine-1-carbonyl)-4-fluorobenzyl)phthalazin-1(2H)-one This compound was made using the procedure described for example 25 (Step 1). Thus, 4-(3-(3-aminoazetidine-1-carbonyl)-4-fluorobenzyl)phthalazin-1(2H)-one (example 3)(200 mg, 0.57 mmol) was reacted with 1-cyclopropylethanone (56 uL, 0.57 mmol) and sodium triacetoxyborohydride (247 mg, 1.17 mmol) to afford the title compound (239 mg, 43%).

$^1$H-NMR (CDCl$_3$, 400 MHz): δ 11.18 (s, 1H), 8.49-8.47 (m, 1H), 7.79-7.72 (m, 3H), 7.52-7.50 (m, 1H), 7.33-7.29 (m, 1H), 7.01 (t, 1H), 4.40 (m, 1H), 4.29 (s, 2H), 3.79 (m, 1H), 1.93 (br, 1H), 1.83 (m, 1H), 1.14 (m, 3H), 0.70-0.40 (m, 3H), 0.15-0.04 (m, 2H).

Example 43

4-(3-(3-(bicyclo[2.2.1]heptan-2-ylamino)azetidine-1-carbonyl)-4-fluorobenzyl)phthalazin-1(2H)-one; (I-43)

Step 1: Preparation of 4-(3-(3-(bicyclo[2.2.1]heptan-2-ylamino)azetidine-1-carbonyl)-4-fluorobenzyl)phthalazin-1(2H)-one This compound was made using the procedure described for example 25 (Step 1). Thus, 4-(3-(3-aminoazetidine-1-carbonyl)-4-fluorobenzyl)phthalazin-1(2H)-one (example 3)(200 mg, 0.57 mmol) was reacted with norcamphor (62 mg, 0.57 mmol) and sodium triacetoxyborohydride (247 mg, 1.17 mmol) to afford the title compound (48 mg, 19%).

$^1$H-NMR (MeOD, 400 MHz): δ 8.37 (d, 1H), 7.92 (d, 1H), 7.82-7.88 (m, 2H), 7.48-7.50 (m, 1H), 7.41-7.43 (m, 1H), 7.14 (t, 1H), 4.38 (s, 2H), 4.28-4.37 (m, 1H), 4.09-4.26 (m, 1H), 3.70-3.91 (m, 2H), 3.61-3.69 (m, 1H), 2.88-2.95 (m, 1H), 2.14-2.23 (m, 2H), 1.73-1.94 (m, 2H), 1.48-1.71 (m, 2H), 1.22-1.40 (m, 4H).

Example 44

4-(3-(3-(sec-butyl amino)azetidine-1-carbonyl)-4-fluorobenzyl)phthalazin-1(2H)-one; (I-44)

Step 1: Preparation of 4-(3-(3-(sec-butylamino)azetidine-1-carbonyl)-4-fluorobenzyl)phthalazin-1(2H)-one This compound was made using the procedure described for example 25 (Step 1). Thus, 4-(3-(3-aminoazetidine-1-carbonyl)-4-fluorobenzyl)phthalazin-1(2H)-one (example 3)(200 mg, 0.57 mmol) was reacted with butan-2-one (51 uL, 0.57 mmol) and sodium triacetoxyborohydride (247 mg, 1.17 mmol) to afford the title compound (74 mg, 32%).

$^1$H-NMR (CDCl$_3$, 400 MHz): δ 10.58 (s, 1H), 8.49-8.45 (m, 1H), 7.80-7.71 (m, 3H), 7.52-7.49 (dd, 1H), 7.33-7.30 (m, 1H), 7.01 (t, 1H), 4.44-4.35 (m, 1H), 4.28 (s, 2H), 4.22-4.14 (m, 1H), 3.86-3.73 (m, 3H), 2.59-2.52 (m, 1H), 1.48-1.24 (m, 3H), 1.02-0.98 (m, 3H), 0.91-0.86 (m, 3H).

Example 45

4-(3-(3-((dicyclopropylmethyl)amino)azetidine-1-carbonyl)-4-fluorobenzyl)phthalazin-1(2H)-one; (I-45)

Step 1: Preparation of 4-(3-(3-((dicyclopropylmethyl)amino)azetidine-1-carbonyl)-4-fluorobenzyl)phthalazin-1(2H)-one This compound was made using the procedure described for example 25 (Step 1). Thus, 4-(3-(3-aminoazetidine-1-carbonyl)-4-fluorobenzyl)phthalazin-1(2H)-one (example 3)(200 mg, 0.57 mmol) was reacted with dicyclopropylmethanone (43 uL, 0.57 mmol) and sodium triacetoxyborohydride (247 mg, 1.17 mmol) to afford the title compound (28 mg, 11%).

$^1$H-NMR (CDCl$_3$, 400 MHz): δ 10.63 (s, 1H), 8.50-8.45 (m, 1H), 7.87-7.71 (m, 3H), 7.52-7.50 (m, 1H), 7.33-7.31 (m, 1H), 7.01 (t, 1H), 4.41-4.37 (m, 1H), 4.28 (s, 2H), 4.20-4.16 (m, 1H), 3.99-3.93 (m, 1H), 3.89-3.76 (m, 2H), 1.74 (br, 1H), 1.08 (t, 1H), 0.85-0.77 (m, 2H), 0.54-0.42 (m, 4H), 0.24-0.18 (m, 2H), 0.08-0.04 (m, 2H).

Example 46

4-(4-fluoro-3-(3-((4-ethylpentan-2-yl)amino)azetidine-1-carbonyl)benzyl)phthalazin-1(2H)-one; (I-46)

Step 1: Preparation of 4-(4-fluoro-3-(3-((4-methylpentan-2-yl)amino)azetidine-1-carbonyl)benzyl)phthalazin-1(2H)-one This compound was made using the procedure described for example 25 (Step 1). Thus, 4-(3-(3-aminoazetidine-1-carbonyl)-4-fluorobenzyl)phthalazin-1(2H)-one (example 3)(200 mg, 0.57 mmol) was reacted with 4-methylpentan-2-one (57 mg, 0.57 mmol) and sodium triacetoxyborohydride (247 mg, 1.17 mmol) to afford the title compound (104 mg, 42%).

¹H-NMR (MeOD, 400 MHz): δ 8.37-8.35 (m, 1H), 7.95-7.92 (m, 1H), 7.87-7.82 (m, 2H), 7.51-7.49 (m, 1H), 7.45-7.43 (m, 1H), 7.16 (q, 1H), 4.37 (s, 2H), 4.34-4.32 (m, 1H), 4.19-4.17 (m, 1H), 3.84-3.82 (m, 3H), 2.78-2.76 (m, 1H), 1.71-1.68 (m, 1H), 1.32-1.27 (m, 2H), 1.03-0.99 (m, 3H), 0.92-0.86 (m, 6H).

Example 47

4-(4-fluoro-3-(3-((3-hydroxybutan-2-yl)amino)azetidine-1-carbonyl)benzyl)phthalazin-1(2H)-one; (I-47)

Step 1: Preparation of 4-(4-fluoro-3-(3-((3-hydroxybutan-2-yl)amino)azetidine-1-carbonyl)benzyl)phthalazin-1(2H)-one This compound was made using the procedure described for example 25 (Step 1). Thus, 4-(3-(3-aminoazetidine-1-carbonyl)-4-fluorobenzyl)phthalazin-1(2H)-one (example 3)(200 mg, 0.57 mmol) was reacted with 3-hydroxybutan-2-one (49 uL, 0.57 mmol) and sodium triacetoxyborohydride (247 mg, 1.17 mmol) to afford the title compound (60 mg, 25%).
¹H-NMR (MeOD, 400 MHz): δ 8.38-8.36 (m, 1H), 7.94-7.92 (m, 1H), 7.88-7.80 (m, 2H), 7.52-7.49 (m, 1H), 7.46-7.44 (m, 1H), 7.16-7.11 (m, 1H), 4.37 (s, 2H), 4.35-4.32 (m, 1H), 4.19-4.16 (m, 1H), 3.91-3.89 (m, 3H), 2.04-1.99 (m, 2H), 1.15-1.12 (m, 3H), 0.12-0.95 (m, 3H).

Example 48

4-(4-fluoro-3-(3-(pentan-2-yl amino)azetidine-1-carbonyl)benzyl)phthalazin-1(2H)-one; (I-48)

Step 1: Preparation of 4-(4-fluoro-3-(3-(pentan-2-ylamino)azetidine-1-carbonyl)benzyl)phthalazin-1(2H)-one This compound was made using the procedure described for example 25 (Step 1). Thus, 4-(3-(3-aminoazetidine-1-carbonyl)-4-fluorobenzyl)phthalazin-1(2H)-one (example 3)(200 mg, 0.57 mmol) was reacted with pentan-2-one (49 mg, 0.57 mmol) and sodium triacetoxyborohydride (247 mg, 1.17 mmol) to afford the title compound (113 mg, 51%).
¹H-NMR (CDCl₃, 400 MHz): δ 10.55 (s, 1H), 8.49-8.45 (m, 1H), 7.80-7.71 (m, 3H), 7.50 (d, 1H), 7.33-7.29 (m, 1H), 7.01 (t, 1H), 4.42-4.36 (m, 1H), 4.21-4.11 (m, 1H), 3.85-3.72 (m, 3H), 2.66-2.59 (m, 1H), 1.40-1.25 (m, 5H), 1.02-0.98 (m, 3H), 0.92-0.88 (m, 3H).

Example 49

4-(4-fluoro-3-(3-((1-(1-methylcyclopropyl)ethyl)amino)azetidine-1-carbonyl)benz yl)phthalazin-1(2H)-one; (I-49)

Step 1: Preparation of 4-(4-fluoro-3-(3-((1-(1-methylcyclopropyl)ethyl)amino)azetidine-1-carbonyl)benzyl)phthalazin-1(2H)-one This compound was made using the procedure described for example 25 (Step 1). Thus, 4-(3-(3-aminoazetidine-1-carbonyl)-4-fluorobenzyl)phthalazin-1(2H)-one (example 3)(200 mg, 0.57 mmol) was reacted with 1-(1-methylcyclopropyl)ethanone (63 uL, 0.57 mmol) and sodium triacetoxyborohydride (247 mg, 1.17 mmol) to afford the title compound (37 mg, 16%).

¹H-NMR (CDCl₃, 400 MHz): δ 10.22 (s, 1H), 8.48-8.45 (m, 1H), 7.78-7.71 (m, 3H), 7.50-7.49 (m, 1H), 7.33-7.29 (m, 1H), 7.02 (t, 1H), 4.40-4.34 (m, 1H), 4.27 (s, 2H), 4.15 (t, 1H), 3.84-3.73 (m, 3H), 1.85-1.79 (m, 1H), 1.41 (br, 1H), 1.10-1.07 (dd, 3H), 0.97-0.95 (d, 3H).

Example 50

4-(4-fluoro-3-(3-((3,3,3-tri fluoro-2-ethylpropyl)amino)azetidine-1-carbonyl)benzyl)phthalazin-1(2H)-one; (I-50)

Step 1: Preparation of 4-(4-fluoro-3-(3-((3,3,3-trifluoro-2-methylpropyl)amino)azetidine-1-carbonyl)benzyl)phthalazin-1(2H)-one This compound was made using the procedure described for example 25 (Step 1). Thus, 4-(3-(3-aminoazetidine-1-carbonyl)-4-fluorobenzyl)phthalazin-1(2H)-one (example 3)(200 mg, 0.57 mmol) was reacted with 3,3,3-trifluoro-2-methylpropanal (0.1 uL, 0.57 mmol) and sodium triacetoxyborohydride (247 mg, 1.17 mmol) to afford the title compound (137 mg, 52%).
¹H-NMR (MeOD, 400 MHz): δ 8.26 (d, 1H), 7.72-7.84 (m, 3H), 7.33-7.41 (m, 2H), 7.04 (t, 1H), 4.28 (s, 2H), 4.18 (t, 1H), 4.02-4.05 (m, 1H), 3.71-3.76 (m, 1H), 3.63-3.67 (m, 1H), 3.54-3.58 (m, 1H), 2.65-2.70 (m, 1H), 2.32-2.38 (m, 2H), 1.05-1.07 (m, 3H).

Example 51

4-(3-(3-(allyl amino)azetidine-1-carbonyl)-4-fluorobenzyl)phthalazin-1(2H)-one; (I-51)

Step 1: Preparation of 4-(3-(3-(allylamino)azetidine-1-carbonyl)-4-fluorobenzyl)phthalazin-1(2H)-one This compound was made using the procedure described for example 25 (Step 1). Thus, 4-(3-(3-aminoazetidine-1-carbonyl)-4-fluorobenzyl)phthalazin-1(2H)-one (example 3)(200 mg, 0.57 mmol) was reacted with acrylaldehyde (38 uL, 0.57 mmol) and sodium triacetoxyborohydride (247 mg, 1.17 mmol) to afford the title compound (147 mg, 66%).
¹H-NMR (CDCl₃, 400 MHz): δ 10.02 (s, 1H), 8.40-8.38 (m, 1H), 7.72-7.64 (m, 3H), 7.44-7.42 (m, 1H), 7.25-7.22 (m, 1H), 6.97-6.93 (m, 1H), 5.79 (m, 1H), 5.13-5.03 (m, 2H), 4.30-4.27 (m, 1H), 4.20 (s, 2H), 4.10-4.08 (m, 1H), 3.83-3.79 (m, 1H), 3.72-3.65 (m, 2H), 3.14 (d, 2H).

Example 52

4-(4-fluoro-3-(3-(isopentylamino)azetidine-1-carbonyl)benzyl)phthalazin-1(2H)-one; (I-52)

Step 1: Preparation of 4-(4-fluoro-3-(3-(isopentylamino)azetidine-1-carbonyl)benzyl)phthalazin-1(2H)-one This compound was made using the procedure described for example 25 (Step 1). Thus, 4-(3-(3-aminoazetidine-1-carbonyl)-4-fluorobenzyl)phthalazin-1(2H)-one (example 3)(200 mg, 0.57 mmol) was reacted with 3-methylbutanal (61 uL, 0.57 mmol) and sodium triacetoxyborohydride (247 mg, 1.17 mmol) to afford the title compound (190 mg, 79%).
¹H-NMR (CDCl₃, 400 MHz): δ 10.14 (s, 1H), 8.47-8.45 (m, 1H), 7.79-7.71 (m, 3H), 7.50 (m, 1H), 7.33-7.29 (m, 1H), 7.02 (t, 1H), 4.36 (t, 1H), 4.27 (s, 2H), 4.18 (t, 1H), 3.88-3.68 (m, 3H), 2.56 (m, 2H), 1.62 (m, 1H), 1.51 (br, 1H), 1.38-1.35 (m, 2H), 0.90-0.88 (dd, 6H).

Example 53

4-(3-(3-(butylamino)azetidine-1-carbonyl)-4-fluorobenzyl)phthalazin-1(2H)-one; (I-53)

Step 1: Preparation of 4-(3-(3-(butylamino)azetidine-1-carbonyl)-4-fluorobenzyl)phthalazin-1(2H)-one This compound was made using the procedure described for example 25 (Step 1). Thus, 4-(3-(3-aminoazetidine-1-carbonyl)-4-fluorobenzyl)phthalazin-1(2H)-one (example 3)(200 mg, 0.57 mmol) was reacted with butyraldehyde (51 uL, 0.57 mmol) and sodium triacetoxyborohydride (247 mg, 1.17 mmol) to afford the title compound (198 mg, 85%).

$^1$H-NMR (CDCl$_3$, 400 MHz): δ 10.28 (s, 1H), 8.40-8.38 (m, 1H), 7.72-7.66 (m, 1H), 7.44-7.41 (m, 1H), 7.24-7.22 (m, 1H), 6.97-6.92 (m, 1H), 4.30-4.27 (m, 1H), 4.20 (s, 2H), 4.11-4.09 (m, 1H), 3.81-3.79 (m, 1H), 3.72-3.70 (m, 1H), 3.64-3.62 (m, 1H), 2.50-2.46 (m, 2H), 2.02 (s, 1H), 1.40-1.37 (m, 2H), 1.30-1.24 (m, 2H), 0.86-0.80 (m, 5H).

Example 54

4-(4-fluoro-3-(3-((3-ethylbut-2-en-1-yl)amino)azetidine-1-carbonyl)benzyl)phthalazin-1(2H)-one; (I-54)

Step 1: Preparation of 4-(4-fluoro-3-(3-((3-methylbut-2-en-1-yl)amino)azetidine-1-carbonyl)benzyl) phthalazin-1(2H)-one This compound was made using the procedure described for example 25 (Step 1). Thus, 4-(3-(3-aminoazetidine-1-carbonyl)-4-fluorobenzyl)phthalazin-1(2H)-one (example 3)(200 mg, 0.57 mmol) was reacted with 3-methylbut-2-enal (55 uL, 0.57 mmol) and sodium triacetoxyborohydride (247 mg, 1.17 mmol) to afford the title compound (146 mg, 61%).

$^1$H-NMR (MeOD, 400 MHz): δ 8.36 (d, 1H), 7.79-7.94 (m, 3H), 7.43-7.51 (m, 2H), 7.13 (t, 1H), 5.19 (brs, 1H), 4.37 (s, 2H), 4.26 (t, 1H), 4.13 (t, 1H), 3.83-3.87 (m, 1H), 3.74-3.78 (m, 1H), 3.63-3.66 (m, 1H), 3.11 (d, 2H), 1.71 (s, 3H), 1.64 (s, 3H).

Example 55

4-(3-(3-((cyclopentylmethyl)amino)azetidine-1-carbonyl)-4-fluorobenzyl)phthalazin-1(2H)-one; (I-55)

Step 1: Preparation of 4-(3-(3-((cyclopentylmethyl)amino)azetidine-1-carbonyl)-4-fluorobenzyl) phthalazin-1(2H)-one This compound was made using the procedure described for example 25 (Step 1). Thus, 4-(3-(3-aminoazetidine-1-carbonyl)-4-fluorobenzyl)phthalazin-1(2H)-one (example 3)(200 mg, 0.57 mmol) was reacted with cyclopentanecarbaldehyde (61 uL, 0.57 mmol) and sodium triacetoxyborohydride (247 mg, 1.17 mmol) to afford the title compound (178 mg, 72%).

$^1$H-NMR (MeOD, 400 MHz): δ 8.38-8.36 (m, 1H), 7.94-7.93 (m, 1H), 7.89-7.82 (m, 2H), 7.51-7.43 (m, 2H), 7.17-7.12 (m, 1H), 4.38 (s, 2H), 4.29-4.28 (m, 1H), 4.15-4.13 (m, 1H), 3.88-3.87 (m, 1H), 3.79-3.77 (m, 1H), 3.66-3.64 (m, 1H), 2.45-2.42 (m, 2H), 1.98-1.95 (m, 1H), 1.81-1.79 (m, 2H), 1.65-1.56 (m, 4H), 1.18-1.16 (m, 2H).

Example 56

4-(4-fluoro-3-(3-((4,4,4-trifluorobutyl)amino)azetidine-1-carbonyl)benzyl)phthalazin-1(2)-one; (I-56)

Step 1: Preparation of 4-(4-fluoro-3-(3-((4,4,4-trifluorobutyl)amino)azetidine-1-carbonyl)benzyl) phthalazin-1(2H)-one This compound was made using the procedure described for example 25 (Step 1). Thus, 4-(3-(3-aminoazetidine-1-carbonyl)-4-fluorobenzyl)phthalazin-1(2H)-one (example 3)(200 mg, 0.57 mmol) was reacted with 4,4,4-trifluorobutanol (72 mg, 0.57 mmol) and sodium triacetoxyborohydride (247 mg, 1.17 mmol) to afford the title compound (111 mg, 42%).

$^1$H-NMR (MeOD, 400 MHz): δ 8.38-8.35 (m, 1H), 7.95-7.92 (m, 1H), 7.89-7.82 (m, 2H), 7.52-7.50 (m, 1H), 7.45-7.43 (m, 1H), 7.17-7.12 (m, 1H), 4.37 (s, 2H), 4.30-4.28 (m, 1H), 4.16-4.14 (m, 1H), 3.86-3.83 (m, 1H), 3.78-3.76 (m, 1H), 3.68-3.66 (m, 1H), 2.58-2.55 (m, 2H), 2.24-2.17 (m, 2H), 1.74-1.68 (m, 2H).

Example 57

4-(4-fluoro-3-(3-(pentyl amino)azetidine-1-carbonyl) benzyl)phthalazin-1(2H)-one; (I-57)

Step 1: Preparation of 4-(4-fluoro-3-(3-(pentylamino)azetidine-1-carbonyl)benzyl)phthalazin-1 (2H)-one This compound was made using the procedure described for example 25 (Step 1). Thus, 4-(3-(3-aminoazetidine-1-carbonyl)-4-fluorobenzyl)phthalazin-1(2H)-one (example 3)(200 mg, 0.57 mmol) was reacted with pentanal (61 uL, 0.57 mmol) and sodium triacetoxyborohydride (247 mg, 1.17 mmol) to afford the title compound (200 mg, 83%).

$^1$H-NMR (MeOD, 400 MHz): δ 8.38-8.35 (m, 1H), 7.94-7.92 (m, 1H), 7.89-7.82 (m, 2H), 7.51-7.49 (m, 1H), 7.45-7.43 (m, 1H), 7.17-7.12 (m, 1H), 4.37 (s, 2H), 4.30-4.28 (m, 1H), 4.17-4.15 (m, 1H), 3.88-3.86 (m, 1H), 3.80-3.78 (m, 1H), 3.69-3.67 (m, 1H), 2.53-2.49 (m, 2H), 1.51-1.47 (m, 2H), 1.35-1.29 (m, 4H), 0.91 (t, 3H).

Example 58

4-(3-(3-((2-cyclopropylethyl)amino)azetidine-1-carbonyl)-4-fluorobenzyl)phthalazin-1(2H)-one; (I-58)

Step 1: Preparation of 4-(3-(3-((2-cyclopropylethyl) amino)azetidine-1-carbonyl)-4-fluorobenzyl) phthalazin-1(2H)-one This compound was made using the procedure described for example 25 (Step 1). Thus, 4-(3-(3-aminoazetidine-1-carbonyl)-4-fluorobenzyl)phthalazin-1(2H)-one (example 3)(200 mg, 0.57 mmol) was reacted with 2-cyclopropylacetaldehyde (48 mg, 0.57 mmol) and sodium triacetoxyborohydride (247 mg, 1.17 mmol) to afford the title compound (240 mg, 69%).

$^1$H-NMR (MeOD, 400 MHz): δ 8.38-8.36 (m, 1H), 7.95-7.93 (m, 1H), 7.89-7.82 (m, 2H), 7.52-7.50 (m, 1H), 7.45-

7.43 (m, 1H), 7.17-7.15 (m, 1H), 4.38 (s, 2H), 4.30-4.29 (m, 1H), 4.15-4.14 (m, 1H), 3.87-3.86 (m, 1H), 3.78-3.77 (m, 1H), 3.68-3.66 (m, 1H), 2.60-2.56 (m, 2H), 1.39-1.34 (m, 2H), 0.72-0.71 (m, 1H), 0.46-0.42 (m, 2H), 0.06-0.04 (m, 2H).

Example 59

4-(4-fluoro-3-(3-(propyl amino)azetidine-1-carbonyl)benzyl)phthalazin-1(2H)-one; (I-59)

Step 1: Preparation of 4-(4-fluoro-3-(3-(propylamino)azetidine-1-carbonyl)benzyl)phthalazin-1(2H)-one This compound was made using the procedure described for example 25 (Step 1). Thus, 4-(3-(3-aminoazetidine-1-carbonyl)-4-fluorobenzyl)phthalazin-1(2H)-one (example 3)(200 mg, 0.57 mmol) was reacted with propionaldehyde (42 uL, 0.57 mmol) and sodium triacetoxyborohydride (247 mg, 1.17 mmol) to afford the title compound (191 mg, 85%).
$^1$H-NMR (MeOD, 400 MHz): δ 10.39 (s, 1H), 8.47-8.45 (m, 1H), 7.80-7.72 (m, 3H), 7.51-7.48 (m, 1H), 7.33-7.29 (m, 1H), 7.04-6.99 (m, 1H), 4.39-4.34 (m, 1H), 4.27 (s, 2H), 4.19-4.17 (m, 1H), 3.89-3.85 (m, 1H), 3.81-3.77 (m, 1H), 3.71-3.70 (m, 1H), 2.55-2.50 (m, 2H), 1.52-1.47 (m, 2H), 0.94-0.91 (m, 3H).

Example 60

4-(4-fluoro-3-(3-(methyl(pyridin-4-ylmethyl)amino)azetidine-1-carbonyl)benzyl)phthalazin-1(2H)-one; (I-60)

Step 1: Preparation of 4-(4-fluoro-3-(3-((pyridin-4-ylmethyl)amino)azetidine-1-carbonyl)benzyl)phthalazin-1(2H)-one isonicotinaldehyde (26 uL, 0.28 mmol) was added to a solution of 4-(3-(3-aminoazetidine-1-carbonyl)-4-fluorobenzyl)phthalazin-1(2H)-one (example 3)(100 mg, 0.28 mmol) in 1,2-dichloroethane (1.1 mL) and stirred for 30 min then acetic acid (31 uL, 0.54 mmol) and sodium triacetoxyborohydride (114 mg, 0.54 mmol) was added to the reaction mixture at 0° C. and stirred for 12 hours. The reaction mixture was concentrated in vacuum, added 2N NaOH(aq) and extracted into dichloromethane. The combined organic layers were dried over MgSO$_4$, filtered, evaporated in vacuum and purified using silica chromatography to afford the intermediate compound 4-(4-fluoro-3-(3-((pyridin-4-ylmethyl)amino)azetidine-1-carbonyl)benzyl)phthalazin-1(2H)-one (108 mg, 87%).

Step 2: Preparation of 4-(4-fluoro-3-(3-(methyl(pyridin-4-ylmethyl)amino)azetidine-1-carbonyl)benzyl)phthalazin-1(2H)-one K$_2$CO$_3$ (51 mg, 0.48 mmol) and iodomethane (33 uL, 0.48 mmol) was added to a solution of the intermediate compound (Step 1)(108 mg, 0.24 mmol) in DMF (1.5 mL) and stirred for 3 hours. The reaction mixture was concentrated in vacuum, added dichloromethane and washed sat. NH$_4$Cl (aq) and water. The combined organic layers were dried over MgSO$_4$, filtered, evaporated in vacuum and purified using silica chromatography to afford the title compound (99 mg, 91%).
$^1$H-NMR (MeOD, 400 MHz): δ 8.47 (d, 2H), 8.36 (d, 2H), 7.94 (d, 1H), 7.78-7.91 (m, 2H), 7.40-7.55 (m, 3H), 7.15 (t, 1H), 4.38 (s, 2H), 4.18-4.25 (m, 1H), 3.97-4.14 (m, 2H), 3.80-3.90 (m, 1H), 3.42-3.54 (m, 3H), 2.08 (s, 3H).

Example 61

(R)-4-(4-fluoro-3-(3-(methyl(pyridin-4-ylmethyl)amino)pyrrolidine-1-carbonyl)benzyl)phthalazin-1(2H)-one; (I-61)

Step 1: Preparation of (R)-4-(4-fluoro-3-(3-((pyridin-4-ylmethyl)amino)pyrrolidine-1-carbonyl)benzyl)phthalazin-1(2H)-one This compound was made using the procedure described for example 60 (Step 1). Thus, (R)-4-(3-(3-aminopyrrolidine-1-carbonyl)-4-fluorobenzyl)phthalazin-1(2H)-one (example 1)(100 mg, 0.28 mmol) was reacted with isonicotinaldehyde (26 uL, 0.28 mmol) and sodium triacetoxyborohydride (114 mg, 0.54 mmol) to afford the intermediate compound (R)-4-(4-fluoro-3-(3-((pyridin-4-ylmethyl)amino)pyrrolidine-1-carbonyl)benzyl)phthalazin-1(2H)-one (106 mg, 83%).

Step 2: Preparation of (R)-4-(4-fluoro-3-(3-(methyl(pyridin-4-ylmethyl)amino)pyrrolidine-1-carbonyl)benzyl)phthalazin-1(2H)-one This compound was made using the procedure described for example 60 (Step 2). Thus, this intermediate compound (Step 1)(106 mg, 0.23 mmol) was reacted with K$_2$CO$_3$ (51 mg, 0.48 mmol) and iodomethane (33 uL, 0.48 mmol) to afford the title compound (98 mg, 91%).
$^1$H-NMR (DMSO, 400 MHz): δ 12.61 (s, 1H), 8.51-8.47 (m, 2H), 8.26 (t, 1H), 7.97 (m, 1H), 7.92-7.78 (m, 2H), 7.45-7.33 (m, 3H), 7.24 (m, 2H), 4.32 (s, 2H), 3.76 (m, 1H), 3.51 (m, 3H), 3.30 (s, 2H), 3.08 (m, 1H), 1.92 (s, 3H), 1.81 (m, 2H), Example 62

(S)-4-(4-fluoro-3-(3-(methyl(pyridin-4-ylmethyl)amino)pyrrolidine-1-carbonyl)benzyl)phthalazin-1(2H)-one; (I-62)

Step 1: Preparation of (S)-4-(4-fluoro-3-(3-((pyridin-4-ylmethyl)amino)pyrrolidine-1-carbonyl)benzyl)phthalazin-1(2H)-one This compound was made using the procedure described for example 60 (Step 1). Thus, (S)-4-(3-(3-aminopyrrolidine-1-carbonyl)-4-fluorobenzyl)phthalazin-1(2H)-one (example 2)(100 mg, 0.23 mmol) was reacted with isonicotinaldehyde (33 uL, 0.23 mmol) and sodium triacetoxyborohydride (114 mg, 0.54 mmol) to afford the intermediate compound (S)-4-(4-fluoro-3-(3-((pyridin-4-ylmethyl)amino)pyrrolidine-1-carbonyl)benzyl)phthalazin-1(2H)-one (106 mg, 83%)).

Step 2: Preparation of (S)-4-(4-fluoro-3-(3-(methyl(pyridin-4-ylmethyl)amino)pyrrolidine-1-carbonyl)benzyl)phthalazin-1(2H)-one This compound was made using the procedure described for example 60 (Step 2). Thus, this intermediate compound (Step 1)(106 mg, 0.24 mmol) was reacted with K$_2$CO$_3$ (51 mg, 0.48 mmol) and iodomethane (33 uL, 0.48 mmol) to afford the title compound (98 mg, 91%).

$^1$H-NMR (DMSO, 400 MHz): δ 12.61 (s, 1H), 8.51-8.47 (m, 2H), 8.26 (t, 1H), 7.97 (m, 1H), 7.92-7.78 (m, 2H), 7.45-7.33 (m, 3H), 7.24 (m, 2H), 4.32 (s, 2H), 3.76 (m, 1H), 3.51 (m, 3H), 3.30 (s, 2H), 3.08 (m, 1H), 1.92 (s, 3H), 1.81 (m, 2H), 1.19 (m, 1H).

Example 63

(S)-4-(4-fluoro-3-(3-(methyl(pyridin-2-ylmethyl) amino)pyrrolidine-1-carbonyl)benzyl)phthalazin-1 (2H)-one; (I-63)

Step 1: Preparation of (S)-4-(4-fluoro-3-(3-((pyridin-2-ylmethyl)amino)pyrrolidine-1-carbonyl)benzyl)phthalazin-1(2H)-one This compound was made using the procedure described for example 60 (Step 1). Thus, (S)-4-(3-(3-aminopyrrolidine-1-carbonyl)-4-fluorobenzyl)phthalazin-1(2H)-one (example 2)(100 mg, 0.23 mmol) was reacted with picolinaldehyde (33 uL, 0.23 mmol) and sodium triacetoxyborohydride (114 mg, 0.54 mmol) to afford the intermediate compound (S)-4-(4-fluoro-3-(3-((pyridin-2-ylmethyl)amino)pyrrolidine-1-carbonyl)benzyl)phthalazin-1 (2H)-one (85 mg, 81%).

Step 2: Preparation of (S)-4-(4-fluoro-3-(3-(methyl (pyridin-2-ylmethyl)amino)pyrrolidine-1-carbonyl) benzyl)phthalazin-1(2H)-one This compound was made using the procedure described for example 60 (Step 2). Thus, this intermediate compound (Step 1)(85 mg, 0.19 mmol) was reacted with K$_2$CO$_3$ (51 mg, 0.37 mmol) and iodomethane (23 uL, 0.37 mmol) to afford the title compound (79 mg, 88%).

$^1$H-NMR (MeOD, 400 MHz): δ 10.82 (s, 0.4H), 10.40 (s, 0.6H), 8.62 (dd, 1H), 8.46 (m, 1H), 7.75 (m, 3H), 7.52 (m, 1H), 7.37 (m, 2H), 7.17 (m, 1H), 7.0 (m, 1H), 4.15 (s, 2H), 3.96 (m, 1H), 3.89 (m, 1H), 3.74 (d, 1H), 3.63 (m, 2H), 3.46 (m, 1H), 3.41 (m, 1H), 2.21 (s, 2H), 1.93 (m, 3H).

Example 64

(R)-4-(4-fluoro-3-(3-(methyl(pyridin-2-ylethyl) amino)pyrrolidine-1-carbonyl)benzyl)phthalazin-1 (2H)-one; (I-64)

Step 1: Preparation of (R)-4-(4-fluoro-3-(3-((pyridin-2-ylmethyl)amino)pyrrolidine-1-carbonyl)benzyl)phthalazin-1(2H)-one This compound was made using the procedure described for example 60 (Step 1). Thus, (R)-4-(3-(3-aminopyrrolidine-1-carbonyl)-4-fluorobenzyl)phthalazin-1(2H)-one (example 1)(100 mg, 0.23 mmol) was reacted with picolinaldehyde (33 uL, 0.23 mmol) and sodium triacetoxyborohydride (114 mg, 0.54 mmol) to afford the intermediate compound (R)-4-(4-fluoro-3-(3-((pyridin-2-ylmethyl)amino)pyrrolidine-1-carbonyl)benzyl)phthalazin-1 (2H)-one (85 mg, 81%).

Step 2: Preparation of (R)-4-(4-fluoro-3-(3-(methyl (pyridin-2-ylmethyl)amino)pyrrolidine-1-carbonyl) benzyl)phthalazin-1(2H)-one This compound was made using the procedure described for example 60 (Step 2). Thus, this intermediate compound (Step 1)(85 mg, 0.19 mmol) was reacted with K$_2$CO$_3$ (51 mg, 0.37 mmol) and iodomethane (23 uL, 0.37 mmol) to afford the title compound (79 mg, 88%).

$^1$H-NMR (MeOD, 400 MHz): δ 10.82 (s, 0.4H), 10.40 (s, 0.6H), 8.62 (dd, 1H), 8.46 (m, 1H), 7.75 (m, 3H), 7.52 (m, 1H), 7.37 (m, 2H), 7.17 (m, 1H), 7.0 (m, 1H), 4.15 (s, 2H), 3.96 (m, 1H), 3.89 (m, 1H), 3.74 (d, 1H), 3.63 (m, 2H), 3.46 (m, 1H), 3.41 (m, 1H), 2.21 (s, 2H), 1.93 (m, 3H).

Example 65

4-(4-fluoro-3-(3-(methyl(pyridin-2-ylmethyl)amino) azetidine-1-carbonyl)benzyl)phthalazin-1(2H)-one; (I-65)

Step 1: Preparation of 4-(4-fluoro-3-(3-((pyridin-2-ylmethyl)amino)azetidine-1-carbonyl)benzyl) phthalazin-1(2H)-one This compound was made using the procedure described for example 60 (Step 1). Thus, 4-(3-(3-aminoazetidine-1-carbonyl)-4-fluorobenzyl)phthalazin-1(2H)-one (example 3)(100 mg, 0.28 mmol) was reacted with picolinaldehyde (26 uL, 0.28 mmol) and sodium triacetoxyborohydride (114 mg, 0.54 mmol) to afford the intermediate compound 4-(4-fluoro-3-(3-((pyridin-2-ylmethyl)amino)azetidine-1-carbonyl)benzyl)phthalazin-1(2H)-one (108 mg, 87%).

Step 2: Preparation of 4-(4-fluoro-3-(3-(methyl (pyridin-2-ylmethyl)amino)azetidine-1-carbonyl) benzyl)phthalazin-1(2H)-one This compound was made using the procedure described for example 60 (Step 2). Thus, this intermediate compound (Step 1)(108 mg, 0.24 mmol) was reacted with K$_2$CO$_3$ (51 mg, 0.48 mmol) and iodomethane (33 uL, 0.48 mmol) to afford the title compound (99 mg, 91%).

$^1$H-NMR (MeOD, 400 MHz): δ 8.47 (d, 1H), 8.35 (d, 1H), 7.94 (d, 1H), 7.78-7.89 (m, 3H), 7.43-7.54 (m, 3H), 7.30-7.35 (m, 1H), 7.14 (t, 1H), 4.38 (s, 2H), 4.17-4.22 (m, 1H), 3.95-4.06 (m, 2H), 3.87-3.94 (m, 1H), 3.57 (s, 2H), 3.44-3.51 (m, 1H), 2.18 (s, 3H).

Example 66

4-(4-fluoro-3-(3-(methyl(pyridin-3-ylmethyl)amino) azetidine-1-carbonyl)benzyl)phthalazin-1(2H)-one; (I-66)

Step 1: Preparation of 4-(4-fluoro-3-(3-((pyridin-3-ylmethyl)amino)azetidine-1-carbonyl)benzyl) phthalazin-1(2H)-one This compound was made using the procedure described for example 60 (Step 1). Thus, 4-(3-(3-aminoazetidine-1-carbonyl)-4-fluorobenzyl)phthalazin-1(2H)-one (example 3)(100 mg, 0.28 mmol) was reacted with nicotinaldehyde (26 uL, 0.28 mmol) and sodium triacetoxyborohydride (114 mg, 0.54 mmol) to afford the intermediate compound 4-(4-fluoro-3-(3-((pyridin-3-ylmethyl)amino)azetidine-1-carbonyl)benzyl)phthalazin-1(2H)-one (108 mg, 87%).

Step 2: Preparation of 4-(4-fluoro-3-(3-(methyl (pyridin-3-ylmethyl)amino)azetidine-1-carbonyl) benzyl)phthalazin-1(2H)-one This compound was made using the procedure described for example 60 (Step 2). Thus, this intermediate compound (Step 1)(108 mg, 0.24 mmol) was reacted with K$_2$CO$_3$ (51 mg, 0.48 mmol) and iodomethane (33 uL, 0.48 mmol) to afford the title compound (99 mg, 91%).

$^1$H-NMR (MeOD, 400 MHz): δ 8.43-8.51 (m, 2H), 8.36 (d, 1H), 7.94 (d, 1H), 7.79-7.90 (m, 3H), 7.48-7.53 (m, 1H), 7.39-7.48 (m, 2H), 7.15 (t, 1H), 4.38 (s, 2H), 4.18-4.25 (m, 1H), 3.96-4.10 (m, 2H), 3.89-3.96 (m, 1H), 3.39-3.56 (m, 2H), 2.06 (s, 3H).

Example 67

(S)-4-(4-fluoro-3-(3-(methyl(pyridin-3-ylmethyl) amino)pyrrolidine-1-carbonyl)benzyl)phthalazin-1 (2H)-one; (I-67)

Step 1: Preparation of (S)-4-(4-fluoro-3-(3-((pyridin-3-ylmethyl)amino)pyrrolidine-1-carbonyl)benzyl)phthalazin-1(2H)-one This compound was made using the procedure described for example 60 (Step 1). Thus, (S)-4-(3-(3-aminopyrrolidine-1-carbonyl)-4-fluorobenzyl)phthalazin-1(2H)-one (example 2)(100 mg, 0.23 mmol) was reacted with nicotinaldehyde (26 uL, 0.23 mmol) and sodium triacetoxyborohydride (114 mg, 0.54 mmol) to afford the intermediate compound (S)-4-(4-fluoro-3-(3-((pyridin-3-ylmethyl)amino)pyrrolidine-1-carbonyl)benzyl)phthalazin-1 (2H)-one (86 mg, 82%).

Step 2: Preparation of (S)-4-(4-fluoro-3-(3-(methyl (pyridin-3-ylmethyl)amino)pyrrolidine-1-carbonyl) benzyl)phthalazin-1(2H)-one This compound was made using the procedure described for example 60 (Step 2). Thus, this intermediate compound (Step 1)(86 mg, 0.19 mmol) was reacted with K$_2$CO$_3$ (52 mg, 0.38 mmol) and iodomethane (24 uL, 0.38 mmol) to afford the title compound (98 mg, 91%).

$^1$H-NMR (MeOD, 400 MHz): δ 10.36 (s, 0.4H), 10.01 (s, 0.6H), 8.46 (m, 3H), 7.73 (m, 3H), 7.40 (m, 1H), 7.38 (m, 3H), 7.04 (m, 1H), 4.27 (s, 2H), 3.89 (m, 1H), 3.67 (m, 3H), 3.47 (m, 3H), 3.12 (m, 1H), 2.13 (m, 5H), 1.87 (m, 1H).

Example 68

(R)-4-(4-fluoro-3-(3-(methyl(pyridin-3-ylmethyl) amino)pyrrolidine-1-carbonyl)benzyl)phthalazin-1 (2H)-one; (I-68)

Step 1: Preparation of (R)-4-(4-fluoro-3-(3-((pyridin-3-ylmethyl)amino)pyrrolidine-1-carbonyl)benzyl)phthalazin-1(2H)-one This compound was made using the procedure described for example 60 (Step 1). Thus, (R)-4-(3-(3-aminopyrrolidine-1-carbonyl)-4-fluorobenzyl)phthalazin-1(2H)-one (example 1)(100 mg, 0.23 mmol) was reacted with nicotinaldehyde (26 uL, 0.23 mmol) and sodium triacetoxyborohydride (114 mg, 0.54 mmol) to afford the intermediate compound (R)-4-(4-fluoro-3-(3-((pyridin-3-ylmethyl)amino)pyrrolidine-1-carbonyl)benzyl)phthalazin-1 (2H)-one (86 mg, 82%).

Step 2: Preparation of (R)-4-(4-fluoro-3-(3-(methyl (pyridin-3-ylmethyl)amino)pyrrolidine-1-carbonyl) benzyl)phthalazin-1(2H)-one This compound was made using the procedure described for example 60 (Step 2). Thus, this intermediate compound (Step 1)(86 mg, 0.19 mmol) was reacted with K$_2$CO$_3$ (52 mg, 0.38 mmol) and iodomethane (24 uL, 0.38 mmol) to afford the title compound (98 mg, 91%).

$^1$H-NMR (MeOD, 400 MHz): δ 10.36 (s, 0.4H), 10.01 (s, 0.6H), 8.46 (m, 3H), 7.73 (m, 3H), 7.40 (m, 1H), 7.38 (m, 3H), 7.04 (m, 1H), 4.27 (s, 2H), 3.89 (m, 1H), 3.67 (m, 3H), 3.47 (m, 3H), 3.12 (m, 1H), 2.13 (m, 3H), 1.87 (m, 1H).

Example 69

4-(3-(3-(cyclopropyl(methyl)amino)azetidine-1-carbonyl)-4-fluorobenzyl)phthalazin-1(2H)-one; (I-69)

Step 1: Preparation of 4-(3-(3-(cyclopropylamino) azetidine-1-carbonyl)-4-fluorobenzyl)phthalazin-1 (2H)-one This compound was made using the procedure described for example 60 (Step 1). Thus, 4-(3-(3-aminoazetidine-1-carbonyl)-4-fluorobenzyl)phthalazin-1(2H)-one (example 3)(100 mg, 0.23 mmol) was reacted with (1-ethoxycyclopropoxy)trimethylsilane(46 uL, 0.23 mmol) and sodium triacetoxyborohydride (114 mg, 0.54 mmol) to afford the intermediate compound 4-(3-(3-(cyclopropylamino)azetidine-1-carbonyl)-4-fluorobenzyl)phthalazin-1(2H)-one (58 mg, 71%).

Step 2: Preparation of 4-(3-(3-(cyclopropyl(methyl) amino)azetidine-1-carbonyl)-4-fluorobenzyl) phthalazin-1(2H)-one This compound was made using the procedure described for example 60 (Step 2). Thus, this intermediate compound (Step 1)(58 mg, 0.16 mmol) was reacted with K$_2$CO$_3$ (44 mg, 0.32 mmol) and iodomethane (33 uL, 0.32 mmol) to afford the title compound (62 mg, 95%).

$^1$H-NMR (MeOD, 400 MHz): δ 8.32-8.39 (d, 1H), 7.89-7.95 (d, 1H), 7.78-7.88 (m, 2H), 7.46-7.53 (m, 1H), 7.39-7.45 (m, 1H), 7.14 (t, 1H), 4.37 (s, 2H), 4.14-4.22 (m, 1H), 4.05-4.13 (m, 2H), 3.98-4.03 (m, 2H), 3.54-3.63 (m, 1H), 2.26 (s, 3H), 0.34-0.56 (m, 4H).

Example 70

4-(3-(3-(cyclopropyl(ethyl)amino)azetidine-1-carbonyl)-4-fluorobenzyl)phthalazin-1(2H)-one; (I-70)

Step 1: Preparation of 4-(3-(3-(cyclopropylamino) azetidine-1-carbonyl)-4-fluorobenzyl)phthalazin-1 (2H)-one This compound was made using the procedure described for example 60 (Step 1) to afford the intermediate compound 4-(3-(3-(cyclopropylamino)azetidine-1-carbonyl)-4-fluorobenzyl)phthalazin-1(2H)-one (58 mg, 71%).

Step 2: Preparation of 4-(3-(3-(cyclopropyl(ethyl) amino)azetidine-1-carbonyl)-4-fluorobenzyl) phthalazin-1(2H)-one This compound was made using the procedure described for example 60 (Step 2). Thus, this intermediate compound (Step 1)(58 mg, 0.16 mmol) was reacted with K$_2$CO$_3$ (44 mg, 0.32 mmol) and iodoethane (33 uL, 0.32 mmol) to afford the title compound (58 mg, 91%).

$^1$H-NMR (MeOD, 400 MHz): δ 8.32-8.40 (m, 1H), 7.90-7.95 (m, 1H), 7.77-7.89 (m, 2H), 7.46-7.54 (m, 1H), 7.30-

7.45 (m, 1H), 7.14 (t, 1H), 4.36 (s, 2H), 3.95-4.24 (m, 4H), 3.73-3.84 (m, 1H), 2.60-2.71 (m, 2H), 1.68-1.78 (m, 1H), 1.19-1.26 (m, 1H), 1.01-1.10 (m, 3H), 0.35-0.58 (m, 4H).

Example 71

4-(3-(3-(cyclobutyl(methyl)amino)azetidine-1-carbonyl)-4-fluorobenzyl)phthalazin-1(2H)-one; (I-71)

Step 1: Preparation of 4-(3-(3-(cyclobutylamino) azetidine-1-carbonyl)-4-fluorobenzyl)phthalazin-1 (2H)-one This compound was made using the procedure described for example 60 (Step 1). Thus, 4-(3-(3-aminoazetidine-1-carbonyl)-4-fluorobenzyl)phthalazin-1(2H)-one (example 3)(100 mg, 0.23 mmol) was reacted with cyclobutanone (17 uL, 0.23 mmol) and sodium triacetoxyborohydride (114 mg, 0.54 mmol) to afford the intermediate compound 4-(3-(3-(cyclobutylamino)azetidine-1-carbonyl)-4-fluorobenzyl) phthalazin-1(2H)-one (84 mg, 90%).

Step 2: Preparation of 4-(3-(3-(cyclobutyl(methyl) amino)azetidine-1-carbonyl)-4-fluorobenzyl) phthalazin-1(2H)-one This compound was made using the procedure described for example 60 (Step 2). Thus, this intermediate compound (Step 1)(84 mg, 0.21 mmol) was reacted with $K_2CO_3$ (57 mg, 0.41 mmol) and iodomethane (25 uL, 0.41 mmol) to afford the title compound (82 mg, 93%).

$^1$H-NMR (MeOD, 400 MHz): δ 8.36 (d, 1H), 7.93 (d, 1H), 7.79-7.89 (m, 2H), 7.48-7.54 (m, 1H), 7.42 (d, 1H), 7.15 (t, 1H), 4.37 (s, 2H), 4.08-4.18 (m, 1H), 3.98-4.04 (m, 1H), 3.89-3.99 (m, 2H), 3.35-3.43 (m, 1H), 2.80-2.90 (m, 1H), 2.06 (s, 3H), 1.81-1.97 (m, 4H), 1.59-1.72 (m, 2H).

Example 72

4-(3-(3-(cyclopentyl(prop-2-yn-1-yl)amino)azetidine-1-carbonyl)-4-fluorobenzyl)phthalazin-1(2H)-one; (I-72)

Step 1: Preparation of 4-(3-(3-(cyclopentylamino) azetidine-1-carbonyl)-4-fluorobenzyl)phthalazin-1 (2H)-one This compound was made using the procedure described for example 60 (Step 1). Thus, 4-(3-(3-aminoazetidine-1-carbonyl)-4-fluorobenzyl)phthalazin-1(2H)-one (example 3)(100 mg, 0.23 mmol) was reacted with cyclopentanone (20 uL, 0.23 mmol) and sodium triacetoxyborohydride (114 mg, 0.54 mmol) to afford the intermediate compound 4-(3-(3-(cyclopentylamino)azetidine-1-carbonyl)-4-fluorobenzyl)phthalazin-1(2H)-one (74 mg, 77%).

Step 2: Preparation of 4-(3-(3-(cyclopentyl(prop-2-yn-1-yl)amino)azetidine-1-carbonyl)-4-fluorobenzyl) phthalazin-1(2H)-one This compound was made using the procedure described for example 60 (Step 2). Thus, this intermediate compound (Step 1)(74 mg, 0.18 mmol) was reacted with $K_2CO_3$ (49 mg, 0.35 mmol) and 1N solution of propargyl bromide in toluene (0.35 mL, 0.35 mmol) to afford the title compound (67 mg, 81%).

$^1$H-NMR (CDCl$_3$, 400 MHz): δ 10.32 (s, 1H), 8.48-8.46 (m, 1H), 7.80-7.71 (m, 3H), 7.51-7.48 (m, 1H), 7.33-7.29 (m, 1H), 7.01 (t, 1H), 4.29-4.25 (m, 3H), 4.12-3.99 (m, 3H), 3.81-3.74 (m, 1H), 3.52-3.39 (m, 2H), 2.96-2.89 (m, 1H), 2.16 (m, 1H), 1.83-1.51 (m, 6H), 1.41-1.30 (m, 2H)

Example 73

4-(3-(3-(3,3-difluoropyrrolidin-1-yl)azetidine-1-carbonyl)-4-fluorobenzyl)phthalazin-1(2H)-one; (I-73)

Step 1: Preparation of 4-(4-fluoro-3-(3-oxoazetidine-1-carbonyl)benzyl)phthalazin-1(2H)-one 4-(4-fluoro-3-(3-hydroxyazetidine-1-carbonyl)benzyl) phthalazin-1(2H)-one (example 6)(200 mg, 0.57 mmol) was dissolved in dichloromethane (2.5 mL) and 1,4-dioxane (1 mL). Dess-Mart in periodinane (DMP, 484 mg, 1.14 mmol) was added at 0° C., after stirring at room temperature for 12 h. The reaction mixture added dichloromethane and washed with aqueous sodium hydroxide and water. The combined organic layers were dried over MgSO$_4$, filtered, evaporated in vacuum to afford the intermediate compound 4-(4-fluoro-3-(3-oxoazetidine-1-carbonyl)benzyl)phthalazin-1(2H)-one (162 mg, 81%).

Step 2: Preparation of 4-(3-(3-(3,3-difluoropyrrolidin-1-yl)azetidine-1-carbonyl)-4-fluorobenzyl) phthalazin-1(2H)-one 3,3-difluoropyrrolidine (43 uL, 0.46 mmol) was added to a solution of the intermediate compound (Step 1)(162 mg, 0.46 mmol) in 1,2-dichloroethane/methanol (2 mL/1 mL) and stirred for 30 min then acetic acid (31 uL, 0.54 mmol) and sodium triacetoxyborohydride (227 mg, 1.07 mmol) was added to the reaction mixture at 0° C. and stirred for 12 hours. The reaction mixture was concentrated in vacuum, added 2N NaOH(aq) and extracted into dichloromethane. The combined organic layers were dried over MgSO$_4$, filtered, evaporated in vacuum and purified using silica chromatography to afford the title compound (134 mg, 66%).

$^1$H-NMR (DMSO, 400 MHz): δ 12.62 (s, 1H), 8.26 (d, 1H), 7.99 (d, 1H), 7.90 (t, 1H), 7.84 (t, 1H), 7.45 (d, 2H), 7.23 (t, 1H), 4.33 (s, 2H), 4.11 (m, 1H), 4.07-0.03 (m, 1H), 3.96 (t, 1H), 3.89-3.85 (m, 1H), 3.81-3.78 (m, 1H), 2.90 (t, 2H), 2.69-2.65 (m, 2H), 2.30-2.19 (m, 2H).

Example 74

4-(4-fluoro-3-(3-(4-fluoropiperidin-1-yl)azetidine-1-carbonyl)benzyl)phthalazin-1(2H)-one; (I-74)

Step 1: Preparation of 4-(4-fluoro-3-(3-oxoazetidine-1-carbonyl)benzyl)phthalazin-1(2H)-one This compound was made using the procedure described for example 73 (Step 1) to afford the intermediate compound 4-(4-fluoro-3-(3-oxoazetidine-1-carbonyl)benzyl) phthalazin-1(2H)-one (81 mg, 162%).

Step 2: Preparation of 4-(4-fluoro-3-(3-(4-fluoropiperidin-1-yl)azetidine-1-carbonyl)benzyl)phthalazin-1 (2H)-one This compound was made using the procedure described for example 73 (Step 2). Thus, this intermediate compound (Step 1)(162 mg, 0.46 mmol) was reacted with 4-fluoropiperidine (43 uL, 0.46 mmol) and sodium triacetoxyborohydride (227 mg, 1.07 mmol) to afford the title compound (145 mg, 72%).

$^1$H-NMR (DMSO, 400 MHz): δ 12.61 (s, 1H), 8.26 (d, 1H), 7.99 (d, 1H), 7.89 (t, 1H), 7.83 (t, 1H), 7.48-7.42 (m, 2H), 7.22 (t, 1H), 4.78-4.60 (m, 1H), 4.33 (s, 2H), 4.05-4.01 (m, 1H), 3.91 (t, 1H), 3.81-3.77 (m, 1H), 3.74-3.70 (m, 1H), 2.41-2.31 (m, 2H), 2.25-2.12 (m, 2H), 1.91-1.77 (m, 2H), 1.75-1.64 (m, 2H).

Example 75

4-(3-([1,3'-biazetidine]-1'-carbonyl)-4-fluorobenzyl)phthalazin-1(2H)-one; (I-75)

Step 1: Preparation of 4-(4-fluoro-3-(3-oxoazetidine-1-carbonyl)benzyl)phthalazin-1(2H)-one This compound was made using the procedure described for example 73 (Step 1) to afford the intermediate compound 4-(4-fluoro-3-(3-oxoazetidine-1-carbonyl)benzyl)phthalazin-1(2H)-one (81 mg, 162%).

Step 2: Preparation of 4-(3-([1,3'-biazetidine]-1'-carbonyl)-4-fluorobenzyl)phthalazin-1(2H)-one This compound was made using the procedure described for example 73 (Step 2). Thus, this intermediate compound (Step 1)(162 mg, 0.46 mmol) was reacted with azetidine (28 uL, 0.46 mmol) and sodium triacetoxyborohydride (227 mg, 1.07 mmol) to afford the title compound (113 mg, 74%).

$^1$H-NMR (DMSO, 400 MHz): δ 12.61 (s, 1H), 8.26 (d, 1H), 7.78 (d, 1H), 7.89 (t, 1H), 7.83 (t, 1H), 7.45 (m, 2H), 7.22 (t, 1H), 4.33 (d, 2H), 4.11 (m, 1H), 3.97 (t, 1H), 3.87 (t, 1H), 3.68 (m, 1H), 3.60 (t, 1H), 3.10 (m, 4H), 1.95 (t, 2H).

Example 76

4-(4-fluoro-3-(3-(pyrrolidin-1-yl)azetidine-1-carbonyl)benzyl)phthalazin-1(2H)-one; (I-76)

Step 1: Preparation of 4-(4-fluoro-3-(3-oxoazetidine-1-carbonyl)benzyl)phthalazin-1(2H)-one This compound was made using the procedure described for example 73 (Step 1) to afford the intermediate compound 4-(4-fluoro-3-(3-oxoazetidine-1-carbonyl)benzyl)phthalazin-1(2H)-one (81 mg, 162%).

Step 2: Preparation of 4-(4-fluoro-3-(3-(pyrrolidin-1-yl)azetidine-1-carbonyl)benzyl)phthalazin-1(2H)-one This compound was made using the procedure described for example 73 (Step 2). Thus, this intermediate compound (Step 1)(162 mg, 0.46 mmol) was reacted with pyrrolidine (38 uL, 0.46 mmol) and sodium triacetoxyborohydride (227 mg, 1.07 mmol) to afford the title compound (159 mg, 85%).

$^1$H-NMR (MeOD, 400 MHz): δ 8.37-8.35 (m, 1H), 7.94 (d, 1H), 7.98 (d, 1H), 7.92-7.82 (m, 2H), 7.48-7.42 (m, 2H), 7.22 (t, 1H), 4.34 (s, 2H), 4.07-4.03 (m, 1H), 3.94 (t, 1H), 3.85-3.81 (m, 1H), 3.76-3.73 (m, 1H), 3.27-3.23 (m, 1H), 2.38 (d, 4H), 1.69 (s, 4H).

Example 77

4-(4-fluoro-3-(3-(piperidin-1-yl)azetidine-1-carbonyl)benzyl)phthalazin-1(2H)-one; (I-77)

Step 1: Preparation of 4-(4-fluoro-3-(3-oxoazetidine-1-carbonyl)benzyl)phthalazin-1(2H)-one This compound was made using the procedure described for example 73 (Step 1) to afford the intermediate compound 4-(4-fluoro-3-(3-oxoazetidine-1-carbonyl)benzyl)phthalazin-1(2H)-one (81 mg, 162%).

Step 2: Preparation of 4-(4-fluoro-3-(3-(piperidin-1-yl)azetidine-1-carbonyl)benzyl)phthalazin-1(2H)-one This compound was made using the procedure described for example 73 (Step 2). Thus, this intermediate compound (Step 1)(162 mg, 0.46 mmol) was reacted with piperidine (43 uL, 0.46 mmol) and sodium triacetoxyborohydride (227 mg, 1.07 mmol) to afford the title compound (162 mg, 85%).

$^1$H-NMR (DMSO, 400 MHz): δ 12.62 (s, 1H), 8.25 (d, 1H), 8.01 (d, 1H), 7.88 (t, 1H), 7.82 (t, 1H), 7.48-7.39 (m, 2H), 7.21 (t, 1H), 4.33 (s, 2H), 4.10-4.08 (m, 1H), 3.95 (t, 1H), 3.85 (t, 1H), 3.69-3.65 (m, 1H), 3.61-3.55 (m, 1H), 2.42 (t, 4H), 1.55-1.49 (m, 6H).

Example 78

4-(4-fluoro-3-(3-(4-methylpiperazin-1-yl)azetidine-1-carbonyl)benzyl)phthalazin-1(2H)-one; (I-78)

Step 1: Preparation of 4-(4-fluoro-3-(3-oxoazetidine-1-carbonyl)benzyl)phthalazin-1(2H)-one This compound was made using the procedure described for example 73 (Step 1) to afford the intermediate compound 4-(4-fluoro-3-(3-oxoazetidine-1-carbonyl)benzyl)phthalazin-1(2H)-one (81 mg, 162%).

Step 2: Preparation of 4-(4-fluoro-3-(3-(4-methylpiperazin-1-yl)azetidine-1-carbonyl)benzyl)phthalazin-1(2H)-one This compound was made using the procedure described for example 73 (Step 2). Thus, this intermediate compound (Step 1)(162 mg, 0.46 mmol) was reacted with 1-methylpiperazine (50 uL, 0.46 mmol) and sodium triacetoxyborohydride (227 mg, 1.07 mmol) to afford the title compound (90 mg, 45%).

$^1$H-NMR (MeOD, 400 MHz): δ 8.37-8.35 (m, 1H), 7.95-7.93 (m, 1H), 7.89-7.81 (m, 2H), 7.57-7.40 (m, 2H), 7.15 (t, 1H), 4.38 (s, 2H), 4.21-4.02 (m, 2H), 3.97-3.82 (m, 2H), 3.65 (m, 1H), 2.94-2.80 (m, 6H), 2.59 (s, 3H).

Example 79

4-(4-fluoro-3-(3-(phenylamino)azetidine-1-carbonyl)benzyl)phthalazin-1(2H)-one; (I-79)

Step 1: Preparation of 4-(4-fluoro-3-(3-oxoazetidine-1-carbonyl)benzyl)phthalazin-1(2H)-one This compound was made using the procedure described for example 73 (Step 1) to afford the intermediate compound 4-(4-fluoro-3-(3-oxoazetidine-1-carbonyl)benzyl) phthalazin-1(2H)-one (81 mg, 162%).

Step 2: Preparation of 4-(4-fluoro-3-(3-(phenylamino)azetidine-1-carbonyl)benzyl)phthalazin-1 (2H)-one This compound was made using the procedure described for example 73 (Step 2). Thus, this intermediate compound (Step 1)(162 mg, 0.46 mmol) was reacted with aniline (42 uL, 0.46 mmol), titanium(IV) epoxide (Ti[OCH$_2$(CH$_3$)$_4$], 96 mL, 46 mmol) and sodium triacetoxyborohydride (227 mg, 1.0 mmol) to afford the title compound (43 mg, 22%).

$^1$H-NMR (DMSO, 400 MHz): δ 12.60 (s, 1H), 8.25 (d, 1H), 7.97 (d, 1H), 7.89 (t, 1H), 7.82 (t, 1H), 7.41 (m, 1H), 7.33 (m, 1H), 7.23 (t, 1H), 7.06 (t, 2H), 6.59 (d, 2H), 6.51 (t, 1H), 4.38 (m, 1H), 4.33 (s, 2H), 4.28-4.19 (m, 2H), 3.80 (dd, 1H), 3.70 (m, 1H).

Example 80

4-(4-fluoro-3-(3-((1-(trifluoromethyl)cyclopropyl) amino)azetidine-1-carbonyl)benzyl)phthalazin-1 (2H)-one; (I-80)

Step 1: Preparation of 4-(4-fluoro-3-(3-oxoazetidine-1-carbonyl)benzyl)phthalazin-1(2H)-one This compound was made using the procedure described for example 73 (Step 1) to afford the intermediate compound 4-(4-fluoro-3-(3-oxoazetidine-1-carbonyl)benzyl) phthalazin-1(2H)-one (81 mg, 162%).

Step 2: Preparation of 4-(4-fluoro-3-(3-((1-(trifluoromethyl)cyclopropyl)amino)azetidine-1-carbonyl) benzyl)phthalazin-1(2H)-one This compound was made using the procedure described for example 73 (Step 2). Thus, this intermediate compound (Step 1)(162 mg, 0.46 mmol) was reacted with 1-(trifluoromethyl)cyclopropylamine (74 mg, 0.46 mmol) and sodium triacetoxyborohydride (227 mg, 1.07 mmol) to afford the title compound (51 mg, 24%).

$^1$H-NMR (MeOD, 400 MHz): δ 8.25 (d, 1H), 7.83 (d, 1H), 7.71-7.76 (m, 2H), 7.33-7.39 (m, 1H), 7.31-7.40 (m, 1H), 7.03 (t, 1H), 4.25 (s, 2H), 4.20-4.26 (m, 1H), 4.01-4.06 (m, 1H), 3.66-3.80 (m, 3H), 0.97-0.99 (m, 2H), 0.81-0.83 (m, 2H).

Example 81

4-(4-fluoro-3-(3-(prop-2-yn-1-ylamino)azetidine-1-carbonyl)benzyl)phthalazin-1(2H)-one; (I-81)

Step 1: Preparation of 4-(4-fluoro-3-(3-oxoazetidine-1-carbonyl)benzyl)phthalazin-1(2H)-one This compound was made using the procedure described for example 73 (Step 1) to afford the intermediate compound 4-(4-fluoro-3-(3-oxoazetidine-1-carbonyl)benzyl) phthalazin-1(2H)-one (81 mg, 162%).

Step 2: Preparation of 4-(4-fluoro-3-(3-(prop-2-yn-1-ylamino)azetidine-1-carbonyl)benzyl)phthalazin-1 (2H)-one This compound was made using the procedure described for example 73 (Step 2). Thus, this intermediate compound (Step 1)(162 mg, 0.46 mmol) was reacted with propargylamine (29 uL, 0.46 mmol) and sodium triacetoxyborohydride (227 mg, 1.07 mmol) to afford the title compound (134 mg, 66%).

$^1$H-NMR (CDCl$_3$, 400 MHz): δ 10.40 (s, 1H), 8.48-8.46 (m, 1H), 7.79-7.71 (m, 3H), 7.52-7.50 (m, 1H), 7.32-7.30 (m, 1H), 7.02 (t, 1H), 4.43-4.38 (m, 1H), 4.28 (s, 2H), 4.23-4.20 (m, 1H), 4.00-3.93 (m, 1H), 3.88-3.85 (m, 2H), 3.42 (q, 2H), 2.21 (m, 1H).

Example 82

(S)-4-(4-fluoro-3-(3-((1-methoxypropan-2-yl)amino) azetidine-1-carbonyl)benzyl)phthalazin-1(2H)-one; (I-82)

Step 1: Preparation of 4-(4-fluoro-3-(3-oxoazetidine-1-carbonyl)benzyl)phthalazin-1(2H)-one This compound was made using the procedure described for example 73 (Step 1) to afford the intermediate compound 4-(4-fluoro-3-(3-oxoazetidine-1-carbonyl)benzyl) phthalazin-1(2H)-one (81 mg, 162%).

Step 2: Preparation of (S)-4-(4-fluoro-3-(3-((1-methoxypropan-2-yl)amino)azetidine-1-carbonyl) benzyl)phthalazin-1(2H)-one This compound was made using the procedure described for example 73 (Step 2). Thus, this intermediate compound (Step 1)(162 mg, 0.46 mmol) was reacted with (S)-1-methoxypropane-2-amine (48 uL, 0.46 mmol) and sodium triacetoxyborohydride (227 mg, 1.07 mmol) to afford the title compound (125 mg, 64%).

$^1$H-NMR (MeOD, 400 MHz): δ 8.38-8.35 (m, 1H), 7.95-7.93 (m, 1H), 7.89-7.82 (m, 2H), 7.52-7.50 (m, 1H), 7.45-7.43 (m, 1H), 7.14 (t, 1H), 4.38 (s, 2H), 4.12-4.10 (m, 1H), 4.18-4.15 (m, 1H), 3.84-3.77 (m, 3H), 3.22-3.19 (m, 1H), 2.89-2.87 (m, 1H), 2.03 (s, 3H), 1.00 (t, 3H).

Example 83

(R)-4-(4-fluoro-3-(3-((1-ethoxypropan-2-yl)amino) azetidine-1-carbonyl)benzyl)phthalazin-1(2H)-one; (I-83)

Step 1: Preparation of 4-(4-fluoro-3-(3-oxoazetidine-1-carbonyl)benzyl)phthalazin-1(2H)-one This compound was made using the procedure described for example 73 (Step 1) to afford the intermediate compound 4-(4-fluoro-3-(3-oxoazetidine-1-carbonyl)benzyl) phthalazin-1(2H)-one (81 mg, 162%).

Step 2: Preparation of (R)-4-(4-fluoro-3-(3-((1-methoxypropan-2-yl)amino)azetidine-1-carbonyl) benzyl)phthalazin-1(2H)-one This compound was made using the procedure described for example 73 (Step 2). Thus, this intermediate compound (Step 1)(162 mg, 0.46 mmol) was reacted with (R)-1-methoxypropane-2-amine (48 uL, 0.4 mmol) and sodium triacetoxyborohydride (227 mg, 1.07 mmol) to afford the title compound (125 mg, 64%).

$^1$H-NMR (MeOD, 400 MHz): δ 8.38-8.35 (m, 1H), 7.95-7.93 (m, 1H), 7.89-7.82 (m, 2H), 7.52-7.50 (m, 1H), 7.45-7.43 (m, 1H), 7.14 (t, 1H), 4.38 (s, 2H), 4.12-4.10 (m, 1H), 4.18-4.15 (m, 1H), 3.84-3.77 (m, 3H), 3.22-3.19 (m, 1H), 2.89-2.87 (m, 1H), 2.03 (s, 3H), 1.00 (t, 3H).

Example 84

4-(4-fluoro-3-(3-((1-(hydroxymethyl)cyclopropyl) amino)azetidine-1-carbonyl)benzyl)phthalazin-1 (2H)-one; (I-84)

Step 1: Preparation of 4-(4-fluoro-3-(3-oxoazetidine-1-carbonyl)benzyl)phthalazin-1(2H)-one This compound was made using the procedure described for example 73 (Step 1) to afford the intermediate compound 4-(4-fluoro-3-(3-oxoazetidine-1-carbonyl)benzyl) phthalazin-1(2H)-one (81 mg, 162%).

Step 2: Preparation of 4-(4-fluoro-3-(3-((1-(hydroxymethyl)cyclopropyl)amino)azetidine-1-carbonyl)benzyl)phthalazin-1(2H)-one This compound was made using the procedure described for example 73 (Step 2). Thus, this intermediate compound (Step 1)(162 mg, 0.46 mmol) was reacted with (1-aminocyclopropyl)methanol (40 mg, 0.46 mmol) and sodium triacetoxyborohydride (227 mg, 1.07 mmol) to afford the title compound (84 mg, 43%).
$^1$H-NMR (MeOD, 400 MHz): δ 8.35-8.34 (m, 1H), 7.95-7.82 (m, 3H), 7.51-7.44 (m, 2H), 7.13 (t, 1H), 4.37-4.33 (m, 3H), 4.19-4.17 (m, 1H), 3.90-3.86 (m, 3H), 1.29-1.27 (m, 1H), 0.57-0.54 (m, 2H), 0.52-0.50 (m, 2H).

Example 85

4-(4-fluoro-3-(3-((1-methylcyclopropyl)amino)azetidine-1-carbonyl)benzyl)phthalazin-1(2H)-one; (I-85)

Step 1: Preparation of 4-(4-fluoro-3-(3-oxoazetidine-1-carbonyl)benzyl)phthalazin-1(2H)-one This compound was made using the procedure described for example 73 (Step 1) to afford the intermediate compound 4-(4-fluoro-3-(3-oxoazetidine-1-carbonyl)benzyl) phthalazin-1(2H)-one (81 mg, 162%).

Step 2: Preparation of 4-(4-fluoro-3-(3-((1-methylcyclopropyl)amino)azetidine-1-carbonyl)benzyl) phthalazin-1(2H)-one This compound was made using the procedure described for example 73 (Step 2). Thus, this intermediate compound (Step 1)(162 mg, 0.46 mmol) was reacted with 1-methylcyclopropanamine (43 uL, 0.46 mmol) and sodium triacetoxyborohydride (227 mg, 1.07 mmol) to afford the title compound (35 mg, 19%).
$^1$H-NMR (MeOD, 400 MHz): δ 8.36 (d, 1H), 7.93 (d, 1H), 7.80-7.86 (m, 2H), 7.42-7.52 (m, 2H), 7.14 (t, 1H), 4.32-4.37 (m, 3H), 4.16 (t, 1H), 3.78-3.88 (m, 3H), 1.29 (s, 3H), 0.51-0.57 (m, 2H, 0.33-0.39 (m, 2H).

Example 86

(R)-4-(3-(3-((3,3-dimethylbutan-2-yl)amino)azetidine-1-carbonyl)-4-fluorobenzyl)phthalazin-1(2H)-one; (I-86)

Step 1: Preparation of 4-(4-fluoro-3-(3-oxoazetidine-1-carbonyl)benzyl)phthalazin-1(2H)-one This compound was made using the procedure described for example 73 (Step 1) to afford the intermediate compound 4-(4-fluoro-3-(3-oxoazetidine-1-carbonyl)benzyl) phthalazin-1(2H)-one (81 mg, 162%).

Step 2: Preparation of (R)-4-(3-(3-((3,3-dimethylbutan-2-yl)amino)azetidine-1-carbonyl)-4-fluorobenzyl)phthalazin-1(2H)-one This compound was made using the procedure described for example 73 (Step 2). Thus, this intermediate compound (Step 1)(162 mg, 0.46 mmol) was reacted with (R)-3,3-dimethylbutan-2-amine (55 uL, 0.46 mmol) and sodium triacetoxyborohydride (227 mg, 1.07 mmol) to afford the title compound (110 mg, 55%).
$^1$H-NMR (MeOD, 400 MHz): δ 8.39 (d, 1H), 7.87-8.38 (m, 3H), 7.43-7.53 (m, 2H), 7.17 (t, 1H), 4.41 (s, 2H), 4.28-4.40 (m, 1H), 4.09-4.18 (m, 1H), 3.71-3.90 (m, 3H), 2.17-2.27 (m, 1H), 0.94-0.98 (m, 12H).

Example 87

(S)-4-(3-(3-((3,3-dimethylbutan-2-yl)amino)azetidine-1-carbonyl)-4-fluorobenzyl)phthalazin-1(2H)-one; (I-87)

Step 1: Preparation of 4-(4-fluoro-3-(3-oxoazetidine-1-carbonyl)benzyl)phthalazin-1(2H)-one This compound was made using the procedure described for example 73 (Step 1) to afford the intermediate compound 4-(4-fluoro-3-(3-oxoazetidine-1-carbonyl)benzyl) phthalazin-1(2H)-one (81 mg, 162%).

Step 2: Preparation of (S)-4-(3-(3-((3,3-dimethylbutan-2-yl)amino)azetidine-1-carbonyl)-4-fluorobenzyl)phthalazin-1(2H)-one This compound was made using the procedure described for example 73 (Step 2). Thus, this intermediate compound (Step 1)(162 mg, 0.46 mmol) was reacted with (S)-3,3-dimethylbutan-2-amine (55 uL, 0.46 mmol) and sodium triacetoxyborohydride (227 mg, 1.07 mmol) to afford the title compound (110 mg, 55%).
$^1$H-NMR (CDCl$_3$, 400 MHz): δ 10.28 (d, 1H), 8.48-8.46 (m, 1H), 7.79-7.70 (m, 3H), 7.50 (d, 1H), 7.32-7.28 (m, 1H), 7.01 (t, 1H), 4.43-4.32 (m, 1H), 4.27 (s, 2H), 4.21-4.09 (m, 1H), 3.84-3.70 (m, 3H), 2.26-2.14 (m, 1H), 0.96-0.90 (m, 3H), 0.88-0.86 (dd, 9H).

Example 88

(R)-4-(4-fluoro-3-(3-((3-ethylbutan-2-yl)amino)azetidine-1-carbonyl)benzyl)phthalazin-1(2H)-one; (I-88)

Step 1: Preparation of 4-(4-fluoro-3-(3-oxoazetidine-1-carbonyl)benzyl)phthalazin-1(2H)-one This compound was made using the procedure described for example 73 (Step 1) to afford the intermediate compound 4-(4-fluoro-3-(3-oxoazetidine-1-carbonyl)benzyl) phthalazin-1(2H)-one (81 mg, 162%).

Step 2: Preparation of (R)-4-(4-fluoro-3-(3-((3-methylbutan-2-yl)amino)azetidine-1-carbonyl)benzyl)phthalazin-1(2H)-one This compound was made using the procedure described for example 73 (Step 2). Thus, this intermediate compound (Step 1)(162 mg, 0.46 mmol) was reacted with (R)-3-methylbutan-2-amine (53 uL, 0.46 mmol) and sodium triacetoxyborohydride (227 mg, 1.07 mmol) to afford the title compound (113 mg, 58%).

$^1$H-NMR (MeOD, 400 MHz): δ 8.39 (d, 1H), 7.83-8.38 (m, 3H), 7.44-7.52 (m, 2H), 7.17 (t, 1H), 4.63 (brs, 2H), 4.40 (s, 2H), 3.76-3.86 (m, 3H), 2.44-2.46 (m, 1H), 1.64-1.67 (m, 1H), 0.86-0.96 (m, 9H).

Example 89

(S)-4-(4-fluoro-3-(3-((3-methylbutan-2-yl)amino)azetidine-1-carbonyl)benzyl)phthalazin-1(2H)-one; (I-89)

Step 1: Preparation of 4-(4-fluoro-3-(3-oxoazetidine-1-carbonyl)benzyl)phthalazin-1(2H)-one This compound was made using the procedure described for example 73 (Step 1) to afford the intermediate compound 4-(4-fluoro-3-(3-oxoazetidine-1-carbonyl)benzyl)phthalazin-1(2H)-one (81 mg, 162%).

Step 2: Preparation of (S)-4-(4-fluoro-3-(3-((3-methylbutan-2-yl)amino)azetidine-1-carbonyl)benzyl)phthalazin-1(2H)-one This compound was made using the procedure described for example 73 (Step 2). Thus, this intermediate compound (Step 1)(162 mg, 0.46 mmol) was reacted with (S)-3-methylbutan-2-amine (53 uL, 0.46 mmol) and sodium triacetoxyborohydride (227 mg, 1.07 mmol) to afford the title compound (113 mg, 58%).

$^1$H-NMR (CDCl$_3$, 400 MHz): δ 10.61 (s, 1H), 8.48-8.46 (m, 1H), 7.80-7.71 (m, 3H), 7.53-7.47 (m, 1H), 7.32-7.30 (m, 1H), 7.01 (t, 1H), 4.38 (m, 1H), 4.28 (s, 2H), 4.15 (m, 1H), 3.84-3.71 (m, 3H), 2.45 (m, 1H), 1.59 (m, 1H), 0.94-0.83 (m, 9H).

Example 90

4-(4-fluoro-3-(3-((1-(methoxymethyl)cyclopropyl)amino)azetidine-1-carbonyl)benzyl)phthalazin-1(2H)-one; (I-90)

Step 1: Preparation of 4-(4-fluoro-3-(3-oxoazetidine-1-carbonyl)benzyl)phthalazin-1(2H)-one This compound was made using the procedure described for example 73 (Step 1) to afford the intermediate compound 4-(4-fluoro-3-(3-oxoazetidine-1-carbonyl)benzyl)phthalazin-1(2H)-one (81 mg, 162%).

Step 2: Preparation of 4-(4-fluoro-3-(3-((1-(methoxymethyl)cyclopropyl)amino)azetidine-1-carbonyl)benzyl)phthalazin-1(2H)-one This compound was made using the procedure described for example 73 (Step 2). Thus, the intermediate compound (Step 1)(162 mg, 0.46 mmol) was reacted with 1-(methoxymethyl)cyclopropanamine (46 mg, 0.46 mmol), and sodium triacetoxyborohydride (227 mg, 1.07 mmol) to afford the title compound (78 mg, 39%)

$^1$H-NMR (MeOD, 400 MHz): δ 8.37-8.35 (m, 1H), 7.95-7.93 (m, 1H), 7.89-7.82 (m, 2H), 7.50-7.43 (m, 2H), 7.16-7.13 (m, 1H), 4.37 (s, 2H), 7.36-7.33 (m, 1H), 7.15-7.14 (m, 1H), 3.87-3.82 (m, 3H), 3.31 (s, 3H), 1.29 (br, 2H), 0.60-0.59 (m, 2H), 0.53-0.51 (m, 2H).

Example 91

4-(3-(3-(but-3-yn-1-ylamino)azetidine-1-carbonyl)-4-fluorobenzyl)phthalazin-1(2H)-one; (I-91)

Step 1: Preparation of 4-(4-fluoro-3-(3-oxoazetidine-1-carbonyl)benzyl)phthalazin-1(2H)-one This compound was made using the procedure described for example 73 (Step 1) to afford the intermediate compound 4-(4-fluoro-3-(3-oxoazetidine-1-carbonyl)benzyl)phthalazin-1(2H)-one (81 mg, 162%).

Step 2: Preparation of 4-(3-(3-(but-3-yn-1-ylamino)azetidine-1-carbonyl)-4-fluorobenzyl)phthalazin-1(2H)-one This compound was made using the procedure described for example 73 (Step 2). Thus, the intermediate compound (Step 1)(162 mg, 0.46 mmol) was reacted with but-3-yn-1-amine (38 uL, 0.46 mmol), and sodium triacetoxyborohydride (227 mg, 1.07 mmol) to afford the title compound (145 mg, 78%).

$^1$H-NMR (MeOD, 400 MHz): δ 8.38-8.35 (m, 1H), 7.94-7.82 (m, 3H), 7.52-7.43 (m, 2H), 7.17-7.14 (m, 1H), 4.37 (s, 2H), 4.32-4.29 (m, 1H), 4.15-4.13 (m, 1H), 3.88-3.69 (m, 3H), 2.69-2.66 (m, 2H), 2.34-2.31 (m, 3H).

Example 92

4-(4-fluoro-3-(3-((2-ethylallyl)amino)azetidine-1-carbonyl)benzyl)phthalazin-1(2H)-one; (I-92)

Step 1: Preparation of 4-(4-fluoro-3-(3-oxoazetidine-1-carbonyl)benzyl)phthalazin-1(2H)-one This compound was made using the procedure described for example 73 (Step 1) to afford the intermediate compound 4-(4-fluoro-3-(3-oxoazetidine-1-carbonyl)benzyl)phthalazin-1(2H)-one (81 mg, 162%).

Step 2: Preparation of 4-(4-fluoro-3-(3-((2-methylallyl)amino)azetidine-1-carbonyl)benzyl)phthalazin-1(2H)-one This compound was made using the procedure described for example 73 (Step 2). Thus, the intermediate compound (Step 1)(162 mg, 0.46 mmol) was reacted with 2-methylprop-2-en-1-amine (35 uL, 0.46 mmol), and sodium triacetoxyborohydride (227 mg, 1.07 mmol) to afford the title compound (83 mg, 45%).

$^1$H-NMR (MeOD, 400 MHz): δ 8.38 (d, 1H), 8.36 (d, 1H), 7.81-7.95 (m, 2H), 7.44-7.50 (m, 1H), 7.11-7.17 (m, 1H), 4.38 (brs, 2H), 4.26-4.30 (m, 1H), 4.11-4.13 (m, 1H), 3.85-3.88 (m, 1H), 3.76-3.78 (m, 1H), 3.66-3.69 (m, 1H), 3.34 (s, 2H), 3.08 (s, 2H), 1.25 (s, 3H).

Example 93

4-(4-fluoro-3-(3-((3-hydroxy-2,2-dimethylpropyl)amino)azetidine-1-carbonyl)benzyl)phthalazin-1(2H)-one; (I-93)

Step 1: Preparation of 4-(4-fluoro-3-(3-oxoazetidine-1-carbonyl)benzyl)phthalazin-1(2H)-one This compound was made using the procedure described for example 73 (Step 1) to afford the intermediate compound 4-(4-fluoro-3-(3-oxoazetidine-1-carbonyl)benzyl) phthalazin-1(2H)-one (81 mg, 162%).

Step 2: Preparation of 4-(4-fluoro-3-(3-((3-hydroxy-2,2-dimethylpropyl)amino)azetidine-1-carbonyl) benzyl)phthalazin-1(2H)-one This compound was made using the procedure described for example 73 (Step 2). Thus, the intermediate compound (Step 1)(162 mg, 0.46 mmol) was reacted with 3-amino-2, 2-dimethylpropan-1-ol (47 mg, 0.46 mmol), and sodium triacetoxyborohydride (227 mg, 1.07 mmol) to afford the title compound (24 mg, 12%).

$^1$H-NMR (CDCl$_3$, 400 MHz): δ 11.53 (br, 1H), 8.46 (m, 1H), 7.78-7.72 (m, 3H), 7.51-7.49 (m, 1H), 7.34-7.29 (m, 1H), 7.01 (t, 1H), 4.36-4.32 (m, 3H), 4.18-4.10 (m, 1H), 3.90-3.78 (m, 2H), 3.67 (m, 1H), 2.53-2.45 (m, 5H), 0.93 (s, 3H), 0.91 (s, 3H).

Example 94

1-(((1-(2-fluoro-5-((4-oxo-3,4-dihydrophthalazin-1-yl)ethyl)benzoyl)azetidin-3-yl)amino)methyl)cyclopropanecarbonitrile; (I-94)

Step 1: Preparation of 4-(4-fluoro-3-(3-oxoazetidine-1-carbonyl)benzyl)phthalazin-1(2H)-one This compound was made using the procedure described for example 73 (Step 1) to afford the intermediate compound 4-(4-fluoro-3-(3-oxoazetidine-1-carbonyl)benzyl) phthalazin-1(2H)-one (81 mg, 162%).

Step 2: Preparation of 1-(((1-(2-fluoro-5-((4-oxo-3, 4-dihydrophthalazin-1-yl)methyl)benzoyl)azetidin-3-yl)amino)methyl)cyclopropanecarbonitrile This compound was made using the procedure described for example 73 (Step 2). Thus, the intermediate compound (Step 1)(162 mg, 0.46 mmol) was reacted with 1-(aminomethyl)cyclopropanecarbonitrile (44 mg, 0.46 mmol), and sodium triacetoxyborohydride (227 mg, 1.07 mmol) to afford the title compound (91 mg, 46%).

$^1$H-NMR (MeOD, 400 MHz): δ 8.38 (dd, 1H), 8.00 (d, 1H), 7.83-7.92 (m, 2H), 7.54-7.62 (m, 2H), 7.14 (t, 1H), 4.41 (s, 2H), 4.28-4.36 (m, 1H), 4.14-4.18 (m, 1H), 3.71-3.81 (m, 3H), 1.35 (s, 4H).

Example 95

4-(4-fluoro-3-(3-((2,2,2-tri fluoroethyl)amino)azetidine-1-carbonyl)benzyl)phthalazin-1(2H)-one; (I-95)

Step 1: Preparation of 4-(4-fluoro-3-(3-oxoazetidine-1-carbonyl)benzyl)phthalazin-1(2H)-one This compound was made using the procedure described for example 73 (Step 1) to afford the intermediate compound 4-(4-fluoro-3-(3-oxoazetidine-1-carbonyl)benzyl) phthalazin-1(2H)-one (81 mg, 162%).

Step 2: Preparation of 4-(4-fluoro-3-(3-((2,2,2-trifluoroethyl)amino)azetidine-1-carbonyl)benzyl) phthalazin-1(2H)-one This compound was made using the procedure described for example 73 (Step 2). Thus, the intermediate compound (Step 1)(162 mg, 0.46 mmol) was reacted with 2,2,2-trifluoroethaneamine (36 uL, 0.46 mmol), and sodium triacetoxyborohydride (227 mg, 1.07 mmol) to afford the title compound (200 mg, 60%).

$^1$H-NMR (MeOD, 400 MHz): δ 8.38-8.35 (m, 1H), 7.95-7.92 (m, 1H), 7.89-7.82 (m, 2H), 7.52-7.50 (m, 1H), 7.45-7.43 (m, 1H), 7.17-7.12 (m, 1H), 4.37 (s, 2H), 4.30-4.28 (m, 1H), 4.16-4.14 (m, 1H), 3.86-3.83 (m, 1H), 3.78-3.76 (m, 1H), 3.68-3.66 (m, 1H), 2.90-2.83 (m, 2H).

Example 96

(R)-4-(4-fluoro-3-(3-(pyrrolidin-3-ylamino)azetidine-1-carbonyl)benzyl)phthalazin-1(2H)-one; (I-96)

Step 1: Preparation of 4-(4-fluoro-3-(3-oxoazetidine-1-carbonyl)benzyl)phthalazin-1(2H)-one This compound was made using the procedure described for example 73 (Step 1) to afford the intermediate compound 4-(4-fluoro-3-(3-oxoazetidine-1-carbonyl)benzyl) phthalazin-1(2H)-one (81 mg, 162%).

Step 2: Preparation of (R)-tert-butyl-3-((1-(2-fluoro-5-((4-oxo-3,4-dihydrophthalazin-1-yl)methyl)benzoyl)azetidine-3-yl)amino)pyrrolidin-1-carboxylate The intermediate compound (Step 1, 162 mg, 0.46 mmol) was added to a solution of (R)-tert-butyl-3-aminopyrrolidin-1-carboxylate (25 uL, 0.46 mmol) in dichloromethane (3 mL), methanol (1 mL) and stirred for 30 min then acetic acid (36 uL, 0.69 mmol) and sodium triacetoxyborohydride (144 mg, 0.69 mmol) was added to the reaction mixture at 0° C. and stirred for 12 hours. The reaction mixture was concentrated in vacuo, added 2N NaOH(aq) and extracted into dichloromethane. The combined organic layers were dried over MgSO$_4$, filtered, evaporated in vacuo and purified using silica chromatography to afford (R)-tert-butyl-3-((1-(2-fluoro-5-((4-oxo-3,4-dihydrophthalazin-1-yl)methyl) benzoyl)azetidine-3-yl)amino)pyrrolidin-1-carboxylate (122 mg, 43%).

Step 3: Preparation of (R)-4-(4-fluoro-3-(3-(pyrrolidin-3-ylamino)azetidine-1-carbonyl)benzyl) phthalazin-1(2H)-one The intermediate compound (Step 2)(122 mg, 0.20 mmol) in dichloromethane (4 mL) cooled to 0° C. was added 1.0 N HCl solution (0.40 mL, 0.40 mmol), and the mixture was stirred at room temperature for 3 h. The react ion mixture was concentrated in vacuo, added dichloromethane and washed with 2N NaOH(aq) and water. The combined organic layers were dried over MgSO$_4$, filtered, evaporated in vacuo and purified using silica chromatography to afford the title compound (76 mg, 90%).

$^1$H-NMR (MeOD, 400 MHz): δ 8.38-8.36 (m, 1H), 7.95-7.83 (m, 3H), 7.54 (m, 1H), 7.44-7.42 (m, 1H), 7.25 (t, 1H), 4.38 (s, 2H), 4.35-4.33 (m, 1H), 4.19-4.17 (m, 1H), 3.78-3.77 (m, 1H), 3.74-3.71 (m, 2H), 3.36-3.21 (m, 2H), 3.17-3.08 (m, 2H), 2.09-1.99 (m, 1H), 1.82-1.79 (m, 1H), 1.28 (s, 1H).

Example 97

(S)-4-(4-fluoro-3-(3-(pyrrolidin-3-ylamino)azetidine-1-carbonyl)benzyl)phthalazin-1(2H)-one; (I-97)

Step 1: Preparation of 4-(4-fluoro-3-(3-oxoazetidine-1-carbonyl)benzyl)phthalazin-1(2H)-one This compound was made using the procedure described for example 73 (Step 1) to afford the intermediate compound 4-(4-fluoro-3-(3-oxoazetidine-1-carbonyl)benzyl) phthalazin-1(2H)-one (81 mg, 162%).

Step 2: Preparation of (S)-tert-butyl-3-((1-(2-fluoro-5-((4-oxo-3,4-dihydrophthalazin-1-yl)methyl)benzoyl)azetidine-3-yl)amino)pyrrolidin-1-carboxylate This compound was made using the procedure described for example 96 (Step 2). Thus, the intermediate compound (Step 1)(162 mg, 0.46 mmol) was reacted with (S)-tert-butyl-3-aminopyrrolidin-1-carboxylate (25 uL, 0.46 mmol), and sodium triacetoxyborohydride (144 mg, 0.69 mmol) to afford the title compound (122 mg, 43%).

Step 3: Preparation of (S)-4-(4-fluoro-3-(3-(pyrrolidin-3-ylamino)azetidine-1-carbonyl)benzyl) phthalazin-1(2H)-one This compound was made using the procedure described for example 96 (Step 3). Thus, the intermediate compound (Step 2)(122 mg, 0.20 mmol) was reacted with 1.0 N HCl solution (0.40 mL, 0.40 mmol)) to afford the title compound (76 mg, 90%).
$^1$H-NMR (MeOD, 400 MHz): δ 8.38-8.36 (m, 1H), 7.95-7.83 (m, 3H), 7.54 (m, 1H), 7.44-7.42 (m, 1H), 7.25 (t, 1H), 4.38 (s, 2H), 4.35-4.33 (m, 1H), 4.19-4.17 (m, 1H), 3.78-3.77 (m, 1H), 3.74-3.71 (m, 2H), 3.36-3.21 (m, 2H), 3.17-3.08 (m, 2H), 2.09-1.99 (m, 1H), 1.82-1.79 (m, 1H), 1.28 (s, 1H).

Example 98

1-((1-(2-fluoro-5-((4-oxo-3,4-dihydrophthalazin-1-yl)ethyl)benzoyl)azetidin-3-yl)amino)cyclopentanecarbonitrile; (I-98)

Step 1: Preparation of 1-((1-(2-fluoro-5-((4-oxo-3,4-dihydrophthalazin-1-yl)methyl)benzoyl)azetidin-3-yl)amino)cyclopentanecarbonitrile Cyclopentanone (79 uL, 1.17 mmol) was added to a solution of 4-(3-(3-aminoazetidine-1-carbonyl)-4-fluorobenzyl)phthalazin-1(2H)-one (200 mg, 1.17 mmol) in 1,2-dichloroethane (6 mL) and stirred for 30 min then acetic acid (67 uL, 1.17 mmol) and trimethylsilyl cyanide (0.30 mL, 2.34 mmol) was added to the reaction mixture at 0° C. and stirred for 12 hours. The reaction mixture was concentrated in vacuo, added 2N NaOH(aq) and extracted into dichloromethane. The combined organic layers were dried over MgSO$_4$, filtered, evaporated in vacuo and purified using silica chromatography to afford the title compound (328 mg, 63%).
$^1$H-NMR (MeOD, 400 MHz): δ 8.36 (m, 1H), 7.93-7.79 (m, 3H), 7.51-7.43 (m, 2H), 7.14 (t, 1H), 4.43-4.39 (m, 1H), 4.36 (s, 2H), 4.25 (m, 1H), 3.96-3.91 (m, 3H), 2.10-2.02 (m, 2H), 1.86-1.76 (m, 6H).

Example 99

1-((1-(2-fluoro-5-((4-oxo-3,4-dihydrophthalazin-1-yl)ethyl)benzoyl)azetidin-3-yl)amino)cyclobutanecarbonitrile; (I-99)

Step 1: Preparation of 1-((1-(2-fluoro-5-((4-oxo-3,4-dihydrophthalazin-1-yl)methyl)benzoyl)azetidin-3-yl)amino)cyclobutanecarbonitrile This compound was made using the procedure described for example 98 (Step 1). Thus, 4-(3-(3-aminoazetidine-1-carbonyl)-4-fluorobenzyl)phthalazin-1(2H)-one (example 3)(200 mg, 1.17 mmol) was reacted with cyclobutanone (87 uL, 1.17 mmol), trimethylsilyl cyanide (0.30 mL, 2.34 mmol) to afford the title compound (293 mg, 58%).
$^1$H-NMR (MeOD, 400 MHz): δ 8.35 (m, 1H), 7.92-7.78 (m, 3H), 7.50-7.43 (m, 2H), 7.13 (t, 1H), 4.41-4.39 (m, 1H), 4.36 (s, 2H), 4.23 (m, 1H), 3.98-3.92 (m, 2H), 3.85-3.78 (m, 1H), 2.48-2.41 (m, 2H), 2.20-2.02 (m, 2H).

Example 100

2-((1-(2-fluoro-5-((4-oxo-3,4-dihydrophthalazin-1-yl)methyl)benzoyl)azetidin-3-yl)amino)propanenitrile; (I-100)

Step 1: Preparation of 2-((1-(2-fluoro-5-((4-oxo-3,4-dihydrophthalazin-1-yl)methyl)benzoyl)azetidin-3-yl)amino)propanenitrile This compound was made using the procedure described for example 98 (Step 1). Thus, 4-(3-(3-aminoazetidine-1-carbonyl)-4-fluorobenzyl)phthalazin-1(2H)-one (example 3)(200 mg, 1.17 mmol) was reacted with acetaldehyde (70 uL, 1.17 mmol), trimethylsilyl cyanide (0.30 mL, 2.34 mmol) to afford the title compound (336 mg, 71%).
$^1$H-NMR (MeOD, 400 MHz): δ 8.36 (m, 1H), 7.94-7.79 (m, 3H), 7.50-7.44 (m, 2H), 7.14 (t, 1H), 4.41-4.17 (m, 4H), 4.00-3.93 (m, 1H), 3.89-3.66 (m, 3H), 1.42 (d, 3H).

Example 101

2-((1-(2-fluoro-5-((4-oxo-3,4-dihydrophthalazin-1-yl)methyl)benzoyl)azetidin-3-yl)amino)butanenitrile; (I-101)

Step 1: Preparation of 2-((1-(2-fluoro-5-((4-oxo-3,4-dihydrophthalazin-1-yl)methyl)benzoyl)azetidin-3-yl)amino)butanenitrile This compound was made using the procedure described for example 98 (Step 1). Thus, 4-(3-(3-aminoazetidine-1-carbonyl)-4-fluorobenzyl)phthalazin-1(2H)-one (example 3, 200 mg, 1.17 mmol) was reacted with propionaldehyde (84 uL, 1.17 mmol), trimethylsilyl cyanide (0.30 mL, 2.34 mmol) to afford the title compound (294 mg, 60%).
$^1$H-NMR (MeOD, 400 MHz): δ 8.35 (m, 1H), 7.94-7.80 (m, 3H), 7.49-7.44 (m, 2H), 7.14 (t, 1H), 4.40-4.16 (m, 4H), 4.00-3.91 (m, 1H), 3.88-3.76 (m, 2H), 3.61-3.50 (m, 1H), 1.79-1.68 (m, 2H), 1.08-1.01 (m, 3H).

Example 102

2-((1-(2-fluoro-5-((4-oxo-3,4-dihydrophthalazin-1-yl)methyl)benzoyl)azetidin-3-yl)amino)-3-ethylbutanenitrile; (I-102)

Step 1: Preparation of 2-((1-(2-fluoro-5-((4-oxo-3,4-dihydrophthalazin-1-yl)methyl)benzoyl)azetidin-3-yl)amino)-3-methylbutanenitrile This compound was made using the procedure described for example 98 (Step 1). Thus, 4-(3-(3-aminoazetidine-1-carbonyl)-4-fluorobenzyl)phthalazin-1(2H)-one (example 3)(200 mg, 1.17 mmol) was reacted with isobutylaldehyde (0.1 mL, 1.17 mmol), trimethylsilyl cyanide (0.30 mL, 2.34 mmol) to afford the title compound (294 mg, 58%).

¹H-NMR (MeOD, 400 MHz): δ 8.34 (m, 1H), 7.92-7.78 (m, 3H), 7.49-7.44 (m, 2H), 7.13 (t, 1H), 4.39-4.15 (m, 4H), 4.02-3.96 (m, 1H), 3.88-3.76 (m, 2H), 3.46-3.39 (dd, 1H), 1.93 (m, 1H), 1.04-0.87 (m, 6H).

Example 103

2-cyclopropyl-2-((1-(2-fluoro-5-((4-oxo-3,4-dihydrophthalazin-1-yl)methyl)benzoyl)azetidin-3-yl) amino)acetonitrile; (I-103)

Step 1: Preparation of 2-cyclopropyl-2-((1-(2-fluoro-5-((4-oxo-3,4-dihydrophthalazin-1-yl)methyl) benzoyl)azetidin-3-yl)amino)acetonitrile This compound was made using the procedure described for example 98 (Step 1). Thus, 4-(3-(3-aminoazetidine-1-carbonyl)-4-fluorobenzyl)phthalazin-1(2H)-one (example 3)(200 mg, 1.17 mmol) was reacted with cyclopropancabaldehyde (79 uL, 1.17 mmol), trimethylsilyl cyanide (0.30 mL, 2.34 mmol) to afford the title compound (409 mg, 81%).

¹H-NMR (MeOD, 400 MHz): δ 8.35 (m, 1H), 7.93-7.78 (m, 3H), 7.50-7.44 (m, 2H), 7.13 (t, 1H), 4.40-4.17 (m, 4H), 4.01-3.79 (m, 3H), 3.42-3.37 (dd, 1H), 1.17 (m, 1H), 0.65-0.42 (m, 4H).

Example 104

4-(4-fluoro-3-(3-((1-(trifluoromethyl)cyclobutyl) amino)azetidine-1-carbonyl)benzyl)phthalazin-1 (2H)-one; (I-104)

Step 1: Preparation of 4-(4-fluoro-3-(3-((1-(trifluoromethyl)cyclobutyl)amino)azetidine-1-carbonyl) benzyl)phthalazin-1(2H)-one This compound was made using the procedure described for example 98 (Step 1). Thus, 4-(3-(3-aminoazetidine-1-carbonyl)-4-fluorobenzyl)phthalazin-1(2H)-one (example 3)(200 mg, 1.17 mmol) was reacted with cyclobutanone (79 uL, 1.17 mmol), trifluoromethyltrimethylsilane (0.30 mL, 2.34 mmol) to afford the title compound (328 mg, 63%).

¹H-NMR (MeOD, 400 MHz): δ 8.26 (d, 1H), 7.72-7.84 (m, 3H), 7.34-7.41 (m, 2H), 7.04 (t, 1H), 7.71-7.76 (m, 2H), 7.33-7.39 (m, 1H), 7.31-7.40 (m, 1H), 7.03 (t, 1H), 4.25 (s, 2H), 4.20-4.26 (m, 1H), 4.01-4.06 (m, 1H), 3.66-3.80 (m, 3H), 0.97-0.99 (m, 2H), 0.81-0.83 (m, 2H).

Example 105

(S)-4-(4-fluoro-3-(3-(methyl(pyrimidin-2-yl)amino) pyrrolidine-1-carbonyl)benzyl)phthalazin-1(2H)-one; (I-105)

Step 1: Preparation of (S)-4-fluoro-3-(3-(methyl (pyrimidin-2-yl)amino)pyrrolidine-1-carbonyl)benzaldehyde This compound was made using the procedure described for example 11 (Step 1). Thus, (S)—N-methyl-N-(pyrrolidin-3-yl)pyrimidine-2-amine (200 mg, 1.12 mmol) was reacted with 2-fluoro-5-formylbenzoic acid (188 mg, 1.12 mmol), O-(benzotriazole-1-yl)-N,N,N',N'-tetramethyluronium hexafluorophosphate (HBTU, 553 mg, 1.46 mmol), N,N-diisopropyl ethylamine (DIPEA, 0.40 mL, 2.24 mmol) to afford (S)-4-fluoro-3-(3-(methyl(pyrimidin-2-yl)amino) pyrrolidine-1-carbonyl)benzaldehyde (154 mg, 43%).

Step 2: Preparation of (S,Z)-3-(4-fluoro-3-(3-(methyl(pyrimidin-2-yl)amino)pyrrolidine-1-carbonyl)benzylidene)isobenzofuran-1(3H)-one This compound was made using the procedure described for example 11 (Step 2). Thus, the intermediate compound (Step 1)(154 mg, 0.47 mmol) was reacted with dimethyl(3-oxo-1,3-dihydroisobenzofuran-1-yl)phosphonate (114 mg, 0.47 mmol), triethylamine (98 uL, 0.47 mmol) to afford intermediate compound (S,Z)-3-(4-fluoro-3-(3-(methyl(pyrimidin-2-yl)amino)pyrrolidine-1-carbonyl)benzylidene) isobenzofuran-1(3H)-one (107 mg, 51%).

Step 3: Preparation of (S)-4-(4-fluoro-3-(3-(methyl (pyrimidin-2-yl)amino)pyrrolidine-1-carbonyl)benzyl)phthalazin-1(2H)-one)

This compound was made using the procedure described for example 11 (Step 3). Thus, the intermediate compound (Step 2)(107 mg, 0.24 mmol) was reacted with hydrazine monohydrate (23 uL, 0.48 mmol) to afford title compound (55 mg, 50%).

¹H-NMR (CDCl₃, 400 MHz): δ 9.96 (d, 1H), 8.45 (m, 1H), 8.43 (dd, 2H), 7.75 (m, 3H), 7.39 (m, 1H), 7.31 (m, 1H), 7.02 (m, 1H), 6.52 (q, 1H), 5.53 (m, 1H), 4.26 (d, 2H), 3.93 (m, 1H), 3.66 (m, 1H), 3.44 (m, 1H), 3.27 (m, 1H), 3.10 (s, 1.3H), 3.04 (s, 1.7H), 2.21 (m, 1H), 2.06 (m, 1H).

Example 106

(S)-4-(4-fluoro-3-(3-(methyl(pyrimidin-2-yl)amino) pyrrolidine-1-carbonyl)benzyl)phthalazin-1(2H)-one; (I-106)

Step 1: Preparation of (S)-4-fluoro-3-(3-(methyl (pyrimidin-2-yl)amino)pyrrolidine-1-carbonyl)benzaldehyde This compound was made using the procedure described for example 11 (Step 1). Thus, (S)—N-ethyl-N-(pyrrolidin-3-yl)pyrimidine-2-amine (200 mg, 1.12 mmol) was reacted with 2-fluoro-5-formylbenzoic acid (175 mg, 1.04 mmol), O-(benzotriazole-1-yl)-N,N,N,N-tetramethyluronium hexafluorophosphate (HBTU, 512 mg, 1.35 mmol), N,N-diisopropyl ethylamine (DIPEA, 0.36 mL, 2.08 mmol) to afford (S)-4-fluoro-3-(3-(methyl(pyrimidin-2-yl)amino)pyrrolidine-1-carbonyl)benzaldehyde (149 mg, 42%).

Step 2: Preparation of (S,Z)-3-(4-fluoro-3-(3-(methyl(pyrimidin-2-yl)amino)pyrrolidine-1-carbonyl)benzylidene)isobenzofuran-1(3H)-one This compound was made using the procedure described for example 11 (Step 2). Thus, intermediate compound (Step 1)(149 mg, 0.43 mmol) was dimethyl(3-oxo-1,3-dihydroisobenzofuran-1-yl)phosphate (105 mg, 0.43 mmol), triethylamine (92 uL, 0.66 mmol) to afford (S,Z)-3-(4-fluoro-3-(3-(methyl(pyrimidin-2-yl)amino)pyrrolidine-1-carbonyl) benzylidene)isobenzofuran-1(3H)-one (102 mg, 51%).

Step 3: Preparation of (S)-4-(3-(3-(methyl(pyrimidin-2-yl)amino)pyrrolidine-1-carbonyl)-4-fluorobenzyl)phthalazin-1(2H)-one This compound was made using the procedure described for example 11 (Step 3). Thus, the intermediate compound (Step 2)(102 mg, 0.22 mmol) was reacted with hydrazine monohydrate (21 uL, 0.45 mmol) to afford title compound (53 mg, 50%).

$^1$H-NMR (CDCl$_3$, 400 MHz): δ 10.63 (d, 1H), 8.49 (m, 1H), 8.32 (dd, 2H), 7.73 (m, 3H), 7.39 (m, 1H), 7.28 (m, 1H), 7.02 (m, 1H), 6.50 (m, 1H), 5.13 (dt, 1H), 4.29 (d, 2H), 3.95 (m, 1H), 3.58 (m, 2H), 3.46 (m, 2H), 3.27 (m, 1H), 2.23 (m, 1H), 2.09 (m, 1H), 1.93 (dt, 3H).

Example 107

4-(4-fluoro-3-(3-(methyl(pyrimidin-2-yl)amino)azetidine-1-carbonyl)benzyl)phthalazin-1(2H)-one; (I-107)

Step 1: Preparation of 4-fluoro-3-(3-(methyl(pyrimidin-2-yl)amino)azetidine-1-carbonyl)benzaldehyde This compound was made using the procedure described for example 11 (Step 1). Thus, N-(azetidin-3-yl)-N-methylpyrimidine-2-amine (200 mg, 1.12 mmol) was reacted with 2-fluoro-5-formylbenzoic acid (204 mg, 1.22 mmol), O-(benzotriazole-1-yl)-N,N,N',N'-tetramethyluronium hexafluorophosphate (HBTU, HBTU, 600 mg, 1.58 mmol), N,N-diisopropyl ethylamine (DIPEA, 0.42 mL, 2.44 mmol) to afford 4-fluoro-3-(3-(methyl(pyrimidin-2-yl)amino)azetidine-1-carbonyl)benzaldehyde (149 mg, 42%).

Step 2: Preparation of (Z)-3-(4-fluoro-3-(3-(methyl(pyrimidin-2-yl)amino)azetidine-1-carbonyl)benzylidene)isobenzofuran-1(3H)-one This compound was made using the procedure described for example 11 (Step 2). Thus, the intermediate compound (Step 1)(202 mg, 0.65 mmol) was reacted with dimethyl(3-oxo-1,3-dihydroisobenzofuran-1-yl)phosphonate (156 mg, 0.65 mmol), triethylamine (0.13 mL, 0.96 mmol) to afford intermediate compound (Z)-3-(4-fluoro-3-(3-(methyl(pyrimidin-2-yl)amino)azetidine-1-carbonyl)benzylidene)isobenzofuran-1(3H)-one (169 mg, 61%).

Step 3: Preparation of 4-(4-fluoro-3-(3-(methyl(pyrimidin-2-yl)amino)azetidine-1-carbonyl)benzyl)phthalazin-1(2H)-one This compound was made using the procedure described for example 11 (Step 3). Thus, the intermediate compound (Step 2)(169 mg, 0.39 mmol) was reacted with hydrazine monohydrate (38 uL, 0.79 mmol) to afford title compound (89 mg, 51%).

$^1$H-NMR (CDCl$_3$, 400 MHz): δ 8.53 (dd, 1H), 8.31 (d, 2H), 7.80-7.70 (m, 3H), 7.54 (dd, 1H), 7.34-7.30 (m, 1H), 7.10-7.03 (m, 1H), 6.55 (t, 1H), 5.48-5.41 (m, 1H), 4.52-4.45 (m, 1H), 4.39-4.27 (m, 4H), 4.23-4.12 (m, 1H), 3.21 (s, 3H).

Example 108

4-(4-fluoro-3-(3-(methyl(pyrimidin-2-yl)amino)azetidine-1-carbonyl)benzyl)phthalazin-1(2H)-one; (I-108)

Step 1: Preparation of 4-fluoro-3-(3-(methyl(pyrimidin-2-yl)amino)azetidine-1-carbonyl)benzaldehyde This compound was made using the procedure described for example 11 (Step 1). Thus, N-(azetidin-3-yl)-N-ethylpyrimidine-2-amine (200 mg, 1.12 mmol) was reacted with 2-fluoro-5-formylbenzoic acid (188 mg, 1.12 mmol), O-(benzotriazole-1-yl)-N,N,N',N'-tetramethyluronium hexafluorophosphate (HBTU, 553 mg, 1.45 mmol), N,N-diisopropyl ethylamine (DIPEA, 0.39 mL, 2.24 mmol) to afford 4-fluoro-3-(3-(methyl(pyrimidin-2-yl)amino)azetidine-1-carbonyl)benzaldehyde (195 mg, 53%).

Step 2: Preparation of (Z)-3-(4-fluoro-3-(3-(methyl(pyrimidin-2-yl)amino)azetidine-1-carbonyl)benzylidene)isobenzofuran-1(3H)-one This compound was made using the procedure described for example 11 (Step 2). Thus, the intermediate compound (Step 1)(195 mg, 0.59 mmol) was reacted with dimethyl(3-oxo-1,3-dihydroisobenzofuran-1-yl)phosphonate (144 mg, 0.59 mmol), triethylamine (0.12 mL, 0.89 mmol) to afford intermediate compound (Z)-3-(4-fluoro-3-(3-(methyl(pyrimidin-2-yl)amino)azetidine-1-carbonyl)benzylidene)isobenzofuran-1(3H)-one (161 mg, 61%).

Step 3: Preparation of 4-(4-fluoro-3-(3-(methyl(pyrimidin-2-yl)amino)azetidine-1-carbonyl)benzyl)phthalazin-1(2H)-one This compound was made using the procedure described for example 11 (Step 3). Thus, the intermediate compound (Step 2)(161 mg, 0.36 mmol) was reacted with hydrazine monohydrate (36 uL, 0.73 mmol) to afford title compound (84 mg, 51%).

$^1$H-NMR (CDCl$_3$, 400 MHz): δ 8.53 (dd, 1H), 8.31 (d, 2H), 7.80-7.70 (m, 3H), 7.54 (dd, 1H), 7.34-7.30 (m, 1H), 7.10-7.03 (m, 1H), 6.55 (t, 1H), 5.09-5.01 (m, 1H), 4.55-4.46 (m, 1H), 4.44-4.28 (m, 4H), 4.20-4.13 (m, 1H), 3.82-3.63 (m, 2H), 1.18 (t, 3H).

Example 109

4-(4-fluoro-3-(3-(pyrimidin-2-yl amino)azetidine-1-carbonyl)benzyl)phthalazin-1(2H)-one; (I-109)

Step 1: Preparation of 4-fluoro-3-(3-(pyrimidin-2-ylamino)azetidine-1-carbonyl)benzaldehyde This compound was made using the procedure described for example 11 (Step 1). Thus, N-(azetidin-3-yl)-pyrimidine-2-amine (220 mg, 1.46 mmol) was reacted with 2-fluoro-5-formylbenzoic acid (246 mg, 1.46 mmol), O-(benzotriazole-1-yl)-N,N,N',N'-tetramethyluronium hexafluorophosphate (HBTU, 722 mg, 1.90 mmol), N,N-diisopropyl ethylamine (DIPEA, 0.51 mL, 2.93 mmol) to afford 4-fluoro-3-(3-(pyrimidin-2-ylamino)azetidine-1-carbonyl)benzaldehyde (233 mg, 53%).

Step 2: Preparation of (Z)-3-(4-fluoro-3-(3-(pyrimidin-2-ylamino)azetidine-1-carbonyl)benzylidene)isofuran-1(3H)-one This compound was made using the procedure described for example 11 (Step 2). Thus, the intermediate compound (Step 1)(233 mg, 0.78 mmol) was reacted with dimethyl(3-oxo-1,3-dihydroisobenzofuran-1-yl)phosphonate (188 mg, 0.78 mmol), triethylamine (0.16 mL, 1.16 mmol) to afford intermediate compound (Z)-3-(4-fluoro-3-(3-(pyrimidin-2-ylamino)azetidine-1-carbonyl)benzylidene)isofuran-1(3H)-one (197 mg, 61%).

Step 3: Preparation of 4-(4-fluoro-3-(3-(pyrimidin-2-ylamino)azetidine-1-carbonyl)benzyl)phthalazin-1(2H)-one This compound was made using the procedure described for example 11 (Step 3). Thus, the intermediate compound (Step 2)(197 mg, 0.47 mmol) was reacted with hydrazine monohydrate (46 uL, 0.95 mmol) to afford title compound (104 mg, 51%).

$^1$H-NMR (DMSO, 400 MHz): δ 7.45 (d, 2H), 7.41 (d, 1H), 7.14 (d, 1H), 7.06-6.96 (m, 3H), 6.63-6.62 (m, 2H), 6.40-6.35 (m, 1H), 5.80 (t, 1H), 3.78-3.70 (m, 1H), 3.49-3.44 (m, 3H), 3.40-3.36 (m, 1H), 3.12-3.08 (m, 1H), 3.05-3.01 (m, 1H).

Example 110

(S)-4-(4-fluoro-3-(3-(pyrimidin-2-ylamino)pyrrolidine-1-carbonyl)benzyl)phthalazin-1(2H)-one; (I-110)

Step 1: Preparation of (S)-4-fluoro-3-(3-(pyrimidin-2-ylamino)pyrrolidine-1-carbonyl)benzaldehyde This compound was made using the procedure described for example 11 (Step 1). Thus, (S)—N-(pyrrolidin-3-yl)pyrimidine-2-amine (300 mg, 1.82 mmol) was reacted with 2-fluoro-5-formylbenzoic acid (307 mg, 1.82 mmol), O-(benzotriazole-1-yl)-N,N,N',N'-tetramethyluronium hexafluorophosphate (HBTU, 900 mg, 2.38 mmol), N,N-diisopropyl ethylamine (DIPEA, 0.64 mL, 3.65 mmol) to afford (S)-4-fluoro-3-(3-(pyrimidin-2-ylamino)pyrrolidine-1-carbonyl)benzaldehyde (252 mg, 44%).

Step 2: Preparation of (S,Z)-3-(4-fluoro-3-(3-(pyrimidin-2-ylamino)pyrrolidine-1-carbonyl)benzylidene)isofuran-1(3H)-one This compound was made using the procedure described for example 11 (Step 2). Thus, the intermediate compound (Step 1)(252 mg, 0.80 mmol) was reacted with dimethyl(3-oxo-1,3-dihydroisobenzofuran-1-yl)phosphonate (195 mg, 0.80 mmol), triethylamine (0.17 mL, 1.20 mmol) to afford intermediate compound (S,Z)-3-(4-fluoro-3-(3-(pyrimidin-2-ylamino)pyrrolidine-1-carbonyl)benzylidene)isofuran-1(3H)-one (138 mg, 40%).

Step 3: Preparation of (S)-4-(4-fluoro-3-(3-(pyrimidin-2-ylamino)pyrrolidine-1-carbonyl)benzyl)phthalazin-1(2H)-one This compound was made using the procedure described for example 11 (Step 3). Thus, the intermediate compound (Step 2)(138 mg, 0.32 mmol) was reacted with hydrazine monohydrate (32 uL, 0.65 mmol) to afford title compound (73 mg, 51%).

$^1$H-NMR (CDCl$_3$, 400 MHz): δ 10.74 (d, 1H), 8.46 (m, 1H), 8.32 (dd, 2H), 7.73 (m, 3H), 7.40 (m, 1H), 7.28 (m, 1H), 7.01 (q, 1H), 6.60 (m, 1H), 5.60 (m, 1H), 4.60 (m, 1H), 4.27 (d, 2H), 4.03 (dd, 0.4H), 3.84 (m, 0.6H), 3.73 (m, 1H), 3.49 (m, 1H), 3.41 (m, 1H), 3.25 (m, 1H), 2.28 (m, 1H), 1.95 (m, 1H).

Example 111

(S)-4-(3-(3-((6-chloropyridazin-3-yl)(methyl)amino)pyrrolidine-1-carbonyl)-4-fluorobenzyl)phthalazin-1(2H)-one; (I-111)

Step 1: Preparation of (S)-3-(3-((6-chloropyridazin-3-yl)(methyl)amino)pyrrolidine-1-carbonyl)-4-fluorobenzaldehyde This compound was made using the procedure described for example 11 (Step 1). Thus, (S)-6-chloro-N-methyl-N-(pyrrolidin-3-yl)pyridazin-3-amine (120 mg, 0.71 mmol) was reacted with 2-fluoro-5-formylbenzoic acid (118 mg, 0.71 mmol), O-(benzotriazole-1-yl)-N,N,N',N'-tetramethyluronium hexafluorophosphate (HBTU, 348 mg, 0.91 mmol), N,N-diisopropyl ethylamine (DIPEA, 0.25 mL, 1.41 mmol) to afford (S)-3-(3-((6-chloropyridazin-3-yl)(methyl)amino)pyrrolidine-1-carbonyl)-4-fluorobenzaldehyde (115 mg, 45%).

Step 2: Preparation of (S,Z)-3-(3-(3-((6-chloropyridazin-3-yl)(methyl)amino)pyrrolidine-1-carbonyl)-4-fluorobenzylidene)isofuran-1(3H)-one This compound was made using the procedure described for example 11 (Step 2). Thus, the intermediate compound (Step 1)(115 mg, 0.31 mmol) was reacted with dimethyl(3-oxo-1,3-dihydroisobenzofuran-1-yl)phosphonate (77 mg, 0.31 mmol), triethylamine (66 uL, 0.48 mmol) to afford intermediate compound (S,Z)-3-(3-(3-((6-chloropyridazin-3-yl)(methyl)amino)pyrrolidine-1-carbonyl)-4-fluorobenzylidene)isofuran-1(3H)-one (85 mg, 56%).

Step 3: Preparation of (S)-4-(3-(3-((6-chloropyridazin-3-yl)(methyl)amino)pyrrolidine-1-carbonyl)-4-fluorobenzyl)phthalazin-1(2H)-one This compound was made using the procedure described for example 11 (Step 3). Thus, the intermediate compound (Step 2)(85 mg, 0.18 mmol) was reacted with hydrazine monohydrate (17 uL, 0.36 mmol) to afford title compound (46 mg, 52%).

$^1$H-NMR (CDCl$_3$, 400 MHz): δ 10.68 (d, 1H), 8.45 (m, 1H), 7.76 (m, 3H), 7.37 (m, 1H), 7.28 (m, 1H), 6.83 (d, 1H), 7.05 (q, 1H), 6.83 (q, 1H), 5.57 (m, 0.4H), 5.39 (m, 0.6H), 4.29 (d, 2H), 3.92 (m, 1H), 3.66 (m, 2H), 3.50 (m, 1H), 3.26 (m, 1H), 2.91 (s, 1.5H), 2.96 (s, 1.5H), 2.24 (m, 2H).

Example 112

(S)-4-(3-(3-((6-chloropyridazin-3-yl)amino)pyrrolidine-1-carbonyl)-4-fluorobenz yl)phthalazin-1(2H)-one; (I-112)

Step 1: Preparation of (S)-3-(3-((6-chloropyridazin-3-yl)amino)pyrrolidine-1-carbonyl)-4-fluorobenzaldehyde This compound was made using the procedure described for example 11 (Step 1). Thus, (S)-6-chloro-N-(pyrrolidin-3-yl)pyridazin-3-amine (200 mg, 1.01 mmol) was reacted with 2-fluoro-5-formylbenzoic acid (169 mg, 1.01 mmol), O-(benzotriazole-1-yl)-N,N,N',N'-tetramethyluronium hexafluorophosphate (HBTU, 496 mg, 1.31 mmol), N,N-diisopropyl ethylamine (DIPEA, 0.35 mL, 2.01 mmol) to afford (S)-3-(3-((6-chloropyridazin-3-yl)amino)pyrrolidine-1-carbonyl)-4-fluorobenzaldehyde (158 mg, 45%).

Step 2: Preparation of (S,Z)-3-(3-(3-((6-chloropyridazin-3-yl)amino)pyrrolidine-1-carbonyl)-4-fluoro benzylidene) isofuran-1(3H)-one This compound was made using the procedure described for example 11 (Step 2). Thus, the intermediate compound (Step 1)(158 mg, 0.45 mmol) was reacted with dimethyl(3-oxo-1,3-dihydroisobenzofuran-1-yl)phosphonate (109 mg, 0.45 mmol), triethylamine (95 uL, 0.68 mmol) to afford intermediate compound (S,Z)-3-(3-(3-((6-chloropyridazin-3-yl)amino)pyrrolidine-1-carbonyl)-4-fluoro benzylidene) isofuran-1(3H)-one (117 mg, 56%).

Step 3: Preparation of (S)-4-(3-(3-((6-chloropyridazin-3-yl)amino)pyrrolidine-1-carbonyl)-4-fluorobenzyl)phthalazin-1(2H)-one This compound was made using the procedure described for example 11 (Step 3). Thus, the intermediate compound (Step 2)(117 mg, 0.25 mmol) was reacted with hydrazine monohydrate (25 uL, 0.50 mmol) to afford title compound (64 mg, 52%).

$^1$H-NMR (CDCl$_3$, 400 MHz): δ 10.83 (d, 1H), 8.41 (m, 1H), 7.72 (m, 3H), 7.35 (m, 1H), 7.02 (m, 2H), 6.67 (dd, 1H), 5.37 (m, 1H), 4.57 (m, 1H), 4.27 (dd, 2H), 3.77 (m, 1H), 3.43 (m, 2H), 3.23 (m, 2H), 2.02 (m, 1H).

Example 113

(S)-4-(4-fluoro-3-(3-(methyl(pyridazin-3-yl)amino)pyrrolidine-1-carbonyl)benzyl)phthalazin-1(2H)-one; (I-113)

Step 1: Preparation of (S)-4-fluoro-3-(3-(methyl(pyridazin-3-yl)amino)pyrrolidine-1-carbonyl)benzaldehyde This compound was made using the procedure described for example 11 (Step 1). Thus, (S)—N-methyl-N-(pyrrolidin-3-yl)pyridazin-3-amine (200 mg, 1.22 mmol) was reacted with 2-fluoro-5-formylbenzoic acid (204 mg, 1.22 mmol), O-(benzotriazole-1-yl)-N,N,N',N'-tetramethyluronium hexafluorophosphate (HBTU, 600 mg, 1.58 mmol), N,N-diisopropyl ethylamine (DIPEA, 0.42 mL, 2.43 mmol) to afford (S)-4-fluoro-3-(3-(methyl(pyridazin-3-yl)amino)pyrrolidine-1-carbonyl)benzaldehyde (172 mg, 45%).

Step 2: Preparation of (S,Z)-3-(4-fluoro-3-(3-(methyl(pyridazin-3-yl)amino)pyrrolidine-1-carbonyl)benzylidene)isofuran-1(3H)-one This compound was made using the procedure described for example 11 (Step 2). Thus, the intermediate compound (Step 1)(172 mg, 0.55 mmol) was reacted with dimethyl(3-oxo-1,3-dihydroisobenzofuran-1-yl)phosphonate (132 mg, 0.55 mmol), triethylamine (0.12 mL, 0.55 mmol) to afford intermediate compound (S,Z)-3-(4-fluoro-3-(3-(methyl(pyridazin-3-yl)amino)pyrrolidine-1-carbonyl)benzylidene)isofuran-1(3H)-one (132 mg, 56%).

Step 3: Preparation of (S)-4-(4-fluoro-3-(3-(methyl(pyridazin-3-yl)amino)pyrrolidine-1-carbonyl)benzyl)phthalazin-1(2H)-one This compound was made using the procedure described for example 11 (Step 3). Thus, the intermediate compound (Step 2)(132 mg, 0.31 mmol) was reacted with hydrazine monohydrate (30 uL, 0.61 mmol) to afford title compound (71 mg, 52%).

$^1$H-NMR (CDCl$_3$, 400 MHz): δ 10.68 (d, 1H), 8.6 (m, 1H), 8.45 (m, 1H), 7.75 (m, 3H), 7.37 (m, 2H), 7.20 (m, 1H), 7.04 (m, 1H), 6.67 (dd, 1H), 4.65 (m, 2H), 4.27 (d, 2H), 3.91 (m, 2H), 3.48 (m, 1H), 3.22 (m, 1H), 2.40 (m, 1H), 2.02 (m, 1H).

Example 114

4-(3-(3-((6-chloropyridazin-3-yl)amino)azetidine-1-carbonyl)-4-fluorobenzyl)phthalazin-1(2)-one; (I-114)

Step 1: Preparation of 3-(3-((6-chloropyridazin-3-yl)amino)azetidine-1-carbonyl)-4-fluorobenzaldehyde This compound was made using the procedure described for example 11 (Step 1). Thus, N-(azetidin-3-yl)-6-chloropyridazin-3-amine (200 mg, 1.08 mmol) was reacted with 2-fluoro-5-formylbenzoic acid (182 mg, 1.08 mmol), O-(benzotriazole-1-yl)-N,N,N',N'-tetramethyluronium hexafluorophosphate (HBTU, 534 mg, 1.40 mmol), N,N-diisopropyl ethylamine (DIPEA, 0.38 mL, 2.17 mmol) to afford 3-(3-((6-chloropyridazin-3-yl)amino)azetidine-1-carbonyl)-4-fluorobenzaldehyde (184 mg, 51%).

Step 2: Preparation of (Z)-3-(3-(3-((6-chloropyridazin-3-yl)amino)azetidine-1-carbonyl)-4-fluorobenzylidene) isofuran-1(3H)-one This compound was made using the procedure described for example 11 (Step 2). Thus, the intermediate compound (Step 1)(184 mg, 0.55 mmol) was reacted with dimethyl(3-oxo-1,3-dihydroisobenzofuran-1-yl)phosphonate (133 mg, 0.55 mmol), triethylamine (0.12 mL, 0.83 mmol) to afford intermediate compound (Z)-3-(3-(3-((6-chloropyridazin-3-yl)amino)azetidine-1-carbonyl)-4-fluorobenz ylidene)isofuran-1(3H)-one (146 mg, 59%).

Step 3: Preparation of 4-(3-(3-((6-chloropyridazin-3-yl)amino)azetidine-1-carbonyl)-4-fluorobenzyl)phthalazin-1(2H)-one This compound was made using the procedure described for example 11 (Step 3). Thus, the intermediate compound (Step 2)(146 mg, 0.33 mmol) was reacted with hydrazine monohydrate (32 uL, 0.66 mmol) to afford title compound (82 mg, 54%).

$^1$H-NMR (CDCl$_3$, 400 MHz): δ 10.16 (s, 1H), 8.47-8.42 (m, 1H), 7.79-7.67 (m, 4H), 7.47 (dd, 1H), 7.35-7.31 (m, 1H), 7.18 (d, 1H), 7.04-6.99 (m, 1H), 6.72 (d, 1H), 5.29-5.25 (m, 1H), 4.87-4.73 (m, 1H), 4.65-4.59 (m, 1H), 4.47-4.43 (m, 1H), 4.31-4.26 (m, 3H), 4.09-4.05 (m, 1H), 3.92-3.88 (m, 1H).

Example 115

4-(3-(3-((6-chloropyridazin-3-yl)(ethyl)amino)azetidine-1-carbonyl)-4-fluorobenzyl) phthalazin-1(2H)-one; (I-115)

Step 1: Preparation of 3-(3-((6-chloropyridazin-3-yl)(methyl)amino)azetidine-1-carbonyl)-4-fluorobenzaldehyde This compound was made using the procedure described for example 11 (Step 1). Thus, N-(azetidin-3-yl)-6-chloro- N-methylpyridazin-3-amine (200 mg, 1.00 mmol) was reacted with 2-fluoro-5-formylbenzoic acid (169 mg, 1.00 mmol), O-(benzotriazole-1-yl)-N,N,N',N'-tetramethyluronium hexafluorophosphate (HBTU, 496 mg, 1.31 mmol), N,N-diisopropyl ethylamine (DIPEA, 0.35 mL, 2.01 mmol) to afford 3-(3-((6-chloropyridazin-3-yl)(methyl)amino)azetidine-1-carbonyl)-4-fluorobenzaldehyde (179 mg, 51%).

Step 2: Preparation of (Z)-3-(3-(3-((6-chloropyridazin-3-yl)(methyl)amino)azetidine-1-carbonyl)-4-fluorobenzylidene) isofuran-1(3H)-one This compound was made using the procedure described for example 11 (Step 2). Thus, the intermediate compound (Step 1)(179 mg, 0.51 mmol) was reacted with dimethyl(3-oxo-1,3-dihydroisobenzofuran-1-yl)phosphonate (124 mg, 0.51 mmol), triethylamine (0.11 mL, 0.77 mmol) to afford intermediate compound (Z)-3-(3-(3-((6-chloropyridazin-3-yl)(methyl)amino)azetidine-1-carbonyl)-4-fluorobenzylidene)isofuran-1(3H)-one (140 mg, 59%).

Step 3: Preparation of 4-(3-(3-((6-chloropyridazin-3-yl)(methyl)amino)azetidine-1-carbonyl)-4-fluorobenzyl) phthalazin-1(2H)-one This compound was made using the procedure described for example 11 (Step 3). Thus, the intermediate compound (Step 2)(140 mg, 0.30 mmol) was reacted with hydrazine monohydrate (30 uL, 0.60 mmol) to afford title compound (78 mg, 54%).
$^1$H-NMR (CDCl$_3$, 400 MHz): δ 10.16 (s, 1H), 8.47-8.42 (m, 1H), 7.79-7.67 (m, 4H), 7.47 (dd, 1H), 7.35-7.31 (m, 1H), 7.18 (d, 1H), 7.04-6.99 (m, 1H), 6.72 (d, 1H), 5.21-5.15 (m, 1H), 4.87-4.73 (m, 1H), 4.65-4.59 (m, 1H), 4.47-4.43 (m, 1H), 4.31-4.26 (m, 3H), 4.09-4.05 (m, 1H), 3.92-3.88 (m, 1H), 3.06 (s, 3H).

Example 116

4-(3-(3-(cyclobutyl(pyrimidin-2-yl)amino)azetidine-1-carbonyl)-4-fluorobenzyl)phthalazin-1(2H)-one; (I-116)

Step 1: Preparation of 3-(3-(cyclobutyl(pyrimidin-2-yl)amino)azetidine-1-carbonyl)-4-fluorobenzaldehyde This compound was made using the procedure described for example 11 (Step 1). Thus, N-(azetidin-3-yl)-N-cyclobutylpyrimidine-2-amine (500 mg, 2.44 mmol) was reacted with 2-fluoro-5-formylbenzoic acid (411 mg, 2.44 mmol), O-(benzotriazole-1-yl)-N,N,N',N'-tetramethyluronium hexafluorophosphate (HBTU, 1.2 g, 3.18 mmol), N,N-diisopropyl ethylamine (DIPEA, 0.86 mL, 4.89 mmol) to afford 3-(3-(cyclobutyl(pyrimidin-2-yl)amino)azetidine-1-carbonyl)-4-fluorobenzaldehyde (442 mg, 51%).

Step 2: Preparation of (Z)-3-(3-(3-(cyclobutyl(pyrimidin-2-yl)amino)azetidine-1-carbonyl)-4-fluorobenzylidene) isofuran-1(3H)-one This compound was made using the procedure described for example 11 (Step 2). Thus, the intermediate compound (Step 1)(442 mg, 1.24 mmol) was reacted with dimethyl(3-oxo-1,3-dihydroisobenzofuran-1-yl)phosphonate (302 mg, 1.24 mmol), triethylamine (0.26 mL, 1.87 mmol) to afford intermediate compound (Z)-3-(3-(3-(cyclobutyl(pyrimidin-2-yl)amino)azetidine-1-carbonyl)-4-fluorobenzylidene)isofuran-1(3H)-one (288 mg, 49%).

Step 3: Preparation of 4-(3-(3-(cyclobutyl(pyrimidin-2-yl)amino)azetidine-1-carbonyl)-4-fluorobenzyl) phthalazin-1(2H)-one This compound was made using the procedure described for example 11 (Step 3). Thus, the intermediate compound (Step 2)(288 mg, 0.62 mmol) was reacted with hydrazine monohydrate (60 uL, 1.22 mmol) to afford title compound (124 mg, 42%).
$^1$H-NMR (CDCl$_3$, 400 MHz): δ 8.46-8.44 (m, 1H), 8.28 (d, 2H), 7.75-7.72 (m, 3H), 7.52-7.49 (m, 1H), 7.36-7.28 (m, 1H), 7.04-6.99 (m, 1H), 6.55 (t, 1H), 4.97-4.90 (m, 1H), 4.82-4.74 (m, 1H), 4.66-4.62 (m, 1H), 4.47-4.43 (m, 1H), 4.31-4.26 (m, 3H), 4.17-4.13 (m, 1H), 2.25-2.01 (m, 5H).

Example 117

4-(4-fluoro-3-(3-(pyridazin-3-ylamino)azetidine-1-carbonyl)benzyl)phthalazin-1(2H)-one; (I-117)

Step 1: Preparation of 4-fluoro-3-(3-(pyridazin-3-ylamino)azetidine-1-carbonyl)benzaldehyde This compound was made using the procedure described for example 11 (Step 1). Thus, N-(azetidin-3-yl)pyridazin-3-amine (200 mg, 1.33 mmol) was reacted with 2-fluoro-5-formylbenzoic acid (224 mg, 1.33 mmol), O-(benzotriazole-1-yl)-N,N,N',N'-tetramethyluronium hexafluorophosphate (HBTU, 656 mg, 1.73 mmol), N,N-diisopropyl ethylamine (DIPEA, 0.46 mL, 2.66 mmol) to afford 4-fluoro-3-(3-(pyridazin-3-ylamino)azetidine-1-carbonyl)benzaldehyde (203 mg, 51%).

Step 2: Preparation of (Z)-3-(4-fluoro-3-(3-(pyridazin-3-ylamino)azetidine-1-carbonyl)benzylidene)isofuran-1(3H)-one This compound was made using the procedure described for example 11 (Step 2). Thus, the intermediate compound (Step 1)(203 mg, 0.68 mmol) was reacted with dimethyl(3-oxo-1,3-dihydroisobenzofuran-1-yl)phosphonate (164 mg, 0.68 mmol), triethylamine (0.14 mL, 1.02 mmol) to afford intermediate compound (Z)-3-(4-fluoro-3-(3-(pyridazin-3-ylamino)azetidine-1-carbonyl)benzylidene)isofuran-1(3H)-one (172 mg, 61%).

Step 3: Preparation of 4-(4-fluoro-3-(3-(pyridazin-3-ylamino)azetidine-1-carbonyl)benzyl)phthalazin-1(2H)-one This compound was made using the procedure described for example 11 (Step 3). Thus, the intermediate compound (Step 2)(172 mg, 0.41 mmol) was reacted with hydrazine monohydrate (40 uL, 0.82 mmol) to afford title compound (93 mg, 52%).
$^1$H-NMR (CDCl$_3$, 400 MHz): δ 10.86 (s, 1H), 8.58-8.57 (m, 1H), 8.44 (d, 1H), 7.78-7.69 (m, 3H), 7.48-7.46 (m, 1H), 7.35-7.31 (m, 1H), 7.18-7.15 (m, 1H), 7.00 (t, 1H), 6.70 (d, 1H), 5.68 (brs, 1H), 4.81-4.74 (m, 1H), 4.61-4.42 (m, 2H), 4.26 (s, 2H), 4.11-4.07 (m, 1H), 3.93-3.90 (m, 1H).

Example 118

(R)-4-(3-(3-((6-chloropyridazin-3-yl)amino)pyrrolidine-1-carbonyl)-4-fluorobenzyl) phthalazin-1(2H)-one; (I-118)

Step 1: Preparation of (R)-3-(3-((6-chloropyridazin-3-yl)amino)pyrrolidine-1-carbonyl)-4-fluorobenzaldehyde This compound was made using the procedure described for example 11 (Step 1). Thus, (R)-6-chloro-N-(pyrrolidin-3-yl)pyridazin-3-amine (200 mg, 1.00 mmol) was reacted with 2-fluoro-5-formylbenzoic acid (169 mg, 1.00 mmol), O-(benzotriazole-1-yl)-N,N,N',N'-tetramethyluronium hexafluorophosphate (HBTU, 496 mg, 1.31 mmol), N,N-diisopropyl ethylamine (DIPEA, 0.35 mL, 2.01 mmol) to afford (R)-3-(3-((6-chloropyridazin-3-yl)amino)pyrrolidine-1-carbonyl)-4-fluorobenzaldehyde (179 mg, 51%).

Step 2: Preparation of (R,Z)-3-(3-(3-((6-chloropyridazin-3-yl)amino)pyrrolidine-1-carbonyl)-4-fluorobenzylidene) isofuran-1(3H)-one This compound was made using the procedure described for example 11 (Step 2). Thus, the intermediate compound (Step 1)(179 mg, 0.51 mmol) was reacted with dimethyl(3-oxo-1,3-dihydroisobenzofuran-1-yl)phosphonate (124 mg, 0.51 mmol), triethylamine (0.1 mL, 0.77 mmol) to afford intermediate compound (R,Z)-3-(3-(3-((6-chloropyridazin-3-yl)amino)pyrrolidine-1-carbonyl)-4-fluoro benzylidene) isofuran-1(3H)-one (146 mg, 61%).

Step 3: Preparation of (R)-4-(3-(3-((6-chloropyridazin-3-yl)amino)pyrrolidine-1-carbonyl)-4-fluorobenzyl) phthalazin-1(2H)-one This compound was made using the procedure described for example 11 (Step 3). Thus, the intermediate compound (Step 2)(146 mg, 0.31 mmol) was reacted with hydrazine monohydrate (30 uL, 0.31 mmol) to afford title compound (78 mg, 52%).

$^1$H-NMR (CDCl$_3$, 400 MHz): δ 10.85 (s, 0.6H), 10.61 (s, 0.4H), 8.43 (m, 1H), 7.79-7.66 (m, 3.5H), 7.32 (m, 1.5H), 7.15-6.98 (m, 2H), 6.69 (d, 0.4H), 6.58 (d, 0.6H), 5.37 (t, 1H), 4.65 (m, 0.4H), 4.58 (m, 0.6H), 4.26 (d, 2H), 3.99-3.83 (m, 1H), 3.79-3.66 (m, 2H), 3.43 (m, 0.5H), 3.25 (dd, 0.5H), 2.32 (m, 1H), 2.04 (m, 1H).

Example 119

(R)-4-(3-(3-((6-chloropyridazin-3-yl)(methyl)amino)pyrrolidine-1-carbonyl)-4-fluorobenzyl) phthalazin-1(2H)-one; (I-119)

Step 1: Preparation of (R)-3-(3-((6-chloropyridazin-3-yl)(methyl)amino)pyrrolidine-1-carbonyl)-4-fluorobenzaldehyde This compound was made using the procedure described for example 11 (Step 1). Thus, (R)-6-chloro-N-methyl-N-(pyrrolidin-3-yl)pyridazin-3-amine (200 mg, 0.94 mmol) was reacted with 2-fluoro-5-formylbenzoic acid (158 mg, 0.94 mmol), 0-(benzotriazole-1-yl)-N,N,N',N'-tetramethyluronium hexafluorophosphate (HBTU, 463 mg, 1.22 mmol), N,N-diisopropyl ethylamine (DIPEA, 0.33 mL, 1.88 mmol) to afford (R)-3-(3-((6-chloropyridazin-3-yl)(methyl)amino)pyrrolidine-1-carbonyl)-4-fluorobenzaldehyde (174 mg, 51%).

Step 2: Preparation of (R,Z)-3-(3-(3-((6-chloropyridazin-3-yl)methyl)amino)pyrrolidine-1-carbonyl)-4-fluorobenzylidene) isofuran-1(3H)-one This compound was made using the procedure described for example 11 (Step 2). Thus, the intermediate compound (Step 1)(174 mg, 0.48 mmol) was reacted with dimethyl(3-oxo-1,3-dihydroisobenzofuran-1-yl)phosphonate (116 mg, 0.48 mmol), triethylamine (0.1 mL, 0.72 mmol) to afford intermediate compound (R,Z)-3-(3-(3-((6-chloropyridazin-3-yl)methyl)amino)pyrrolidine-1-carbonyl)-4-fluorobenzylidene)isofuran-1(3H)-one (140 mg, 61%).

Step 3: Preparation of (R)-4-(3-(3-((6-chloropyridazin-3-yl)(methyl)amino)pyrrolidine-1-carbonyl)-4-fluorobenzyl) phthalazin-1(2H)-one This compound was made using the procedure described for example 11 (Step 3). Thus, the intermediate compound (Step 2)(140 mg, 0.29 mmol) was reacted with hydrazine monohydrate (29 uL, 0.59 mmol) to afford title compound (74 mg, 52%).

$^1$H-NMR (CDCl$_3$, 400 MHz): δ 10.42 (s, 0.6H), 10.29 (s, 0.4H), 8.46 (m, 1H), 7.81-7.70 (m, 3H), 7.38 (m, 1H), 7.34-7.24 (m, 1H), 7.22 (d, 1H), 7.03 (m, 1H), 6.82 (dd, 1H), 5.58 (m, 0.5H), 5.41 (m, 0.5H), 4.29 (s, 0.8H), 4.28 (s, 1.2H), 3.92 (m, 1H), 3.74-3.61 (m, 2H), 3.44 (m, 0.5H), 3.26 (dd, 0.5H), 2.99 (s, 1.2H), 2.94 (s, 1.8H), 2.32-2.04 (m, 2H).

Example 120

(R)-4-(4-fluoro-3-(3-(pyrimidin-2-ylamino)pyrrolidine-1-carbonyl)benzyl)phthalazin-1(2H)-one; (I-120)

Step 1: Preparation of (R)-4-fluoro-3-(3-(pyrimidin-2-ylamino)pyrrolidine-1-carbonyl)benzaldehyde This compound was made using the procedure described for example 11 (Step 1). Thus, (R)—N-(pyrrolidin-3-yl) pyrimidine-2-amine (200 mg, 1.22 mmol) was reacted with 2-fluoro-5-formylbenzoic acid (205 mg, 1.22 mmol), 0-(benzotriazole-1-yl)-N,N,N',N'-tetramethyluronium hexafluorophosphate (HBTU, 600 mg, 1.58 mmol), N,N-diisopropyl ethylamine (DIPEA, 0.42 mL, 2.44 mmol) to afford (R)-4-fluoro-3-(3-(pyrimidin-2-ylamino)pyrrolidine-1-carbonyl)benzaldehyde (195 mg, 51%).

Step 2: Preparation of (R,Z)-3-(4-fluoro-3-(3-(pyrimidin-2-ylamino)pyrrolidine-1-carbonyl)benzylidene) isofuran-1(3H)-one This compound was made using the procedure described for example 11 (Step 2). Thus, the intermediate compound (Step 1)(195 mg, 0.62 mmol) was reacted with dimethyl(3-oxo-1,3-dihydroisobenzofuran-1-yl)phosphonate (150 mg, 0.62 mmol), triethylamine (0.13 mL, 0.94 mmol) to afford intermediate compound (R,Z)-3-(4-fluoro-3-(3-(pyrimidin-2-ylamino)pyrrolidine-1-carbonyl)benzylidene)isofuran-1(3H)-one (163 mg, 61%).

Step 3: Preparation of (R)-4-(4-fluoro-3-(3-(pyrimidin-2-ylamino)pyrrolidine-1-carbonyl)benzyl) phthalazin-1(2H)-one This compound was made using the procedure described for example 11 (Step 3). Thus, the intermediate compound (Step 2)(163 mg, 0.38 mmol) was reacted with hydrazine monohydrate (37 uL, 0.76 mmol) to afford title compound (88 mg, 52%).
$^1$H-NMR (CDCl$_3$, 400 MHz): δ 10.73 (s, 0.6H), 10.51 (s, 0.4H), 8.42 (s, 1H), 8.30 (dd, 2H), 7.78-7.68 (m, 3H), 7.41 (m, 1H), 7.28 (m, 1H), 7.03 (q, 1H), 6.59 (m, 1H), 5.57 (dd, 1H), 4.63 (m, 0.4H), 4.53 (m, 0.6H), 4.27 (s, 0.8H), 4.26 (s, 1.2H), 4.02 (dd, 0.4H), 3.88-3.68 (m, 1.6H), 3.62 (dd, 0.4H), 3.52-3.40 (m, 1H), 3.26 (d, 0.6H), 2.37-2.24 (m, 1H), 2.08-1.95 (m, 1H).

Example 121

(R)-4-(3-(3-(methyl(pyrimidin-2-yl)amino)pyrrolidine-1-carbonyl)-4-fluorobenzyl) phthalazin-1(2H)-one; (I-121)

Step 1: Preparation of (R)-3-(3-(methyl(pyrimidin-2-yl)amino)pyrrolidine-1-carbonyl)-4-fluorobenzaldehyde This compound was made using the procedure described for example 11 (Step 1). Thus, (R)—N-ethyl-N-(pyrrolidin-3-yl)pyrimidine-2-amine (220 mg, 1.14 mmol) was reacted with 2-fluoro-5-formylbenzoic acid (158 mg, 0.94 mmol), 0-(benzotriazole-1-yl)-N,N,N',N'-tetramethyluronium hexafluorophosphate (HBTU, 564 mg, 1.49 mmol), N,N-diisopropyl ethylamine (DIPEA, 0.40 mL, 2.29 mmol) to afford (R)-3-(3-(methyl(pyrimidin-2-yl)amino)pyrrolidine-1-carbonyl)-4-fluorobenzaldehyde (200 mg, 51%).

Step 2: Preparation of (R,Z)-3-(3-(3-(methyl(pyrimidin-2-yl)amino)pyrrolidine-1-carbonyl)-4-fluorobenzylidene) isofuran-1(3H)-one This compound was made using the procedure described for example 11 (Step 2). Thus, the intermediate compound (Step 1)(200 mg, 0.58 mmol) was reacted with dimethyl(3-oxo-1,3-dihydroisobenzofuran-1-yl)phosphonate (141 mg, 0.58 mmol), triethylamine (0.12 mL, 0.87 mmol) to afford intermediate compound (R,Z)-3-(3-(3-(methyl(pyrimidin-2-yl)amino)pyrrolidine-1-carbonyl)-4-fluorobenzylidene)isofuran-1(3H)-one (163 mg, 61%).

Step 3: Preparation of (R)-4-(3-(3-(methyl(pyrimidin-2-yl)amino)pyrrolidine-1-carbonyl)-4-fluorobenzyl) phthalazin-1(2H)-one This compound was made using the procedure described for example 11 (Step 3). Thus, the intermediate compound (Step 2)(163 mg, 0.36 mmol) was reacted with hydrazine monohydrate (34 uL, 0.72 mmol) to afford title compound (87 mg, 52%).
$^1$H-NMR (CDCl$_3$, 400 MHz): δ 10.43 (s, 0.5H), 10.38 (s, 0.5H), 8.47 (m, 1H), 8.30 (m, 2H), 7.81-7.68 (m, 3H), 7.39 (dd, 1H), 7.28 (m, 1H), 7.03 (m, 1H), 6.51 (m, 1H), 5.37-5.18 (m, 1H), 4.29 (s, 0.8H), 4.27 (s, 1.2H), 4.02-3.90 (m, 1H), 3.67-3.53 (m, 2H), 3.52-3.37 (m, 2.5H), 3.27 (t, 0.5H), 2.22 (m, 1H), 2.13 (m, 1H), 1.22 (t, 1.5H), 1.16 (t, 1.5H).

Example 122

(R)-4-(4-fluoro-3-(3-(pyridazin-3-ylamino)pyrrolidine-1-carbonyl)benzyl)phthalazin-1(2H)-one; (I-122)

Step 1: Preparation of (R)-4-fluoro-3-(3-(pyridazin-3-ylamino)pyrrolidine-1-carbonyl)benzaldehyde This compound was made using the procedure described for example 11 (Step 1). Thus, (R)—N-(pyrrolidin-3-yl)pyridazin-3-amine (200 mg, 1.34 mmol) was reacted with 2-fluoro-5-formylbenzoic acid (225 mg, 1.34 mmol), 0-(benzotriazole-1-yl)-N,N,N',N'-tetramethyluronium hexafluorophosphate (HBTU, 660 mg, 1.74 mmol), N,N-diisopropyl ethylamine (DIPEA, 0.47 mL, 2.68 mmol) to afford (R)-4-fluoro-3-(3-(pyridazin-3-ylamino)pyrrolidine-1-carbonyl)benzaldehyde (214 mg, 51%).

Step 2: Preparation of (R,Z)-3-(4-fluoro-3-(3-(pyridazin-3-ylamino)pyrrolidine-1-carbonyl)benzylidene) isofuran-1(3H)-one This compound was made using the procedure described for example 11 (Step 2). Thus, the intermediate compound (Step 1)(214 mg, 0.68 mmol) was reacted with dimethyl(3-oxo-1,3-dihydroisobenzofuran-1-yl)phosphonate (165 mg, 0.68 mmol), triethylamine (0.14 mL, 1.02 mmol) to afford intermediate compound (R,Z)-3-(4-fluoro-3-(3-(pyridazin-3-ylamino)pyrrolidine-1-carbonyl)benzylidene)isofuran-1(3H)-one (179 mg, 61%).

Step 3: Preparation of (R)-4-(4-fluoro-3-(3-(pyridazin-3-ylamino)pyrrolidine-1-carbonyl)benzyl) phthalazin-1(2H)-one This compound was made using the procedure described for example 11 (Step 3). Thus, the intermediate compound (Step 2)(179 mg, 0.42 mmol) was reacted with hydrazine monohydrate (41 uL, 0.84 mmol) to afford title compound (97 mg, 52%).
$^1$H-NMR (CDCl$_3$, 400 MHz): δ 10.88 (s, 0.6H), 10.49 (s, 0.4H), 8.58 (m, 1H), 8.44 (m, 1H), 7.74 (m, 3H), 7.39-7.25 (m, 2H), 7.17 (m, 1H), 7.02 (m, 1H), 6.71 (d, 0.4H), 6.63 (d, 0.6H), 5.30 (m, 0.4H), 5.00 (m, 0.6H), 4.28 (s, 0.8H), 4.26 (s, 1.2H), 4.02 (m, 0.6H), 3.87 (m, 1.4H), 3.79-3.64 (m, 1H), 3.52-3.42 (m, 0.5H), 3.25 (m, 0.5H), 2.43-2.26 (m, 1H), 2.07 (m, 1H).

Example 123

(R)-4-(4-fluoro-3-(3-(methyl(pyridazin-3-yl)amino) pyrrolidine-1-carbonyl)benzyl) phthalazin-1(2H)-one; (I-123)

Step 1: Preparation of (R)-4-fluoro-3-(3-(methyl(pyridazin-3-yl)amino)pyrrolidine-1-carbonyl)benzaldehyde This compound was made using the procedure described for example 11 (Step 1). Thus, (R)—N-methyl-N-(pyrrolidin-3-yl)pyridazin-3-amine (200 mg, 1.12 mmol) was reacted with 2-fluoro-5-formylbenzoic acid (188 mg, 1.12 mmol), O-(benzotriazole-1-yl)-N,N,N',N'-tetramethyluronium hexafluorophosphate (HBTU, 553 mg, 1.46 mmol), N,N-diisopropyl ethylamine (DIPEA, 0.39 mL, 2.24 mmol)

to afford (R)-4-fluoro-3-(3-(methyl(pyridazin-3-yl)amino) pyrrolidine-1-carbonyl)benzaldehyde (187 mg, 51%).

Step 2: Preparation of (R,Z)-3-(4-fluoro-3-(3-(methyl(pyridazin-3-yl)amino)pyrrolidine-1-carbonyl)benzylidene) isofuran-1(3H)-one This compound was made using the procedure described for example 11 (Step 2). Thus, the intermediate compound (Step 1)(187 mg, 0.57 mmol) was reacted with dimethyl(3-oxo-1,3-dihydroisobenzofuran-1-yl)phosphonate (138 mg, 0.57 mmol), triethylamine (0.12 mL, 0.86 mmol) to afford intermediate compound (R,Z)-3-(4-fluoro-3-(3-(methyl (pyridazin-3-yl)amino)pyrrolidine-1-carbonyl)benzylidene) isofuran-1(3H)-one (155 mg, 61%).

Step 3: Preparation of (R)-4-(4-fluoro-3-(3-(methyl (pyridazin-3-yl)amino)pyrrolidine-1-carbonyl)benzyl) phthalazin-1(2H)-one This compound was made using the procedure described for example 11 (Step 3). Thus, the intermediate compound (Step 2)(155 mg, 0.35 mmol) was reacted with hydrazine monohydrate (34 uL, 0.70 mmol) to afford title compound (83 mg, 52%).
$^1$H-NMR (CDCl$_3$, 400 MHz): δ 10.70 (s, 0.6H), 10.25 (s, 0.4H), 8.61 (m, 1H), 8.46 (m, 1H), 7.81-7.70 (m, 3H), 7.39 (m, 1H), 7.33-7.21 (m, 2H), 7.08-6.97 (m, 1H), 6.81 (m, 1H), 5.74 (m, 0.4H), 5.52 (m, 0.6H), 4.29 (s, 0.8H), 4.27 (s, 1.2H), 3.92 (m, 1H), 3.75-3.63 (m, 2H), 3.52-3.39 (m, 0.4H), 3.24 (dd, 0.6H), 2.99 (s, 1.2H), 2.94 (s, 1.8H), 2.25 (m, 1H), 2.08 (m, 1H).

Example 124

(R)-4-(4-fluoro-3-(3-(thiazol-2-ylamino)pyrrolidine-1-carbonyl)benzyl)phthalazin-1(2H)-one; (I-124)

Step 1: Preparation of (R)-4-fluoro-3-(3-(thiazol-2-ylamino)pyrrolidine-1-carbonyl)benzaldehyde This compound was made using the procedure described for example 11 (Step 1). Thus, (R)—N-(pyrrolidine-3-yl) thiazol-2-amine (200 mg, 1.18 mmol) was reacted with 2-fluoro-5-formylbenzoic acid (198 mg, 1.18 mmol), 0-(benzotriazole-1-yl)-N,N,N',N'-tetramethyluronium hexafluorophosphate (HBTU, 582 mg, 1.54 mmol), N,N-diisopropyl ethylamine (DIPEA, 0.42 mL, 2.36 mmol) to afford (R)-4-fluoro-3-(3-(thiazol-2-ylamino)pyrrolidine-1-carbonyl)benzaldehyde (170 m g, 45%).

Step 2: Preparation of (R,Z)-3-(4-fluoro-3-(3-(thiazol-2-ylamino)pyrrolidine-1-carbonyl)benzylidene) isofuran-1(3H)-one This compound was made using the procedure described for example 11 (Step 2). Thus, the intermediate compound (Step 1)(170 mg, 0.53 mmol) was reacted with dimethyl(3-oxo-1,3-dihydroisobenzofuran-1-yl)phosphonate (128 mg, 0.53 mmol), triethylamine (0.11 mL, 0.80 mmol) to afford intermediate compound (R,Z)-3-(4-fluoro-3-(3-(thiazol-2-ylamino)pyrrolidine-1-carbonyl)benzylidene) isofuran-1 (3H)-one (125 mg, 54%).

Step 3: Preparation of (R)-4-(4-fluoro-3-(3-(thiazol-2-ylamino)pyrrolidine-1-carbonyl)benzyl) phthalazin-1(2H)-one This compound was made using the procedure described for example 11 (Step 3). Thus, the intermediate compound (Step 2)(125 mg, 0.29 mmol) was reacted with hydrazine monohydrate (28 uL, 0.57 mmol) to afford title compound (67 mg, 52%).
$^1$H-NMR (MeOD, 400 MHz): δ 8.36 (m, 1H), 7.85 (m, 3H), 7.39 (m, 2H), 7.15 (m, 1H), 6.96 (dd, 1H), 6.58 (dd, 1H), 4.41 (m, 2H), 3.71 (m, 3H), 3.40 (m, 1H), 3.21 (m, 1H), 2.29 (m, 1H), 2.04 (m, 1H).

Example 125

(R)-4-(3-(3-((5-ethynylpyrimidin-2-yl)amino)pyrrolidine-1-carbonyl)-4-fluorobenzyl) phthalazin-1 (2H)-one; (I-125)

Step 1: Preparation of (R)-3-(3-((5-ethynylpyrimidin-2-yl)amino)pyrrolidine-1-carbonyl)-4-fluorobenzaldehyde This compound was made using the procedure described for example 11 (Step 1). Thus, (R)-5-ethynyl-N-(pyrrolidin-3-yl)pyrimidine-2-amine (230 mg, 1.22 mmol) was reacted with 2-fluoro-5-formylbenzoic acid (205 mg, 1.22 mmol), 0-(benzotriazole-1-yl)-N,N,N',N'-tetramethyluronium hexafluorophosphate (HBTU, 602 mg, 1.59 mmol), N,N-diisopropyl ethylamine (DIPEA, 0.43 mL, 2.44 mmol) to afford (R)-3-(3-((5-ethynylpyrimidin-2-yl)amino)pyrrolidine-1-carbonyl)-4-fluorobenzaldehyde (210 mg, 51%).

Step 2: Preparation of (R,Z)-3-(3-(3-((5-ethynylpyrimidin-2-yl)amino)pyrrolidine-1-carbonyl)-4-fluorobenzylidene) isofuran-1(3H)-one This compound was made using the procedure described for example 11 (Step 2). Thus, the intermediate compound (Step 2)(210 mg, 0.62 mmol) was reacted with dimethyl(3-oxo-1,3-dihydroisobenzofuran-1-yl)phosphonate (150 mg, 0.62 mmol), triethylamine (0.13 mL, 0.93 mmol) to afford intermediate compound (R,Z)-3-(3-(3-((5-ethynylpyrimidin-2-yl)amino)pyrrolidine-1-carbonyl)-4-fluorobenzylidene)isofuran-1(3H)-one (164 mg, 58%).

Step 3: Preparation of (R)-4-(3-(3-((5-ethynylpyrimidin-2-yl)amino)pyrrolidine-1-carbonyl)-4-fluorobenzyl) phthalazin-1(2H)-one This compound was made using the procedure described for example 11 (Step 3). Thus, the intermediate compound (Step 2)(164 mg, 0.36 mmol) was reacted with hydrazine monohydrate (36 uL, 0.72 mmol) to afford title compound (103 mg, 61%).
$^1$H-NMR (CDCl$_3$, 400 MHz): δ 10.10-0.93 (dd, 1H), 8.41-8.38 (m, 3H), 7.78-7.68 (m, 3H), 7.41-7.37 (m, 1H), 7.32-7.27 (m, 1H), 7.04-7.02 (m, 1H), 5.48-5.44 (m, 1H), 4.66-4.51 (m, 1H), 4.27 (s, 2H), 4.03 (m, 0.5H), 3.85-3.39 (m, 3H), 3.28-3.26 (m, 0.5H), 3.19 (m, 2H), 2.40-2.23 (m, 1H), 2.17-1.93 (m, 1H).

Example 126

(R)-2-((1-(2-fluoro-5-((4-oxo-3,4-dihydrophthalazin-1-yl)ethyl)benzoyl)pyrrolidin-3-yl) amino)pyrimidine-5-carbonitrile; (I-126)

Step 1: Preparation of (R)-2-((1-(2-fluoro-5-formylbenzoyl)pyrrolidin-3-yl)amino)pyrimidine-5-carbonitrile This compound was made using the procedure described for example 11 (Step 1). Thus, (R)-2-(pyrrolidin-3-ylamino)

pyrimidine-5-carbonitrile (230 mg, 1.22 mmol) was reacted with 2-fluoro-5-formylbenzoic acid (205 mg, 1.22 mmol), O-(benzotriazole-1-yl)-N,N,N',N'-tetramethyluronium hexafluorophosphate (HBTU, 602 mg, 1.59 mmol), N,N-diisopropyl ethylamine (DIPEA, 0.43 mL, 2.44 mmol) to afford (R)-3-(3-((5-ethynylpyrimidin-2-yl)amino)pyrrolidine-1-carbonyl)-4-fluorobenzaldehyde (210 mg, 51%).

Step 2: Preparation of (R,Z)-2-((1-(2-fluoro-5-((3-oxoisofuran-1(3H)-ylidene)methyl)benzol)pyrrolidin-3-yl) amino)pyrimidine-5-carbonitrile This compound was made using the procedure described for example 11 (Step 2). Thus, the intermediate compound (Step 1)(210 mg, 0.63 mol) was reacted with dimethyl(3-oxo-1,3-dihydroisobenzofuran-1-yl)phosphonate (150 mg, 0.63 mmol), triethylamine (0.13 mL, 0.93 mmol) to afford intermediate compound (R,Z)-2-((1-(2-fluoro-5-((3-oxoisofuran-1(3H)-ylidene)methyl)benzoyl)pyrrolidin-3-yl) amino)pyrimidine-5-carbonitrile (164 mg, 58%).

Step 3: Preparation of (R)-2-((1-(2-fluoro-5-((4-oxo-3,4-dihydrophthalazin-1-yl)methyl)benzoyl) pyrrolidin-3-yl) amino)pyrimidine-5-carbonitrile This compound was made using the procedure described for example 11 (Step 3). Thus, the intermediate compound (Step 2)(164 mg, 0.36 mmol) was reacted with hydrazine monohydrate (164 mg, 0.36 mmol) to afford title compound (103 mg, 61%).
$^1$H-NMR (CDCl$_3$, 400 MHz): δ 9.93-9.81 (m, 1H), 8.50-8.43 (m, 2H), 7.79-7.62 (m, 3H), 7.41-7.27 (m, 3H), 7.07-6.99 (m, 1H), 5.83-5.76 (m, 1H), 4.71-4.55 (m, 1H), 4.27 (d, 2H), 4.05-4.00 (m, 0.5H), 3.88-3.62 (m, 2H), 3.52-3.44 (m, 1H), 3.29-3.25 (m, 0.5H), 2.42-2.28 (m, 1H), 2.09-1.96 (m, 1H).

Example 127

(R)-2-((1-(2-fluoro-5-((4-oxo-3,4-dihydrophthalazin-1-yl)ethyl)benzoyl)pyrrolidin-3-yl) amino)nicotinonitrile; (I-127)

Step 1: Preparation of (R)-2-((1-(2-fluoro-5-formylbenzoyl)pyrrolidine-3-yl)amino)nicotinonitrile This compound was made using the procedure described for example 11 (Step 1). Thus, (R)-2-(pyrrolidin-3-ylamino) nicotinonitrile (300 mg, 1.59 mmol) was reacted with 2-fluoro-5-formylbenzoic acid (205 mg, 1.22 mmol), O-(benzotriazole-1-yl)-N,N,N',N'-tetramethyluronium hexafluorophosphate (HBTU, 785 mg, 2.07 mmol), N,N-diisopropyl ethylamine (DIPEA, 0.55 mL, 3.18 mmol) to afford (R)-2-((1-(2-fluoro-5-formylbenzoyl)pyrrolidine-3-yl)amino)nicotinonitrile (275 mg, 51%).

Step 2: Preparation of (R,Z)-2-((1-(2-fluoro-5-((3-oxoisofuran-1(3H)-ylidene)methyl)benzoyl)pyrrolidine-3-yl) amino)nicotinonitrile This compound was made using the procedure described for example 11 (Step 2). Thus, the intermediate compound (Step 1)(275 mg, 0.81 mmol) was reacted with dimethyl(3-oxo-1,3-dihydroisobenzofuran-1-yl)phosphonate (196 mg, 0.81 mmol), triethylamine (1.7 mL, 1.22 mmol) to afford intermediate compound (R,Z)-2-((1-(2-fluoro-5-((3-oxoisofuran-1(3H)-ylidene)methyl)benzoyl)pyrrolidine-3-yl) amino)nicotinonitrile (155 mg, 42%).

Step 3: Preparation of (R)-2-((1-(2-fluoro-5-((4-oxo-3,4-dihydrophthalazin-1-yl)methyl)benzoyl) pyrrolidin-3-yl) amino)nicotinonitrile This compound was made using the procedure described for example 11 (Step 3). Thus, the intermediate compound (Step 2)(155 mg, 0.34 mmol) was reacted with hydrazine monohydrate (34 uL, 0.68 mmol) to afford title compound (78 mg, 49%).
$^1$H-NMR (DMSO, 400 MHz): δ 12.59 (d, 1H), 8.28 (m, 2H), 7.85 (m, 4H), 7.38 (m, 2H), 7.22 (m, 2H), 6.72 (m, 1H), 4.57 (m, 1H), 4.32 (d, 2H), 3.75 (m, 1H), 3.46 (m, 2H), 3.21 (m, 1H), 2.10 (m, 2H).

Example 128

(R)-4-(4-fluoro-3-(3-(pyridin-2-ylamino)pyrrolidine-1-carbonyl)benzyl)phthalazin-1(2H)-one; (I-128)

Step 1: Preparation of (R)-4-fluoro-3-(3-(pyridin-2-ylamino)pyrrolidine-1-carbonyl)benzaldehyde This compound was made using the procedure described for example 11 (Step 1). Thus, (R)—N-(pyrrolidin-3-yl) pyridine-2-amine (250 mg, 0.92 mmol) was reacted with 2-fluoro-5-formylbenzoic acid (154 mg, 0.92 mmol), O-(benzotriazole-1-yl)-N,N,N',N'-tetramethyluronium hexafluorophosphate (HBTU, 453 mg, 1.19 mmol), N,N-diisopropyl ethylamine (DIPEA, 0.32 mL, 1.83 mmol) to afford (R)-4-fluoro-3-(3-(pyridin-2-ylamino)pyrrolidine-1-carbonyl)benzaldehyde (178 m g, 62%).

Step 2: Preparation of (R,Z)-3-(4-fluoro-3-(3-(pyridin-2-ylamino)pyrrolidine-1-carbonyl)benzylidene) isofuran-1(3H)-one This compound was made using the procedure described for example 11 (Step 2). Thus, the intermediate compound (Step 1)(178 mg, 0.57 mmol) was reacted with dimethyl(3-oxo-1,3-dihydroisobenzofuran-1-yl)phosphonate (138 mg, 0.57 mmol), triethylamine (0.12 mL, 0.85 mmol) to afford intermediate compound (R,Z)-3-(4-fluoro-3-(3-(pyridin-2-ylamino)pyrrolidine-1-carbonyl)benzylidene) isofuran-1 (3H)-one (144 mg, 59%).

Step 3: Preparation of (R)-4-(4-fluoro-3-(3-(pyridin-2-ylamino)pyrrolidine-1-carbonyl)benzyl) phthalazin-1(2H)-one This compound was made using the procedure described for example 11 (Step 3). Thus, the intermediate compound (Step 2)(144 mg, 0.34 mmol) was reacted with hydrazine monohydrate (33 uL, 0.67 mmol) to afford title compound (91 mg, 61%).
$^1$H-NMR (MeOD, 400 MHz): δ 8.35-8.31 (m, 1H), 7.95-7.93 (m, 1H), 7.88-7.81 (m, 2H), 7.76-7.73 (m, 1H), 7.45-7.39 (m, 3H), 7.34-7.32 (m, 1H), 7.15-7.08 (m, 2H), 4.67-4.30 (m, 1H), 4.38-4.31 (d, 2H), 3.98-3.12 (m, 5H), 2.35-2.19 (m, 1H), 2.06-1.88 (m, 1H).

Example 129

(R)-2-((1-(2-fluoro-5-((4-oxo-3,4-dihydrophthalazin-1-yl)methyl)benzoyl)pyrrolidin-3-yl) amino)-N,N-dimethylnicotinamide; (I-129)

Step 1: Preparation of (R)-2-((1-(2-fluoro-5-formylbenzoyl)pyrrolidin-3-yl)amino)-N,N-dimethylnicotinamide This compound was made using the procedure described for example 11 (Step 1). Thus, (R)—N,N-dimethyl-2-(pyrrolidin-3-ylamino)nicotinamide (320 mg, 1.36 mmol) was reacted with 2-fluoro-5-formylbenzoic acid (300 mg, 1.36 mmol), O-(benzotriazole-1-yl)-N,N,N',N'-tetramethyluronium hexafluorophosphate (HBTU, 673 mg, 1.77 mmol), N,N-diisopropyl ethylamine (DIPEA, 0.48 mL, 2.73 mmol) to afford (R)-2-((1-(2-fluoro-5-formylbenzoyl)pyrrolidin-3-yl)amino)-N,N-dimethylnicotinamide (220 mg, 42%).

Step 2: Preparation of (R,Z)-2-((1-(2-fluoro-5-((3-oxoisofuran-1(3H)-ylidene)methyl)benzoyl)pyrrolidin-3-yl) amino)-N,N-dimethylnicotinamide This compound was made using the procedure described for example 11 (Step 2). Thus, the intermediate compound (Step 1)(220 mg, 0.57 mmol) was reacted with dimethyl(3-oxo-1,3-dihydroisobenzofuran-1-yl)phosphonate (139 mg, 0.57 mmol), triethylamine (0.2 mL, 0.86 mmol) to afford intermediate compound (R,Z)-2-((1-(2-fluoro-5-((3-oxoisofuran-1(3H)-ylidene)methyl)benzoyl)pyrrolidin-3-yl)amino)-N,N-dimethylnicotinamide (109 mg, 38%).

Step 3: Preparation of (R)-2-((1-(2-fluoro-5-((4-oxo-3,4-dihydrophthalazin-1-yl)methyl)benzoyl)pyrrolidin-3-yl) amino)-N,N-dimethylnicotinamide This compound was made using the procedure described for example 11 (Step 3). Thus, the intermediate compound (Step 2)(109 mg, 0.22 mmol) was reacted with hydrazine monohydrate (22 uL, 0.44 mmol) to afford title compound (39 mg, 35%).
$^1$H-NMR (MeOD, 400 MHz): δ 8.36 (m, 1H), 7.88 (m, 4H), 7.44 (m, 3H), 7.13 (m, 1H), 6.69 (m, 1H), 4.56 (m, 1H), 4.36 (d, 2H), 3.85 (m, 1H), 3.55 (m, 2H), 3.21 (m, 1H), 3.02 (s, 6H), 2.30 (m, 1H), 2.07 (m, 1H).

Example 130

(R)-4-(3-(3-((5-bromopyridin-2-yl)amino)pyrrolidine-1-carbonyl)-4-fluorobenzyl) phthalazin-1(2H)-one; (I-130)

Step 1: Preparation of (R)-3-(3-((5-bromopyrimidin-2-yl)amino)pyrrolidine-1-carbonyl)-4-fluorobenzaldehyde This compound was made using the procedure described for example 11 (Step 1). Thus, (R)-5-bromo-N-(pyrrolidin-3-yl)pyrimidine-2-amine (320 mg, 1.32 mmol) was reacted with 2-fluoro-5-formylbenzoic acid (221 mg, 1.32 mmol), O-(benzotriazole-1-yl)-N,N,N',N'-tetramethyluronium hexafluorophosphate (HBTU, 649 mg, 1.71 mmol), N,N-diisopropyl ethylamine (DIPEA, 0.46 mL, 2.63 mmol) to afford (R)-3-(3-((5-bromopyrimidin-2-yl)amino)pyrrolidine-1-carbonyl)-4-fluorobenzaldehyde (274 mg, 53%).

Step 2: Preparation of (R,Z)-3-(4-fluoro-3-(3-((5-bromopyrimidin-2-yl)aminopyrrolidine-1-carbonyl) benzylidene) isofuran-1(3H)-one This compound was made using the procedure described for example 11 (Step 2). Thus, the intermediate compound (Step 1)(274 mg, 0.70 mmol) was reacted with dimethyl(3-oxo-1,3-dihydroisobenzofuran-1-yl)phosphonate (169 mg, 0.70 mmol), triethylamine (0.15 mL, 1.04 mmol) to afford intermediate compound (R,Z)-3-(4-fluoro-3-(3-((5-bromopyrimidin-2-yl)aminopyrrolidine-1-carbonyl)benzylidene)isofuran-1(3H)-one (217 mg, 61%).

Step 3: Preparation of (R)-4-(4-fluoro-3-(3-((5-bromopyrimidin-2-yl)aminopyrrolidine-1-carbonyl) benzyl) phthalazin-1(2H)-one This compound was made using the procedure described for example 11 (Step 3). Thus, the intermediate compound (Step 2)(217 mg, 0.43 mmol) was reacted with hydrazine monohydrate (45 uL, 0.86 mmol) to afford title compound (131 mg, 59%).
$^1$H-NMR (CDCl$_3$, 400 MHz): δ 9.93-9.81 (m, 1H), 8.50-8.43 (m, 2H), 7.79-7.62 (m, 3H), 7.41-7.27 (m, 3H), 7.07-6.99 (m, 1H), 5.83-5.76 (m, 1H), 4.71-4.55 (m, 1H), 4.27 (d, 2H), 4.05-4.00 (m, 0.5H), 3.88-3.62 (m, 2H), 3.52-3.44 (m, 1H), 3.29-3.25 (m, 0.5H), 2.42-2.28 (m, 1H), 2.09-1.96 (m, 1H).

Example 131

(R)-4-(4-fluoro-3-(3-((5-(trifluoromethyl)pyridin-2-yl)amino)pyrrolidine-1-carbonyl) benzyl)phthalazin-1(2H)-one; (I-131)

Step 1: Preparation of (R)-4-fluoro-3-(3-((5-(trifluoromethylpyridin-2-yl)aminopyrrolidine-1-carbonyl) benzaldehyde This compound was made using the procedure described for example 11 (Step 1). Thus, (R)—N-(pyrrolidin-3-yl)-5-(trifluoromethyl-2-amine (200 mg, 0.86 mmol) was reacted with 2-fluoro-5-formylbenzoic acid (145 mg, 0.86 mmol), O-(benzotriazole-1-yl)-N,N,N',N'-tetramethyluronium hexafluorophosphate (HBTU, 426 mg, 1.12 mmol), N,N-diisopropyl ethylamine (DIPEA, 0.31 mL, 1.72 mmol) to afford (R)-4-fluoro-3-(3-((5-(trifluoromethylpyridin-2-yl)aminopyrrolidine-1-carbonyl)benzaldehyde (174 mg, 53%).

Step 2: Preparation of (R,Z)-3-(4-fluoro-3-(3-((5-(trifluoromethylpyridin-2-yl)amino)pyrrolidine-1-carbonyl) benzylidene)isofuran-1(3H)-one This compound was made using the procedure described for example 11 (Step 2). Thus, the intermediate compound (Step 1)(174 mg, 0.46 mmol) was reacted with dimethyl(3-oxo-1,3-dihydroisobenzofuran-1-yl)phosphonate (111 mg, 0.46 mmol), triethylamine (96 uL, 0.69 mmol) to afford intermediate compound R,Z)-3-(4-fluoro-3-(3-((5-(trifluoromethylpyridin-2-yl)amino)pyrrolidine-1-carbonyl)benzylidene)isofuran-1(3H)-one (139 mg, 61%).

Step 3: Preparation of (R)-4-(4-fluoro-3-(3-((5-(trifluoromethyl)pyridin-2-yl)amino)pyrrolidine-1-carbonyl) benzyl)phthalazin-1(2H)-one This compound was made using the procedure described for example 11 (Step 3). Thus, the intermediate compound (Step 2)(139 mg, 0.28 mmol) was reacted with hydrazine monohydrate (28 uL, 0.56 mmol) to afford title compound (85 mg, 59%).

¹H-NMR (DMSO, 400 MHz): δ 12.59 (d, 1H), 8.29 (m, 2H), 7.85 (m, 3H), 7.62 (m, 2H), 7.39 (m, 2H), 7.20 (m, 1H), 6.58 (m, 1H), 4.38 (m, 1H), 4.32 (d, 2H), 3.75 (m, 1H), 3.47 (m, 2H), 3.21 (m, 1H), 2.20 (m, 1H), 1.92 (m, 1H).

Example 132

(R)-4-(4-fluoro-3-(3-((4-(tri fluoroethyl)pyridin-2-yl)amino)pyrrolidine-1-carbonyl) benzyl)phthalazin-1(2H)-one; (I-132)

Step 1: Preparation of (R)-4-fluoro-3-(3-((4-(trifluoromethyl)pyridin-2-yl)amino)pyrrolidine-1-carbonyl) benzaldehyde This compound was made using the procedure described for example 11 (Step 1). Thus, (R)—N-(pyrrolidin-3-yl)-4-(trifluoromethyl)pyridine-2-amine (200 mg, 0.86 mmol) was reacted with 2-fluoro-5-formylbenzoic acid (145 mg, 0.86 mmol), 0-(benzotriazole-1-yl)-N,N,N',N'-tetramethyluronium hexafluorophosphate (HBTU, 426 mg, 1.12 mmol), N,N-diisopropyl ethylamine (DIPEA, 0.31 mL, 1.72 mmol) to afford (R)-4-fluoro-3-(3-((4-(trifluoromethyl)pyridin-2-yl)amino)pyrrolidine-1-carbonyl)benzaldehyde (174 mg, 53%).

Step 2: Preparation of (R,Z)-3-(4-fluoro-3-(3-((4-(trifluoromethyl)pyridin-2-yl)amino)pyrrolidine-1-carbonyl) benzylidene)isofuran-1(3H)-one This compound was made using the procedure described for example 11 (Step 2). Thus, the intermediate compound (Step 1)(174 mg, 0.46 mmol) was reacted with dimethyl(3-oxo-1,3-dihydroisobenzofuran-1-yl)phosphonate (111 mg, 0.46 mmol), triethylamine (96 uL, 0.69 mmol) to afford intermediate compound (R,Z)-3-(4-fluoro-3-(3-((4-(trifluoromethyl)pyridin-2-yl)amino)pyrrolidine-1-carbonyl)benzylidene)isofuran-1(3H)-one (139 mg, 61%).

Step 3: Preparation of (R)-4-(4-fluoro-3-(3-((4-(trifluoromethyl)pyridin-2-yl)amino)pyrrolidine-1-carbonyl) benzyl)phthalazin-1(2H)-one This compound was made using the procedure described for example 11 (Step 3). Thus, the intermediate compound (Step 2)(139 mg, 0.28 mmol) was reacted with hydrazine monohydrate (28 uL, 0.56 mmol) to afford title compound (85 mg, 59%).

¹H-NMR (DMSO, 400 MHz): δ 12.59 (d, 1H), 8.29 (m, 2H), 7.85 (m, 3H), 7.62 (m, 2H), 7.39 (m, 2H), 7.20 (m, 1H), 6.58 (m, 1H), 4.38 (m, 1H), 4.32 (d, 2H), 3.75 (m, 1H), 3.47 (m, 2H), 3.21 (m, 1H), 2.20 (m, 1H), 1.92 (m, 1H).

Example 133

4-(3-(3-(benzylamino)azetidine-1-carbonyl)-4-fluorobenzyl)phthalazin-1(2H)-one; I-133

Step 1: Preparation of 4-(3-(3-(benzylamino)azetidine-1-carbonyl)-4-fluorobenzyl)phthalazin-1(2H)-one Benzyl bromide (0.10 mL, 0.86 mmol) and K₂CO₃ (119 mg, 0.86 mmol) was added to a suspension of the example 3 product (150 mg, 0.43 mmol) in dimethylformamide (DMF, 8 mL) and stirred for 8 hours at 80° C. The reaction was cooled to room temperature and concentrated in vacuo, added dichloromethane and washed a solution of sodium bicarbonate and water. The combined organic layers were dried over MgSO₄, filtered, evaporated in vacuo and purified using silica chromatography to afford title compound (86 mg, 45%).

¹H-NMR (CDCl₃, 400 MHz): δ 10.17 (s, 1H), 8.47-8.46 (m, 1H), 7.82-7.72 (m, 3H), 7.54-7.50 (m, 1H), 7.37-7.31 (m, 5H), 7.06-7.01 (m, 1H), 4.37-4.32 (m, 1H), 4.29 (s, 2H), 4.19-4.16 (m, 1H), 3.89-3.73 (m, 5H).

Example 134

4-(4-fluoro-3-(3-((3,3,3-tri fluoropropyl)amino)azetidine-1-carbonyl)benzyl)phthalazin-1(2H)-one; (I-134)

Step 1: Preparation of 4-(4-fluoro-3-(3-((3,3,3-trifluoropropyl)amino)azetidine-1-carbonyl)benzyl) phthalazin-1(2H)-one This compound was made using the procedure described for example 133 (Step 1). Thus, 4-(3-(3-aminoazetidin-1-carbonyl)-4-fluorobenzyl)phthalazin-1(2H)-one (150 mg, 0.43 mmol) was reacted with 3-bromo-1,1,1-trifluoropropan (0.25 mL, 0.86 mmol), K₂CO₃ (119 mg, 0.86 mmol) to afford title compound (98 mg, 51%).

¹H-NMR (MeOD, 400 MHz): δ 8.38-8.35 (m, 1H), 7.95-7.92 (m, 1H), 7.89-7.82 (m, 2H), 7.52-7.50 (m, 1H), 7.45-7.43 (m, 1H), 7.17-7.12 (m, 1H), 4.37 (s, 2H), 4.30-4.28 (m, 1H), 4.16-4.14 (m, 1H), 3.86-3.83 (m, 1H), 3.78-3.76 (m, 1H), 3.68-3.66 (m, 1H), 2.48-2.42 (m, 2H), 1.92-1.85 (m, 2H).

Example 135

(R)-4-(3-(3-(azetidin-1-yl)pyrrolidine-1-carbonyl)-4-fluorobenzyl) phthalazin-1(2H)-one; (I-135)

Step 1: Preparation of (S)-1-(2-fluoro-5-((4-oxo-3,4-dihydrophthalazin-1-yl)methyl)benzoyl) pyrrolidine-3-ylmethansulfonate The example 5 intermediate compound (S)-4-(4-fluoro-3-(3-hydroxypyrrolidine-1-carbonyl)benzyl)phthalazin-1(2H)-one (539 mg, 1.25 mmol) in dichloromethane (7 mL) cooled to 0° C. was added triethylamine (0.1 mL, 1.50 mmol), methanesulfonyl chloride (MsCl, 0.11 mL, 1.38 mmol), and the mixture was stirred at room temperature for 3 h. The reaction mixture was concentrated in vacuo, added dichloromethane and washed with aqueous sodium bicarbonate and water. The combined organic layers were dried over MgSO₄, filtered, evaporated in vacuo to afford (S)-1-(2-fluoro-5-((4-oxo-3,4-dihydrophthalazin-1-yl)methyl) benzoyl)pyrrolidine-3-ylmethanesulfonate (434 mg, 78%).

Step 2: Preparation of (R)-4-(3-(3-(azetidin-1-yl) pyrrolidine-1-carbonyl)-4-fluorobenzyl)phthalazin-1(2H)-one The intermediate compound (Step 1)(434 mg, 0.97 mmol) in dimethylformamide (DMF, 5 mL) was added azetidine (0.20 mL, 2.93 mmol), Li₂CO₃ (216 mg, 2.93 mmol) and the mixture was stirred at 80° C. for 16 h. The reaction mixture was concentrated in vacuo, added dichloromethane and washed with aqueous ammonium chloride and water. The combined organic layers were dried over MgSO$_4$, filtered, evaporated in vacuo and purified using silica chromatography to afford the title compound (117 mg, 45%).

$^1$H-NMR (DMSO, 400 MHz): δ 12.61 (s, 1H), 8.26 (d, 1H), 7.96 (t, 1H), 7.91-7.80 (m, 2H), 7.46-7.35 (m, 1H), 7.25-7.18 (m, 1H), 4.33 (s, 2H), 3.73-3.58 (m, 1H), 3.44-3.39 (m, 1H), 3.27-3.19 (m, 1H), 3.13-3.08 (m, 1H), 2.98 (t, 1H), 2.86 (d, 1H), 2.77-2.61 (m, 1H), 2.16 (t, 2H), 2.03 (t, 2H), 1.77-1.62 (m, 2H).

Example 136

(R)-4-(3-([1,3'-bipyrrolidine]-1'-carbonyl)-4-fluorobenzyl)phthalazin-1(2H)-one; (I-136)

Step 1: Preparation of (S)-1-(2-fluoro-5-((4-oxo-3,4-dihydrophthalazin-1-yl)methyl)benzoyl) pyrrolidine-3-ylmethansulfonate The intermediate compound (S)-1-(2-fluoro-5-((4-oxo-3,4-dihydrophthalazin-1-yl)methyl)benzoyl)pyrrolidine-3-yl-methansulfonate was made using the procedure described for example 135 (Step 1) in a yield of 78% (434 mg).

Step 2: Preparation of (R)-4-(3-([1,3'-bipyrrolidine]-1'-carbonyl)-4-fluorobenzyl)phthalazin-1(2H)-one This compound was made using the procedure described for example 135 (Step 2). Thus, the intermediate compound (Step 1)(434 mg, 0.97 mmol) was reacted with pyrrolidine (0.22 mL, 2.93 mmol), Li$_2$CO$_3$ (216 mg, 2.93 mmol) to afford title compound (130 mg, 32%).

$^1$H-NMR (MeOD, 400 MHz): δ 8.35 (d, 1H), 7.93 (d, 1H), 7.90-7.79 (m, 2H), 7.54-7.44 (m, 1H), 7.42-7.37 (m, 1H), 7.18-7.11 (m, 1H), 4.37 (s, 2H), 3.85-3.74 (m, 1H), 2.65 (t, 2H), 2.57-2.50 (m, 1H), 2.40 (t, 1H), 2.23-2.07 (m, 1H), 1.97-1.90 (m, 1H), 1.85 (m, 2H), 1.76 (m, 2H).

Example 137

(R)-4-(4-fluoro-3-(3-(piperidin-1-yl)pyrrolidine-1-carbonyl)benzyl)phthalazin-1(2H)-one; (I-137)

Step 1: Preparation of (S)-1-(2-fluoro-5-((4-oxo-3,4-dihydrophthalazin-1-yl)methyl)benzoyl) pyrrolidine-3-ylmethansulfonate The intermediate compound (S)-1-(2-fluoro-5-((4-oxo-3,4-dihydrophthalazin-1-yl)methyl)benzoyl)pyrrolidine-3-yl-methansulfonate was made using the procedure described for example 135 (Step 1) in a yield of 78% (434 mg).

Step 2: Preparation of (R)-4-(4-fluoro-3-(3-(piperidin-1-yl)pyrrolidine-1-carbonyl)benzyl)phthalazin-1(2H)-one This compound was made using the procedure described for example 135 (Step 2). Thus, the intermediate compound (Step 1)(434 mg, 0.97 mmol) was reacted with piperidine (0.10 mL, 2.93 mmol), Li$_2$CO$_3$ (216 mg, 2.93 mmol) to afford title compound (88 mg, 21%).

$^1$H-NMR (DMSO, 400 MHz): δ 12.61 (s, 1H), 8.26 (d, 1H), 7.97 (d, 1H), 7.91-7.80 (m, 2H), 7.46-7.39 (m, 1H), 7.38-7.35 (m, 1H), 7.25-7.19 (m, 1H), 4.32 (s, 2H), 3.75-3.59 (m, 1H), 3.39-3.36 (m, 0.5H), 3.29-3.12 (m, 2H), 2.97 (t, 0.5H), 2.83-2.71 (m, 1H), 2.42-2.28 (m, 3H), 2.15-1.98 (m, 2H), 1.73-1.63 (m, 1H), 1.51-1.29 (m, 6H).

Example 138

(R)-4-(4-fluoro-3-(3-(p-tolyl amino)pyrrolidine-1-carbonyl)benzyl)phthalazin-1(2H)-one; (I-138)

Step 1: Preparation of (R)-4-fluoro-3-(3-(p-tolylamino)pyrrolidine-1-carbonyl)benzaldehyde This compound was made using the procedure described for example 11 (Step 1). Thus, (R)-4-fluoro-3-(3-(p-tolylamino)pyrrolidine-1-carbonyl)benzaldehyde (200 mg, 1.13 mmol) was reacted with 2-fluoro-5-formylbenzoic acid (190 mg, 1.13 mmol), 0-(benzotriazole-1-yl)-N,N,N',N'-tetramethyluronium hexafluorophosphate (HBTU, 559 mg, 1.48 mmol), N,N-diisopropyl ethylamine (DIPEA, 0.40 mL, 2.27 mmol) to afford (R)-4-fluoro-3-(3-(p-tolylamino)pyrrolidine-1-carbonyl)benzaldehyde (230 mg, 62%).

Step 2: Preparation of (R,Z)-3-(4-fluoro-3-(3-(p-tolylamino)pyrrolidine-1-carbonyl)benzylidene) isobenzofuran-1(3H)-one This compound was made using the procedure described for example 11 (Step 2). Thus, the intermediate compound (Step 1)(230 mg, 0.70 mmol) was reacted with dimethyl(3-oxo-1,3-dihydroisobenzofuran-1-yl)phosphonate (170 mg, 0.70 mmol), triethylamine (0.15 mL, 1.10 mmol) to afford intermediate compound (R,Z)-3-(4-fluoro-3-(3-(p-tolylamino)pyrrolidine-1-carbonyl)benzylidene)isobenzofuran-1(3H)-one (190 mg, 61%).

Step 3: Preparation of (R)-4-(4-fluoro-3-(3-(p-tolylamino)pyrrolidine-1-carbonyl)benzyl)phthalazin-1 (2H)-one This compound was made using the procedure described for example 11 (Step 3). Thus, the intermediate compound (Step 2)(190 mg, 0.43 mmol) was reacted with hydrazine monohydrate (42 uL, 0.86 mmol) to afford title compound (129 mg, 66%).

$^1$H-NMR (DMSO, 400 MHz): δ 12.59 (d, 1H), 8.26 (m, 1H), 7.85 (m, 3H), 7.60 (m, 1H), 7.36 (m, 1H), 7.20 (m, 1H), 6.88 (dd, 2H), 6.48 (dd, 2H), 5.60 (m, 1H), 4.32 (d, 2H), 3.91 (m, 2H), 3.52 (m, 2H), 3.11 (m, 1H), 2.14 (m, 1H), 2.12 (s, 3H), 1.90 (m, 1H).

Example 139

(R)-4-(4-fluoro-3-(3-(phenylamino)pyrrolidine-1-carbonyl)benzyl)phthalazin-1(2H)-one; (I-139)

Step 1: Preparation of (R)-4-fluoro-3-(3-(phenylamino)pyrrolidine-1-carbonyl)benzaldehyde This compound was made using the procedure described for example 11 (Step 1). Thus, (R)—N-phenylpyrrolidine-3-amine (200 mg, 1.23 mmol) was reacted with 2-fluoro-5-formylbenzoic acid (207 mg, 1.23 mmol), O-(benzotriazole-1-yl)-N,N,N',N'-tetramethyluronium hexafluorophosphate (HBTU, 607 mg, 1.60 mmol), N,N-diisopropyl ethylamine (DIPEA, 0.43 mL, 2.46 mmol) to afford (R)-4-fluoro-3-(3-(phenylamino)pyrrolidine-1-carbonyl)benzaldehyde (238 mg, 62%).

Step 2: Preparation of (R,Z)-3-(4-fluoro-3-(3-(phenylamino)pyrrolidine-1-carbonyl)benzylidene)isobenzofuran-1(3H)-one This compound was made using the procedure described for example 11 (Step 2). Thus, the intermediate compound (Step 1)(238 mg, 0.76 mmol) was reacted with dimethyl(3-oxo-1,3-dihydroisobenzofuran-1-yl)phosphonate (185 mg, 0.76 mmol), triethylamine (0.16 mL, 1.14 mmol) to afford intermediate compound (R,Z)-3-(4-fluoro-3-(3-(phenylamino)pyrrolidine-1-carbonyl)benzylidene)isobenzofuran-1(3H)-one (200 mg, 61%).

Step 3: Preparation of (R)-4-(4-fluoro-3-(3-(phenylamino)pyrrolidine-1-carbonyl)benzyl)phthalazin-1(2H)-one This compound was made using the procedure described for example 11 (Step 3). Thus, the intermediate compound (Step 2)(200 mg, 0.47 mmol) was reacted with hydrazine monohydrate (46 uL, 0.94 mmol) to afford title compound (136 mg, 66%).

$^1$H-NMR (MeOD, 400 MHz): δ 8.39-8.34 (m, 1H), 7.97-7.70 (m, 3H), 7.50-7.33 (m, 2H), 7.19-7.07 (m, 3H), 6.70-6.57 (m, 3H), 4.40 (s, 1H), 4.33 (s, 1H), 4.17-4.05 (m, 1H), 3.95-3.79 (m, 1H), 3.72-3.47 (m, 2H), 3.41-3.16 (m, 1H), 2.37-2.20 (m, 1H), 2.09-1.91 (m, 1H).

Example 140

4-(4-fluoro-3-(3-(pyrrolidin-1-ylmethyl)azetidine-1-carbonyl)benzyl)phthalazin-1(2H)-one; (I-140)

Step 1: Preparation of (1-(2-fluoro-5-((4-oxo-3,4-dihydrophthalazin-1-yl)methyl)benzoyl)azetidine-3-yl) methylmethanesulfonate The intermediate compound (example 7) 4-(4-fluoro-3-(3-(hydroxymethyl)azetidine-1-carbonyl)benzyl)phthalazin-1(2H)-one (460 mg, 1.25 mmol) in dichloromethane (7 mL) cooled to 0° C. was added triethylamine (0.1 mL, 1.50 mmol), methanesulfonyl chloride (MsCl, 0.11 mL, 1.38 mmol), and the mixture was stirred at room temperature for 3 h. The reaction mixture was concentrated in vacuo, added dichloromethane and washed with aqueous sodium bicarbonate and water. The combined organic layers were dried over MgSO$_4$, filtered, evaporated in vacuo to afford (1-(2-fluoro-5-((4-oxo-3,4-dihydrophthalazin-1-yl)methyl)benzoyl)azetidine-3-yl)methylmethansulfonate (417 mg, 75%).

Step 2: Preparation of 4-(4-fluoro-3-(3-(pyrrolidin-1-ylmethyl)azetidine-1-carbonyl)benzyl)phthalazin-1(2H)-one The intermediate compound (Step 1)(417 mg, 0.94 mmol) in 1,4-dioxane (5 mL) was added pyrrolidine (0.27 mL, 4.00 mmol) and the mixture was stirred at 80° C. for 16 h. The reaction mixture was concentrated in vacuo, added dichloromethane and washed with aqueous ammonium chloride and water. The combined organic layers were dried over MgSO$_4$, filtered, evaporated in vacuo and purified using silica chromatography to afford the title compound (138 mg, 35%).

$^1$H-NMR (CDCl$_3$, 400 MHz): δ 9.85 (s, 1H), 8.46-8.44 (m, 1H), 7.78-7.70 (m, 3H), 7.49-7.47 (m, 1H), 7.32-7.27 (m, 1H), 7.03-6.98 (m, 1H), 4.29-4.24 (m, 3H), 4.14-4.10 (t, 1H), 3.85-3.77 (m, 2H), 2.91-2.64 (m, 3H), 2.48 (s, 4H), 1.77 (s, 4H).

Example 141

4-(4-fluoro-3-(3-(piperidin-1-ylethyl)azetidine-1-carbonyl)benzyl)phthalazin-1(2H)-one; (I-141)

Step 1: Preparation of (1-(2-fluoro-5-((4-oxo-3,4-dihydrophthalazin-1-yl)methyl)benzoyl)azetidine-3-yl) methyl methanesulfonate The intermediate compound (1-(2-fluoro-5-((4-oxo-3,4-dihydrophthalazin-1-yl)methyl)benzoyl)azetidine-3-yl) methyl methansulfonate was made using the procedure described for example 140 (Step 1) in a yield of 75% (417 mg).

Step 2: Preparation of 4-(4-fluoro-3-(3-(piperidin-1-ylmethyl)azetidine-1-carbonyl)benzyl)phthalazin-1(2H)-one This compound was made using the procedure described for example 140 (Step 2). Thus, the intermediate compound (Step 1)(417 mg, 0.94 mmol) was reacted with piperidine (0.44 mL, 4.00 mmol) to afford title compound (138 mg, 35%).

$^1$H-NMR (CDCl$_3$, 400 MHz): δ 9.94 (s, 1H), 8.46 (m, 1H), 7.78-7.70 (m, 3H), 7.50-7.48 (m, 1H), 7.31-7.27 (m, 1H), 7.01 (t, 1H), 4.27-4.23 (t, 1H), 4.26 (s, 2H), 7.13-4.09 (t, 1H), 3.83-3.70 (m, 2H), 2.88-2.84 (m, 1H), 2.57-2.55 (m, 2H), 2.32 (s, 4H), 1.54 (s, 4H), 1.42 (s, 2H).

Example 142

4-(3-(3-(azetidin-1-ylmethyl)azetidine-1-carbonyl)-4-fluorobenzyl)phthalazin-1(2H)-one; (I-142)

Step 1: Preparation of (1-(2-fluoro-5-((4-oxo-3,4-dihydrophthalazin-1-yl)methyl)benzoyl)azetidine-3-yl) methyl methansulfonate The intermediate compound (1-(2-fluoro-5-((4-oxo-3,4-dihydrophthalazin-1-yl)methyl)benzoyl)azetidine-3-yl) methyl methansulfonate was made using the procedure described for example 140 (Step 1) in a yield of 75% (417 mg).

Step 2: Preparation of 4-(3-(3-(azetidin-1-ylmethyl)azetidine-1-carbonyl)-4-fluorobenzyl)phthalazin-1(2H)-one This compound was made using the procedure described for example 140 (Step 2). Thus, the intermediate compound (Step 1)(417 mg, 0.94 mmol) was reacted with azetidine (0.28 mL, 4.00 mmol) to afford title compound (154 mg, 41%).

$^1$H-NMR (MeOD, 400 MHz): δ 8.36 (d, 1H), 7.94 (d, 1H), 7.84 (m, 2H), 7.50 (m, 2H), 7.13 (t, 1H), 4.38 (s, 2H), 4.19 (t, 1H), 4.09 (m, 1H), 3.74 (m, 2H), 3.30 (m, 4H), 2.69 (m, 3H), 2.14 (t, 2H).

Example 143

4-(3-(3-((cyclopropylamino)methyl)azetidine-1-carbonyl)-4-fluorobenzyl)phthalazin-1(2H)-one; (I-143)

Step 1: Preparation of (1-(2-fluoro-5-((4-oxo-3,4-dihydrophthalazine-1-yl)methyl)benzoyl)azetidine-3-yl) methyl methansulfonate The intermediate compound (1-(2-fluoro-5-((4-oxo-3,4-dihydrophthalazin-1-yl)methyl)benzoyl)azetidine-3-yl) methyl methansulfonate was made using the procedure described for example 140 (Step 1) in a yield of 75% (417 mg).

Step 2: Preparation of 4-(3-(3-((cyclopropylamino)methyl)azetidine-1-carbonyl)-4-fluorobenzyl)phthalazin-1(2H)-one This compound was made using the procedure described for example 140 (Step 2). Thus, the intermediate compound (Step 1)(417 mg, 0.94 mmol) was reacted with cyclopropylamine (0.28 mL, 4.00 mmol) to afford title compound (206 mg, 54%).

$^1$H-NMR (CDCl$_3$, 400 MHz): δ 10.03 (s, 1H), 8.47-8.45 (m, 1H), 7.80-7.71 (m, 3H), 7.52-7.48 (m, 1H), 7.32-7.28 (m, 1H), 7.01 (t, 1H), 4.27 (s, 2H), 4.26-4.22 (m, 1H), 4.10 (t, 1H), 3.85-3.81 (m, 1H), 3.73-3.70 (m, 1H), 2.99-2.88 (m, 2H), 2.81-2.72 (m, 1H), 2.07 (m, 1H), 1.57 (br, 1H), 0.45-0.41 (m, 2H), 0.29-0.26 (m, 2H).

Example 144

4-(4-fluoro-3-(3-((isopropylamino)methyl)azetidine-1-carbonyl)benzyl)phthalazin-1(2H)-one; (I-144)

Step 1: Preparation of (1-(2-fluoro-5-((4-oxo-3,4-dihydrophthalazine-1-yl)methyl)benzoyl)azetidine-3-yl) methyl methansulfonate The intermediate compound (1-(2-fluoro-5-((4-oxo-3,4-dihydrophthalazin-1-yl)methyl)benzoyl)azetidine-3-yl) methyl methansulfonate was made using the procedure described for example 140 (Step 1) in a yield of 75% (417 mg).

Step 2: Preparation of 4-(4-fluoro-3-(3-((isopropylamino)methyl)azetidine-1-carbonyl)benzyl)phthalazin-1(2H)-one This compound was made using the procedure described for example 140 (Step 2). Thus, the intermediate compound (Step 1)(417 mg, 0.94 mmol) was reacted with isopropylamine (0.34 mL, 4.00 mmol) to afford title compound (234 mg, 61%).

$^1$H-NMR (CDCl$_3$, 400 MHz): δ 10.20 (br, 1H), 8.47-8.45 (m, 1H), 7.80-7.70 (m, 3H), 7.51-7.49 (dd, 1H), 7.32-7.28 (m, 1H), 7.01 (t, 1H), 4.27 (s, 2H), 4.28-4.23 (m, 1H), 4.12 (t, 1H), 3.84-3.81 (dd, 1H), 3.75-3.71 (dd, 1H), 2.88-2.69 (m, 4H), 1.05-1.03 (dd, 6H).

Example 145

4-(3-(3-(((cyclopropylmethyl)amino)ethyl)azetidine-1-carbonyl)-4-fluorobenzyl)phthalazin-1(2H)-one; (I-145)

Step 1: Preparation of (1-(2-fluoro-5-((4-oxo-3,4-dihydrophthalazine-1-yl)methyl)benzoyl)azetidine-3-yl) methyl methansulfonate The intermediate compound (1-(2-fluoro-5-((4-oxo-3,4-dihydrophthalazin-1-yl)methyl)benzoyl)azetidine-3-yl) methyl methansulfonate was made using the procedure described for example 140 (Step 1) in a yield of 75% (417 mg).

Step 2: Preparation of 4-(3-(3-(((cyclopropylmethyl)amino)methyl)azetidine-1-carbonyl)-4-fluorobenzyl)phthalazin-1(2H)-one This compound was made using the procedure described for example 140 (Step 2). Thus, the intermediate compound (Step 1)(417 mg, 0.94 mmol) was reacted with cyclopropylmethylamine (0.34 mL, 4.00 mmol) to afford title compound (189 mg, 48%).

$^1$H-NMR (CDCl$_3$, 400 MHz): δ 10.36 (br, 1H), 8.47-8.45 (m, 1H), 7.80-7.71 (m, 3H), 7.51-7.49 (m, 1H), 7.32-7.28 (m, 1H), 7.01 (t, 1H), 4.27-4.24 (m, 3H), 4.13 (t, 1H), 3.86-3.75 (m, 2H), 2.94-2.75 (m, 3H), 2.48-2.46 (dd, 2H), 1.61 (br, 1H), 0.95-0.91 (m, 1H), 0.51-0.46 (m, 2H), 0.12-0.09 (m, 2H).

Example 146

4-(4-fluoro-3-(3-((isobutylamino)methyl)azetidine-1-carbonyl)benzyl)phthalazin-1(2H)-one; (I-146)

Step 1: Preparation of (1-(2-fluoro-5-((4-oxo-3,4-dihydrophthalazine-1-yl)methyl)benzoyl)azetidine-3-yl) methyl methansulfonate The intermediate compound (1-(2-fluoro-5-((4-oxo-3,4-dihydrophthalazin-1-yl)methyl)benzoyl)azetidine-3-yl) methyl methansulfonate was made using the procedure described for example 140 (Step 1) in a yield of 75% (417 mg).

Step 2: Preparation of 4-(4-fluoro-3-(3-((isobutylamino)methyl)azetidine-1-carbonyl)benzyl)phthalazin-1(2H)-one This compound was made using the procedure described for example 140 (Step 2). Thus, the intermediate compound (Step 1)(417 mg, 0.94 mmol) was reacted with 2-methylpropan-1-amine (0.40 mL, 4.00 mmol) to afford title compound (207 mg, 52%).

$^1$H-NMR (CDCl$_3$, 400 MHz): δ 10.69 (br, 1H), 8.47-8.45 (m, 1H), 7.80-7.71 (m, 3H), 7.50-7.48 (m, 1H), 7.32-7.28 (m, 1H), 7.00 (t, 1H), 4.27-4.23 (m, 3H), 4.14 (t, 1H), 3.86-3.78 (m, 2H), 2.93-2.78 (m, 3H), 2.45 (s, 1H), 2.44 (s, 1H), 1.81-1.71 (m, 1H), 0.91 (s, 3H), 0.89 (s, 3H).

Example 147

4-(3-(3-((tert-butylamino)methyl)azetidine-1-carbonyl)-4-fluorobenzyl)phthalazin-1(2H)-one; (I-147)

Step 1: Preparation of (1-(2-fluoro-5-((4-oxo-3,4-dihydrophthalazine-1-yl)methyl)benzoyl)azetidine-3-yl) methyl methansulfonate The intermediate compound (1-(2-fluoro-5-((4-oxo-3,4-dihydrophthalazin-1-yl)methyl)benzoyl)azetidine-3-yl) methyl methansulfonate was made using the procedure described for example 140 (Step 1) in a yield of 75% (417 mg).

Step 2: Preparation of 4-(3-(3-((tert-butylamino)methyl)azetidine-1-carbonyl)-4-fluorobenzyl)phthalazin-1(2H)-one This compound was made using the procedure described for example 140 (Step 2). Thus, the intermediate compound (Step 1)(417 mg, 0.94 mmol) was reacted with 2-methylpropan-2-amine (0.42 mL, 4.00 mmol) to afford title compound (71 mg, 18%).
$^1$H-NMR (CDCl$_3$, 400 MHz): δ 10.49 (br, 1H), 8.47-8.45 (m, 1H), 7.80-7.72 (m, 3H), 7.52-7.48 (m, 1H), 7.31-7.28 (m, 1H), 7.01 (t, 1H), 4.27-4.22 (m, 3H), 4.14 (t, 1H), 2.90-2.75 (m, 3H), 1.14 (s, 9H).

Example 148

4-(3-(3-((cyclobutylamino)methyl)azetidine-1-carbonyl)-4-fluorobenzyl)phthalazin-1(2H)-one; (I-148)

Step 1: Preparation of (1-(2-fluoro-5-((4-oxo-3,4-dihydrophthalazine-1-yl)methyl)benzoyl)azetidine-3-yl) methyl methansulfonate The intermediate compound (1-(2-fluoro-5-((4-oxo-3,4-dihydrophthalazin-1-yl)methyl)benzoyl)azetidine-3-yl) methyl methansulfonate was made using the procedure described for example 140 (Step 1) in a yield of 75% (417 mg).

Step 2: Preparation of 4-(3-(3-((cyclobutylamino)methyl)azetidine-1-carbonyl)-4-fluorobenzyl)phthalazin-1(2H)-one This compound was made using the procedure described for example 140 (Step 2). Thus, the intermediate compound (Step 1)(417 mg, 0.94 mmol) was reacted with cyclobutylamine (0.43 mL, 4.00 mmol) to afford title compound (138 mg, 35%).
$^1$H-NMR (CDCl$_3$, 400 MHz): δ 10.33 (br, 1H), 8.47-8.45 (m, 1H), 7.80-7.71 (m, 3H), 7.50-7.48 (m, 1H), 7.31-7.28 (m, 1H), 7.00 (t, 1H), 4.27-4.22 (m, 3H), 4.11 (t, 1H), 3.83-3.72 (m, 2H), 3.23 (m, 1H), 2.83-2.72 (m, 3H), 2.23-2.17 (m, 2H), 1.71-1.62 (m, 5H).

Example 149

4-(4-fluoro-3-(3-((prop-2-yn-1-ylamino)methyl)azetidine-1-carbonyl)benzyl)phthalazin-1(2H)-one; (I-149)

Step 1: Preparation of (1-(2-fluoro-5-((4-oxo-3,4-dihydrophthalazine-1-yl)methyl)benzoyl)azetidine-3-yl) methyl methansulfonate The intermediate compound (1-(2-fluoro-5-((4-oxo-3,4-dihydrophthalazin-1-yl)methyl)benzoyl)azetidine-3-yl) methyl methansulfonate was made using the procedure described for example 140 (Step 1) in a yield of 75% (417 mg).

Step 2: Preparation of 4-(4-fluoro-3-(3-((prop-2-yn-1-ylamino)methyl)azetidine-1-carbonyl)benzyl)phthalazin-1(2H)-one This compound was made using the procedure described for example 140 (Step 2). Thus, the intermediate compound (Step 1)(417 mg, 0.94 mmol) was reacted with propargylamine (0.27 mL, 4.00 mmol) to afford title compound (163 mg, 43%).
$^1$H-NMR (CDCl$_3$, 400 MHz): δ 10.61 (s, 1H), 8.48-8.46 (m, 1H), 7.80-7.71 (m, 3H), 7.51-7.49 (m, 1H), 7.32-7.28 (m, 1H), 7.01 (t, 1H), 4.28-4.24 (m, 3H), 4.12 (t, 1H), 3.88-3.76 (m, 2H), 3.43 (m, 2H), 3.00-2.87 (m, 2H), 2.78-2.72 (m, 1H), 2.27-2.23 (m, 1H), 1.45 (br, 1H).

Example 150

4-(4-fluoro-3-(3-((phenylamino)ethyl)azetidine-1-carbonyl)benzyl)phthalazin-1(2H)-one; (I-150)

Step 1: Preparation of (1-(2-fluoro-5-((4-oxo-3,4-dihydrophthalazine-1-yl)methyl)benzoyl)azetidine-3-yl) methyl methansulfonate The intermediate compound (1-(2-fluoro-5-((4-oxo-3,4-dihydrophthalazin-1-yl)methyl)benzoyl)azetidine-3-yl) methyl methansulfonate was made using the procedure described for example 140 (Step 1) in a yield of 75% (417 mg).

Step 2: Preparation of 4-(4-fluoro-3-(3-((phenylamino)methyl)azetidine-1-carbonyl)benzyl)phthalazin-1(2H)-one This compound was made using the procedure described for example 140 (Step 2). Thus, the intermediate compound (Step 1)(417 mg, 0.94 mmol) was reacted with aniline (0.36 mL, 4.00 mmol) to afford title compound (45 mg, 11%).
$^1$H-NMR (CDCl$_3$, 400 MHz): δ 11.25 (s, 1H), 8.48-8.46 (m, 1H), 7.77-7.70 (m, 3H), 7.51-7.49 (dd, 1H), 7.33-7.29 (m, 1H), 7.17 (t, 2H), 7.00 (t, 1H), 6.72 (t, 1H), 6.59 (m, 2H), 4.31-4.27 (m, 3H), 4.17-4.09 (m, 1H), 3.39-3.78 (m, 2H), 3.41-3.31 (m, 2H), 2.95-2.89 (m, 1H).

Example 151

1-((((1-(2-fluoro-5-((4-oxo-3,4-dihydrophthalazin-1-yl)methyl)benzoyl)azetidin-3-yl) methyl)amino)methyl)cyclopropanecarbonitrile; (I-151)

Step 1: Preparation of (1-(2-fluoro-5-((4-oxo-3,4-dihydrophthalazine-1-yl)methyl)benzoyl)azetidine-3-yl) methyl methansulfonate The intermediate compound (1-(2-fluoro-5-((4-oxo-3,4-dihydrophthalazin-1-yl)methyl)benzoyl)azetidine-3-yl)

methyl methansulfonate was made using the procedure described for example 140 (Step 1) in a yield of 75% (417 mg).

Step 2: Preparation of 1-(((1-(2-fluoro-5-((4-oxo-3,4-dihydrophthalazin-1-yl)methyl)benzoyl)azetidin-3-yl)methyl)amino)methyl)cyclopropanecarbonitrile This compound was made using the procedure described for example 140 (Step 2). Thus, the intermediate compound (Step 1)(417 mg, 0.94 mmol) was reacted with 1-(aminomethyl)cyclopropanecarbonitrile (384 mg, 4.00 mmol) to afford title compound (121 mg, 29%).
$^1$H-NMR (MeOD, 400 MHz): δ 8.36 (d, 1H), 7.82-7.95 (m, 3H), 7.44-7.46 (m, 2H), 7.13 (t, 1H), 4.37 (s, 2H), 4.21 (t, 1H), 4.10 (t, 1H), 3.74-3.85 (m, 2H), 2.80-2.87 (m, 3H), 2.68-2.70 (m, 2H), 1.20 (s, 2H), 0.95 (s, 2H).

Example 152

1-(((1-(2-fluoro-5-((4-oxo-3,4-dihydrophthalazin-1-yl)methyl)benzoyl)azetidin-3-yl) methyl)amino) cyclopropanecarbonitrile; (I-152)

Step 1: Preparation of (1-(2-fluoro-5-((4-oxo-3,4-dihydrophthalazine-1-yl)methyl)benzoyl)azetidine-3-yl) methyl methansulfonate The intermediate compound (1-(2-fluoro-5-((4-oxo-3,4-dihydrophthalazin-1-yl)methyl)benzoyl)azetidine-3-yl) methyl methansulfonate was made using the procedure described for example 140 (Step 1) in a yield of 75% (417 mg).

Step 2: Preparation of 1-(((1-(2-fluoro-5-((4-oxo-3,4-dihydrophthalazin-1-yl)methyl)benzoyl)azetidin-3-yl) methyl)amino)cyclopropanecarbonitrile This compound was made using the procedure described for example 140 (Step 2). Thus, the intermediate compound (Step 1)(417 mg, 0.94 mmol) was reacted with 1-aminocyclopropanecarbonitrile (474 mg, 4.00 mmol) to afford title compound (44 mg, 11%).
$^1$H-NMR (CDCl$_3$, 400 MHz): δ 10.39 (s, 1H), 8.48-8.46 (m, 1H), 7.77-7.72 (m, 3H), 7.53-7.49 (m, 1H), 7.35-7.29 (m, 1H), 7.02 (t, 1H), 4.28 (s, 2H), 4.27-4.09 (m, 2H), 3.86-3.69 (m, 2H), 2.75 (m, 1H), 1.90 (m, 1H), 1.64 (s, 2H), 1.23 (m, 2H), 1.00 (m, 2H).

Example 153

4-(3-(3-((cyclopropyl(prop-2-yn-1-yl)amino)methyl) azetidine-1-carbonyl)-4-fluorobenzyl)phthalazin-1 (2H)-one; (I-153)

Step 1: Preparation of 4-(3-(3-((cyclopropyl(prop-2-yn-1-yl)amino)methyl)azetidine-1-carbonyl)-4-fluorobenzyl)phthalazin-1(2H)-one 4-(3-(3-((cyclopropylamino)methyl)azetidine-1-carbonyl)-4-fluorobenzyl)phthalazin-1(2H)-one (example 144) (126 mg, 0.52 mmol) in dimethylformamide (DMF, 3 mL) was added Na$_2$CO$_3$ (63 mg, 1.56 mmol), 3-bromoprop-1-yn (0.16 mL, 2.60 mmol) and the mixture was stirred at room temperature for 3 h. The reaction mixture was concentrated in vacuo, added dichloromethane and washed with aqueous ammonium chloride and water. The combined organic layers were dried over MgSO$_4$, filtered, evaporated in vacuo and purified using silica chromatography to afford the title compound (190 mg, 82%).
$^1$H-NMR (CDCl$_3$, 400 MHz): δ 11.08 (s, 1H), 8.49-8.47 (m, 1H), 7.79-7.71 (m, 3H), 7.51-7.49 (m, 1H), 7.32-7.29 (m, 1H), 7.01 (t, 1H), 4.29 (s, 2H), 4.26-4.05 (m, 2H), 3.83-3.68 (m, 2H), 3.40 (m, 2H), 2.96-2.87 (m, 3H), 2.23 (m, 1H), 1.98-1.95 (m, 1H), 0.53-0.48 (m, 2H), 0.34-0.31 (m, 2H).

Example 154

4-(3-(3-((cyclopropyl(methyl)amino)methyl)azetidine-1-carbonyl)-4-fluorobenzyl)phthalazin-1(2H)-one; (I-154)

Step 1: Preparation of 4-(3-(3-((cyclopropyl (methyl)amino)methyl)azetidine-1-carbonyl)-4-fluorobenzyl)phthalazin-1(2H)-one This compound was made using the procedure described for example 153 (Step 1). Thus, the intermediate compound (example 144) 4-(3-(3-((cyclopropylamino)methyl)azetidine-1-carbonyl)-4-fluorobenzyl)-phthalazin-1(2H)-one (150 mg, 0.34 mmol) was reacted with Na$_2$CO$_3$ (78 mg, 0.74 mmol) and methyl iodide (46 uL, 0.74 mmol) to afford the title compound (121 mg, 85%).
$^1$H-NMR (CDCl$_3$, 400 MHz): δ 10.91 (s, 1H), 8.49-8.47 (m, 1H), 7.79-7.71 (m, 3H), 7.51-7.49 (m, 1H), 7.32-7.28 (m, 1H), 7.00 (t, 1H), 4.28 (s, 2H), 4.26-4.04 (m, 2H), 3.81-3.66 (m, 2H), 2.96-2.87 (m, 1H), 2.81-2.74 (m, 3H), 1.03 (m, 1H), 0.49-0.41 (m, 2H), 0.34-0.26 (m, 2H).

Example 155

4-(3-(3-((cyclopropyl(ethyl)amino)methyl)azetidine-1-carbonyl)-4-fluorobenzyl)phthalazin-1(2H)-one; (I-155)

Step 1: Preparation of 4-(3-(3-((cyclopropyl(ethyl) amino)methyl)azetidine-1-carbonyl)-4-fluorobenzyl) phthalazin-1(2H)-one This compound was made using the procedure described for example 153 (Step 1). Thus, the intermediate compound (example 144) 4-(3-(3-((cyclopropylamino)methyl)azetidine-1-carbonyl)-4-fluorobenzyl)-phthalazin-1(2H)-one (150 mg, 0.34 mmol) was reacted with Na$_2$CO$_3$ (78 mg, 0.74 mmol) and ethyl iodide (49 uL, 0.74 mmol) to afford the title compound (113 mg, 77%).
$^1$H-NMR (CDCl$_3$, 400 MHz): δ 10.60 (s, 1H), 8.48-8.46 (m, 1H), 7.79-7.71 (m, 3H), 7.51-7.49 (m, 1H), 7.32-7.28 (m, 1H), 7.01 (t, 1H), 4.28 (s, 2H), 4.26-4.04 (m, 2H), 3.81-3.66 (m, 2H), 2.96-2.87 (m, 1H), 2.81-2.74 (m, 2H), 2.65-2.60 (m, 2H), 1.64 (m, 1H), 1.03 (m, 1H), 0.49-0.41 (m, 2H), 0.34-0.26 (m, 2H).

Example 156

4-(3-(3-(cyclobutylamino)azetidine-1-carbonyl)-4-fluorobenzyl)phthalazin-1(2H)-one hydrochloride; (I-156)

Step 1: Preparation of 4-(3-(3-(cyclobutylamino) azetidine-1-carbonyl)-4-fluorobenzyl)phthalazin-1 (2H)-one hydrochloride The intermediate compound (example 25) 4-(3-(3-(cyclobutylamino)azetidine-1-carbonyl)-4-fluorobenzyl)

phthalazin-1(2H)-one (100 mg, 0.25 mmol) in dichloromethane (3 mL) cooled to 0° C. was added 1N solution of hydrochloric acid (0.50 mL, 0.50 mmol). After stirring at room temperature for 1 h, the solvents were evaporated to afford title compound (102 mg, 93%).

$^1$H-NMR (DMSO, 400 MHz): δ 12.61 (s, 1H), 9.23 (d, 2H), 8.26 (d, 1H), 7.97 (d, 1H), 7.89 (t, 1H), 7.83 (t, 1H), 7.50-7.21 (m, 2H), 7.21 (t, 1H), 4.33 (s, 2H), 4.10 (t, 1H), 3.97 (t, 1H), 3.67-3.51 (m, 3H), 3.08 (m, 1H), 2.76 (m, 1H), 1.99 (t, 2H), 1.69-1.46 (m, 4H).

Example 157

4-(3-(3-(cyclopropylamino)azetidine-1-carbonyl)-4-fluorobenzyl)phthalazin-1(2H)-one hydrochloride; (I-157)

Step 1: Preparation of 4-(3-(3-(cyclopropylamino) azetidine-1-carbonyl)-4-fluorobenzyl)phthalazin-1 (2H)-one hydrochloride This compound was made using the procedure described for example 156 (Step 1). Thus, the intermediate compound (example 26) 4-(3-(3-(cyclopropylcyclopropylamino)azetidine-1-carbonyl)-4-fluorobenzyl)phthalazin-1(2H)-one (100 mg, 0.25 mmol) was reacted with 1N solution of hydrochloric acid (0.50 mL, 0.50 mmol) to afford the title compound (97 mg, 91%).

$^1$H-NMR (MeOD, 400 MHz): δ 8.36 (d, 1H), 7.93 (d, 1H), 7.79-7.89 (m, 2H), 7.48-7.54 (m, 1H), 7.42 (d, 1H), 7.15 (t, 1H), 4.00-4.05 (m, 2H), 3.75-3.80 (m, 2H), 3.34-3.39 (m, 1H), 3.12 (s, 2H), 1.32-1.36 (m, 1H), 0.64-0.72 (m, 2H), 0.41-0.46 (m, 2H).

Example 158

4-(3-(3-(cyclopentylamino)azetidine-1-carbonyl)-4-fluorobenzyl)phthalazin-1(2H)-one hydrochloride; (I-158)

Step 1: Preparation of 4-(3-(3-(cyclopentylamino) azetidine-1-carbonyl)-4-fluorobenzyl)phthalazin-1 (2H)-one hydrochloride This compound was made using the procedure described for example 156 (Step 1). Thus, the intermediate compound (example 27) 4-(3-(3-(cyclopentylamino)azetidine-1-carbonyl)-4-fluorobenzyl)phthalazin-1(2H)-one (117 mg, 0.24 mmol) was reacted with 1N solution of hydrochloric acid (0.48 mL, 0.48 mmol) to afford the title compound (99 mg, 90%).

$^1$H-NMR (DMSO, 400 MHz): δ 12.60 (s, 1H), 9.23 (d, 2H), 8.26 (d, 1H), 7.97 (d, 1H), 7.89 (t, 1H), 7.83 (t, 1H), 7.44-7.50 (m, 1H), 7.40 (d, 1H), 7.21 (t, 1H), 4.33 (s, 2H), 4.13 (t, 1H), 4.00 (t, 1H), 3.54-3.70 (m, 3H), 2.82-2.91 (m, 1H), 1.52-1.67 (m, 4H), 1.43 (brs, 2H), 1.10-1.27 (m, 2H).

Example 159

4-(4-fluoro-3-(3-(isopropylamino)azetidine-1-carbonyl)benzyl)phthalazin-1(2H)-one hydrochloride; (I-159)

Step 1: Preparation of 4-(4-fluoro-3-(3-(isopropylamino)azetidine-1-carbonyl)benzyl)phthalazin-1 (2H)-one hydrochloride This compound was made using the procedure described for example 156 (Step 1). Thus, the intermediate compound (example 32) 4-(4-fluoro-3-(3-(isopropylamino)azetidine-1-carbonyl)benzyl)phthalazin-1(2H)-one (100 mg, 0.25 mmol) was reacted with 1N solution of hydrochloric acid (0.50 mL, 0.50 mmol) to afford the title compound (102 mg, 95%).

$^1$H-NMR (DMSO, 400 MHz): δ 12.61 (s, 1H), 9.23 (d, 2H), 8.27-8.25 (m, 1H), 7.97 (d, 1H), 7.91-7.81 (m, 2H), 7.48-7.44 (m, 1H), 7.41-7.39 (m, 1H), 7.21 (t, 1H), 4.33 (s, 2H), 4.15-4.10 (m, 2H), 3.66-3.59 (m, 3H), 3.17 (d, 1H), 2.68-2.61 (m, 1H), 0.92-0.83 (m, 6H).

Example 160

4-(3-(3-((cyclopropylethyl)amino)azetidine-1-carbonyl)-4-fluorobenzyl)phthalazin-1(2H)-one hydrochloride; (I-160)

Step 1: Preparation of 4-(3-(3-((cyclopropylmethyl) amino)azetidine-1-carbonyl)-4-fluorobenzyl) phthalazin-1(2H)-one hydrochloride This compound was made using the procedure described for example 156 (Step 1). Thus, the intermediate compound (example 33) 4-(3-(3-((cyclopropylmethyl)amino)azetidine-1-carbonyl)-4-fluorobenzyl)phthalazin-1(2H)-one (100 mg, 0.25 mmol) was reacted with 1N solution of hydrochloric acid (0.50 mL, 0.50 mmol) to afford the title compound (98 mg, 89%).

$^1$H-NMR (DMSO, 400 MHz): δ 12.61 (s, 1H), 9.23 (d, 2H), 8.28-7.97 (m, 2H), 7.91-7.81 (m, 2H), 7.48-7.40 (m, 2H), 7.22 (m, 1H), 4.33 (s, 2H), 4.13-3.98 (m, 2H), 3.70-3.56 (m, 3H), 2.29 (m, 2H), 0.83-0.72 (m, 1H), 0.37-0.32 (m, 2H), 0.06 (m, 2H).

Example 161

4-(4-fluoro-3-(3-(isobutylamino)azetidine-1-carbonyl)benzyl)phthalazin-1(2H)-one hydrochloride; (I-161)

Step 1: Preparation of 4-(4-fluoro-3-(3-(isobutylamino)azetidine-1-carbonyl)benzyl)phthalazin-1 (2H)-onehydrochloride This compound was made using the procedure described for example 156 (Step 1). Thus, the intermediate compound (example 35) 4-(4-fluoro-3-(3-(isobutylamino)azetidine-1-carbonyl)benzyl)phthalazin-1(2H)-one (100 mg, 0.24 mmol) was reacted with 1N solution of hydrochloric acid (0.48 mL, 0.48 mmol) to afford the title compound (101 mg, 95%).

$^1$H-NMR (MeOD, 400 MHz): δ 8.38-8.35 (m, 1H), 7.95-7.93 (m, 1H), 7.89-7.82 (m, 2H), 7.51-7.49 (m, 1H), 7.45-7.43 (m, 1H), 7.15 (t, 1H), 4.38 (s, 2H), 4.28-4.26 (m, 1H), 4.16-4.12 (m, 1H), 3.88-3.84 (m, 1H), 3.79-3.75 (m, 1H), 3.66-3.64 (m, 1H), 2.31-2.28 (m, 2H), 1.71-1.68 (m, 1H), 0.91 (dd, 6H).

Example 162

4-(4-fluoro-3-(3-((1-hydroxypropan-2-yl)amino) azetidine-1-carbonyl)benzyl)phthalazin-1(2)-one hydrochloride; (I-162)

Step 1: Preparation of 4-(4-fluoro-3-(3-((1-hydroxypropan-2-yl)amino)azetidine-1-carbonyl)benzyl) phthalazin-1(2H)-one hydrochloride This compound was made using the procedure described for example 156 (Step 1). Thus, the intermediate compound (example 36) 4-(4-fluoro-3-(3-((1-hydroxypropan-2-yl)amino)azetidine-1-carbonyl)benzyl)phthalazin-1(2H)-one (100 mg, 0.24 mmol) was reacted with 1N solution of hydrochloric acid (0.48 mL, 0.48 mmol) to afford the title compound (91 mg, 85%).

$^{1}$H-NMR (MeOD, 400 MHz): δ 8.36-8.34 (m, 1H), 7.94-7.92 (m, 1H), 7.88-7.81 (m, 2H), 7.50-7.49 (m, 1H), 7.46-7.44 (m, 1H), 7.16-7.11 (m, 1H), 4.36 (s, 2H), 4.35-4.33 (m, 1H), 4.20-4.17 (m, 1H), 3.90-3.3.83 (m, 3H), 3.46-3.43 (m, 1H), 3.39-3.36 (m, 1H), 2.77-2.75 (m, 1H), 1.95 (s, 1H), 1.02 (q, 3H).

Example 163

4-(3-(3-(butylamino)azetidine-1-carbonyl)-4-fluorobenzyl)phthalazin-1(2H)-one hydrochloride; (I-163)

Step 1: Preparation of 4-(3-(3-(butylamino)azetidine-1-carbonyl)-4-fluorobenzyl)phthalazin-1(2H)-one hydrochloride This compound was made using the procedure described for example 156 (Step 1). Thus, the intermediate compound (example 53) 4-(3-(3-(butylamino)azetidine-1-carbonyl)benzyl)phthalazin-1(2H)-one (100 mg, 0.24 mmol) was reacted with 1N solution of hydrochloric acid (0.48 mL, 0.48 mmol) to afford the title compound (104 mg, 98%).

$^{1}$H-NMR (CDCl$_3$, 400 MHz): δ 10.28 (s, 1H), 9.19 (d, 2H), 8.40-8.38 (m, 1H), 7.72-7.66 (m, 1H), 7.44-7.41 (m, 1H), 7.24-7.22 (m, 1H), 6.97-6.92 (m, 1H), 4.30-4.27 (m, 1H), 4.20 (s, 2H), 4.11-4.09 (m, 1H), 3.81-3.79 (m, 1H), 3.72-3.70 (m, 1H), 3.64-3.62 (m, 1H), 2.50-2.46 (m, 2H), 2.02 (s, 1H), 1.40-1.37 (m, 2H), 1.30-1.24 (m, 2H), 0.86-0.80 (m, 5H).

Example 164

4-(3-([1,3'-biazetidine]-1'-carbonyl)-4-fluorobenzyl)phthalazin-1(2H)-one hydrochloride; (I-164)

Step 1: Preparation of 4-(3-([1,3'-biazetidine]-1'-carbonyl)-4-fluorobenzyl)phthalazin-1(2H)-onehydrochloride This compound was made using the procedure described for example 156 (Step 1). Thus, the intermediate compound (example 75) 4-(3-([1,3'-biazetidine]-1'-carbonyl)-4-fluorobenzyl)phthalazin-1(2H)-one (100 mg, 0.25 mmol) was reacted with 1N solution of hydrochloric acid (0.50 mL, 0.50 mmol) to afford the title compound (88 mg, 82%).

$^{1}$H-NMR (DMSO, 400 MHz): δ 12.61 (s, 1H), 9.23 (d, 2H), 8.26 (d, 1H), 7.78 (d, 1H), 7.89 (t, 1H), 7.83 (t, 1H), 7.45 (m, 2H), 7.22 (t, 1H), 4.33 (d, 2H), 4.11 (m, 1H), 3.97 (t, 1H), 3.87 (t, 1H), 3.68 (m, 1H), 3.60 (t, 1H), 3.10 (m, 4H), 1.95 (t, 2H).

Example 165

(R)-4-(4-fluoro-3-(3-((1-methoxypropan-2-yl)amino)azetidine-1-carbonyl)benzyl) phthalazin-1(2H)-one hydrochloride; (I-165)

Step 1: Preparation of (R)-4-(4-fluoro-3-(3-((1-methoxypropan-2-yl)amino)azetidine-1-carbonyl)benzyl) phthalazin-1(2H)-one hydrochloride This compound was made using the procedure described for example 156 (Step 1). Thus, the intermediate compound (example 83) (R)-4-(4-fluoro-3-(3-((1-methoxypropan-2-yl)amino)azetidine-1-carbonyl)benzyl)phthalazin-1(2H)-one (117 mg, 0.23 mmol) was reacted with 1N solution of hydrochloric acid (0.46 mL, 0.46 mmol) to afford the title compound (93 mg, 88%).

$^{1}$H-NMR (MeOD, 400 MHz): δ 8.38-8.35 (m, 1H), 7.95-7.93 (m, 1H), 7.89-7.82 (m, 2H), 7.52-7.50 (m, 1H), 7.45-7.43 (m, 1H), 7.14 (t, 1H), 4.38 (s, 2H), 4.12-4.10 (m, 1H), 4.18-4.15 (m, 1H), 3.84-3.77 (m, 3H), 3.22-3.19 (m, 1H), 2.89-2.87 (m, 1H), 2.03 (s, 3H), 1.00 (t, 3H).

Example 166

1-((1-(2-fluoro-5-((4-oxo-3,4-dihydrophthalazin-1-yl)methyl)benzoyl)azetidin-3-yl) amino)cyclobutanecarbonitrile hydrochloride; (I-166)

Step 1: Preparation of 1-((1-(2-fluoro-5-((4-oxo-3,4-dihydrophthalazin-1-yl)methyl)benzoyl)azetidin-3-yl) amino)cyclobutanecarbonitrilehydrochloride This compound was made using the procedure described for example 156 (Step 1). Thus, the intermediate compound (example 99) 1-((1-(2-fluoro-5-((4-oxo-3,4-dihydrophthalazin-1-yl)methyl)benzoyl)azetidin-3-yl)amino)cyclobutanecarbonitrile (100 mg, 0.23 mmol) was reacted with 1N solution of hydrochloric acid (0.46 mL, 0.46 mmol) to afford the title compound (86 mg, 79%).

$^{1}$H-NMR (MeOD, 400 MHz): δ 8.35 (m, 1H), 7.92-7.78 (m, 3H), 7.50-7.43 (m, 2H), 7.13 (t, 1H), 4.41-4.39 (m, 1H), 4.36 (s, 2H), 4.23 (m, 1H), 3.98-3.92 (m, 2H), 3.85-3.78 (m, 1H), 2.48-2.41 (m, 2H), 2.20-2.02 (m, 2H).

Example 167

(R)-4-(3-(3-(azetidin-1-yl)pyrrolidine-1-carbonyl)-4-fluorobenzyl)phthalazin-1(2H)-one hydrochloride; (I-167)

Step 1: Preparation of (R)-4-(3-(3-(azetidin-1-yl)pyrrolidine-1-carbonyl)-4-fluorobenzyl)phthalazin-1(2H)-one hydrochloride This compound was made using the procedure described for example 156 (Step 1). Thus, the intermediate compound (example 135) (R)-4-(3-(3-(azetidin-1-yl)pyrrolidine-1-carbonyl)-4-fluorobenzyl)phthalazin-1(2H)-one (100 mg, 0.24 mmol) was reacted with 1N solution of hydrochloric acid (0.48 mL, 0.48 mmol) to afford the title compound (99 mg, 93%).

$^{1}$H-NMR (DMSO, 400 MHz): δ 12.61 (s, 1H), 9.23 (d, 2H), 8.26 (d, 1H), 7.96 (t, 1H), 7.91-7.80 (m, 2H), 7.46-7.35 (m, 1H), 7.25-7.18 (m, 1H), 4.33 (s, 2H), 3.73-3.58 (m, 1H), 3.44-3.39 (m, 1H), 3.27-3.19 (m, 1H), 3.13-3.08 (m, 1H), 2.98 (t, 1H), 2.86 (d, 1H), 2.77-2.61 (m, 1H), 2.16 (t, 2H), 2.03 (t, 2H), 1.77-1.62 (m, 2H).

Example 168

4-(4-fluoro-3-(3-(pyrrolidin-1-ylethyl)azetidine-1-carbonyl)benzyl)phthalazin-1(2H)-one hydrochloride; (I-168)

Step 1: Preparation of 4-(4-fluoro-3-(3-(pyrrolidin-1-ylmethyl)azetidine-1-carbonyl)benzyl)phthalazin-1(2H)-one hydrochloride This compound was made using the procedure described for example 156 (Step 1). Thus, the intermediate compound (example 140)-(4-fluoro-3-(3-(pyrrolidin-1-ylmethyl)azetidine-1-carbonyl)benzyl)phthalazin-1(2H)-one (100 mg, 0.23 mmol) was reacted with 1N solution of hydrochloric acid (0.46 mL, 0.46 mmol) to afford the title compound (96 mg, 91%).

$^1$H-NMR (CDCl$_3$, 400 MHz): δ 9.85 (s, 1H), 9.19 (d, 2H), 8.46-8.44 (m, 1H), 7.78-7.70 (m, 3H), 7.49-7.47 (m, 1H), 7.32-7.27 (m, 1H), 7.03-6.98 (m, 1H), 4.29-4.24 (m, 3H), 4.14-4.10 (t, 1H), 3.85-3.77 (m, 2H), 2.91-2.64 (m, 3H), 2.48 (s, 4H), 1.77 (s, 4H).

Example 169

4-(4-fluoro-3-(3-(piperidin-1-ylmethyl)azetidine-1-carbonyl)benzyl)phthalazin-1(2H)-one hydrochloride; (I-169)

Step 1: Preparation of 4-(4-fluoro-3-(3-(piperidin-1-ylmethyl)azetidine-1-carbonyl)benzyl)phthalazin-1(2H)-one hydrochloride This compound was made using the procedure described for example 156 (Step 1). Thus, the intermediate compound (example 142) 4-(4-fluoro-3-(3-(piperidin-1-ylmethyl)azetidine-1-carbonyl)benzyl)phthalazin-1(2H)-one (100 mg, 0.23 mmol) was reacted with 1N solution of hydrochloric acid (0.46 mL, 0.46 mmol) to afford the title compound (105 mg, 97%).

$^1$H-NMR (CDCl$_3$, 400 MHz): δ 9.94 (s, 1H), 9.19 (d, 2H), 8.46 (m, 1H), 7.78-7.70 (m, 3H), 7.50-7.48 (m, 1H), 7.31-7.27 (m, 1H), 7.01 (t, 1H), 4.27-4.23 (t, 1H), 4.26 (s, 2H), 7.13-4.09 (t, 1H), 3.83-3.70 (m, 2H), 2.88-2.84 (m, 1H), 2.57-2.55 (m, 2H), 2.32 (s, 4H), 1.54 (s, 4H), 1.42 (s, 2H).

Example 170

4-(3-(3-(azetidin-1-ylmethyl)azetidine-1-carbonyl)-4-fluorobenzyl)phthalazin-1(2H)-one hydrochloride; (I-170)

Step 1: Preparation of 4-(3-(3-(azetidin-1-ylmethyl)azetidine-1-carbonyl)-4-fluorobenzyl)phthalazin-1(2H)-one hydrochloride This compound was made using the procedure described for example 156 (Step 1). Thus, the intermediate compound (example 143) 4-(3-(3-(azetidin-1-ylmethyl)azetidine-1-carbonyl)-4-fluorobenzyl)phthalazin-1(2H)-one (100 mg, 0.24 mmol) was reacted with 1N solution of hydrochloric acid (0.48 mL, 0.48 mmol) to afford the title compound (101 mg, 95%).

$^1$H-NMR (400 MHz, MeOD): δ 8.36 (d, 1H), 7.94 (d, 1H), 7.84 (m, 2H), 7.50 (m, 2H), 7.13 (t, 1H), 4.38 (s, 2H), 4.19 (t, 1H), 4.09 (m, 1H), 3.74 (m, 2H), 3.30 (m, 4H), 2.69 (m, 3H), 2.14 (t, 2H).

Example 171

4-(3-(3-((cyclopropylamino)methyl)azetidine-1-carbonyl)-4-fluorobenzyl)phthalazin-1(2H)-one hydrochloride; (I-171)

Step 1: Preparation of 4-(3-(3-((cyclopropylamino)methyl)azetidine-1-carbonyl)-4-fluorobenzyl)phthalazin-1(2H)-one hydrochloride This compound was made using the procedure described for example 156 (Step 1). Thus, the intermediate compound (example 25) 4-(3-(3-((cyclopropylamino)methyl)azetidine-1-carbonyl)-4-fluorobenzyl)phthalazin-1(2H)-one (100 mg, 0.25 mmol) was reacted with 1N solution of hydrochloric acid (0.50 mL, 0.50 mmol) to afford the title compound (99 mg, 91%).

$^1$H-NMR (CDCl$_3$, 400 MHz): δ 10.03 (s, 1H), 9.18 (d, 2H), 8.47-8.45 (m, 1H), 7.80-7.71 (m, 3H), 7.52-7.48 (m, 1H), 7.32-7.28 (m, 1H), 7.01 (t, 1H), 4.27 (s, 2H), 4.26-4.22 (m, 1H), 4.10 (t, 1H), 3.85-3.81 (m, 1H), 3.73-3.70 (m, 1H), 2.99-2.88 (m, 2H), 2.81-2.72 (m, 1H), 2.07 (m, 1H), 1.57 (br, 1H), 0.45-0.41 (m, 2H), 0.29-0.26 (m, 2H).

Example 172

4-(4-fluoro-3-(3-((isopropylamino)methyl)azetidine-1-carbonyl)benzyl)phthalazin-1(2H)-one hydrochloride; (I-172)

Step 1: Preparation of 4-(4-fluoro-3-(3-((isopropylamino)methyl)azetidine-1-carbonyl)benzyl)phthalazin-1(2H)-one hydrochloride This compound was made using the procedure described for example 156 (Step 1). Thus, the intermediate compound (example 145) 4-(4-fluoro-3-(3-((isopropylamino)methyl)azetidine-1-carbonyl)benzyl)phthalazin-1(2H)-one (100 mg, 0.24 mmol) was reacted with 1N solution of hydrochloric acid (0.48 mL, 0.48 mmol) to afford the title compound (95 mg, 89%).

$^1$H-NMR (CDCl$_3$, 400 MHz): δ 10.20 (br, 1H), 9.19 (d, 2H), 8.47-8.45 (m, 1H), 7.80-7.70 (m, 3H), 7.51-7.49 (dd, 1H), 7.32-7.28 (m, 1H), 7.01 (t, 1H), 4.27 (s, 2H), 4.28-4.23 (m, 1H), 4.12 (t, 1H), 3.84-3.81 (dd, 1H), 3.75-3.71 (dd, 1H), 2.88-2.69 (m, 4H), 1.05-1.03 (dd, 6H).

Example 173

4-(3-(3-(((cyclopropyl)ethyl)amino)ethyl)azetidine-1-carbonyl)-4-fluorobenzyl)phthalazin-1(2H)-one hydrochloride; (I-173)

Step 1: Preparation of 4-(3-(3-(((cyclopropylmethyl)amino)methyl)azetidine-1-carbonyl)-4-fluorobenzyl)phthalazin-1(2H)-one hydrochloride This compound was made using the procedure described for example 156 (Step 1). Thus, the intermediate compound (example 146) 4-(3-(3-(((cyclopropylmethyl)amino)methyl)azetidine-1-carbonyl)-4-fluorobenzyl)phthalazin-1(2H)-one (100 mg, 0.23 mmol) was reacted with 1N solution of hydrochloric acid (0.46 mL, 0.46 mmol) to afford the title compound (94 mg, 90%).

$^1$H-NMR (CDCl$_3$, 400 MHz): δ 10.36 (br, 1H), 9.18 (d, 2H), 8.47-8.45 (m, 1H), 7.80-7.71 (m, 3H), 7.51-7.49 (m, 1H), 7.32-7.28 (m, 1H), 7.01 (t, 1H), 4.27-4.24 (m, 3H), 4.13 (t, 1H), 3.86-3.75 (m, 2H), 2.94-2.75 (m, 3H), 2.48-2.46 (dd, 2H), 1.61 (br, 1H), 0.95-0.91 (m, 1H), 0.51-0.46 (m, 2H), 0.12-0.09 (m, 2H).

Example 174

4-(4-fluoro-3-(3-((isobutylamino)methyl)azetidine-1-carbonyl)benzyl)phthalazin-1(2H)-one hydrochloride; (I-174)

Step 1: Preparation of 4-(4-fluoro-3-(3-((isobutylamino)methyl)azetidine-1-carbonyl)benzyl)phthalazin-1(2H)-one hydrochloride This compound was made using the procedure described for example 156 (Step 1). Thus, the intermediate compound (example 147) 4-(4-fluoro-3-(3-((isobutylamino)methyl)azetidine-1-carbonyl)benzyl)phthalazin-1(2H)-one (100 mg, 0.23 mmol) was reacted with 1N solution of hydrochloric acid (0.46 mL, 0.46 mmol) to afford the title compound (101 mg, 93%).

$^1$H-NMR (CDCl$_3$, 400 MHz): δ 10.69 (br, 1H), 9.20 (d, 2H), 8.47-8.45 (m, 1H), 7.80-7.71 (m, 3H), 7.50-7.48 (m, 1H), 7.32-7.28 (m, 1H), 7.00 (t, 1H), 4.27-4.23 (m, 3H), 4.14 (t, 1H), 3.86-3.78 (m, 2H), 2.93-2.78 (m, 3H), 2.45 (s, 1H), 2.44 (s, 1H), 1.81-1.71 (m, 1H), 0.91 (s, 3H), 0.89 (s, 3H).

Example 175

4-(3-(3-((cyclobutylamino)ethyl)azetidine-1-carbonyl)-4-fluorobenzyl)phthalazin-1(2H)-one hydrochloride; (I-175)

Step 1: Preparation of 4-(3-(3-((cyclobutylamino)methyl)azetidine-1-carbonyl)-4-fluorobenzyl)phthalazin-1(2H)-one hydrochloride This compound was made using the procedure described for example 156 (Step 1). Thus, the intermediate compound (example 149) 4-(3-(3-((cyclobutylamino)methyl)azetidine-1-carbonyl)-4-fluorobenzyl)phthalazin-1(2H)-one (100 mg, 0.24 mmol) was reacted with 1N solution of hydrochloric acid (0.48 mL, 0.48 mmol) to afford the title compound (99 mg, 91%).

$^1$H-NMR (CDCl$_3$, 400 MHz): δ 10.33 (br, 1H), 9.19 (d, 2H), 8.47-8.45 (m, 1H), 7.80-7.71 (m, 3H), 7.50-7.48 (m, 1H), 7.31-7.28 (m, 1H), 7.00 (t, 1H), 4.27-4.22 (m, 3H), 4.11 (t, 1H), 3.83-3.72 (m, 2H), 3.23 (m, 1H), 2.83-2.72 (m, 3H), 2.23-2.17 (m, 2H), 1.71-1.62 (m, 5H).

Example 176

4-(4-fluoro-3-(3-((prop-2-yn-1-ylamino)methyl)azetidine-1-carbonyl)benzyl)phthalazin-1(2H)-one hydrochloride; (I-176)

Step 1: Preparation of 4-(4-fluoro-3-(3-((prop-2-yn-1-ylamino)methyl)azetidine-1-carbonyl)benzyl)phthalazin-1(2H)-one hydrochloride This compound was made using the procedure described for example 156 (Step 1). Thus, the intermediate compound (example 150) 4-(4-fluoro-3-(3-((prop-2-yn-1-ylamino)methyl)azetidine-1-carbonyl)benzyl)phthalazin-1(2H)-one (100 mg, 0.25 mmol) was reacted with 1N solution of hydrochloric acid (0.50 mL, 0.50 mmol) to afford the title compound (96 mg, 88%).

$^1$H-NMR (CDCl$_3$, 400 MHz): δ 10.61 (s, 1H), 9.19 (d, 2H), 8.48-8.46 (m, 1H), 7.80-7.71 (m, 3H), 7.51-7.49 (m, 1H), 7.32-7.28 (m, 1H), 7.01 (t, 1H), 4.28-4.24 (m, 3H), 4.12 (t, 1H), 3.88-3.76 (m, 2H), 3.43 (m, 2H), 3.00-2.87 (m, 2H), 2.78-2.72 (m, 1H), 2.27-2.23 (m, 1H), 1.45 (br, 1H).

Experiment 1

In Vitro Test for Antitumoral Activity

To ecaluate the in vitro test, the invented compounds (from I-1 to I-155) were determined as follows and showed table 1, 2, 3, 4 and 5.

1. Determination of Cellular PAR Levels

Cellular PAR assay was performed to measure cellular PARP inhibitory activity of the compounds in the present invention. Hela human cervical cancer cells cultured in Minimum Essential Medium with Earle's Balanced Salts (MEM/EBSS) containing 10% FBS were seeded into 96-well cell culture plates, and incubated for 1 day at 37° C. under 5% CO$_2$ atmosphere. After the invented compounds serially diluted in DMSO were added to each well, and then DNA damage was provoked by addition of H$_2$O$_2$ solution in H$_2$O. Cellular PAR levels were determined and EC$_{50}$ was calculated by using PAR antibody and detection solution.

TABLE 1

| Compound | EC$_{50}$ Cellular PAR [EC$_{50}$, nM] |
|---|---|
| WO2004080976A1 Example 168 | A |
| I-8 | B |
| I-9 | B |
| I-10 | A |
| I-11 | B |
| I-12 | A |
| I-13 | A |
| I-14 | B |
| I-15 | C |
| I-16 | C |
| I-17 | A |
| I-18 | A |
| I-19 | A |
| I-20 | B |
| I-21 | B |
| I-22 | A |
| I-23 | C |
| I-24 | C |
| I-25 | A |
| I-26 | A |
| I-27 | A |
| I-28 | A |
| I-29 | B |
| I-30 | B |
| I-31 | A |
| I-32 | A |
| I-33 | A |
| I-34 | C |
| I-35 | A |
| I-36 | B |
| I-37 | A |
| I-38 | A |
| I-39 | B |
| I-40 | A |
| I-41 | A |
| I-42 | A |
| I-43 | A |
| I-44 | A |
| I-45 | A |
| I-46 | A |
| I-47 | B |
| I-48 | A |
| I-49 | A |
| I-50 | A |
| I-51 | A |
| I-52 | A |
| I-53 | A |
| I-54 | A |
| I-55 | A |
| I-56 | A |
| I-57 | A |
| I-58 | A |
| I-59 | A |
| I-60 | B |
| I-61 | A |
| I-62 | A |
| I-63 | B |
| I-64 | B |
| I-65 | B |
| I-66 | A |
| I-67 | B |
| I-68 | B |
| I-69 | A |

TABLE 1-continued

| Compound | EC$_{50}$ Cellular PAR [EC$_{50}$, nM] |
|---|---|
| I-70 | A |
| I-71 | A |
| I-72 | C |
| I-73 | A |
| I-74 | A |
| I-75 | A |
| I-76 | A |
| I-77 | A |
| I-78 | B |
| I-79 | A |
| I-80 | A |
| I-81 | A |
| I-82 | A |
| I-83 | A |
| I-84 | B |
| I-85 | A |
| I-86 | A |
| I-87 | B |
| I-88 | A |
| I-89 | A |
| I-90 | A |
| I-91 | A |
| I-92 | A |
| I-93 | B |
| I-94 | B |
| I-95 | A |
| I-96 | C |
| I-97 | C |
| I-98 | A |
| I-99 | A |
| I-100 | A |
| I-101 | A |
| I-102 | A |
| I-103 | B |
| I-104 | A |
| I-105 | A |
| I-106 | C |
| I-107 | A |
| I-108 | B |
| I-109 | A |
| I-110 | A |
| I-111 | B |
| I-112 | B |
| I-113 | B |
| I-114 | B |
| I-115 | B |
| I-116 | B |
| I-118 | B |
| I-119 | C |
| I-120 | A |
| I-121 | C |
| I-122 | B |
| I-123 | B |
| I-124 | B |
| I-125 | B |
| I-126 | A |
| I-127 | C |
| I-128 | A |
| I-129 | D |
| I-130 | A |
| I-131 | B |
| I-132 | A |
| I-133 | B |
| I-134 | B |
| I-135 | A |
| I-136 | A |
| I-137 | B |
| I-138 | B |
| I-139 | B |
| I-140 | A |
| I-141 | A |
| I-142 | A |
| I-143 | A |
| I-144 | A |
| I-145 | A |
| I-146 | A |
| I-147 | B |
| I-148 | A |
| I-149 | A |
| I-150 | B |
| I-151 | B |
| I-152 | D |
| I-153 | B |
| I-154 | A |
| I-155 | A |

Range A: EC$_{50}$ ≤ 5 nM
Range B: 5 nM < EC$_{50}$ ≤ 50 nM
Range C: 50 nM < EC$_{50}$ ≤ 300 nM
Range D: 300 nM < EC$_{50}$ ≤ 1,000 nM
Range E: EC$_{50}$ > 1,000 nM According to the above table 1, the compounds in the present invent ion showed potent cellular PARP inhibitory activity in cellular PAR assay.

2. Cell Viability Assay (MDA-MB-436)

Cell viability assay was performed by using MDA-MB-436 cell line to measure cytotoxicity of compounds in the present invention. MDA-MB-436 breast cancer cell line was seeded into 96-well plates at 37° C. under 5% CO$_2$ atmosphere using DMEM/F12 (Gibco) containing 10% FBS (Hyclone). After 24 hr incubation, cells were treated with the invented compounds at various concentrations for 6 days. The medium was changed every 3 day. 6 days later, A fluorescence reagent was used to determine the IC$_{50}$ values.

TABLE 2

| Compound | IC$_{50}$ MDA-MB-436 [nM] |
|---|---|
| WO2004080976A1 Example 168 | B |
| WO2004080976A1 Example 168 | B |
| I-14 | C |
| I-19 | C |
| I-22 | C |
| I-24 | D |
| I-25 | B |
| I-26 | B |
| I-27 | A |
| I-28 | B |
| I-29 | D |
| I-30 | C |
| I-31 | B |
| I-32 | A |
| I-33 | A |
| I-34 | D |
| I-35 | A |
| I-36 | B |
| I-37 | B |
| I-38 | B |
| I-39 | D |
| I-40 | B |
| I-41 | A |
| I-42 | A |
| I-43 | B |
| I-44 | A |
| I-45 | B |
| I-46 | B |
| I-48 | A |
| I-49 | B |
| I-50 | C |
| I-51 | B |
| I-52 | A |
| I-53 | A |
| I-54 | B |

TABLE 2-continued

| Compound | IC$_{50}$ MDA-MB-436 [nM] |
|---|---|
| I-55 | B |
| I-56 | D |
| I-57 | B |
| I-58 | B |
| I-59 | B |
| I-61 | C |
| I-66 | C |
| I-69 | C |
| I-70 | C |
| I-71 | C |
| I-73 | C |
| I-74 | B |
| I-75 | B |
| I-76 | B |
| I-77 | C |
| I-78 | D |
| I-79 | C |
| I-80 | A |
| I-81 | C |
| I-82 | B |
| I-83 | B |
| I-84 | C |
| I-85 | A |
| I-86 | B |
| I-87 | D |
| I-88 | A |
| I-89 | B |
| I-90 | C |
| I-91 | C |
| I-92 | B |
| I-93 | C |
| I-94 | D |
| I-95 | C |
| I-96 | D |
| I-98 | D |
| I-99 | B |
| I-100 | D |
| I-101 | D |
| I-102 | D |
| I-103 | D |
| I-104 | D |
| I-109 | D |
| I-110 | D |
| I-111 | D |
| I-112 | D |
| I-113 | D |
| I-114 | D |
| I-115 | D |
| I-116 | D |
| I-118 | D |
| I-120 | A |
| I-121 | D |
| I-124 | C |
| I-125 | A |
| I-126 | B |
| I-128 | B |
| I-129 | D |
| I-130 | A |
| I-131 | C |
| I-132 | A |
| I-133 | C |
| I-134 | C |
| I-135 | B |
| I-136 | B |
| I-137 | C |
| I-138 | D |
| I-140 | A |
| I-141 | B |
| I-142 | B |
| I-143 | A |
| I-144 | A |
| I-145 | B |
| I-146 | B |
| I-147 | D |
| I-148 | A |
| I-149 | A |
| I-150 | C |
| I-151 | D |
| I-153 | D |
| I-154 | D |
| I-155 | C |

Range A: IC$_{50}$ ≤ 5 nM
Range B: 5 nM < IC$_{50}$ ≤ 50 nM
Range C: 50 nM < IC$_{50}$ ≤ 300 nM
Range D: 300 nM < IC$_{50}$ ≤ 1,000 nM
Range E: IC$_{50}$ > 1,000 nM According to the above table 2, the compounds in the present invent ion showed potent growth inhibition of cancer cells in cell cytotoxicity assay using MDA-MB-436 breast cancer cell line.

3. Cell Viability Assay (Capan-1)

Cell viability assay was performed by using Capan-1 cell line to measure cytotoxicity of compounds in the present invention. Capan-1 pancreatic cancer cell line was seeded into 96-well plates at 37° C. under 5% CO atmosphere using IMDM (Sigma) containing 10% FBS (Hyclone). After 24 hr incubation, cells were treated with the invented compounds at various concentrations for 10 days. After 7-day incubation, the medium was changed. 10 days later, A fluorescence reagent was used to determine the IC$_{50}$ values.

TABLE 3

| Compound | IC$_{50}$, Capan-1 [nM] |
|---|---|
| WO2004080976A1 Example 168 | D |
| WO2004080976A1 Example 168 | D |
| I-25 | D |
| I-26 | D |
| I-27 | C |
| I-28 | D |
| I-31 | C |
| I-32 | C |
| I-33 | D |
| I-35 | D |
| I-40 | D |
| I-36 | D |
| I-41 | D |
| I-42 | D |
| I-43 | D |
| I-44 | D |
| I-53 | D |
| I-80 | C |
| I-82 | D |
| I-83 | D |
| I-132 | B |
| I-140 | D |
| I-141 | D |
| I-142 | D |
| I-143 | C |
| I-146 | D |
| I-149 | D |
| I-99 | D |
| I-100 | D |

Range A: IC$_{50}$ ≤ 5 nM
Range B: 5 nM < IC$_{50}$ ≤ 50 nM
Range C: 50 nM < IC$_{50}$ ≤ 300 nM
Range D: 300 nM < IC$_{50}$ ≤ 1,000 nM
Range E: IC$_{50}$ > 1,000 nM According to the above table 3, the compounds in the present invent ion showed potent growth inhibition of cancer cells in cell cytotoxicity assay using Capan-1 pancreatic cancer cell line.

4. Cell Viability Assay (LNCap)

Cell viability assay was performed by using LNCaP cell line to measure cytotoxicity of compounds in the present invention. LNCaP prostate cancer cell line was seeded into 96-well plates at 37° C. under 5% $CO_2$ atmosphere using RPMI-1640 (Hyclone) containing 10% FBS (Hyclone). After 24 hr incubation, cells were treated with the invented compounds at various concentrations for 11 days. The medium was changed every 3 to 4 day. 11 days later, A fluorescence reagent was used to determine the $IC_{50}$ values.

TABLE 4

| Compound | $IC_{50}$ LNCap [nM] |
|---|---|
| WO2004080976A1 Example 168 | E |
| I-27 | C |
| I-32 | C |
| I-33 | D |
| I-35 | E |
| I-53 | E |
| I-80 | C |
| I-83 | E |
| I-99 | D |
| I-114 | B |
| I-131 | B |
| I-146 | E |
| I-149 | E |

Range A: $IC_{50} \leq 5$ nM
Range B: 5 nM $< IC_{50} \leq 50$ nM
Range C: 50 nM $< IC_{50} \leq 300$ nM
Range D: 300 nM $< IC_{50} \leq 1,000$ nM
Range E: $IC_{50} > 1,000$ nM According to the above table 4, the compounds in the present invent ion showed potent growth inhibition of cancer cells in cell cytotoxicity assay using LNCaP prostate cancer cell line.

5. Tankyrase-1 Enzyme Assay

Tankyrase-1 enzyme assay was performed to determine Tankyrase-1 inhibitory activity of compounds in the present invention. The enzymatic reaction was conducted by coating the plate with substrates of tankyrase-1, and then the plate was washed. Compounds in the present invent ion serially diluted in DMSO were added to the reaction buffer activating tankyrase-1, and incubated for 1 hr at room temperature. After stopping the reaction, the plate was washed, and streptavidin-HRP was added to each well. $IC_{50}$ was calculated by adding chemiluminescent substrate and immediately reading the sample in a microplate reader (Biotek).

TABLE 5

| Compound | IC50 Tankyrase-1 [nM] |
|---|---|
| WO2004080976A1 Example 168 | E |
| I-27 | E |
| I-32 | E |
| I-33 | E |
| I-99 | D |
| I-114 | E |
| I-130 | C |
| I-147 | E |
| I-150 | E |

Range A: $IC_{50} \leq 5$ nM
Range B: 5 nM $< IC_{50} \leq 50$ nM
Range C: 50 nM $< IC_{50} \leq 300$ nM
Range D: 300 nM $< IC_{50} \leq 1,000$ nM
Range E: $IC_{50} > 1,000$ nM According to the above table 5, the compounds in the prevent invention exhibited strong inhibitory activity against tankyrase-1.

Experiment 2

In Vivo Test for Antitumoral Activity

To evaluate the in vivo antitumoral efficacy, the invented compounds (I-80~171) was determined as a result to follows.

Capan-1 Human pancreatic cancer cells were established as subcutaneous xenografts by injection of $8 \times 10^6$ cells into the flanks of adult female Balb/c nude mice. Mice with established tumors (160-250 $mm^3$) were selected for study (n=6/treatment group). The test compounds were formulated in DW and administered orally (po) at a dose of 30~200 mg/kg. The vehicle alone was administered to control groups. Animals were dosed 5 days per week (Monday through Friday) for 3 consecutive weeks.

Animals were weighed and tumor size was determined twice weekly by caliper measurements, and tumor volumes were calculated (volume=$[l \times w^2]/2$ ($mm^3$), where l and w refer to the larger and smaller dimensions collected at each measurement). The mean tumor volumes of each group were calculated. The change in mean treated tumor volume was divided by the change in mean control tumor volume, multiplied by 100 and subtracted from 100% to give the tumor growth inhibition for each group.

TABLE 6

| Compound | Does | Schedule | % TGI |
|---|---|---|---|
| WO2004080976A1 Example 168 | 200 mg/kg | po qd × 5 | 53.5 |
| I-80 | 100 mg/kg | po qd × 5 | 75.9 |
| I-80 | 200 mg/kg | po qd × 5 | 103.9 |
| I-159 | 100 mg/kg | po qd × 5 | 59.4 |
| I-159 | 200 mg/kg | po qd × 5 | 69.4 |
| I-158 | 100 mg/kg | po qd × 5 | 44.9 |
| I-158 | 200 mg/kg | po qd × 5 | 80.9 |
| I-160 | 100 mg/kg | po qd × 5 | 55.8 |
| I-160 | 200 mg/kg | po qd × 5 | 88.2 |
| I-171 | 30 mg/kg | po qd × 5 | 42.1 |
| I-171 | 60 mg/kg | po qd × 5 | 69.7 |

As can be seen from table 6, the selected compounds showed useful tumor growth inhibition.

Experiment 3

Mouse Pharmacokinetics

To ecaluate the pharmacokinetics test, the invented compounds (from I-25 to I-1171) were determined as follows. Blood samples are collected at 15, 30, 60, 120, 240, 480, 1140 min. Quantification is by using a LC-MS/MS method specific to the selected compound. Pharmarcokinetics parameters are calculated using WinNonLinnon compartmental analysis software.

TABLE 7

| Compound | AUC [min*ng/mL] |
|---|---|
| WO2004080976A1 Example 168 | 39,927 |
| I-25 | 49,858 |
| I-26 | 200,772 |
| I-27 | 28,302 |
| I-30 | 31,280 |
| I-33 | 61,268 |
| I-35 | 135,283 |
| I-53 | 74,937 |
| I-75 | 28,516 |
| I-80 | 121,308 |
| I-83 | 34,044 |
| I-99 | 35,139 |
| I-120 | 30,582 |
| I-135 | 9,175 |
| I-140 | 17,724 |
| I-141 | 11,588 |
| I-142 | 5,325 |
| I-143 | 40,367 |
| I-146 | 65,532 |
| I-148 | 28,290 |
| I-149 | 10,138 |
| I-159 | 28,302 |
| I-160 | 135,283 |
| I-161 | 61,268 |
| I-171 | 40,367 |

As can be seen from table 7, the selected compounds showed significant pharmacokinetics in Balb/c male mice.

Experiment 4

Solubility Test

To evaluate the solubility, the invented compounds (I-159, I-161 and I-171) was determined as follows. The compounds was dissolve in water (1 mL, 10 mL and 100 mL) at 25° C. under an atmospheric pressure.

TABLE 8

| Compound | Solvent by volume for one part of soluble by weight. | |
|---|---|---|
| WO2004080976A1 example 168 | From 1000 to 10000 mL | Very slightly soluble |
| I-159 | From 30 to 100 mL | Sparingly soluble |
| I-161 | From 30 to 100 mL | Sparingly soluble |
| I-171 | From 30 to 100 mL | Sparingly soluble |

As can be seen form Table 8. The invented compounds showed significant solubility.

It will be understood that the invention disclosed and defined in this specification extends to all alternative combinations of two or more of the individual features mentioned or evident from the text or drawings. All of these different combinations constitute various alternative aspects of the invention.

INDUSTRIAL APPLICABILITY

The compounds of the present invention are highly active in the suppression of PARP, and according to its pharmaceutical compositions are expected to be useful for therapeutic applications which are improved by suppression of PARP activity, and cancer with mutated BRCA1, BRCA2 and ERG fusion gene in mono or combination treatment with radiation and with chemotherapy.

The invention claimed is:

1. A compound represented by Formula I, racemic, enantiomer, diastereoisomer thereof, or pharmaceutically acceptable salt thereof,

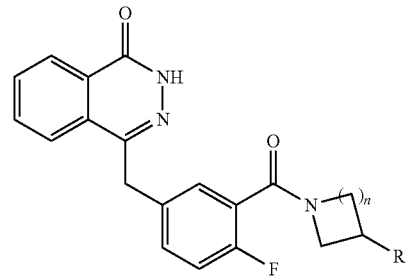

[Formula I]

In the present Formula I,
n is 1 or 2,
R is

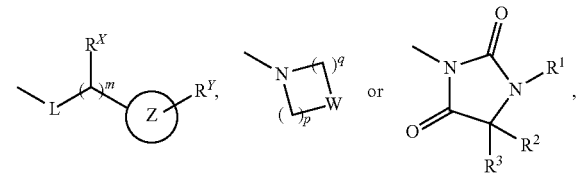

Wherein, when the R is

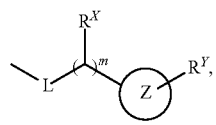

m is 0, 1 or 2,
L is oxygen, methylene, carbonyl, CONHCH$_2$, NR$^{c1}$CH$_2$, NR$^{c2}$CO, NR$^{c3}$, CONR$^{c4}$ or CH$_2$NR$^{c5}$ (especially, R$^{c1}$, R$^{c2}$, R$^{c3}$, R$^{c4}$ and R$^{c5}$ is each independently oxygen, C$_{1-4}$alkylamine, C$_{1-6}$ alkyl, C$_{1-6}$ alkoxy, halo C$_{1-6}$ alkyl, C$_{2-6}$ alkenyl, C$_{2-6}$ alkynyl, C$_{3-8}$ cycloalkyl,
R$^X$ is hydrogen, cyano, hydroxyl, trifluoromethyl, C$_{1-6}$ alkyl or C$_{3-8}$ cycloalkyl,
R$^Y$ is hydrogen, amide, cyano, hydroxyl, trifluoromethyl, halo, ester, C$_{1-4}$ alkylamine, C$_{1-6}$ alkyl, C$_{1-6}$ methoxyalkyl or C$_{2-6}$ alkynyl,
Z is unsubstituted, C$_{1-6}$ alkyl, C$_{1-6}$ methoxyalkyl, C$_{2-6}$ alkenyl, C$_{2-6}$ alkynyl, C$_{3-8}$ cycloalkyl, C$_{3-8}$ cycloalkenyl, C$_{6-10}$ aromatic cycle or 3-8 membered heterocycle having 1-3 nitrogens,
wherein, when the R is

p and q is each independently from 1 to 3,
W is CR$^{d1}$R$^{d2}$ or NR$^{d3}$ (especially, R$^{d1}$, R$^{d2}$ and R$^{d3}$ is each independently hydrogen, fluoro or C$_{1-6}$ alkyl), wherein, when the R is

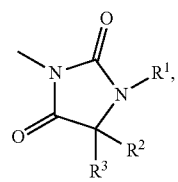

R¹, R² and R³ is each independently hydrogen or $C_{1-6}$ alkyl.

2. The compound according to claim 1,
wherein, L is methylene, carbonyl, $CONHCH_2$, $NR^{c1}CH_2$, $NR^{c2}CO$, $NR^{c3}$, $CONR^{c4}$ or $CH_2NR^{c5}$ (especially, $R^{c1}$, $R^{c2}$, $R^{c3}$, $R^{c4}$ and $R^{c5}$ is each independently hydrogen, $C_{1-6}$alkyl, $C_{2-6}$ alkynyl or $C_{3-8}$ cycloalkyl),
$R^X$ is hydrogen, cyano, hydroxyl, trifluoromethyl, methyl, ethyl or cyclopropyl,
$R^Y$ is hydrogen, dimethylamide, cyano, hydroxyl, trifluoromethyl, halo, ethylester, dimethylamine, methyl, methoxymethyl or propargyl,
Z is unsubstituted, $C_{1-6}$ alkyl, $C_{1-6}$ methoxyalkyl, $C_{2-6}$ alkynyl, $C_{3-8}$ cycloalkyl, $C_{6-10}$ aromatic cycle or 3-8 membered heterocycle having 1-3 nitrogens,
p and q is each independently 1 or 2,
W is $CR^{d1}R^{d2}$ or $NR^{d3}$ (especially $R^{d1}$, $R^{d2}$ and $R^{d3}$ is each independently hydrogen, fluoro or methyl),
R¹, R² and R³ is each independently hydrogen, methyl or ethyl.

3. The compound according to claim 1,
wherein, L is $NR^{c1}CH_2$, $CONR^{c4}$ or $CH_2NR^{c5}$ (especially, $R^{c1}$, $R^{c4}$ and $R^{c5}$ is each independently hydrogen, methyl, ethyl, propyl, propargyl or cyclopropyl),
Z is

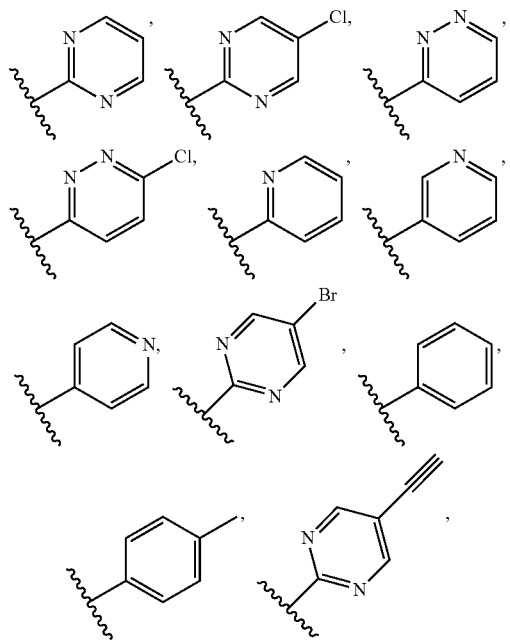

-continued

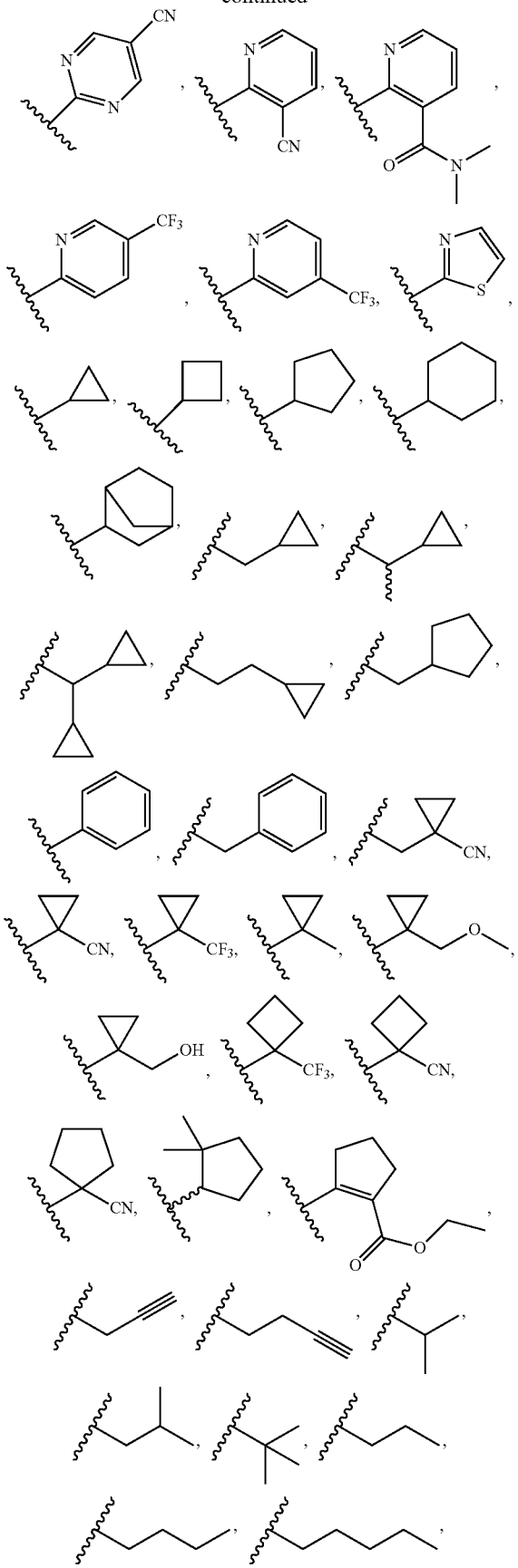

-continued

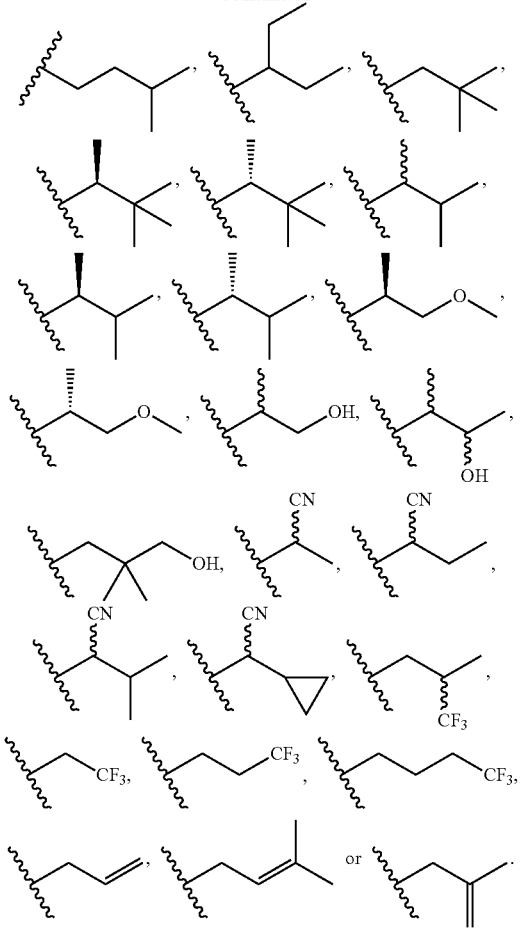

4. The compound according to claim 1, wherein, L is methylene or carbonyl, Z is

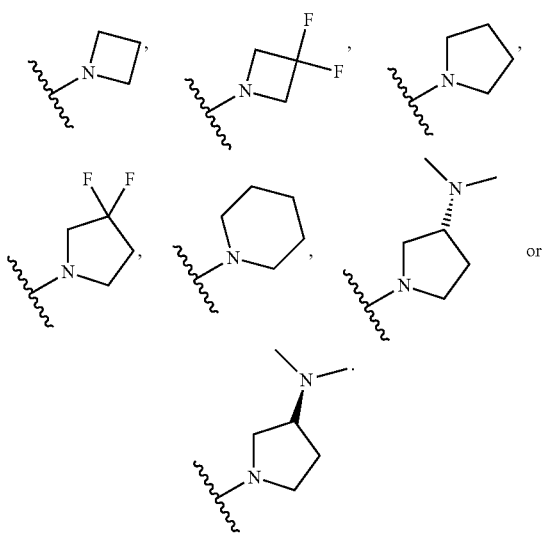

5. The compound according to claim 1, wherein, L is CONHCH$_2$ or NR$^{c2}$CO (especially, R$^{c2}$ is hydrogen, methyl, ethyl or propyl), Z is

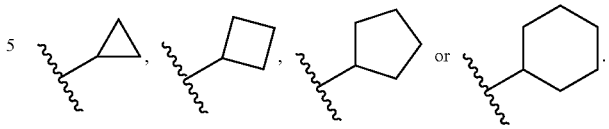

6. The compound according to claim 1, wherein, the present R is

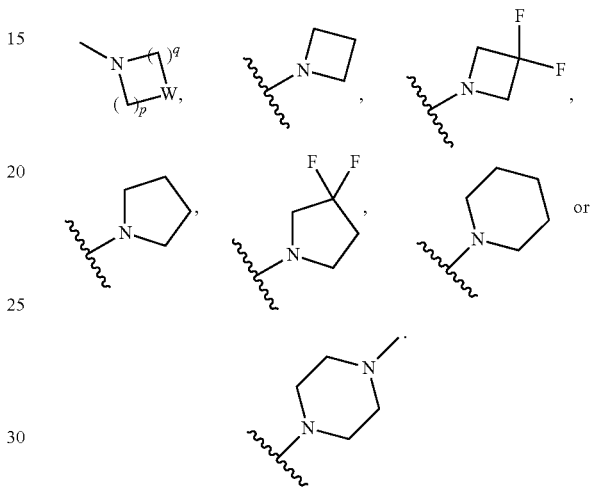

7. The compound according to claim 1, wherein, the compound represented by Formula I is selected from the group Consisting of the following compounds:

(R)-4-(3-(3-aminopyrrolidine-1-carbonyl)-4-fluorobenzyl)phthalazin-1(2H)-one;
(S)-4-(3-(3-aminopyrrolidine-1-carbonyl)-4-fluorobenzyl)phthalazin-1(2H)-one;
4-(3-(3-aminoazetidine-1-carbonyl)-4-fluorobenzyl)phthalazin-1(2H)-one;
(R)-4-(4-fluoro-3-(3-hydroxypyrrolidine-1-carbonyl)benzyl)phthalazin-1(2H)-one;
(S)-4-(4-fluoro-3-(3-hydroxypyrrolidine-1-carbonyl)benzyl)phthalazin-1(2H)-one;
4-(4-fluoro-3-(3-hydroxyazetidine-1-carbonyl)benzyl)phthalazin-1(2H)-one;
4-(4-fluoro-3-(3-(hydroxymethyl)azetidine-1-carbonyl)benzyl)phthalazin-1(2H)-one;
(R)—N-(1-(2-fluoro-5-((4-oxo-3,4-dihydrophthalazin-1-yl)methyl)benzoyl)pyrrolidin-3-yl)cyclopropanecarboxamide;
N-(1-(2-fluoro-5-((4-oxo-3,4-dihydrophthalazin-1-yl)methyl)benzoyl)azetidin-3-yl)cyclopropanecarboxamide;
(S)—N-(1-(2-fluoro-5-((4-oxo-3,4-dihydrophthalazin-1-yl)methyl)benzoyl)pyrrolidin-3-yl)cyclopropanecarboxamide;
(R)—N-(1-(2-fluoro-5-((4-oxo-3,4-dihydrophthalazin-1-yl)methyl)benzoyl)pyrrolidin-3-yl)-N-methylcyclopropanecarboxamide;
N-(1-(2-fluoro-5-((4-oxo-3,4-dihydrophthalazin-1-yl)methyl)benzoyl)azetidin-3-yl)-N-methylcyclopropanecarboxamide;

(S)—N-(1-(2-fluoro-5-((4-oxo-3,4-dihydrophthalazin-1-yl)methyl)benzoyl)pyrrolidin-3-yl)-N-methylcyclopropanecarboxamide;
3-(1-(2-fluoro-5-((4-oxo-3,4-dihydrophthalazin-1-yl)methyl)benzoyl)azetidin-3-yl)-5,5-dimethylimidazolidine-2,4-dione;
(R)-3-(1-(2-fluoro-5-((4-oxo-3,4-dihydrophthalazin-1-yl)methyl)benzoyl)pyrrolidin-3-yl)imidazolidine-2,4-dione;
(R)-1-ethyl-3-(1-(2-fluoro-5-((4-oxo-3,4-dihydrophthalazin-1-yl)methyl)benzoyl)pyrrolidin-3-yl)imidazolidine-2,4-dione;
4-(4-fluoro-3-(3-(4-fluoropiperidine-1-carbonyl)azetidine-1-carbonyl)benzyl)phthalazin-1(2H)-one;
4-(3-(3-(3,3-difluoroazetidine-1-carbonyl)azetidine-1-carbonyl)-4-fluorobenzyl)phthalazin-1(2H)-one;
4-(3-(3-(3,3-difluoropyrrolidine-1-carbonyl)azetidine-1-carbonyl)-4-fluorobenzyl)phthalazin-1(2H)-one;
4-(3-(3-(3,3-difluoropyrrolidine-1-carbonyl)pyrrolidine-1-carbonyl)-4-fluorobenzyl)phthalazin-1(2H)-one;
(R)—N-(cyclopropylmethyl)-1-(2-fluoro-5-((4-oxo-3,4-dihydrophthalazin-1-yl)methyl)benzoyl)pyrrolidine-3-carboxamide;
4-(4-fluoro-3-(3-(pyrrolidine-1-carbonyl)azetidine-1-carbonyl)benzyl)phthalazin-1(2H)-one;
(R)-4-(3-(3-(3-(dimethylamino)pyrrolidine-1-carbonyl)azetidine-1-carbonyl)-4-fluorobenzyl)phthalazin-1(2H)-one;
(S)-4-(3-(3-(3-(dimethylamino)pyrrolidine-1-carbonyl)azetidine-1-carbonyl)-4-fluorobenzyl)phthalazin-1(2H)-one;
4-(3-(3-(cyclobutylamino)azetidine-1-carbonyl)-4-fluorobenzyl)phthalazin-1(2H)-one;
4-(3-(3-(cyclopropylamino)azetidine-1-carbonyl)-4-fluorobenzyl)phthalazin-1(2H)-one;
4-(3-(3-(cyclopentylamino)azetidine-1-carbonyl)-4-fluorobenzyl)phthalazin-1(2H)-one;
4-(3-(3-(cyclohexylamino)azetidine-1-carbonyl)-4-fluorobenzyl)phthalazin-1(2H)-one;
(R)-4-(3-(3-(cyclopropylamino)pyrrolidine-1-carbonyl)-4-fluorobenzyl)phthalazin-1(2H)-one;
(R)-4-(3-(3-(cyclobutylamino)pyrrolidine-1-carbonyl)-4-fluorobenzyl)phthalazin-1(2H)-one;
(R)-4-(3-(3-(cyclopentylamino)pyrrolidine-1-carbonyl)-4-fluorobenzyl)phthalazin-1(2H)-one;
4-(4-fluoro-3-(3-(isopropylamino)azetidine-1-carbonyl)benzyl)phthalazin-1(2H)-one;
4-(3-(3-((cyclopropylmethyl)amino)azetidine-1-carbonyl)-4-fluorobenzyl)phthalazin-1(2H)-one;
4-(3-(3-(bis(cyclopropylmethyl)amino)azetidine-1-carbonyl)-4-fluorobenzyl)phthalazin-1(2H)-one;
4-(4-fluoro-3-(3-(isobutylamino)azetidine-1-carbonyl)benzyl)phthalazin-1(2H)-one;
4-(4-fluoro-3-(3-((1-hydroxypropan-2-yl)amino)azetidine-1-carbonyl)benzyl)phthalazin-1(2H)-one;
4-(4-fluoro-3-(3-(neopentylamino)azetidine-1-carbonyl)benzyl)phthalazin-1(2H)-one;
4-(3-(3-((2,2-dimethylcyclopentyl)amino)azetidine-1-carbonyl)-4-fluorobenzyl)phthalazin-1(2H)-one;
ethyl 2-((1-(2-fluoro-5-((4-oxo-3,4-dihydrophthalazin-1-yl)methyl)benzoyl)azetidin-3-yl)amino)cyclopent-1-enecarboxylate;
4-(4-fluoro-3-(3-(pentan-3-ylamino)azetidine-1-carbonyl)benzyl)phthalazin-1(2H)-one;
4-(4-fluoro-3-(3-((3-methylbutan-2-yl)amino)azetidine-1-carbonyl)benzyl)phthalazin-1(2H)-one;
4-(3-(3-((1-cyclopropylethyl)amino)azetidine-1-carbonyl)-4-fluorobenzyl)phthalazin-1(2H)-one;
4-(3-(3-(bicyclo[2.2.1]heptan-2-ylamino)azetidine-1-carbonyl)-4-fluorobenzyl)phthalazin-1(2H)-one;
4-(3-(3-(sec-butylamino)azetidine-1-carbonyl)-4-fluorobenzyl)phthalazin-1(2H)-one;
4-(3-(3-((dicyclopropylmethyl)amino)azetidine-1-carbonyl)-4-fluorobenzyl)phthalazin-1(2H)-one;
4-(4-fluoro-3-(3-((4-methylpentan-2-yl)amino)azetidine-1-carbonyl)benzyl)phthalazin-1(2H)-one;
4-(4-fluoro-3-(3-((3-hydroxybutan-2-yl)amino)azetidine-1-carbonyl)benzyl)phthalazin-1(2H)-one;
4-(4-fluoro-3-(3-(pentan-2-ylamino)azetidine-1-carbonyl)benzyl)phthalazin-1(2H)-one;
4-(4-fluoro-3-(3-((1-(1-methyl cyclopropyl)ethyl)amino)azetidine-1-carbonyl)benzyl)phthalazin-1(2H)-one;
4-(4-fluoro-3-(3-((3,3,3-trifluoro-2-methylpropyl)amino)azetidine-1-carbonyl)benzyl)phthalazin-1(2H)-one;
4-(3-(3-(allylamino)azetidine-1-carbonyl)-4-fluorobenzyl)phthalazin-1(2H)-one;
4-(4-fluoro-3-(3-(isopentylamino)azetidine-1-carbonyl)benzyl)phthalazin-1(2H)-one;
4-(3-(3-(butylamino)azetidine-1-carbonyl)-4-fluorobenzyl)phthalazin-1(2H)-one;
4-(4-fluoro-3-(3-((3-methylbut-2-en-1-yl)amino)azetidine-1-carbonyl)benzyl)phthalazin-1(2H)-one;
4-(3-(3-((cyclopentylmethyl)amino)azetidine-1-carbonyl)-4-fluorobenzyl)phthalazin-1(2H)-one;
4-(4-fluoro-3-(3-((4,4,4-trifluorobutyl)amino)azetidine-1-carbonyl)benzyl)phthalazin-1(2H)-one;
4-(4-fluoro-3-(3-(pentylamino)azetidine-1-carbonyl)benzyl)phthalazin-1(2H)-one;
4-(3-(3-((2-cyclopropylethyl)amino)azetidine-1-carbonyl)-4-fluorobenzyl)phthalazin-1(2H)-one;
4-(4-fluoro-3-(3-(propylamino)azetidine-1-carbonyl)benzyl)phthalazin-1(2H)-one;
4-(4-fluoro-3-(3-(methyl(pyridin-4-ylmethyl)amino)azetidine-1-carbonyl)benzyl)phthalazin-1(2H)-one;
(R)-4-(4-fluoro-3-(3-(methyl(pyridin-4-ylmethyl)amino)pyrrolidine-1-carbonyl)benzyl)phthalazin-1(2H)-one;
(S)-4-(4-fluoro-3-(3-(methyl(pyridin-4-ylmethyl)amino)pyrrolidine-1-carbonyl)benzyl)phthalazin-1(2H)-one;
(S)-4-(4-fluoro-3-(3-(methyl(pyridin-2-ylmethyl)amino)pyrrolidine-1-carbonyl)benzyl)phthalazin-1(2H)-one;
(R)-4-(4-fluoro-3-(3-(methyl(pyridin-2-ylmethyl)amino)pyrrolidine-1-carbonyl)benzyl)phthalazin-1(2H)-one;
4-(4-fluoro-3-(3-(methyl(pyridin-2-ylmethyl)amino)azetidine-1-carbonyl)benzyl)phthalazin-1(2H)-one;
4-(4-fluoro-3-(3-(methyl(pyridin-3-ylmethyl)amino)azetidine-1-carbonyl)benzyl)phthalazin-1(2H)-one;
(S)-4-(4-fluoro-3-(3-(methyl(pyridin-3-ylmethyl)amino)pyrrolidine-1-carbonyl)benzyl)phthalazin-1(2H)-one;
(R)-4-(4-fluoro-3-(3-(methyl(pyridin-3-ylmethyl)amino)pyrrolidine-1-carbonyl)benzyl)phthalazin-1(2H)-one;
4-(3-(3-(cyclopropyl(methyl)amino)azetidine-1-carbonyl)-4-fluorobenzyl)phthalazin-1(2H)-one;
4-(3-(3-(cyclopropyl(ethyl)amino)azetidine-1-carbonyl)-4-fluorobenzyl)phthalazin-1(2H)-one;
4-(3-(3-(cyclobutyl(methyl)amino)azetidine-1-carbonyl)-4-fluorobenzyl)phthalazin-1(2H)-one;
4-(3-(3-(cyclopentyl(prop-2-yn-1-yl)amino)azetidine-1-carbonyl)-4-fluorobenzyl)phthalazin-1(2H)-one;
4-(3-(3-(3,3-difluoropyrrolidin-1-yl)azetidine-1-carbonyl)-4-fluorobenzyl)phthalazin-1(2H)-one;
4-(4-fluoro-3-(3-(4-fluoropiperidin-1-yl)azetidine-1-carbonyl)benzyl)phthalazin-1(2H)-one;

4-(3-([1,3'-biazetidine]-1'-carbonyl)-4-fluorobenzyl)
  phthalazin-1(2H)-one;
4-(4-fluoro-3-(3-(pyrrolidin-1-yl)azetidine-1-carbonyl)
  benzyl)phthalazin-1(2H)-one;
4-(4-fluoro-3-(3-(piperidin-1-yl)azetidine-1-carbonyl)
  benzyl)phthalazin-1(2H)-one;
4-(4-fluoro-3-(3-(4-methylpiperazin-1-yl)azetidine-1-
  carbonyl)benzyl)phthalazin-1(2H)-one;
4-(4-fluoro-3-(3-(phenylamino)azetidine-1-carbonyl)
  benzyl)phthalazin-1(2H)-one;
4-(4-fluoro-3-(3-((1-(trifluoromethyl)cyclopropyl)amino)
  azetidine-1-carbonyl)benzyl)phthalazin-1(2H)-one;
4-(4-fluoro-3-(3-(prop-2-yn-1-ylamino)azetidine-1-car-
  bonyl)benzyl)phthalazin-1(2H)-one;
(S)-4-(4-fluoro-3-(3-((1-methoxypropan-2-yl)amino)aze-
  tidine-1-carbonyl)benzyl)phthalazin-1(2H)-one;
(R)-4-(4-fluoro-3-(3-((1-methoxypropan-2-yl)amino)aze-
  tidine-1-carbonyl)benzyl)phthalazin-1(2H)-one;
4-(4-fluoro-3-(3-((1-(hydroxymethyl)cyclopropyl)amino)
  azetidine-1-carbonyl)benzyl)phthalazin-1(2H)-one;
4-(4-fluoro-3-(3-((1-methylcyclopropyl)amino)azetidine-
  1-carbonyl)benzyl)phthalazin-1(2H)-one;
(R)-4-(3-(3-((3,3-dimethylbutan-2-yl)amino)azetidine-1-
  carbonyl)-4-fluorobenzyl)phthalazin-1(2H)-one;
(S)-4-(3-(3-((3,3-dimethylbutan-2-yl)amino)azetidine-1-
  carbonyl)-4-fluorobenzyl)phthalazin-1(2H)-one;
(R)-4-(4-fluoro-3-(3-((3-methylbutan-2-yl)amino)azeti-
  dine-1-carbonyl)benzyl)phthalazin-1(2H)-one;
(S)-4-(4-fluoro-3-(3-((3-methylbutan-2-yl)amino)azeti-
  dine-1-carbonyl)benzyl)phthalazin-1(2H)-one;
4-(4-fluoro-3-(3-((1-(methoxymethyl)cyclopropyl)
  amino)azetidine-1-carbonyl)benzyl)phthalazin-1(2H)-
  one;
4-(3-(3-(but-3-yn-1-ylamino)azetidine-1-carbonyl)-4-
  fluorobenzyl)phthalazin-1(2H)-one;
4-(4-fluoro-3-(3-((2-methylallyl)amino)azetidine-1-car-
  bonyl)benzyl)phthalazin-1(2H)-one;
4-(4-fluoro-3-(3-((3-hydroxy-2,2-dimethylpropyl)amino)
  azetidine-1-carbonyl)benzyl)phthalazin-1(2H)-one;
1-(((1-(2-fluoro-5-((4-oxo-3,4-dihydrophthalazin-1-yl)
  methyl)benzoyl)azetidin-3-yl)amino)methyl)cyclopro-
  panecarbonitrile;
4-(4-fluoro-3-(3-((2,2,2-trifluoroethyl)amino)azetidine-
  1-carbonyl)benzyl)phthalazin-1(2H)-one;
(R)-4-(4-fluoro-3-(3-(pyrrolidin-3-ylamino)azetidine-1-
  carbonyl)benzyl)phthalazin-1(2H)-one;
(S)-4-(4-fluoro-3-(3-(pyrrolidin-3-ylamino)azetidine-1-
  carbonyl)benzyl)phthalazin-1(2H)-one;
1-((1-(2-fluoro-5-((4-oxo-3,4-dihydrophthalazin-1-yl)
  methyl)benzoyl)azetidin-3-yl)amino)cyclopentanecar-
  bonitrile;
1-((1-(2-fluoro-5-((4-oxo-3,4-dihydrophthalazin-1-yl)
  methyl)benzoyl)azetidin-3-yl)amino)cyclobutanecar-
  bonitrile;
2-((1-(2-fluoro-5-((4-oxo-3,4-dihydrophthalazin-1-yl)
  methyl)benzoyl)azetidin-3-yl)amino)propanenitrile;
2-((1-(2-fluoro-5-((4-oxo-3,4-dihydrophthalazin-1-yl)
  methyl)benzoyl)azetidin-3-yl)amino)butanenitrile;
2-((1-(2-fluoro-5-((4-oxo-3,4-dihydrophthalazin-1-yl)
  methyl)benzoyl)azetidin-3-yl)amino)-3-methylbu-
  tanenitrile;
2-cyclopropyl-2-((1-(2-fluoro-5-((4-oxo-3,4-dihy-
  drophthalazin-1-yl)methyl)benzoyl)azetidin-3-yl)
  amino)acetonitrile;
4-(4-fluoro-3-(3-((1-(trifluoromethyl)cyclobutyl)amino)
  azetidine-1-carbonyl)benzyl)phthalazin-1(2H)-one;
(S)-4-(4-fluoro-3-(3-(methyl(pyrimidin-2-yl)amino)pyr-
  rolidine-1-carbonyl)benzyl)phthalazin-1(2H)-one;
(S)-4-(4-fluoro-3-(3-(methyl(pyrimidin-2-yl)amino)pyr-
  rolidine-1-carbonyl)benzyl)phthalazin-1(2H)-one;
4-(4-fluoro-3-(3-(methyl(pyrimidin-2-yl)amino)azeti-
  dine-1-carbonyl)benzyl)phthalazin-1(2H)-one;
4-(4-fluoro-3-(3-(methyl(pyrimidin-2-yl)amino)azeti-
  dine-1-carbonyl)benzyl)phthalazin-1(2H)-one;
4-(4-fluoro-3-(3-(pyrimidin-2-ylamino)azetidine-1-car-
  bonyl)benzyl)phthalazin-1(2H)-one;
(S)-4-(4-fluoro-3-(3-(pyrimidin-2-ylamino)pyrrolidine-1-
  carbonyl)benzyl)phthalazin-1(2H)-one;
(S)-4-(3-(3-((6-chloropyridazin-3-yl)(methyl)amino)pyr-
  rolidine-1-carbonyl)-4-fluorobenzyl)phthalazin-1(2H)-
  one;
(S)-4-(3-(3-((6-chloropyridazin-3-yl)amino)pyrrolidine-
  1-carbonyl)-4-fluorobenzyl)phthalazin-1(2H)-one;
(S)-4-(4-fluoro-3-(3-(methyl(pyridazin-3-yl)amino)pyr-
  rolidine-1-carbonyl)benzyl)phthalazin-1(2H)-one;
4-(3-(3-((6-chloropyridazin-3-yl)amino)azetidine-1-car-
  bonyl)-4-fluorobenzyl)phthalazin-1(2H)-one;
4-(3-(3-((6-chloropyridazin-3-yl)(methyl)amino)azeti-
  dine-1-carbonyl)-4-fluorobenzyl)phthalazin-1(2H)-
  one;
4-(3-(3-(cyclobutyl(pyrimidin-2-yl)amino)azetidine-1-
  carbonyl)-4-fluorobenzyl)phthalazin-1(2H)-one;
4-(4-fluoro-3-(3-(pyridazin-3-ylamino)azetidine-1-carbo-
  nyl)benzyl)phthalazin-1(2H)-one;
(R)-4-(3-(3-((6-chloropyridazin-3-yl)amino)pyrrolidine-
  1-carbonyl)-4-fluorobenzyl)phthalazin-1(2H)-one;
(R)-4-(3-(3-((6-chloropyridazin-3-yl)(methyl)amino)pyr-
  rolidine-1-carbonyl)-4-fluorobenzyl)phthalazin-1(2H)-
  one;
(R)-4-(4-fluoro-3-(3-(pyrimidin-2-ylamino)pyrrolidine-
  1-carbonyl)benzyl)phthalazin-1(2H)-one;
(R)-4-(3-(3-(methyl(pyrimidin-2-yl)amino)pyrrolidine-1-
  carbonyl)-4-fluorobenzyl)phthalazin-1(2H)-one;
(R)-4-(4-fluoro-3-(3-(pyridazin-3-ylamino)pyrrolidine-1-
  carbonyl)benzyl)phthalazin-1(2H)-one;
(R)-4-(4-fluoro-3-(3-(methyl(pyridazin-3-yl)amino)pyr-
  rolidine-1-carbonyl)benzyl)phthalazin-1(2H)-one;
(R)-4-(4-fluoro-3-(3-(thiazol-2-ylamino)pyrrolidine-1-
  carbonyl)benzyl)phthalazin-1(2H)-one;
(R)-4-(3-(3-((5-ethynylpyrimidin-2-yl)amino)pyrroli-
  dine-1-carbonyl)-4-fluorobenzyl)phthalazin-1(2H)-
  one;
(R)-2-((1-(2-fluoro-5-((4-oxo-3,4-dihydrophthalazin-1-
  yl)methyl)benzoyl)pyrrolidin-3-yl)amino)pyrimidine-
  5-carbonitrile;
(R)-2-((1-(2-fluoro-5-((4-oxo-3,4-dihydrophthalazin-1-
  yl)methyl)benzoyl)pyrrolidin-3-yl)amino)nicotinoni-
  trile;
(R)-4-(4-fluoro-3-(3-(pyridin-2-ylamino)pyrrolidine-1-
  carbonyl)benzyl)phthalazin-1(2H)-one;
(R)-2-((1-(2-fluoro-5-((4-oxo-3,4-dihydrophthalazin-1-
  yl)methyl)benzoyl)pyrrolidin-3-yl)amino)-N,N-dim-
  ethylnicotinamide;
(R)-4-(3-(3-((5-bromopyrimidin-2-yl)amino)pyrrolidine-
  1-carbonyl)-4-fluorobenzyl)phthalazin-1(2H)-one;
(R)-4-(4-fluoro-3-(3-((5-(trifluoromethyl)pyridin-2-yl)
  amino)pyrrolidine-1-carbonyl)benzyl)phthalazin-1
  (2H)-one;
(R)-4-(4-fluoro-3-(3-((4-(trifluoromethyl)pyridin-2-yl)
  amino)pyrrolidine-1-carbonyl)benzyl)phthalazin-1
  (2H)-one;
4-(3-(3-(benzylamino)azetidine-1-carbonyl)-4-fluoroben-
  zyl)phthalazin-1(2H)-one;

4-(4-fluoro-3-(3-((3,3,3-trifluoropropyl)amino)azetidine-1-carbonyl)benzyl)phthalazin-1(2H)-one;

(R)-4-(3-(3-(azetidin-1-yl)pyrrolidine-1-carbonyl)-4-fluorobenzyl)phthalazin-1(2H)-one;

(R)-4-(3-([1,3'-bipyrrolidine]-1'-carbonyl)-4-fluorobenzyl)phthalazin-1(2H)-one;

(R)-4-(4-fluoro-3-(3-(piperidin-1-yl)pyrrolidine-1-carbonyl)benzyl)phthalazin-1(2H)-one;

(R)-4-(4-fluoro-3-(3-(p-tolylamino)pyrrolidine-1-carbonyl)benzyl)phthalazin-1(2H)-one;

(R)-4-(4-fluoro-3-(3-(phenylamino)pyrrolidine-1-carbonyl)benzyl)phthalazin-1(2H)-one;

4-(4-fluoro-3-(3-(pyrrolidin-1-ylmethyl)azetidine-1-carbonyl)benzyl)phthalazin-1(2H)-one;

4-(4-fluoro-3-(3-(piperidin-1-ylmethyl)azetidine-1-carbonyl)benzyl)phthalazin-1(2H)-one;

4-(3-(3-(azetidin-1-ylmethyl)azetidine-1-carbonyl)-4-fluorobenzyl)phthalazin-1(2H)-one;

4-(3-(3-((cyclopropylamino)methyl)azetidine-1-carbonyl)-4-fluorobenzyl)phthalazin-1(2H)-one;

4-(4-fluoro-3-(3-((isopropylamino)methyl)azetidine-1-carbonyl)benzyl)phthalazin-1(2H)-one;

4-(3-(3-(((cyclopropylmethyl)amino)methyl)azetidine-1-carbonyl)-4-fluorobenzyl)phthalazin-1(2H)-one;

4-(4-fluoro-3-(3-((isobutylamino)methyl)azetidine-1-carbonyl)benzyl)phthalazin-1(2H)-one;

4-(3-(3-((tert-butylamino)methyl)azetidine-1-carbonyl)-4-fluorobenzyl)phthalazin-1(2H)-one;

4-(3-(3-((cyclobutylamino)methyl)azetidine-1-carbonyl)-4-fluorobenzyl)phthalazin-1(2H)-one;

4-(4-fluoro-3-(3-((prop-2-yn-1-ylamino)methyl)azetidine-1-carbonyl)benzyl)phthalazin-1(2H)-one;

4-(4-fluoro-3-(3-((phenylamino)methyl)azetidine-1-carbonyl)benzyl)phthalazin-1(2H)-one;

1-((((1-(2-fluoro-5-((4-oxo-3,4-dihydrophthalazin-1-yl)methyl)benzoyl)azetidin-3-yl)methyl)amino)methyl)cyclopropanecarbonitrile;

1-(((1-(2-fluoro-5-((4-oxo-3,4-dihydrophthalazin-1-yl)methyl)benzoyl)azetidin-3-yl)methyl)amino)cyclopropanecarbonitrile;

4-(3-(3-((cyclopropyl(prop-2-yn-1-yl)amino)methyl)azetidine-1-carbonyl)-4-fluorobenzyl)phthalazin-1(2H)-one;

4-(3-(3-((cyclopropyl(methyl)amino)methyl)azetidine-1-carbonyl)-4-fluorobenzyl)phthalazin-1(2H)-one;

4-(3-(3-((cyclopropyl(ethyl)amino)methyl)azetidine-1-carbonyl)-4-fluorobenzyl)phthalazin-1(2H)-one;

4-(3-(3-(cyclobutylamino)azetidine-1-carbonyl)-4-fluorobenzyl)phthalazin-1(2H)-one hydrochloride;

4-(3-(3-(cyclopropylamino)azetidine-1-carbonyl)-4-fluorobenzyl)phthalazin-1(2H)-one hydrochloride;

4-(3-(3-(cyclopentylamino)azetidine-1-carbonyl)-4-fluorobenzyl)phthalazin-1(2H)-one hydrochloride;

4-(4-fluoro-3-(3-(isopropylamino)azetidine-1-carbonyl)benzyl)phthalazin-1(2H)-one hydrochloride;

4-(3-(3-((cyclopropylmethyl)amino)azetidine-1-carbonyl)-4-fluorobenzyl)phthalazin-1(2H)-one hydrochloride;

4-(4-fluoro-3-(3-(isobutylamino)azetidine-1-carbonyl)benzyl)phthalazin-1(2H)-one hydrochloride;

4-(4-fluoro-3-(3-((1-hydroxypropan-2-yl)amino)azetidine-1-carbonyl)benzyl)phthalazin-1(2H)-one hydrochloride;

4-(3-(3-(butylamino)azetidine-1-carbonyl)-4-fluorobenzyl)phthalazin-1(2H)-one hydrochloride;

4-(3-([1,3'-biazetidine]-1'-carbonyl)-4-fluorobenzyl)phthalazin-1(2H)-one hydrochloride;

(R)-4-(4-fluoro-3-(3-((1-methoxypropan-2-yl)amino)azetidine-1-carbonyl)benzyl)phthalazin-1(2H)-one hydrochloride;

1-((1-(2-fluoro-5-((4-oxo-3,4-dihydrophthalazin-1-yl)methyl)benzoyl)azetidin-3-yl)amino)cyclobutanecarbonitrile hydrochloride;

(R)-4-(3-(3-(azetidin-1-yl)pyrrolidine-1-carbonyl)-4-fluorobenzyl)phthalazin-1(2H)-one hydrochloride;

4-(4-fluoro-3-(3-(pyrrolidin-1-ylmethyl)azetidine-1-carbonyl)benzyl)phthalazin-1(2H)-one hydrochloride;

4-(4-fluoro-3-(3-(piperidin-1-ylmethyl)azetidine-1-carbonyl)benzyl)phthalazin-1(2H)-one hydrochloride;

4-(3-(3-(azetidin-1-ylmethyl)azetidine-1-carbonyl)-4-fluorobenzyl)phthalazin-1(2H)-one hydrochloride;

4-(3-(3-((cyclopropylamino)methyl)azetidine-1-carbonyl)-4-fluorobenzyl)phthalazin-1(2H)-one hydrochloride;

4-(4-fluoro-3-(3-((isopropylamino)methyl)azetidine-1-carbonyl)benzyl)phthalazin-1(2H)-one hydrochloride;

4-(3-(3-(((cyclopropylmethyl)amino)methyl)azetidine-1-carbonyl)-4-fluorobenzyl)phthalazin-1(2H)-one hydrochloride;

4-(4-fluoro-3-(3-((isobutylamino)methyl)azetidine-1-carbonyl)benzyl)phthalazin-1(2H)-one hydrochloride;

4-(3-(3-((cyclobutylamino)methyl)azetidine-1-carbonyl)-4-fluorobenzyl)phthalazin-1(2H)-one hydrochloride; and 4-(4-fluoro-3-(3-((prop-2-yn-1-ylamino)methyl)azetidine-1-carbonyl)benzyl)phthalazin-1(2H)-one hydrochloride.

* * * * *